United States Patent
Bakonyi et al.

(10) Patent No.: US 9,242,989 B2
(45) Date of Patent: *Jan. 26, 2016

(54) COMPOUNDS AS MODULATORS OF RORγ

(71) Applicant: Boehringer Ingelheim International GmbH, Ingelheim am Rhein (DE)

(72) Inventors: Johanna Bakonyi, New Fairfield, CT (US); Steven Richard Brunette, New Milford, CT (US); Delphine Collin, New Milford, CT (US); Robert Owen Hughes, Newtown, CT (US); Xiang Li, New Milford, CT (US); Shuang Liang, Roseville, MN (US); Robert Sibley, North Haven, CT (US); Michael Robert Turner, Danbury, CT (US); Lifen Wu, New Milford, CT (US); Qiang Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/683,682

(22) Filed: Apr. 10, 2015

(65) Prior Publication Data

US 2015/0291607 A1    Oct. 15, 2015

Related U.S. Application Data

(60) Provisional application No. 61/979,231, filed on Apr. 14, 2014.

(51) Int. Cl.
| C07D 487/04 | (2006.01) |
| A61K 31/33 | (2006.01) |
| C07D 475/10 | (2006.01) |

(52) U.S. Cl.
CPC .............. C07D 487/04 (2013.01); A61K 31/33 (2013.01); C07D 475/10 (2013.01)

(58) Field of Classification Search
CPC .................................................... C07D 487/04
See application file for complete search history.

(56) References Cited

U.S. PATENT DOCUMENTS

2005/0010047 A1*   1/2005  Bonnert .............. C07D 475/06
                                                               544/258

FOREIGN PATENT DOCUMENTS

WO    WO 2009/022185    *   2/2009

OTHER PUBLICATIONS

International Search Report, ISA 220, for PCT/US 2015025328 mailed Jul. 1, 2015.
Khan, Bioorganic and Medicinal Chem. Letters, "Small Molecule amides as potent ROR-y selective modulators" vol. 23, 2013, p. 532-536.
Hughes, Bioorganic and Medicinal Chem. Letters, "Investigation of aminopyridiopyrazinones as PDE5 inhibitors: Evaluation of modifications to the central ring system", vol. 19, 2009, p. 4092-4096.

* cited by examiner

Primary Examiner — Shailendra Kumar
(74) Attorney, Agent, or Firm — Michael P. Morris; Edward S. Lazer

(57) ABSTRACT

The present invention encompasses compounds of the formula (I)

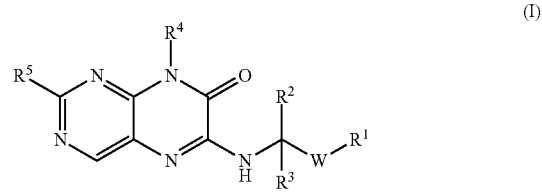

wherein the variables are defined herein which are suitable for the modulation of RORγ and the treatment of diseases related to the modulation of RORγ. The present invention also encompasses processes of making compounds of formula (I) and pharmaceutical preparations containing them.

53 Claims, No Drawings

COMPOUNDS AS MODULATORS OF RORγ

BACKGROUND OF THE INVENTION

1. Technical Field

The present invention relates to novel compounds which modulate the activity of RORγ and their use as medicaments.

2. Background Information

RORγ (retinoic acid receptor related orphan receptor gamma) (also referred to as "RORγt") is a transcription factor belonging to the steroid hormone receptor superfamily (reviewed in Jetten 2006. Adv. Dev Biol. 16: 313-355). RORγ has been identified as a transcriptional factor that is required for the differentiation of T cells and secretion of Interleukin 17 (IL-17) from a subset of T cells termed $Th_{17}$ cells (Ivanov, Cell 2006, 126, 1121-1133). The rationale for the use of a RORγ targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with neutralizing antibodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated $Th_{17}$ T cells via inhibition of RORγ may offer similar therapeutic benefit.

SUMMARY OF THE INVENTION

The invention comprises a novel class of heteroaromatic compounds and methods for making and using the same, said compounds having the general structure of formula (I), wherein the substituent groups are as herein defined:

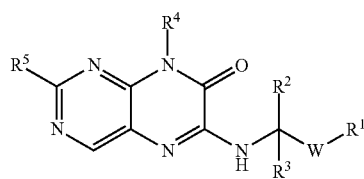

(I)

These compounds are useful for the treatment of autoimmune and allergic disorders in that they exhibit good modulatory effect upon RORγ.

DETAILED DESCRIPTION OF THE INVENTION

Definitions and Conventions Used

Terms that are not specifically defined here have the meanings that would be apparent to a person skilled in the art, in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x number of carbon atoms.

In general, for groups comprising two or more subgroups, unless otherwise indicated the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached. However, if a bond is depicted just prior to the first named subgroup, then that first named subgroup is the radical attachment point, for example, the substituent "—S(O)$_n$C$_{1-6}$alkyl" means a C$_{1-6}$-alkyl-group which is bound to an S(O)$_n$ group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkoxy.

Unlike alkyl, alkenyl, when used alone or in combination, consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl, when used alone or in combination, consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl), when used alone or in combination, is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

Halogen relates to fluorine, chlorine, bromine and/or iodine atoms.

The term "cycloalkyl", when used alone or in combination, refers to a nonaromatic 3 to 12-membered (but preferably, 3 to 6-membered) monocyclic carbocyclic radical or a nonaromatic 6 to 10-membered fused bicyclic, bridged bicyclic, propellane or spirocyclic carbocyclic radical. The $C_{3-12}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[1.1.1] pentane, bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2] octanyl, and bicyclo[3.2.1]octanyl. Non-limiting examples of 6 to 10-membered propellane carbocyclic radicals include but are not limited to [1.1.1.]propellane, [3.3.3]propellane and [3.3.1]propellane. Non-limiting examples of 6 to 10-membered spirocyclic carbocyclic radicals include but are not limited to spiro[3,3]heptanyl, spiro[3,4]octanyl and spiro [4,4]heptanyl.

The term "heterocyclyl", when used alone or in combination, refers to a heterocyclic ring system that contains 2-10 carbon atoms and one to four heteroatom ring atoms chosen from NH, NR', oxygen and sulfur wherein R' is $C_{1-6}$ alkyl and includes stable nonaromatic 4-8 membered monocyclic heterocyclic radical or a stable nonaromatic 6 to 11-membered fused bicyclic, bridged bicyclic or spirocyclic heterocyclic radical. The heterocycle may be either completely saturated or partially unsaturated. In one embodiment the heterocycle is a $C_{3-6}$ heterocycle, i.e., containing 3 to 6 ring carbon atoms. Non-limiting examples of nonaromatic monocyclic heterocyclic radicals include tetrahydrofuranyl, azetidinyl, pyrrolidinyl, pyranyl, tetrahydropyranyl, dioxanyl, thiomorpholinyl, 1,1-dioxo-1.lamda$_6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0] hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro [3,4]octanyl, and 7-aza-spiro[3,4]octanyl. Sulfur and nitrogen may optionally be present in all the possible oxidation stages (sulphur→sulphoxide —SO—, sulphone —$SO_2$—; nitrogen→N-oxide).

The term "aryl", when used alone or in combination, refers to an aromatic hydrocarbon ring containing from six to fourteen carbon ring atoms (e.g., a $C_{6-14}$ aryl, preferably $C_{6-10}$ aryl). The term $C_{6-14}$ aryl includes monocyclic rings, fused rings and bicyclic rings where at least one of the rings is aromatic. Non-limiting examples of $C_{6-14}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heteroaryl", when used alone or in combination, refers to a heteroaromatic ring system that contains 2-10 carbon atoms and 1-4 heteroatom ring atoms selected from N, NH, NR', O and S wherein R' is $C_{1-6}$ alkyl and includes aromatic 5 to 6-membered monocyclic heteroaryls and aromatic 7 to 11-membered heteroaryl bicyclic or fused rings where at least one of the rings is aromatic. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic or fused rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl. Sulfur and nitrogen may optionally be present in all the possible oxidation stages (sulphur→sulphoxide —SO—, sulphone —$SO_2$—; nitrogen→N-oxide).

The compounds of the invention are only those which are contemplated to be chemically stable as will be appreciated by those skilled in the art. For example, a compound which would have a "dangling valency", or a carbanion are not compounds contemplated by the inventive methods disclosed herein.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and their corresponding unsolvated as well as solvated forms with pharmaceutically acceptable solvents such as water, ethanol and the like.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio. Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

By a therapeutically effective amount for the purposes of this invention is meant a quantity of substance that is capable of obviating symptoms of illness or alleviating these symptoms, or which prolong the survival of a treated patient.

Embodiments of the Invention

A general embodiment of the invention is directed to a compound of formula (I) below:

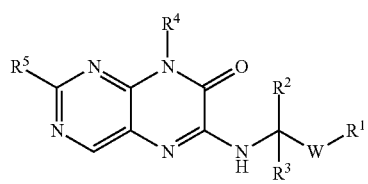

(I)

wherein:
$R^1$ is:
—CN;
—S(O)$_n$R$^6$;
—S(O)NR$^7$R$^8$;
—S(O)(NR$^9$)R$^6$;
—N(R$^9$)C(O)R$^6$;
—N(R$^9$)C(O)OR$^6$;
—N(R$^9$)S(O)$_n$R$^6$;
—C(O)OR$^9$;
—C(O)NR$^7$R$^8$; or
—C(O)R$^9$; or
$R^6$, $R^7$, $R^8$ or $R^9$ of $R^1$ may be cyclized onto W to form a ring; and
$R^2$ and $R^3$ are each independently:
(A) —H;
(B) C$_{1-3}$ alkyl optionally substituted with one, two or three groups selected from:
a) C$_{3-6}$ cycloalkyl;
b) —OR$^9$;
c) —CN;
d) —CF$_3$;
e) -halo;
f) —C(O)OR$^9$;
g) —C(O)N(R$^9$)$_2$;
h) —S(O)$_n$R$^9$; and
i) —S(O)$_n$NR$^7$R$^8$; or
(C) C$_{3-6}$ cycloalkyl;
(D) C$_{3-6}$ heterocyclyl; or
$R^2$ and $R^3$ are taken together with the carbon to which they are attached to form a C$_{3-6}$ carbocyclic ring; or
$R^2$ and $R^3$ are taken together with the carbon to which they are attached to form a C$_{3-6}$ heterocyclic ring; or
$R^2$ or $R^3$ may be cyclized onto W to form a ring;
$R^4$ is:
(A) C$_{1-6}$ alkyl optionally substituted with one, two or three groups selected from:
a) C$_{3-6}$ cycloalkyl;
b) C$_{3-6}$ heterocyclyl;
c) —OR$^9$;
d) —CN;
e) —S(O)$_n$R$^9$;
f) -halo; and
g) —CF$_3$; or
(B) C$_{3-12}$ cycloalkyl optionally substituted with one, two or three groups selected from:
a) C$_{1-6}$ alkyl;
b) —OR$^9$;
c) —CN;
d) —S(O)$_n$R$^9$;
e) -halo; and
f) —CF$_3$; or
(C) aryl, heteroaryl or heterocyclyl each optionally substituted with one, two or three groups selected from:
a) C$_{1-6}$ alkyl;
b) C$_{3-6}$cycloalkyl;
c) —OR$^9$;
d) —CN;
e) —S(O)$_n$R$^9$;
f) -halo; and
g) —CF$_3$;
$R^5$ is aryl, heteroaryl, heterocyclyl or C$_{3-12}$ cycloalkyl each optionally substituted with one, two or three groups selected from:
(A) C$_{1-6}$ alkyl, C$_{3-6}$ cycloalkyl or C$_{3-6}$ heterocyclyl each optionally substituted with one, two or three groups selected from:

a) $C_{3-6}$ cycloalkyl;
  b) $C_{3-6}$ heterocyclyl;
  c) —$OR^9$;
  d) —CN;
  e) —S(O)—$NR^7R^8$
  f) —S(O)—$R^9$;
  g) -halo; and
  h) —$CF_3$; or
(B) —$OR^9$;
(C) —CN;
(D) —$CF_3$;
(E) -halo;
(F) —$S(O)_nNR^7R^8$;
(G) —$S(O)_nR^9$; and
(H) —$NR^7R^8$;
W is aryl, heteroaryl, heterocyclyl, $C_{3-12}$ cycloalkyl, or alkynyl each optionally substituted with one or two groups selected from:
  a) $C_{1-6}$ alkyl;
  b) $C_{3-6}$ cycloalkyl;
  c) —$OR^9$;
  d) —CN;
  e) —$CF_3$;
  f) -halo;
  g) —$NR^7R^8$;
  h) —$C(O)OR^9$; and
  i) —$C(O)N(R^9)_2$;
$R^6$ is selected from:
(A) —OH;
(B) $C_{1-6}$ alkyl optionally substituted with one or two groups selected from:
  a) $C_{3-6}$cycloalkyl;
  b) —$OR^9$;
  c) —CN;
  d) —$CF_3$; and
  e) -halo;
(C) $C_{3-6}$ cycloalkyl; and
(D) —$CF_3$;
$R^7$ and $R^8$ are independently selected from:
(A) —H;
(B) $C_{1-3}$ alkyl optionally substituted with one or two groups selected from:
  a) $C_{3-6}$cycloalkyl;
  b) —$OR^9$;
  c) —CN;
  d) -halo; and
(C) $C_{3-6}$cycloalkyl; or
$R^7$ and $R^8$, together with the nitrogen to which they are bonded, form a saturated ring with 3-6 carbon atoms wherein one carbon atom in said saturated ring may be optionally replaced by —O—, —$NR^9$— or —$S(O)_n$—;
$R^9$ is selected from;
(A) —H;
(B) $C_{1-3}$ alkyl optionally substituted with one or two groups selected from:
  a) $C_{3-6}$cycloalkyl;
  b) —$OR^9$;
  c) —CN;
  d) —$CF_3$; and
  e) -halo; or
(C) $C_{3-6}$cycloalkyl; and
n is 0, 1 or 2;
or a pharmaceutically acceptable salt thereof.

Additional sub-embodiments within the various substituent definitions include the following:

$R^1$ Group Embodiments
(1) $R^1$ is:
  —CN,
  —$S(O)_nR^6$,
  —$S(O)_nNR^7R^8$;
  —$N(H)S(O)_nR^6$; or
  —$S(O)(NH)R^6$; and
wherein:
$R^6$ is:
(A) $C_{1-3}$ alkyl optionally substituted with one or two groups selected from:
  a) $C_{3-6}$cycloalkyl;
  b) —$OR^9$; and
  c) —CN; or
(B) $C_{3-6}$cycloalkyl;
$R^7$ and $R^8$ are each independently:
(A) —H; or
(B) $C_{1-3}$ alkyl; and
$R^9$ is selected from;
(A) —H;
(B) $C_{1-3}$ alkyl; or
(C) $C_{3-6}$cycloalkyl; and
n is 1 or 2.
(2) $R^1$ is:
  —$S(O)_nR^6$,
  —$S(O)_nNR^7R^8$, or
  $S(O)(NH)R^6$; and
wherein:
$R^6$ is:
(A) $C_{1-3}$ alkyl optionally substituted with one or two groups selected from:
  a) $C_{3-6}$cycloalkyl;
  b) —$OR^9$; and
  c) —CN; or
(B) $C_{3-6}$cycloalkyl;
$R^7$ and $R^8$ are each independently:
(A) —H; or
(B) $C_{1-3}$ alkyl; and
$R^9$ is selected from;
(A) —H;
(B) $C_{1-3}$ alkyl; or
(C) $C_{3-6}$cycloalkyl; and
n is 1 or 2.
(3) $R^1$ is —$S(O)_nR^6$, —$S(O)_nNR^7R^8$ or —$S(O)(NH)R^6$; and
$R^6$ is $C_{1-3}$ alkyl; and
$R^7$ and $R^8$ are each independently:
(A) —H; or
(B) $C_{1-3}$ alkyl; and
n is 2.

$R^2$ and $R^3$ Group Embodiments
(1) $R^2$ and $R^3$ are each independently selected from:
(A) —H;
(B) $C_{1-3}$ alkyl optionally substituted with one, two or three groups selected from:
  a) $C_{3-6}$ cycloalkyl;
  b) —$OR^9$; or
  c) -halo; and
$R^2$ and $R^3$ are taken together with the carbon to which they are attached to form a $C_{3-6}$ carbocyclic ring; or
$R^2$ and $R^3$ are taken together with the carbon to which they are attached to form a $C_{3-6}$ heterocyclic ring; and
$R^9$ is selected from:
(A) —H; and
(B) $C_{1-3}$ alkyl.

(2) $R^2$ and $R^3$ are each independently selected from:
    (A) —H; and
    (B) $C_{1-3}$ alkyl;
(3) $R^2$ and $R^3$ are H.

$R^4$ Group Embodiments (1) $R^4$ is:
    (A) $C_{1-6}$ alkyl optionally substituted with one, two or three groups selected from:
        a) $C_{3-6}$ cycloalkyl;
        b) a 4, 5 or 6-membered heterocyclyl;
        c) —$OR^9$;
        d) —CN;
        e) -halo; and
        f) —$CF_3$; or
    (B) $C_{3-6}$ cycloalkyl optionally substituted with one, two or three groups selected from:
        a) $C_{1-6}$ alkyl;
        b) —$OR^9$;
        c) —CN;
        d) -halo; and
        e) —$CF_3$; and
    wherein one carbon in said $C_{3-6}$ cycloalkyl may be optionally replaced by —O—;
    (C) Phenyl; or
    (D) a 4, 5 or 6-membered heterocyclyl;
    $R^9$ is selected from:
    (A) —H; and
    (B) $C_{1-3}$ alkyl.
(2) $R^4$ is:
    (A) $C_{1-6}$ alkyl optionally substituted with one or two groups selected from:
        a) $C_{3-6}$ cycloalkyl;
        b) a 4, 5, or 6-membered heterocyclyl;
        c) —$OR^9$;
        d) —CN;
        e) -halo; and
        f) —$CF_3$; or
    (B) $C_{3-6}$ cycloalkyl optionally substituted with one, two or three groups selected from:
        a) $C_{1-6}$ alkyl;
        b) —$OR^9$;
        c) —CN;
        d) -halo; and
        e) —$CF_3$; or
    (C) Phenyl; or
    (D) a 5 or 6-membered heterocyclyl; and
    $R^9$ is $C_{1-3}$ alkyl.
(3) $R^4$ is:
    (A) $C_{1-6}$ alkyl optionally substituted with one or two groups selected from $C_{3-6}$ cycloalkyl, halo, —$CF_3$, and $C_{1-3}$ alkoxy; or
    (B) $C_{3-6}$ cycloalkyl optionally substituted with one or two groups selected from $C_{1-6}$ alkyl, —$CF_3$, and halo; or
    (C) a 5-membered heterocyclyl.

$R^5$ Group Embodiments (1) $R^5$ is aryl, heteroaryl or heterocyclyl, each optionally substituted with one, two or three groups selected from:
    a) $C_{1-6}$ alkyl;
    b) $C_{3-6}$ cycloalkyl;
    c) —$OR^9$;
    d) —CN;
    e) —$CF_3$;
    f) -halo; and
    g) —$NR^7R^8$; and $R^7$, $R^8$ and $R^9$ are each independently selected from:
    (A) —H; and
    (B) $C_{1-3}$ alkyl.
(2) $R^5$ is:
    (A) phenyl optionally substituted with one, two or three groups selected from:
        a) $C_{1-6}$ alkyl;
        b) $C_{3-6}$ cycloalkyl;
        c) —$OR^9$;
        d) —CN;
        e) —$CF_3$; and
        f) -halo; or
    (B) a 5 or 6-membered heteroaryl optionally substituted with one, two or three groups selected from:
        a) $C_{1-6}$ alkyl;
        b) $C_{3-6}$ cycloalkyl;
        c) —$OR^9$;
        d) —CN;
        e) —$CF_3$;
        f) -halo; and
        g) —$NR^7R^8$; and
    $R^7$, $R^8$ and $R^9$ are each independently selected from:
    (A) —H; and
    (B) $C_{1-3}$ alkyl.
(3) $R^5$ is pyridinyl or pyrimidinyl each optionally substituted with one, two or three groups selected from:
    a) $C_{1-6}$ alkyl;
    b) $C_{3-6}$ cycloalkyl;
    c) —$OR^9$;
    d) —$CF_3$; and
    e) —$NR^7R^8$; and
    $R^7$ and $R^8$ are each independently selected from:
    (A) —H;
    (B) $C_{1-3}$ alkyl; and
    $R^9$ is $C_{1-3}$ alkyl.
(4) $R^5$ is pyrimidinyl optionally substituted with one or two groups selected from:
    a) $C_{1-3}$ alkyl;
    b) $C_{3-5}$ cycloalkyl;
    c) $C_{1-3}$ alkoxy; and
    d) —$CF_3$.

W Group Embodiments (1) W is phenyl, pyridinyl, pyrimidinyl, piperidinyl, piperizinyl, pyrazinyl or $C_{3-12}$ cycloalkyl, each optionally substituted with one or two groups selected from:
    a) $C_{1-6}$ alkyl;
    b) $C_{3-6}$ cycloalkyl;
    c) —$OR^9$;
    d) —CN;
    e) —$CF_3$;
    f) -halo;
    g) —$NR^7R^8$
    h) —$C(O)OR^9$; and
    i) —$C(O)N(R^9)_2$;
    $R^7$, $R^8$ and $R^9$ are each selected from:
    (A) —H; and
    (B) $C_{1-3}$ alkyl.
(2) W is phenyl, pyridinyl, pyrimidinyl or piperidinyl.

Additional embodiments include any possible combinations of the above sub-embodiments for $R^1$, $R^2$, $R^3$, $R^4$, $R^5$, $R^6$, and W.

Additional Subgeneric Embodiments of Formula (I)

Additional subgeneric embodiments of the compounds of formula (I) above include:

(1) A compound of formula (I) as described above, or a pharmaceutically acceptable salt thereof, wherein:

R$^1$ is:
—S(O)nR$^6$,
—S(O)nNR$^7$R$^8$, or
—S(O)(NH)R$^6$;
R$^2$ and R$^3$ are each independently selected from:
(A) —H; and
(B) C$_{1-3}$ alkyl;
R$^4$ is:
(A) C$_{1-6}$ alkyl optionally substituted with one or two groups selected from:
 a) C$_{3-6}$ cycloalkyl;
 b) a 4, 5, or 6-membered heterocyclyl;
 c) —OR$^9$;
 d) —CN;
 e) -halo; and
 f) —CF$_3$;
(B) C$_{3-6}$ cycloalkyl optionally substituted with one, two or three groups selected from:
 a) C$_{1-6}$ alkyl;
 b) —OR$_9$;
 c) —CN;
 d) -halo; and
 e) —CF$_3$;
(C) Phenyl; or
(D) a 5 or 6-membered heterocyclyl;
R$^5$ is:
(A) phenyl optionally substituted with one or two groups selected from:
 a) C$_{1-6}$ alkyl;
 b) C$_{3-6}$ cycloalkyl;
 c) —OR$^9$;
 d) —CN;
 e) —CF$_3$; and
 f) -halo; or
(B) Pyridinyl or pyrimidinyl each optionally substituted with one, two or three groups selected from:
 a) C$_{1-6}$ alkyl;
 b) C$_{3-6}$ cycloalkyl;
 c) —OR$^9$;
 d) —CN;
 e) —CF$_3$;
 f) -halo; and
 g) —NR$^7$R$^8$; and
W is phenyl, pyridinyl, pyrimidinyl, piperidinyl or C$_{3-12}$ cycloalkyl, each optionally substituted with one or two groups selected from:
 a) C$_{1-6}$ alkyl;
 b) C$_{3-6}$ cycloalkyl;
 c) —OR$^9$;
 d) —CN;
 e) —CF$_3$;
 f) -halo;
 g) —NR$^7$R$^8$
 h) —C(O)OR$^9$; and
 i) —C(O)N(R$^9$)$_2$;
R$^6$ is:
(A) C$_{1-3}$ alkyl optionally substituted with one or two groups selected from:
 a) C$_{3-6}$ cycloalkyl;
 b) —OR$^9$ and
 b) —CN; or
(B) C$_{3-6}$ cycloalkyl;
R$^7$, R$^8$ and R$^9$ are each independently:
(A) —H; or
(B) C$_{1-3}$ alkyl; and
n is 2.
(2) A compound of formula (I) as described above, or a pharmaceutically acceptable salt thereof, wherein:
R$^1$ is —S(O)$_n$R$^6$ or —S(O)$_n$NR$^7$R$^8$; and
R$^2$ and R$^3$ are H;
R$^4$ is:
(A) C$_{1-6}$ alkyl optionally substituted with one or two groups selected from C$_{3-6}$ cycloalkyl, —CF$_3$, and C$_{1-3}$ alkoxy; or
(B) C$_{3-6}$ cycloalkyl optionally substituted with one or two groups selected from C$_{1-6}$ alkyl, —CN, and halo; or
(C) 5-membered heterocyclyl;
R$^5$ is pyrimidinyl optionally substituted with one, two or three groups selected from:
 a) C$_{1-6}$ alkyl;
 b) C$_{3-6}$ cycloalkyl;
 c) —OR$^9$;
 d) —CF$_3$; and
 e) —NR$^7$R$^8$;
W is phenyl, pyridinyl, pyrimidinyl or piperidinyl;
R$^6$ is C$_{1-3}$ alkyl;
R$^7$, R$^8$R$^9$ are each independently:
(A) —H; or
(B) C$_{1-3}$ alkyl; and
n is 2.
(3) A compound of formula (I) as described immediately above in (2), or a pharmaceutically acceptable salt thereof, wherein:
R$^5$ is pyrimidinyl optionally substituted with one or two groups selected from:
 a) C$_{1-3}$ alkyl;
 b) C$_{3-5}$ cycloalkyl; and
 c) C$_{1-3}$ alkoxy; and
W is phenyl, pyridinyl, pyrimidinyl or piperidinyl.

Specific compounds falling within the instant invention include the compounds in the following Table I, or their pharmaceutically acceptable salts:

TABLE 1

| Example | Structure | RT (min) | m/z [M + H]$^+$ | m/z [M − H]$^−$ | HPLC Method |
|---|---|---|---|---|---|
| 1 | 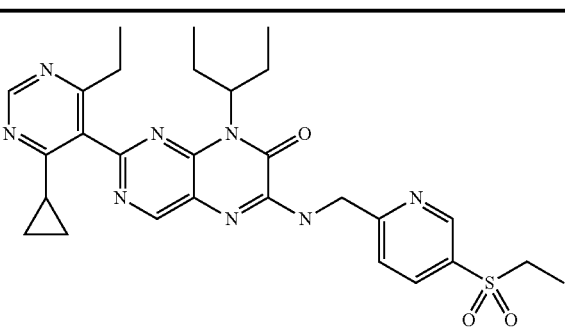 | 1.09 | 563.7 | | A |

TABLE 1-continued

| Example | Structure | RT (min) | m/z [M + H]+ | m/z [M − H]− | HPLC Method |
|---|---|---|---|---|---|
| 2 | 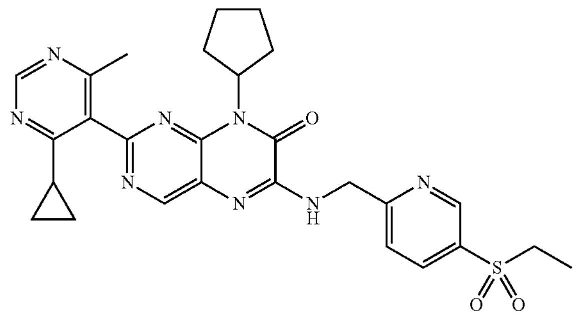 | 0.98 | 547.4 | | A |
| 3 | 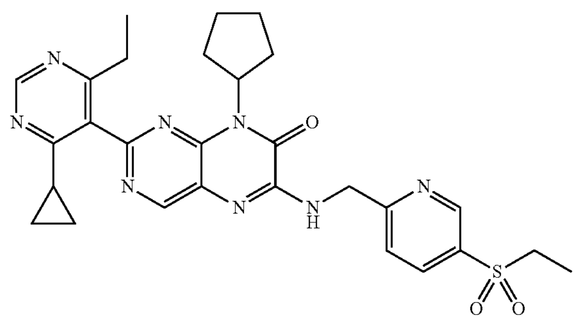 [SMILES: CCc1ncnc(C2CC2)c1-c1ncc2nc(NCc3ccc(S(=O)(=O)CC)cn3)c(=O)n(C3CCCC3)c2n1] | 1.05 | 561.4 | | A |
| 4 | 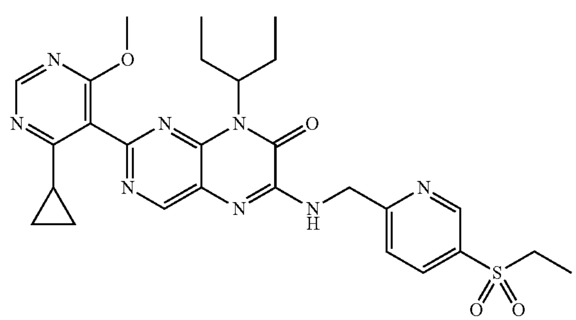 [SMILES: CCC(CC)n1c(=O)c(NCc2ccc(S(=O)(=O)CC)cn2)nc2cnc(-c3c(OC)ncnc3C3CC3)nc21] | 1.08 | 565.5 | | A |
| 5 | 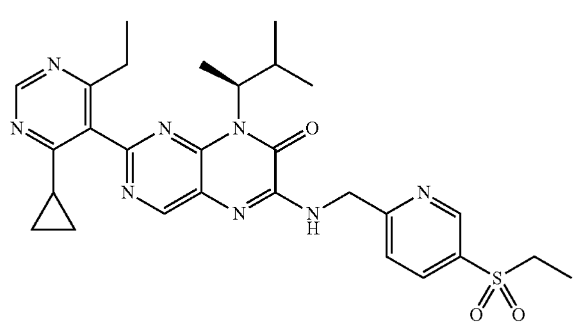 | 1.08 | 563.4 | | A |

TABLE 1-continued

| Example | Structure | RT (min) | m/z [M + H]+ | m/z [M − H]− | HPLC Method |
|---|---|---|---|---|---|
| 6 | 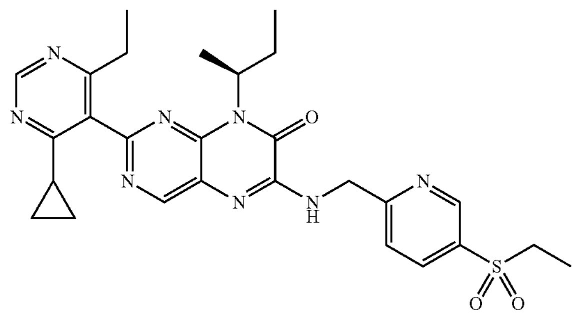 [SMILES: CCc1ncnc(C2CC2)c1-c1ncc2nc(NCc3ccc(S(=O)(=O)CC)cn3)c(=O)n([C@@H](C)CC)c2n1] | 1.05 | 549.3 | | A |
| 7 | 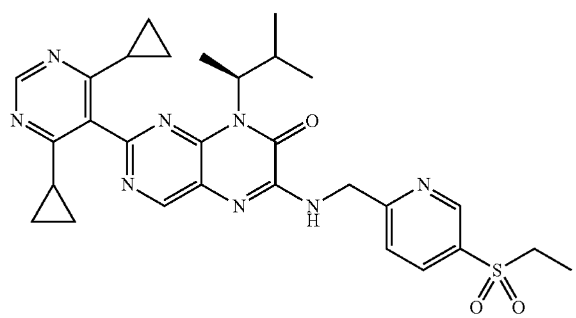 [SMILES: CCS(=O)(=O)c1ccc(CNc2nc3cnc(-c4c(C5CC5)ncnc4C4CC4)nc3n([C@@H](C)C(C)C)c2=O)nc1] | 1.14 | 575.4 | | A |
| 8 | 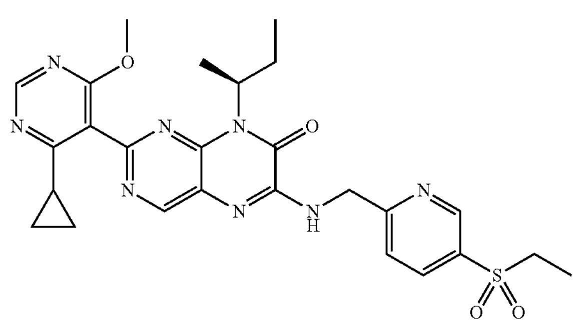 [SMILES: CC[C@H](C)n1c(=O)c(NCc2ccc(S(=O)(=O)CC)cn2)nc2cnc(-c3c(OC)ncnc3C3CC3)nc21] | 1.01 | 551.4 | | A |
| 9 | 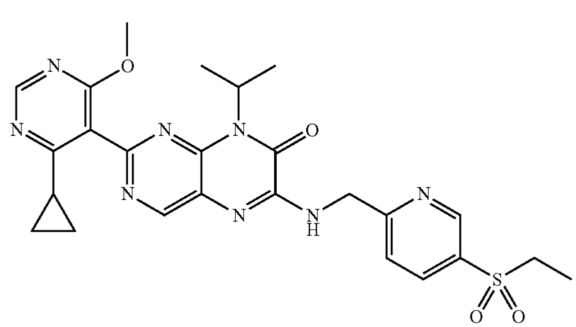 | 1.03 | 537.2 | | A |

TABLE 1-continued

| Example | Structure | RT (min) | m/z [M + H]+ | m/z [M − H]− | HPLC Method |
|---|---|---|---|---|---|
| 10 | 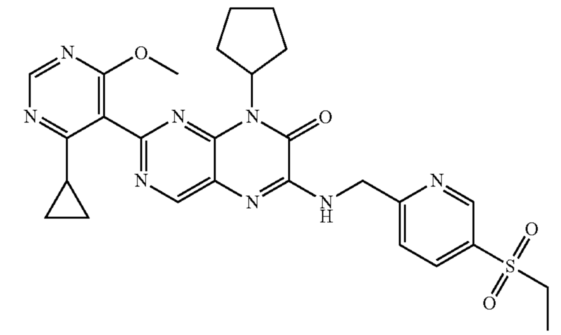 [SMILES: CCS(=O)(=O)c1ccc(CNc2nc3cnc(-c4c(OC)ncnc4C4CC4)nc3n(C3CCCC3)c2=O)nc1] | 1.04 | 563.4 | | A |
| 11 | 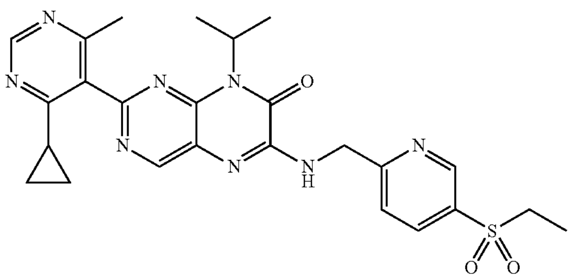 [SMILES: CCS(=O)(=O)c1ccc(CNc2nc3cnc(-c4c(C)ncnc4C4CC4)nc3n(C(C)C)c2=O)nc1] | 0.91 | 521.4 | | A |
| 12 | 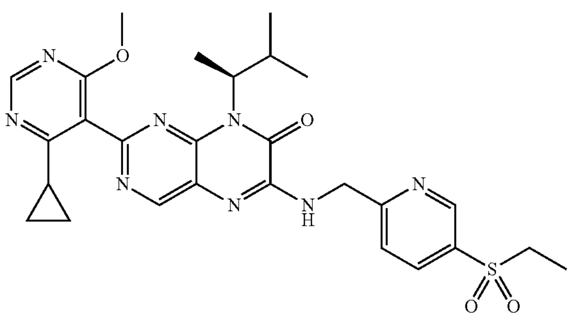 | 1.07 | 565.4 | | A |
| 13 | 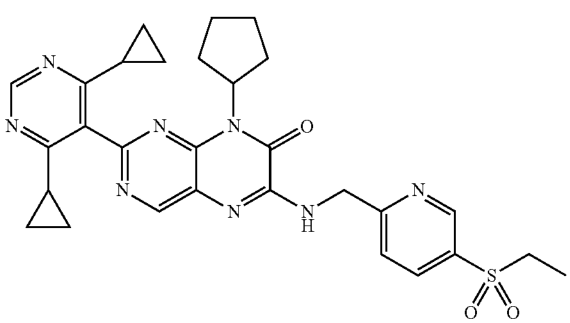 [SMILES: CCS(=O)(=O)c1ccc(CNc2nc3cnc(-c4c(C5CC5)ncnc4C4CC4)nc3n(C3CCCC3)c2=O)nc1] | 1.11 | 573.4 | | A |
| 14 | 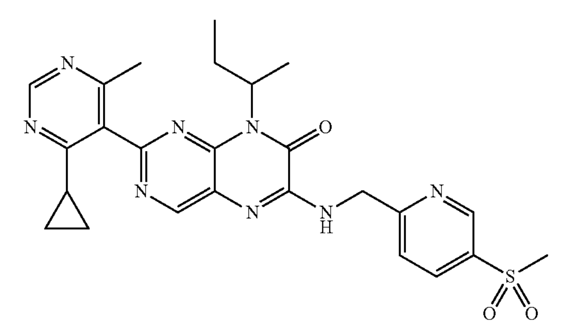 [SMILES: CCC(C)n1c(=O)c(NCc2ccc(S(C)(=O)=O)cn2)nc2cnc(-c3c(C)ncnc3C3CC3)nc21] | 1.01 | 520.3 | | A |

TABLE 1-continued

| Example | Structure | RT (min) | m/z [M + H]+ | m/z [M − H]− | HPLC Method |
|---|---|---|---|---|---|
| 15 | 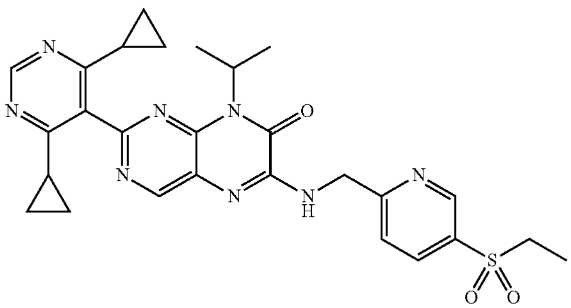 [SMILES: CCS(=O)(=O)c1ccc(CNc2nc3cnc(-c4c(C5CC5)ncnc4C4CC4)nc3n(C(C)C)c2=O)nc1] | 1.02 | 547.4 | | A |
| 16 | 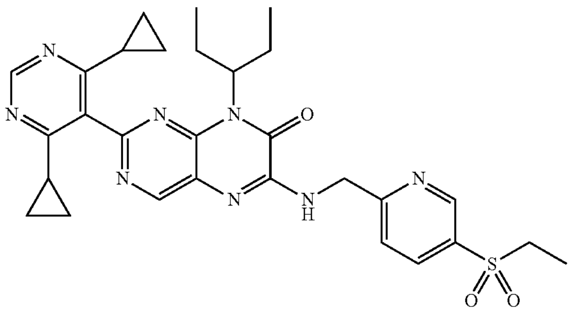 [SMILES: CCC(CC)n1c(=O)c(NCc2ccc(S(=O)(=O)CC)cn2)nc2cnc(-c3c(C4CC4)ncnc3C3CC3)nc21] | 1.15 | 575.4 | | A |
| 17 | 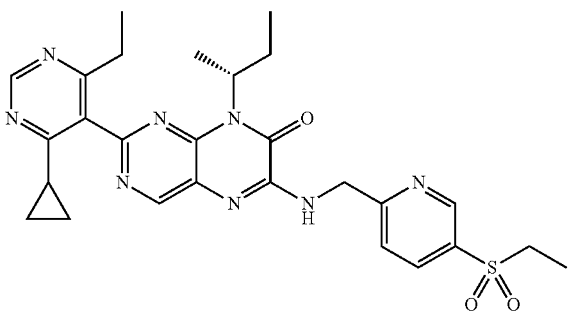 | 1.01 | 551.4 | | A |
| 18 | 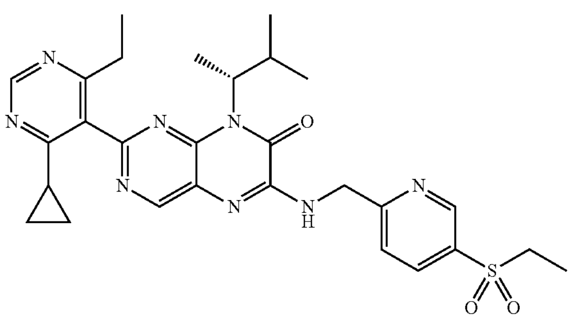 [SMILES: CCc1ncnc(C2CC2)c1-c1ncc2nc(NCc3ccc(S(=O)(=O)CC)cn3)c(=O)n([C@H](C)C(C)C)c2n1] | 1.07 | 563.4 | | A |
| 19 | 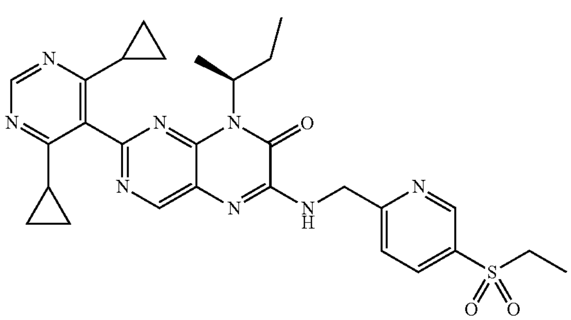 [SMILES: CC[C@H](C)n1c(=O)c(NCc2ccc(S(=O)(=O)CC)cn2)nc2cnc(-c3c(C4CC4)ncnc3C3CC3)nc21] | 1.12 | 561.3 | | A |

TABLE 1-continued

| Example | Structure | RT (min) | m/z [M + H]+ | m/z [M − H]− | HPLC Method |
|---|---|---|---|---|---|
| 20 | 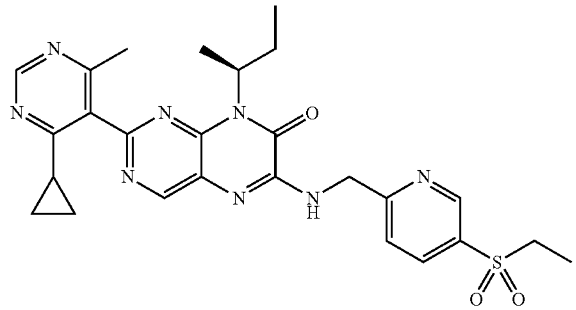 [SMILES: CC[C@H](C)n1c(=O)c(NCc2ccc(S(=O)(=O)CC)cn2)nc2cnc(-c3c(C)ncnc3C3CC3)nc21] | 0.99 | 535.2 | | A |
| 21 | 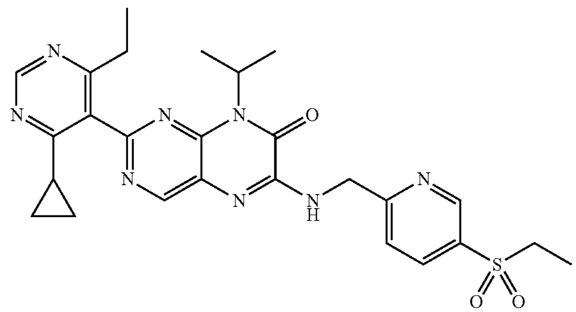 [SMILES: CCc1ncnc(C2CC2)c1-c1ncc2nc(NCc3ccc(S(=O)(=O)CC)cn3)c(=O)n(C(C)C)c2n1] | 0.97 | 535.4 | | A |
| 22 | 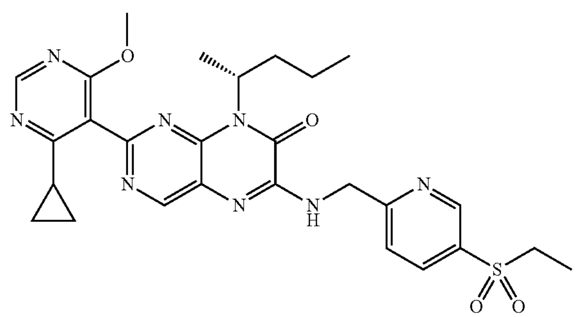 [SMILES: CCC[C@@H](C)n1c(=O)c(NCc2ccc(S(=O)(=O)CC)cn2)nc2cnc(-c3c(OC)ncnc3C3CC3)nc21] | 1.09 | 565.3 | 563.3 | A |
| 23 | 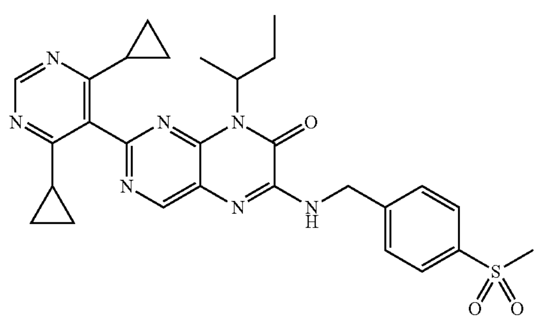 [SMILES: CCC(C)n1c(=O)c(NCc2ccc(S(C)(=O)=O)cc2)nc2cnc(-c3c(C4CC4)ncnc3C3CC3)nc21] | 1.14 | 547.4 | | A |
| 24 | 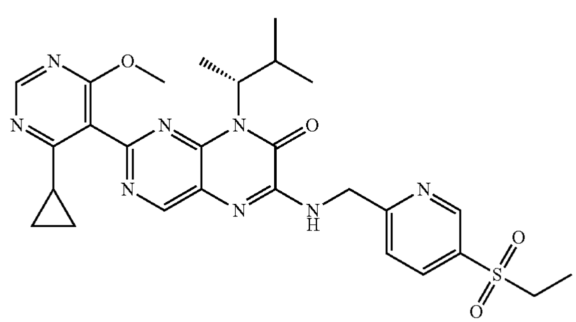 [SMILES: CCS(=O)(=O)c1ccc(CNc2nc3cnc(-c4c(OC)ncnc4C4CC4)nc3n([C@H](C)C(C)C)c2=O)nc1] | 1.07 | 565.4 | | A |

TABLE 1-continued

| Example | Structure | RT (min) | m/z [M + H]+ | m/z [M − H]− | HPLC Method |
|---|---|---|---|---|---|
| 25 | 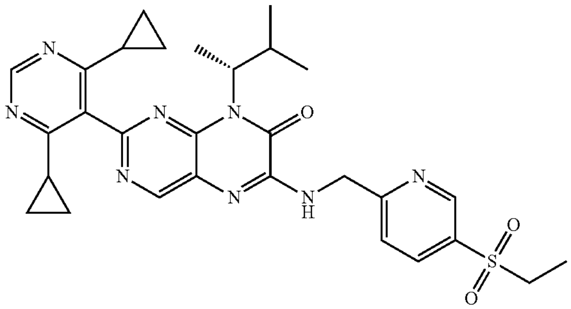 [SMILES: CCS(=O)(=O)c1ccc(CNc2nc3cnc(-c4c(C5CC5)ncnc4C4CC4)nc3n([C@H](C)C(C)C)c2=O)nc1] | 1.14 | 575.4 | | A |
| 26 | 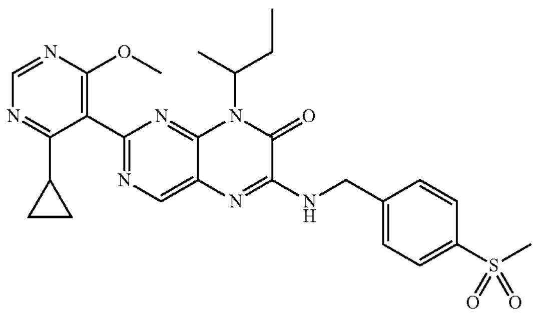 [SMILES: CCC(C)n1c(=O)c(NCc2ccc(S(C)(=O)=O)cc2)nc2cnc(-c3c(OC)ncnc3C3CC3)nc21] | 1.03 | 536.2 | | A |
| 27 | 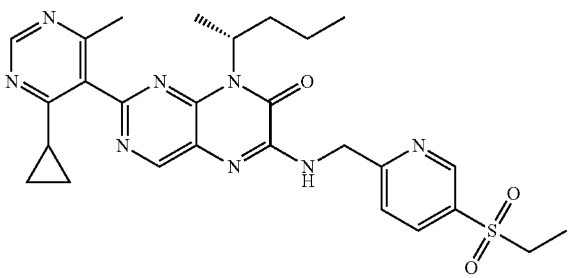 [SMILES: CCC[C@@H](C)n1c(=O)c(NCc2ccc(S(=O)(=O)CC)cn2)nc2cnc(-c3c(C)ncnc3C3CC3)nc21] | 1.03 | 549.2 | 547.1 | A |
| 28 | 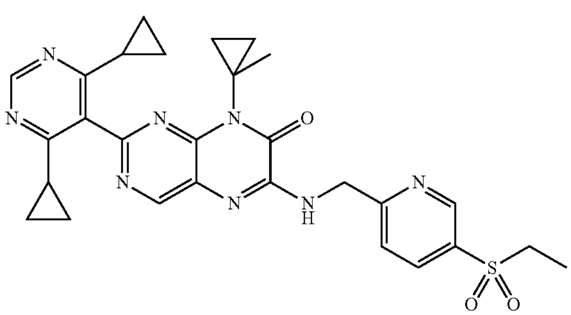 [SMILES: CCS(=O)(=O)c1ccc(CNc2nc3cnc(-c4c(C5CC5)ncnc4C4CC4)nc3n(C3(C)CC3)c2=O)nc1] | 2.06 | 559.4 | 557.4 | B |
| 29 | 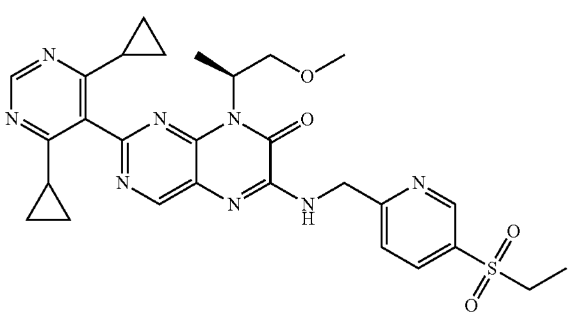 [SMILES: CCS(=O)(=O)c1ccc(CNc2nc3cnc(-c4c(C5CC5)ncnc4C4CC4)nc3n([C@@H](C)COC)c2=O)nc1] | 0.97 | 577.4 | | A |

TABLE 1-continued

| Example | Structure | RT (min) | m/z [M + H]⁺ | m/z [M − H]⁻ | HPLC Method |
|---------|-----------|----------|--------------|--------------|-------------|
| 30 | 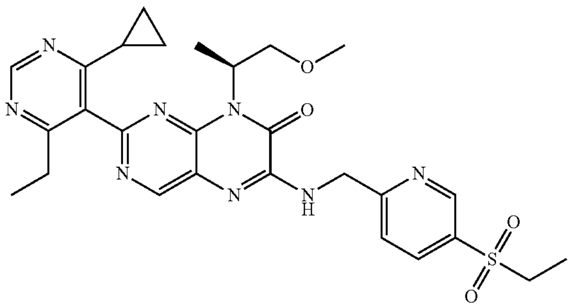 [SMILES: CCc1ncnc(C2CC2)c1-c1ncc2nc(NCc3ccc(S(=O)(=O)CC)cn3)c(=O)n([C@@H](C)COC)c2n1] | 0.91 | 565.4 | | A |
| 31 | 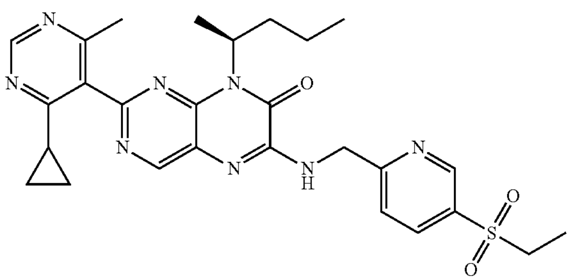 [SMILES: CCC[C@H](C)n1c(=O)c(NCc2ccc(S(=O)(=O)CC)cn2)nc2cnc(-c3c(C)ncnc3C3CC3)nc21] | 1.03 | 549.2 | 547.0 | A |
| 32 | 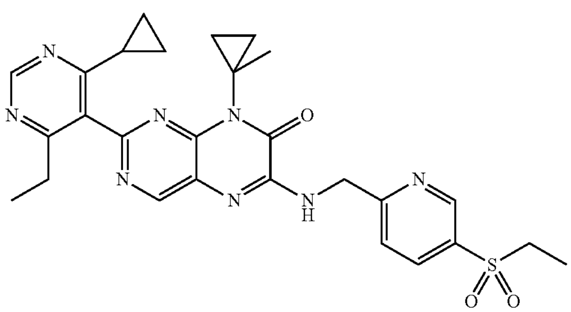 [SMILES: CCc1ncnc(C2CC2)c1-c1ncc2nc(NCc3ccc(S(=O)(=O)CC)cn3)c(=O)n(C3(C)CC3)c2n1] | 1.89 | 547.4 | 545.4 | B |
| 33 | 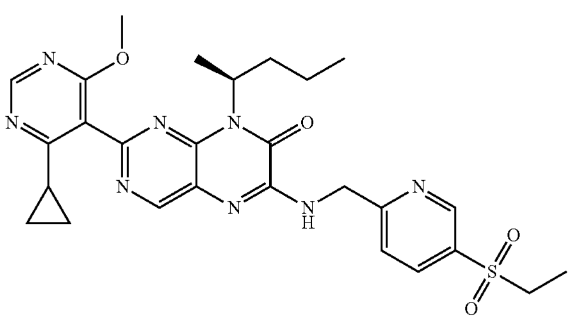 [SMILES: CCC[C@H](C)n1c(=O)c(NCc2ccc(S(=O)(=O)CC)cn2)nc2cnc(-c3c(OC)ncnc3C3CC3)nc21] | 1.09 | 565.3 | 563.3 | A |
| 34 | 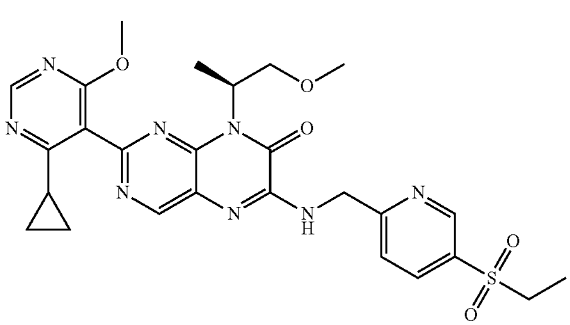 | 0.90 | 567.4 | | A |

TABLE 1-continued

| Example | Structure | RT (min) | m/z [M + H]+ | m/z [M − H]− | HPLC Method |
|---|---|---|---|---|---|
| 35 | 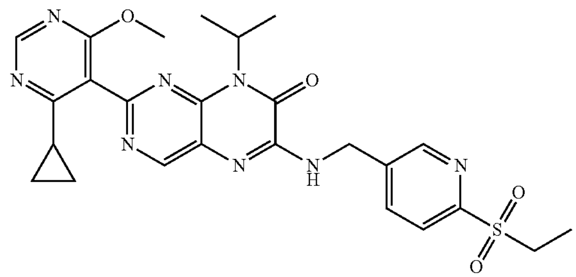 [SMILES: CCS(=O)(=O)c1ccc(CNc2nc3cnc(-c4c(OC)ncnc4C4CC4)nc3n(C(C)C)c2=O)cn1] | 1.05 | 537.2 | | A |
| 36 | 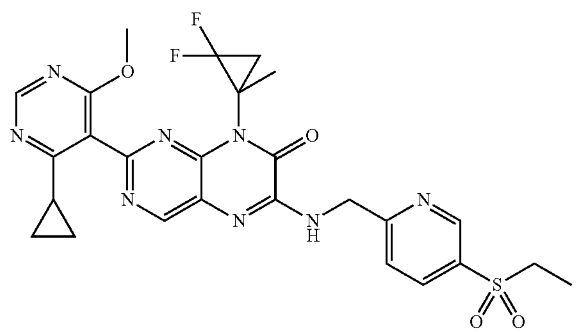 [SMILES: CCS(=O)(=O)c1ccc(CNc2nc3cnc(-c4c(OC)ncnc4C4CC4)nc3n(C3(C)CC3(F)F)c2=O)nc1] | 0.93 | 585.3 | 583.3 | A |
| 37 | 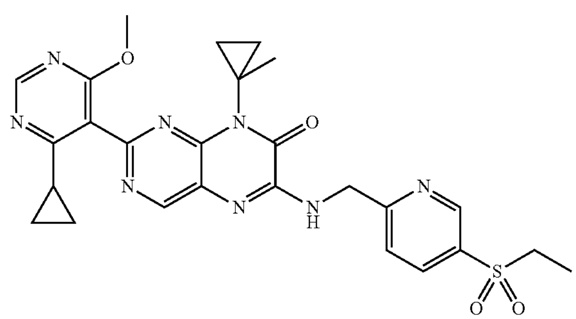 [SMILES: CCS(=O)(=O)c1ccc(CNc2nc3cnc(-c4c(OC)ncnc4C4CC4)nc3n(C3(C)CC3)c2=O)nc1] | 1.85 | 549.4 | 547.4 | B |
| 38 | 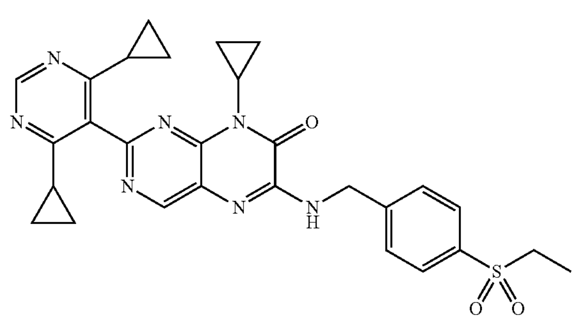 [SMILES: CCS(=O)(=O)c1ccc(CNc2nc3cnc(-c4c(C5CC5)ncnc4C4CC4)nc3n(C3CC3)c2=O)cc1] | 2.06 | 544.4 | 542.4 | B |
| 39 | 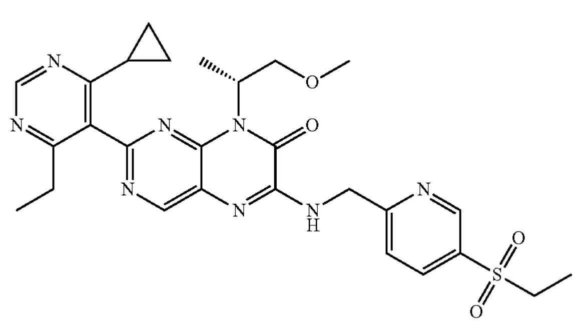 [SMILES: CCc1ncnc(C2CC2)c1-c1ncc2nc(NCc3ccc(S(=O)(=O)CC)cn3)c(=O)n([C@H](C)COC)c2n1] | 0.91 | 565.4 | | A |

TABLE 1-continued
| Example | Structure | RT (min) | m/z [M + H]+ | m/z [M − H]− | HPLC Method |
|---|---|---|---|---|---|
| 40 | 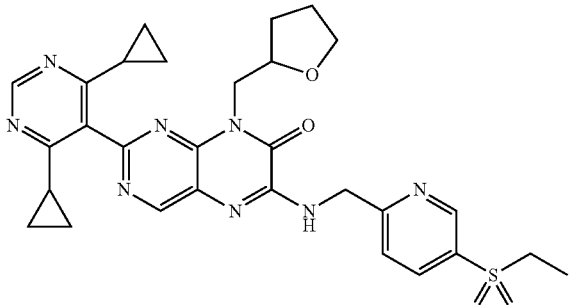 | 0.94 | 589.4 | | A |
| 41 | 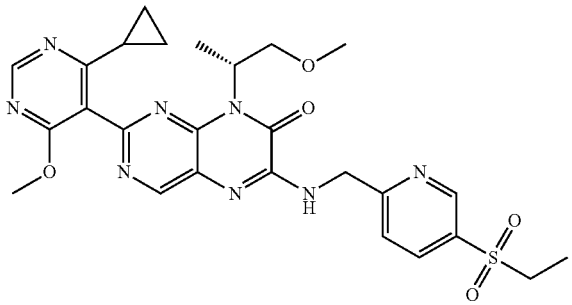 | 0.90 | 567.4 | | A |
| 42 | 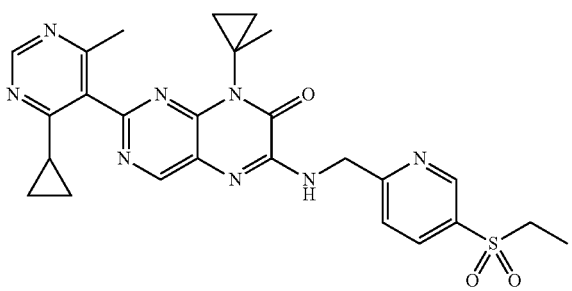 [SMILES: CCS(=O)(=O)c1ccc(CNc2nc3cnc(-c4c(C)ncnc4C4CC4)nc3n(C3(C)CC3)c2=O)nc1] | 2.08 | 559.4 | 557.4 | B |
| 43 | 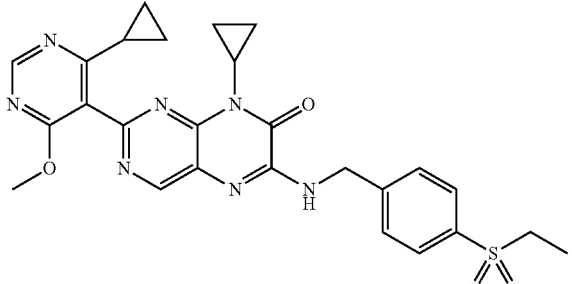 | 1.81 | 534.4 | 532.4 | B |
| 44 | 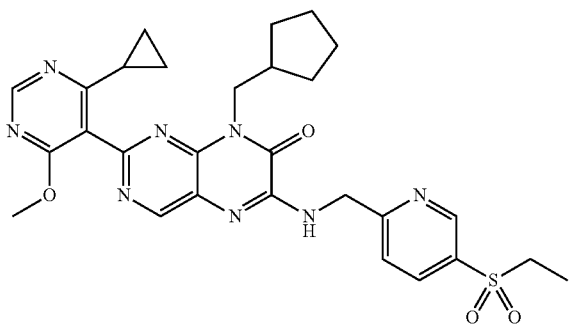 | 0.86 | 579.4 | | A |

TABLE 1-continued

| Example | Structure | RT (min) | m/z [M + H]+ | m/z [M − H]− | HPLC Method |
|---|---|---|---|---|---|
| 45 | 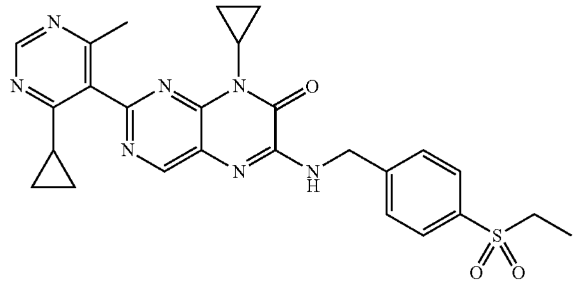 [SMILES: CCS(=O)(=O)c1ccc(CNc2nc3cnc(-c4c(C)ncnc4C4CC4)nc3n(C3CC3)c2=O)cc1] | 1.67 | 518.4 | 516.4 | B |
| 46 | 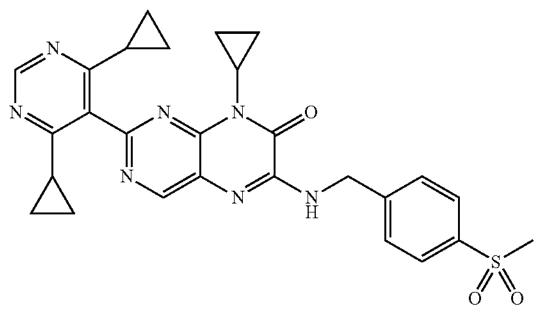 [SMILES: CS(=O)(=O)c1ccc(CNc2nc3cnc(-c4c(C5CC5)ncnc4C4CC4)nc3n(C3CC3)c2=O)cc1] | 1.89 | 530.4 | 528.4 | B |
| 47 | 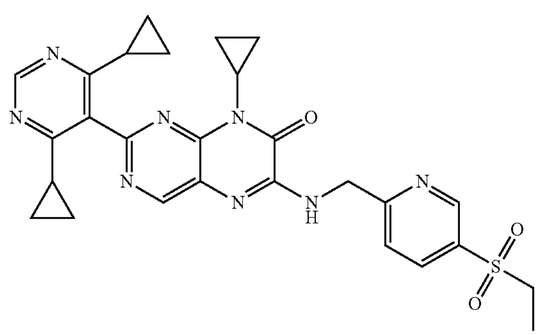 [SMILES: CCS(=O)(=O)c1ccc(CNc2nc3cnc(-c4c(C5CC5)ncnc4C4CC4)nc3n(C3CC3)c2=O)nc1] | 0.85 | 545.1 | 543.2 | A |
| 48 | 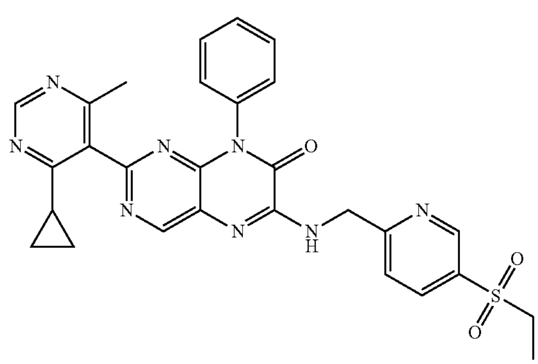 [SMILES: CCS(=O)(=O)c1ccc(CNc2nc3cnc(-c4c(C)ncnc4C4CC4)nc3n(-c3ccccc3)c2=O)nc1] | 0.99 | 555.3 | | A |

TABLE 1-continued

| Example | Structure | RT (min) | m/z [M + H]+ | m/z [M − H]− | HPLC Method |
|---|---|---|---|---|---|
| 49 | 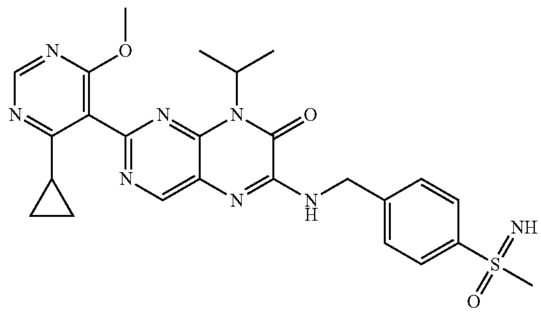 [SMILES: COc1ncnc(C2CC2)c1-c1ncc2nc(NCc3ccc(S(C)(=N)=O)cc3)c(=O)n(C(C)C)c2n1] | 0.94 | 521.1 | | A |
| 50 | 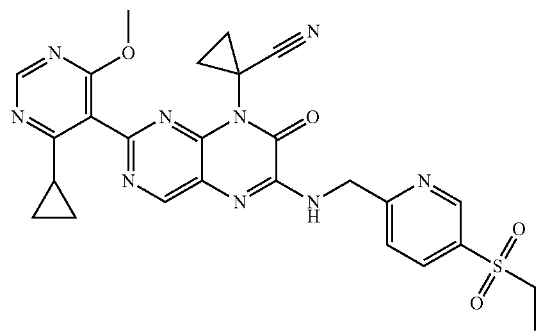 [SMILES: CCS(=O)(=O)c1ccc(CNc2nc3cnc(-c4c(OC)ncnc4C4CC4)nc3n(C3(C#N)CC3)c2=O)nc1] | 0.82 | 560.3 | 558.4 | A |
| 51 | 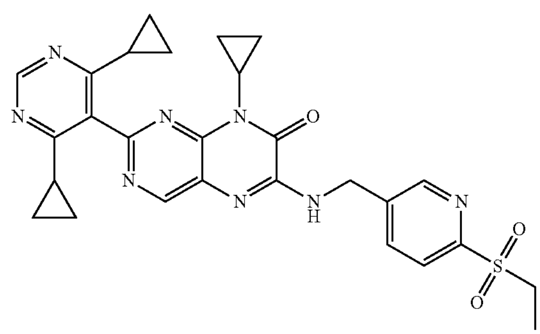 [SMILES: CCS(=O)(=O)c1ccc(CNc2nc3cnc(-c4c(C5CC5)ncnc4C4CC4)nc3n(C3CC3)c2=O)cn1] | 0.85 | 544.7 | 543.1 | A |
| 52 | 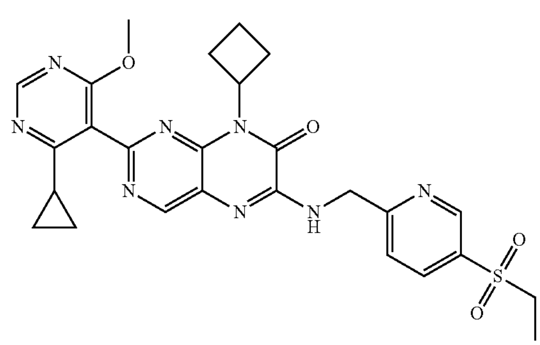 [SMILES: CCS(=O)(=O)c1ccc(CNc2nc3cnc(-c4c(OC)ncnc4C4CC4)nc3n(C3CCC3)c2=O)nc1] | 1.01 | 548.8 | | A |

TABLE 1-continued

| Example | Structure | RT (min) | m/z [M + H]+ | m/z [M − H]− | HPLC Method |
|---|---|---|---|---|---|
| 53 | 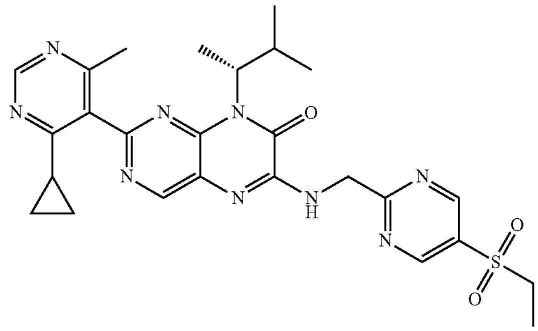 | 1.01 | 549.9 | | A |
| 54 | 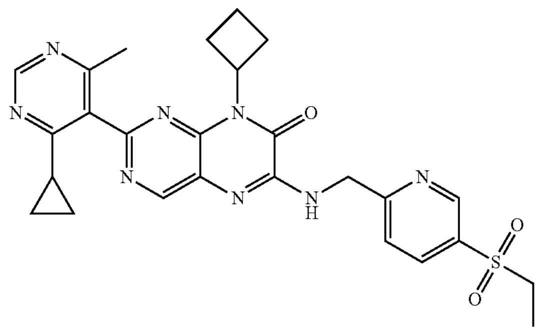 [SMILES: CCS(=O)(=O)c1ccc(CNc2nc3cnc(-c4c(C)ncnc4C4CC4)nc3n(C3CCC3)c2=O)nc1] | 0.94 | 532.8 | | A |
| 55 | 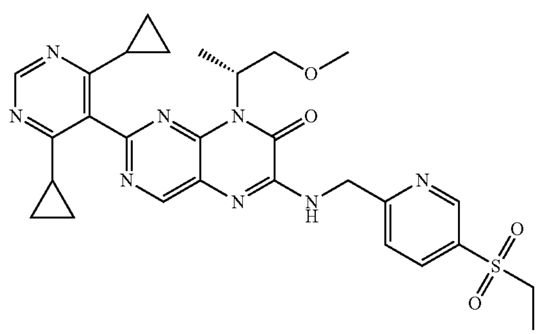 [SMILES: CCS(=O)(=O)c1ccc(CNc2nc3cnc(-c4c(C5CC5)ncnc4C4CC4)nc3n([C@H](C)COC)c2=O)nc1] | 0.97 | 577.4 | | A |
| 56 | 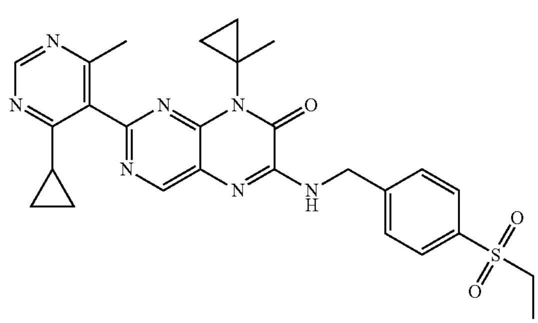 [SMILES: CCS(=O)(=O)c1ccc(CNc2nc3cnc(-c4c(C)ncnc4C4CC4)nc3n(C3(C)CC3)c2=O)cc1] | 1.96 | 532.1 | 530.1 | B |

TABLE 1-continued

| Example | Structure | RT (min) | m/z [M + H]+ | m/z [M − H]− | HPLC Method |
|---|---|---|---|---|---|
| 57 | 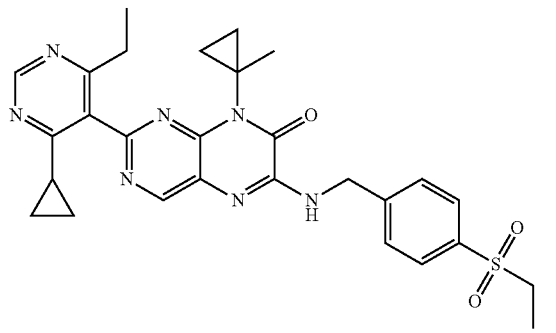 | 2.17 | 546.1 | 544.1 | B |
| 58 | 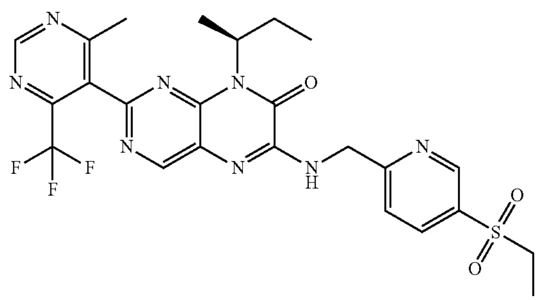 [SMILES: CC[C@H](C)n1c(=O)c(NCc2ccc(S(=O)(=O)CC)cn2)nc2cnc(-c3c(C)ncnc3C(F)(F)F)nc21] | 1.03 | 563.1 | | A |
| 59 | 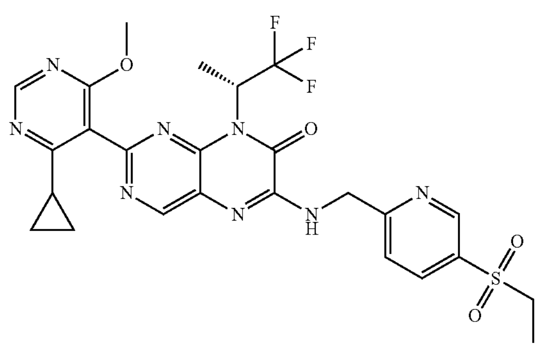 [SMILES: CCS(=O)(=O)c1ccc(CNc2nc3cnc(-c4c(OC)ncnc4C4CC4)nc3n([C@H](C)C(F)(F)F)c2=O)nc1] | 1.01 | 591.1 | 589 | A |
| 60 | 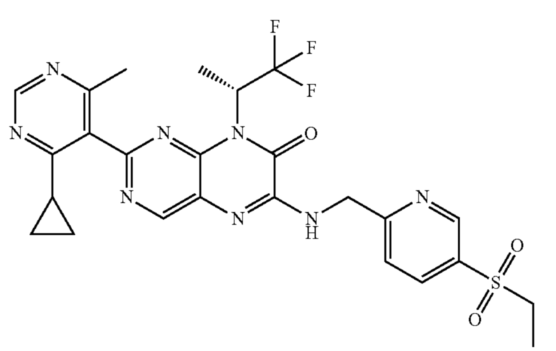 [SMILES: CCS(=O)(=O)c1ccc(CNc2nc3cnc(-c4c(C)ncnc4C4CC4)nc3n([C@H](C)C(F)(F)F)c2=O)nc1] | 0.95 | 575.2 | 573 | A |

TABLE 1-continued

| Example | Structure | RT (min) | m/z [M + H]+ | m/z [M − H]− | HPLC Method |
|---|---|---|---|---|---|
| 61 | 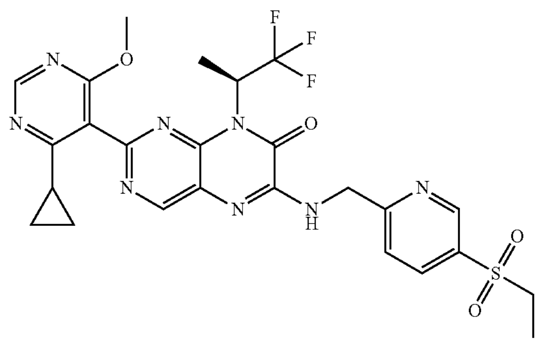 [SMILES: CCS(=O)(=O)c1ccc(CNc2nc3cnc(-c4c(OC)ncnc4C4CC4)nc3n([C@@H](C)C(F)(F)F)c2=O)nc1] | 1.02 | 591.2 | 589 | A |
| 62 | 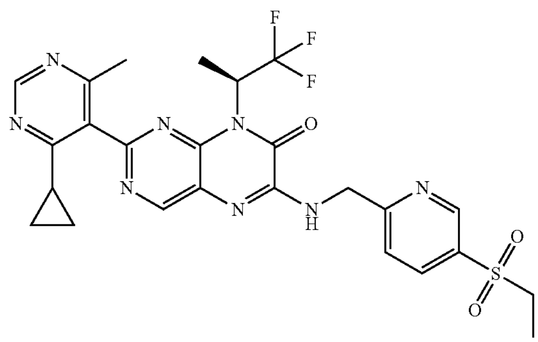 | 0.96 | 575.1 | 573 | A |
| 63 | 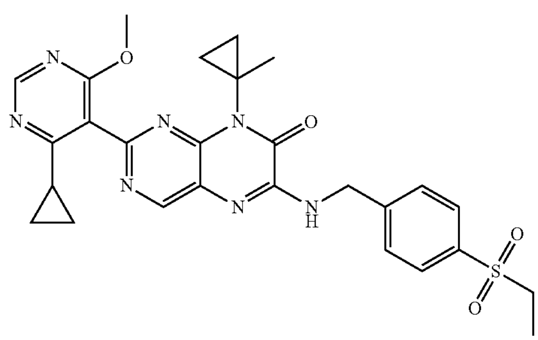 | 2.13 | 548.0 | 546.0 | B |
| 64 | 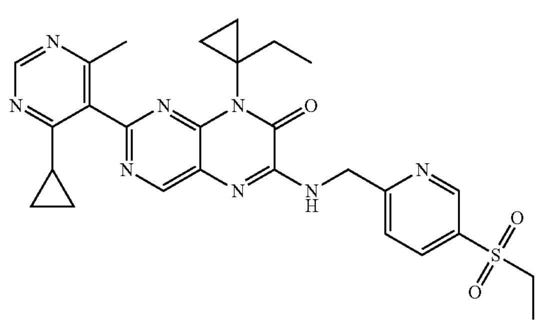 [SMILES: CCC1(n2c(=O)c(NCc3ccc(S(=O)(=O)CC)cn3)nc3cnc(-c4c(C)ncnc4C4CC4)nc32)CC1] | 1.97 | 546.8 | 545.1 | B |

TABLE 1-continued

| Example | Structure | RT (min) | m/z [M + H]+ | m/z [M − H]− | HPLC Method |
|---|---|---|---|---|---|
| 65 | 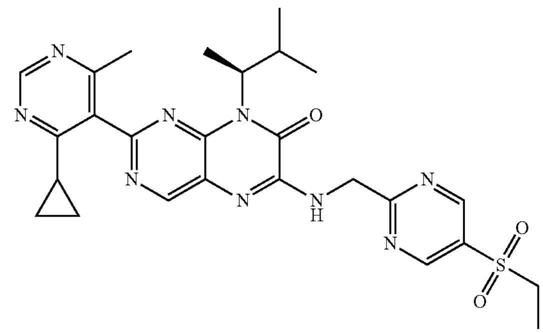 | 1.01 | 550.0 | | A |
| 66 | 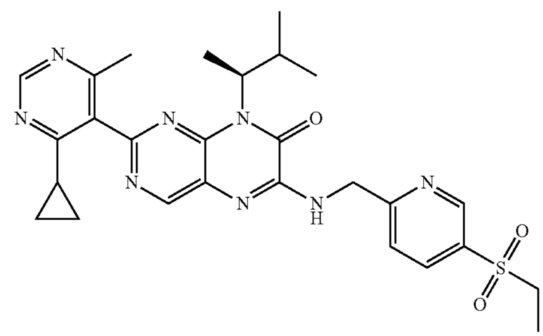 | 1.02 | 548.9 | | A |
| 67 | 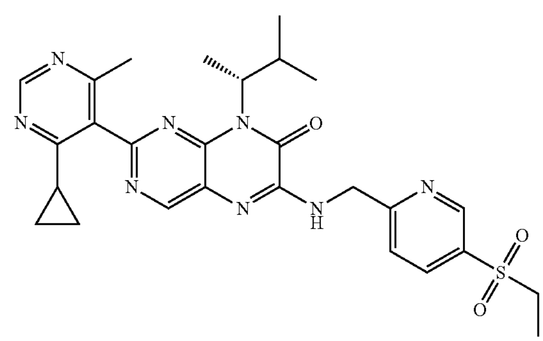 | 1.02 | 548.9 | | A |
| 68 | 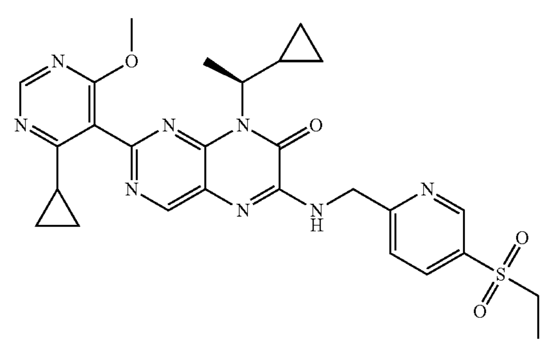 [SMILES: CCS(=O)(=O)c1ccc(CNc2nc3cnc(-c4c(OC)ncnc4C4CC4)nc3n([C@@H](C)C3CC3)c2=O)nc1] | 1.04 | 563.0 | | A |

TABLE 1-continued

| Example | Structure | RT (min) | m/z [M + H]+ | m/z [M − H]− | HPLC Method |
|---|---|---|---|---|---|
| 69 | 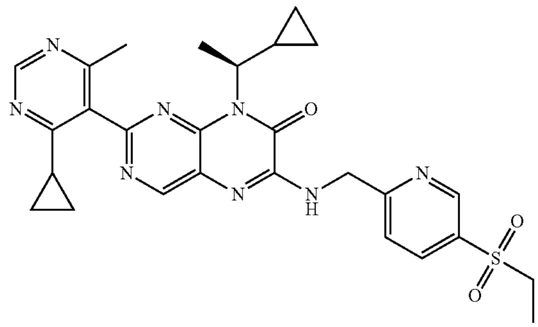 [SMILES: CCS(=O)(=O)c1ccc(CNc2nc3cnc(-c4c(C)ncnc4C4CC4)nc3n([C@@H](C)C3CC3)c2=O)nc1] | 0.98 | 547.3 | | A |
| 70 | 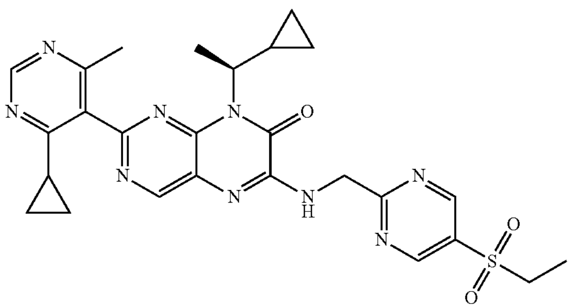 [SMILES: CCS(=O)(=O)c1cnc(CNc2nc3cnc(-c4c(C)ncnc4C4CC4)nc3n([C@@H](C)C3CC3)c2=O)nc1] | 0.98 | 548.0 | | A |
| 71 | 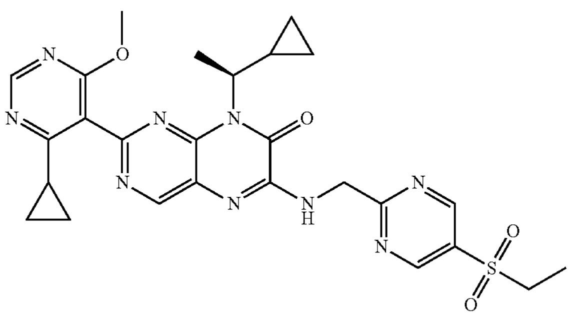 | 1.04 | 564.0 | | A |
| 72 | 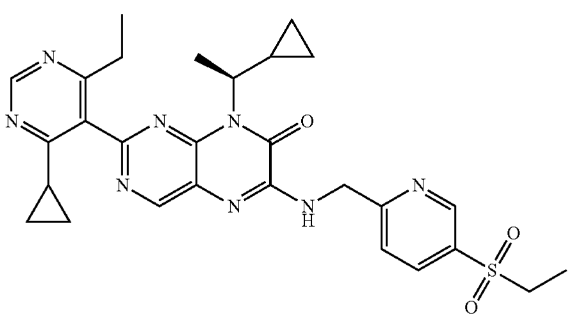 | 1.05 | 560.8 | | A |
| 73 | 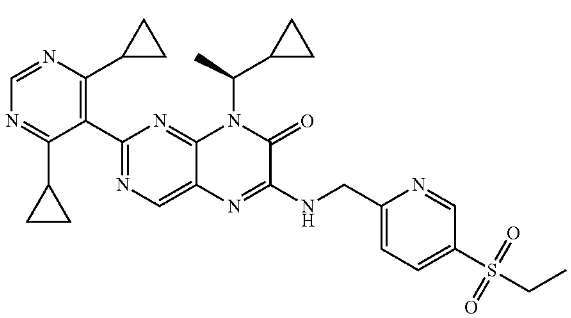 [SMILES: CCS(=O)(=O)c1ccc(CNc2nc3cnc(-c4c(C5CC5)ncnc4C4CC4)nc3n([C@@H](C)C3CC3)c2=O)nc1] | 1.05 | 573.0 | | A |

TABLE 1-continued

| Example | Structure | RT (min) | m/z [M + H]+ | m/z [M − H]− | HPLC Method |
|---|---|---|---|---|---|
| 74 | 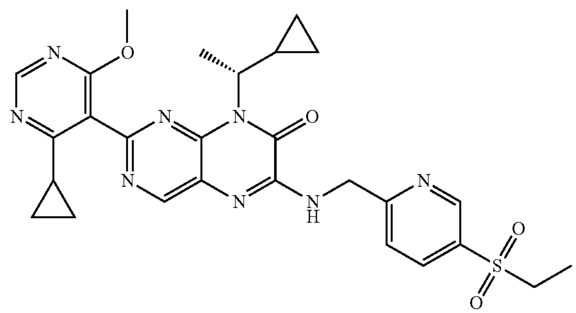 [SMILES: CCS(=O)(=O)c1ccc(CNc2nc3cnc(-c4c(OC)ncnc4C4CC4)nc3n([C@H](C)C3CC3)c2=O)nc1] | 1.05 | 563.0 | | A |
| 75 | 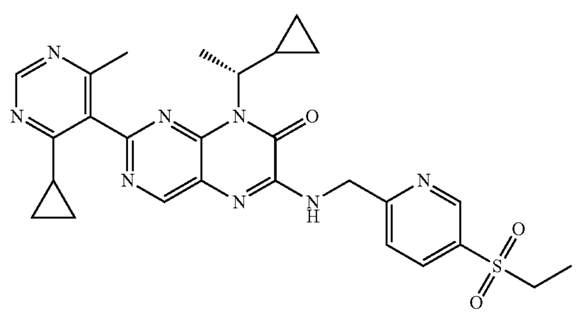 [SMILES: CCS(=O)(=O)c1ccc(CNc2nc3cnc(-c4c(C)ncnc4C4CC4)nc3n([C@H](C)C3CC3)c2=O)nc1] | 0.98 | 546.7 | | A |
| 76 | 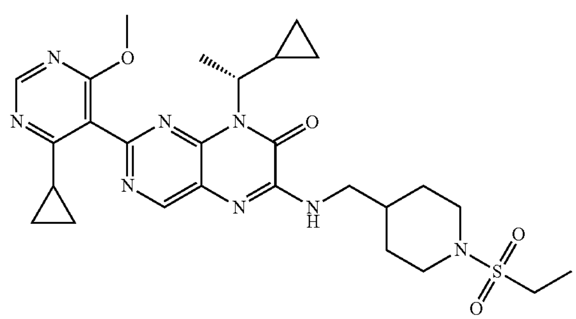 [SMILES: CCS(=O)(=O)N1CCC(CNc2nc3cnc(-c4c(OC)ncnc4C4CC4)nc3n([C@H](C)C3CC3)c2=O)CC1] | 1.11 | 568.8 | | A |
| 77 | 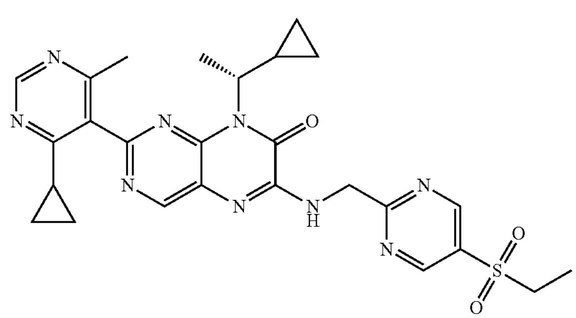 [SMILES: CCS(=O)(=O)c1cnc(CNc2nc3cnc(-c4c(C)ncnc4C4CC4)nc3n([C@H](C)C3CC3)c2=O)nc1] | 0.97 | 547.7 | | A |
| 78 | 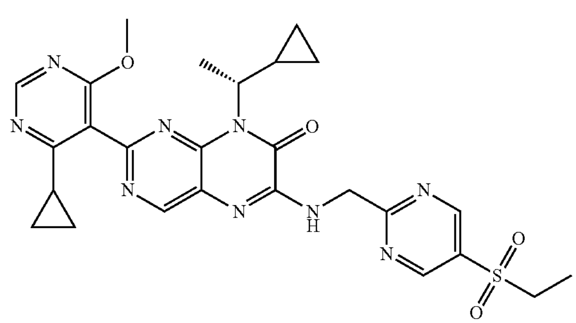 [SMILES: CCS(=O)(=O)c1cnc(CNc2nc3cnc(-c4c(OC)ncnc4C4CC4)nc3n([C@H](C)C3CC3)c2=O)nc1] | 1.04 | 563.8 | | A |

TABLE 1-continued

| Example | Structure | RT (min) | m/z [M + H]+ | m/z [M − H]− | HPLC Method |
|---|---|---|---|---|---|
| 79 | 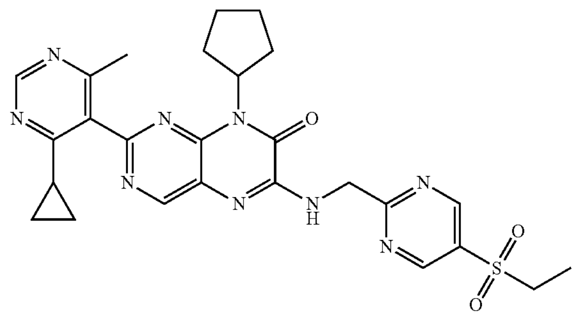 | 0.99 | 547.7 | | A |
| 80 | 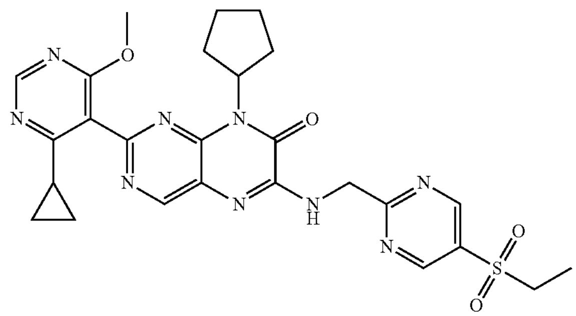 [SMILES: CCS(=O)(=O)c1cnc(CNc2nc3cnc(-c4c(OC)ncnc4C4CC4)nc3n(C3CCCC3)c2=O)nc1] | 1.05 | 563.7 | | A |
| 81 | 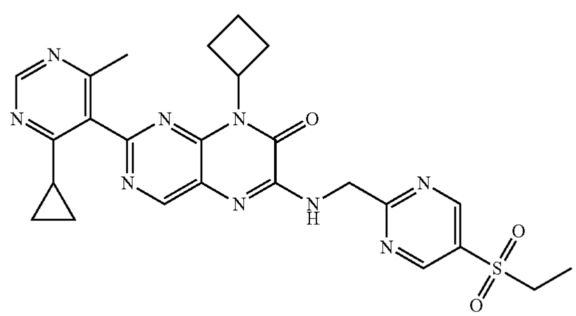 [SMILES: CCS(=O)(=O)c1cnc(CNc2nc3cnc(-c4c(C)ncnc4C4CC4)nc3n(C3CCC3)c2=O)nc1] | 0.94 | 533.8 | | A |
| 82 | 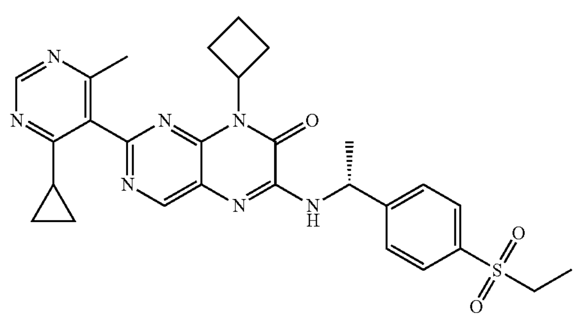 [SMILES: CCS(=O)(=O)c1ccc([C@@H](C)Nc2nc3cnc(-c4c(C)ncnc4C4CC4)nc3n(C3CCC3)c2=O)cc1] | 1.07 | 545.8 | | A |
| 83 | 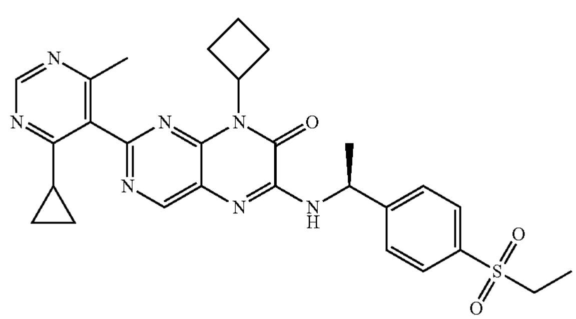 [SMILES: CCS(=O)(=O)c1ccc([C@H](C)Nc2nc3cnc(-c4c(C)ncnc4C4CC4)nc3n(C3CCC3)c2=O)cc1] | 1.07 | 545.9 | | A |

TABLE 1-continued

| Example | Structure | RT (min) | m/z [M + H]+ | m/z [M − H]− | HPLC Method |
|---|---|---|---|---|---|
| 84 | 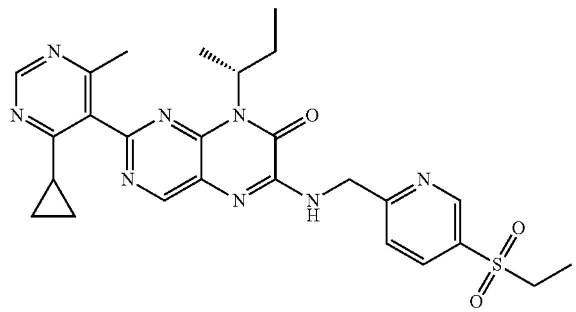 [SMILES: CC[C@@H](C)n1c(=O)c(NCc2ccc(S(=O)(=O)CC)cn2)nc2cnc(-c3c(C)ncnc3C3CC3)nc21] | 0.97 | 535.2 | | A |
| 85 | 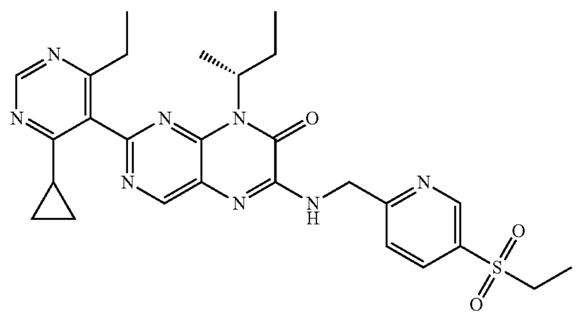 [SMILES: CCc1ncnc(C2CC2)c1-c1ncc2nc(NCc3ccc(S(=O)(=O)CC)cn3)c(=O)n([C@H](C)CC)c2n1] | 1.04 | 549.2 | | A |
| 86 | 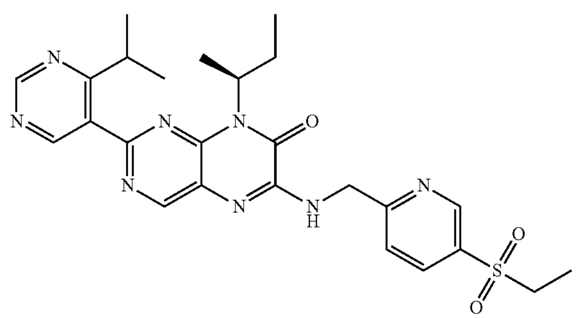 [SMILES: CC[C@H](C)n1c(=O)c(NCc2ccc(S(=O)(=O)CC)cn2)nc2cnc(-c3cncnc3C(C)C)nc21] | 1.05 | 523.2 | | A |
| 87 | 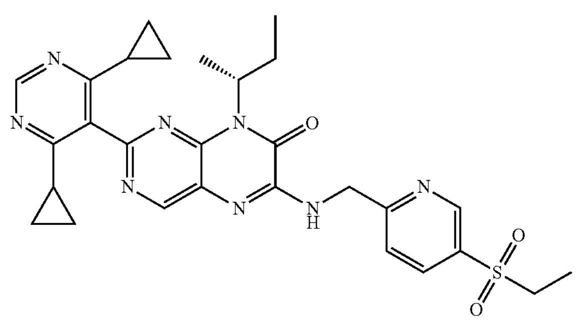 [SMILES: CC[C@@H](C)n1c(=O)c(NCc2ccc(S(=O)(=O)CC)cn2)nc2cnc(-c3c(C4CC4)ncnc3C3CC3)nc21] | 1.11 | 561.2 | | A |
| 88 | 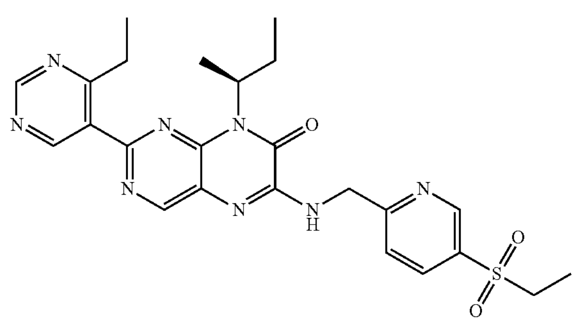 [SMILES: CCc1ncncc1-c1ncc2nc(NCc3ccc(S(=O)(=O)CC)cn3)c(=O)n([C@@H](C)CC)c2n1] | 0.94 | 509.2 | | A |

TABLE 1-continued

| Example | Structure | RT (min) | m/z [M + H]⁺ | m/z [M − H]⁻ | HPLC Method |
|---|---|---|---|---|---|
| 89 | 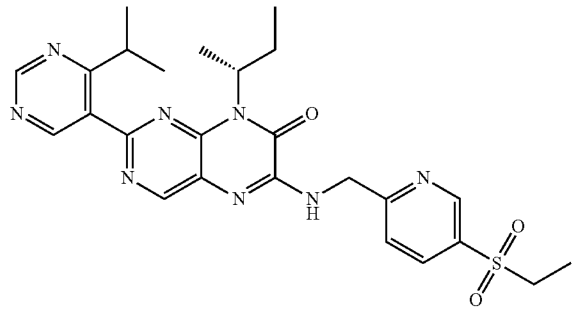 [SMILES: CC[C@@H](C)n1c(=O)c(NCc2ccc(S(=O)(=O)CC)cn2)nc2cnc(-c3cncnc3C(C)C)nc21] | 1.04 | 523.2 | | A |
| 90 | 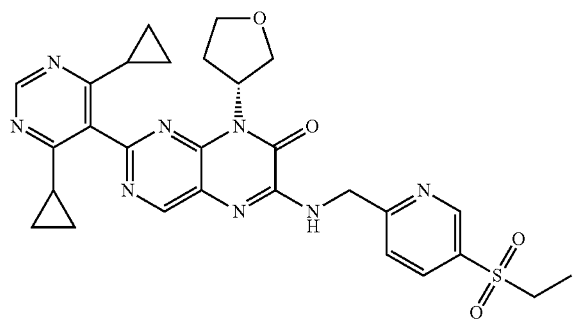 [SMILES: CCS(=O)(=O)c1ccc(CNc2nc3cnc(-c4c(C5CC5)ncnc4C4CC4)nc3n([C@@H]3CCOC3)c2=O)nc1] | 0.89 | 575.2 | | A |
| 91 | 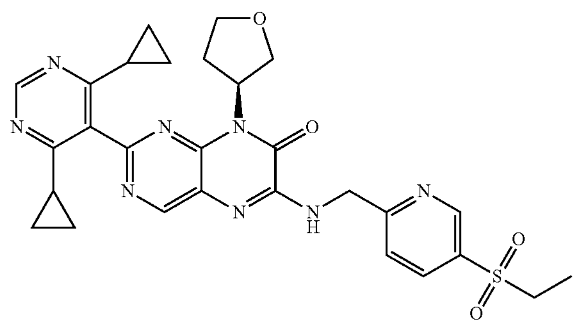 [SMILES: CCS(=O)(=O)c1ccc(CNc2nc3cnc(-c4c(C5CC5)ncnc4C4CC4)nc3n([C@H]3CCOC3)c2=O)nc1] | 0.89 | 575.2 | | A |
| 92 | 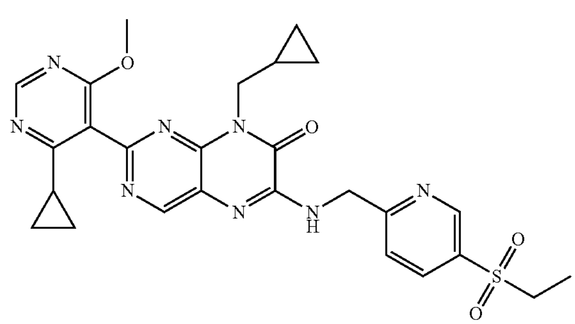 [SMILES: CCS(=O)(=O)c1ccc(CNc2nc3cnc(-c4c(OC)ncnc4C4CC4)nc3n(CC3CC3)c2=O)nc1] | 0.98 | 549.0 | | A |

TABLE 1-continued
| Example | Structure | RT (min) | m/z [M + H]+ | m/z [M − H]− | HPLC Method |
|---|---|---|---|---|---|
| 93 | 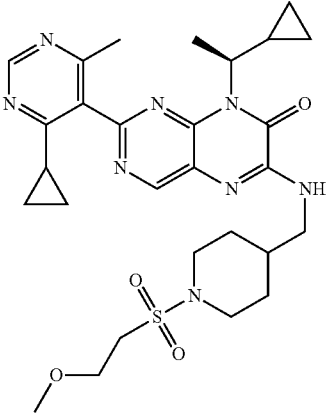 [SMILES: COCCS(=O)(=O)N1CCC(CNc2nc3cnc(-c4c(C)ncnc4C4CC4)nc3n([C@@H](C)C3CC3)c2=O)CC1] | 1.03 | 584.0 | | A |
| 94 | 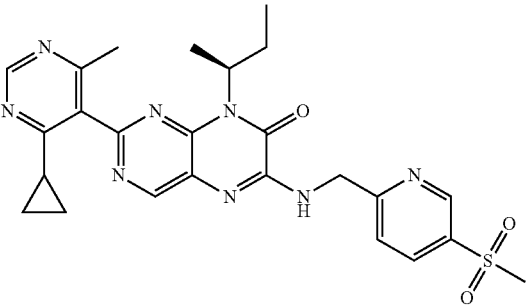 [SMILES: CC[C@H](C)n1c(=O)c(NCc2ccc(S(C)(=O)=O)cn2)nc2cnc(-c3c(C)ncnc3C3CC3)nc21] | 0.89 | 521.5 | | A |
| 95 | 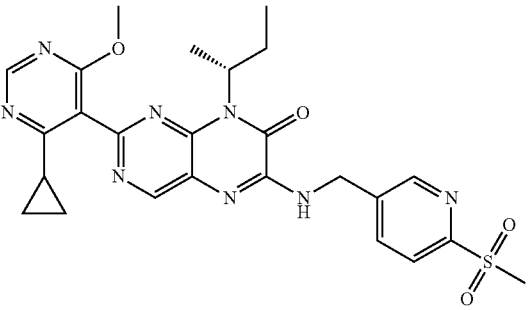 | 0.95 | 537.3 | | A |
| 96 | 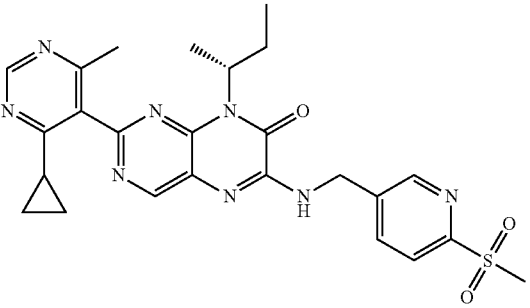 | 0.89 | 521.5 | | A |

TABLE 1-continued

| Example | Structure | RT (min) | m/z [M + H]+ | m/z [M − H]− | HPLC Method |
|---|---|---|---|---|---|
| 97 | 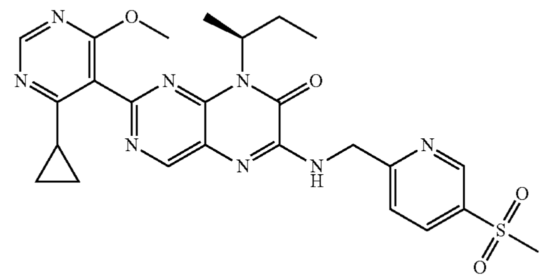 [SMILES: CC[C@H](C)n1c(=O)c(NCc2ccc(S(C)(=O)=O)cn2)nc2cnc(-c3c(OC)ncnc3C3CC3)nc21] | 0.95 | 537.5 | | A |
| 98 | 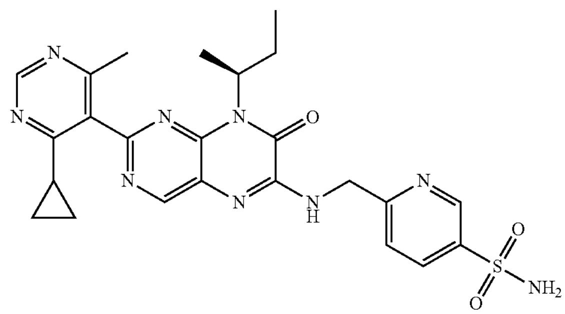 [SMILES: CC[C@H](C)n1c(=O)c(NCc2ccc(S(N)(=O)=O)cn2)nc2cnc(-c3c(C)ncnc3C3CC3)nc21] | 0.83 | 522.5 | | A |
| 99 | 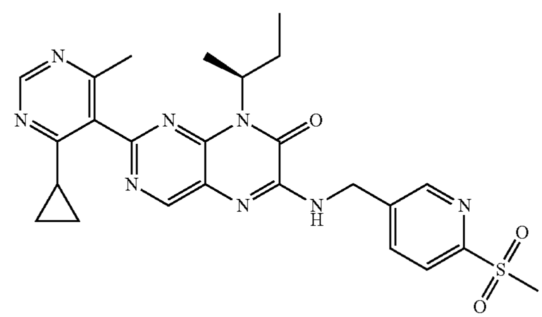 [SMILES: CC[C@H](C)n1c(=O)c(NCc2ccc(S(C)(=O)=O)nc2)nc2cnc(-c3c(C)ncnc3C3CC3)nc21] | 0.89 | 521.5 | | A |
| 100 | 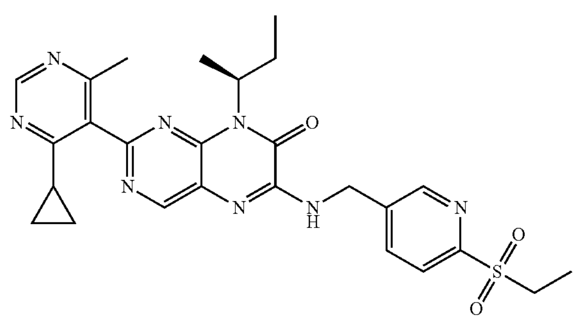 [SMILES: CC[C@H](C)n1c(=O)c(NCc2ccc(S(=O)(=O)CC)nc2)nc2cnc(-c3c(C)ncnc3C3CC3)nc21] | 0.93 | 535.5 | | A |
| 101 | 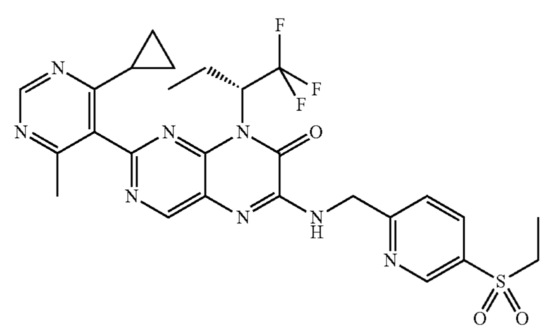 [SMILES: CC[C@@H](n1c(=O)c(NCc2ccc(S(=O)(=O)CC)cn2)nc2cnc(-c3c(C)ncnc3C3CC3)nc21)C(F)(F)F] | 0.98 | 589.4 | | A |

TABLE 1-continued

| Example | Structure | RT (min) | m/z [M + H]+ | m/z [M − H]− | HPLC Method |
|---|---|---|---|---|---|
| 102 | 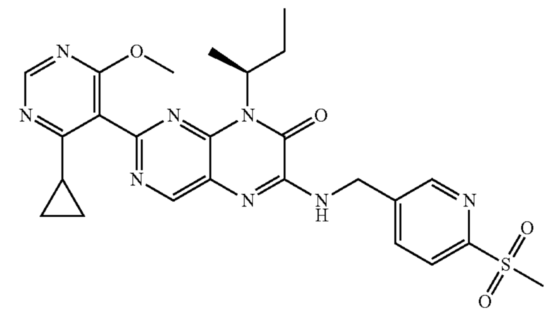 [SMILES: CC[C@H](C)n1c(=O)c(NCc2ccc(S(C)(=O)=O)nc2)nc2cnc(-c3c(OC)ncnc3C3CC3)nc21] | 0.95 | 537.5 | | A |
| 103 | 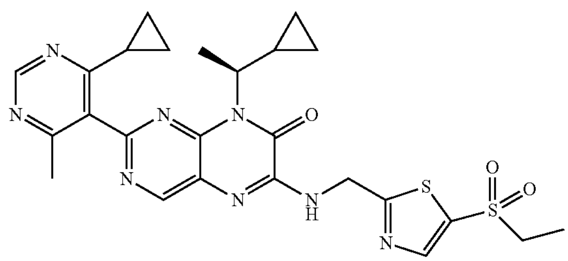 [SMILES: CCS(=O)(=O)c1cnc(CNc2nc3cnc(-c4c(C)ncnc4C4CC4)nc3n([C@@H](C)C3CC3)c2=O)s1] | 2.18 | 553.3 | | B |
| 104 | 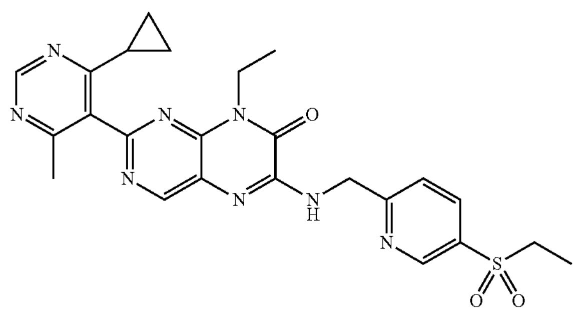 [SMILES: CCn1c(=O)c(NCc2ccc(S(=O)(=O)CC)cn2)nc2cnc(-c3c(C)ncnc3C3CC3)nc21] | 1.67 | 507.0 | | B |
| 105 | 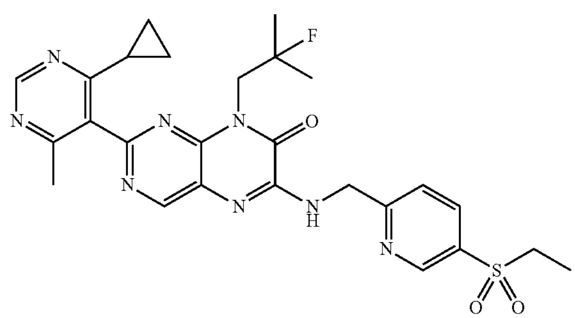 [SMILES: CCS(=O)(=O)c1ccc(CNc2nc3cnc(-c4c(C)ncnc4C4CC4)nc3n(CC(C)(C)F)c2=O)nc1] | 1.80 | 553.5 | | B |
| 106 | 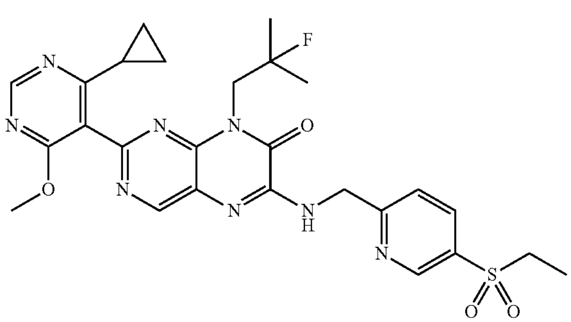 [SMILES: CCS(=O)(=O)c1ccc(CNc2nc3cnc(-c4c(OC)ncnc4C4CC4)nc3n(CC(C)(C)F)c2=O)nc1] | 1.99 | 569.5 | | B |

TABLE 1-continued
| Example | Structure | RT (min) | m/z [M + H]+ | m/z [M − H]− | HPLC Method |
|---|---|---|---|---|---|
| 107 | 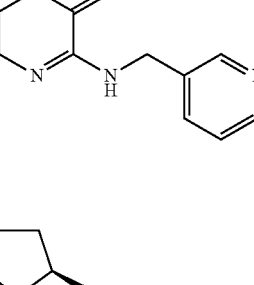 | 0.94 | 537.5 | | A |
| 108 | 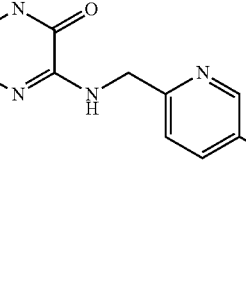 | 0.87 | 588.1 | | A |
| 109 | 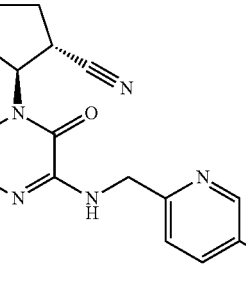 | 0.91 | 588.0 | | A |
| 110 | 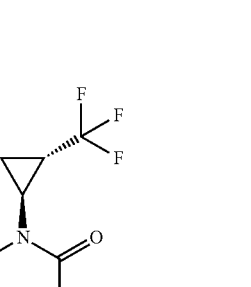 | 0.88 | 603.1 | | A |

TABLE 1-continued

| Example | Structure | RT (min) | m/z [M + H]+ | m/z [M − H]− | HPLC Method |
|---|---|---|---|---|---|
| 111 | 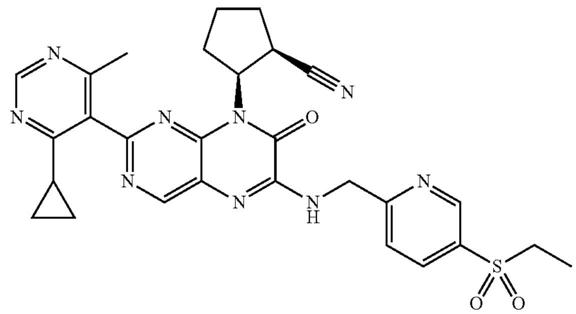 [SMILES: CCS(=O)(=O)c1ccc(CNc2nc3cnc(-c4c(C)ncnc4C4CC4)nc3n([C@H]3CCC[C@H]3C#N)c2=O)nc1] | 0.81 | 572.5 | | A |
| 112 | 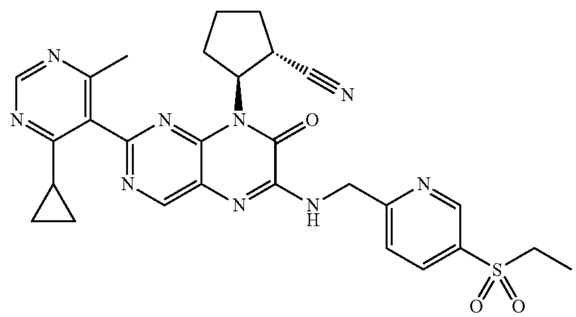 | 0.81 | 572.5 | | A |
| 113 | 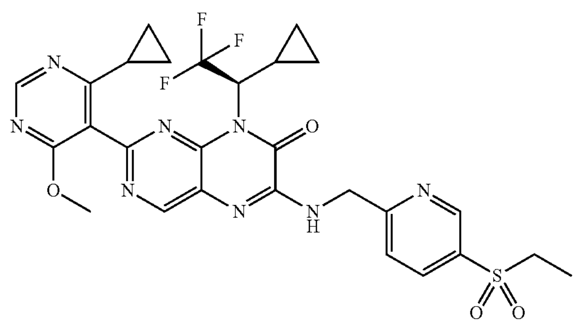 [SMILES: CCS(=O)(=O)c1ccc(CNc2nc3cnc(-c4c(OC)ncnc4C4CC4)nc3n([C@H](C3CC3)C(F)(F)F)c2=O)nc1] | 1.05 | 617.5 | | A |
| 114 | 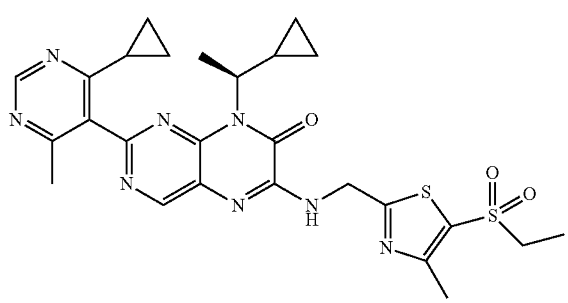 [SMILES: CCS(=O)(=O)c1sc(CNc2nc3cnc(-c4c(C)ncnc4C4CC4)nc3n([C@@H](C)C3CC3)c2=O)nc1C] | 2.28 | 567.5 | | B |
| 115 | 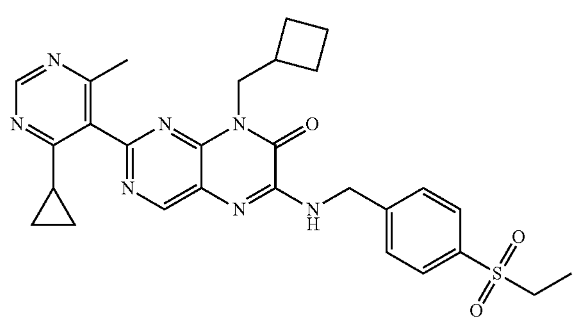 [SMILES: CCS(=O)(=O)c1ccc(CNc2nc3cnc(-c4c(C)ncnc4C4CC4)nc3n(CC3CCC3)c2=O)cc1] | 1.02 | 546.5 | | A |

TABLE 1-continued

| Example | Structure | RT (min) | m/z [M + H]+ | m/z [M − H]− | HPLC Method |
|---|---|---|---|---|---|
| 116 | 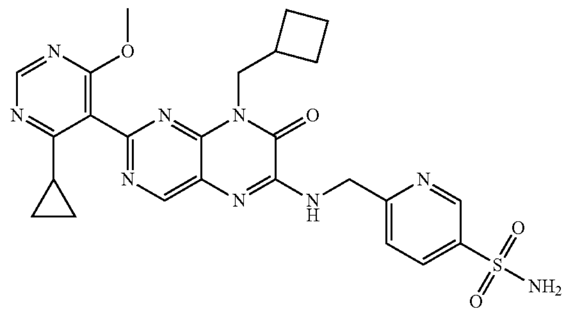 [SMILES: COc1ncnc(C2CC2)c1-c1ncc2nc(NCc3ccc(S(N)(=O)=O)cn3)c(=O)n(CC3CCC3)c2n1] | 0.92 | 550.5 | | A |
| 117 | 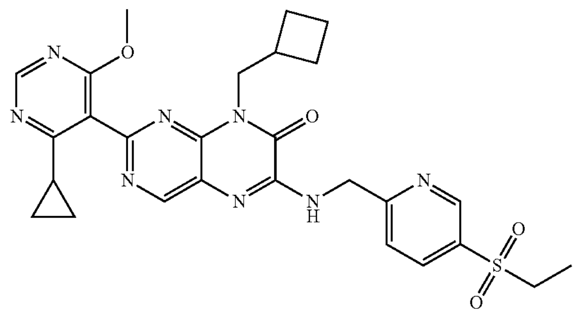 [SMILES: CCS(=O)(=O)c1ccc(CNc2nc3cnc(-c4c(OC)ncnc4C4CC4)nc3n(CC3CCC3)c2=O)nc1] | 1.12 | 563.4 | | A |
| 118 | 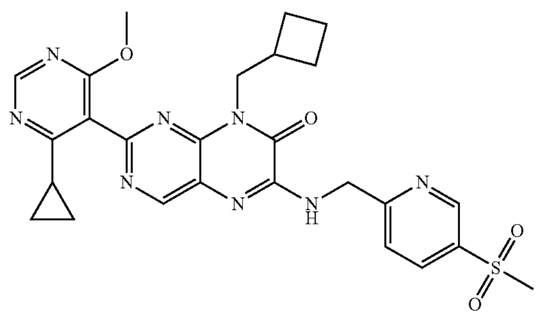 [SMILES: COc1ncnc(C2CC2)c1-c1ncc2nc(NCc3ccc(S(C)(=O)=O)cn3)c(=O)n(CC3CCC3)c2n1] | 0.98 | 549.5 | | A |
| 119 | 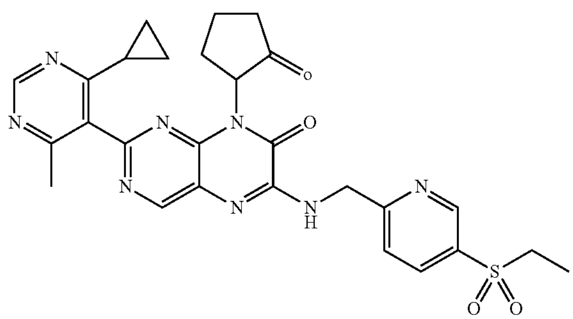 | 0.78 | 561.3 | | A |
| 120 | 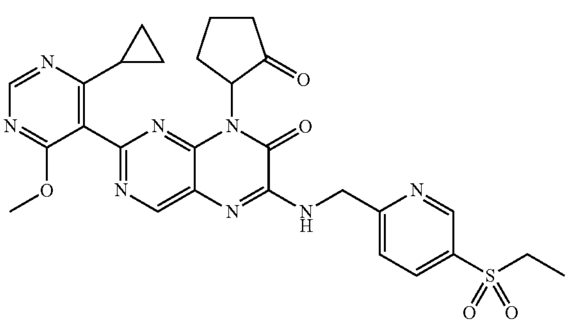 [SMILES: CCS(=O)(=O)c1ccc(CNc2nc3cnc(-c4c(OC)ncnc4C4CC4)nc3n(C3CCCC3=O)c2=O)nc1] | 0.83 | 577.3 | | A |

TABLE 1-continued

| Example | Structure | RT (min) | m/z [M + H]+ | m/z [M − H]− | HPLC Method |
|---|---|---|---|---|---|
| 121 | 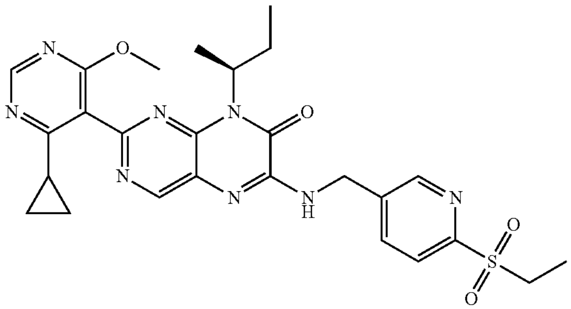 [SMILES: CC[C@H](C)n1c(=O)c(NCc2ccc(S(=O)(=O)CC)nc2)nc2cnc(-c3c(OC)ncnc3C3CC3)nc21] | 2.27 | 551.5 | | B |
| 122 | 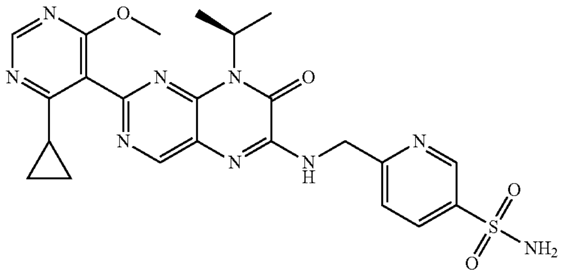 | 0.89 | 538.4 | | A |
| 123 | 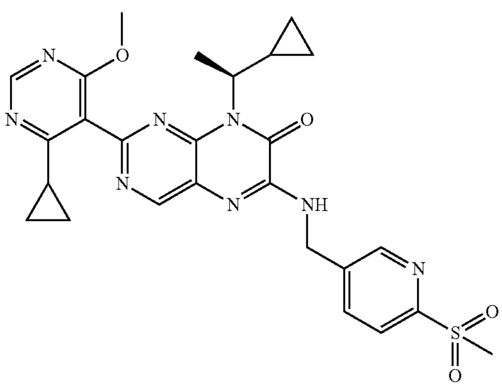 [SMILES: COc1ncnc(C2CC2)c1-c1ncc2nc(NCc3ccc(S(C)(=O)=O)nc3)c(=O)n([C@@H](C)C3CC3)c2n1] | 0.99 | 549.0 | | A |
| 124 | 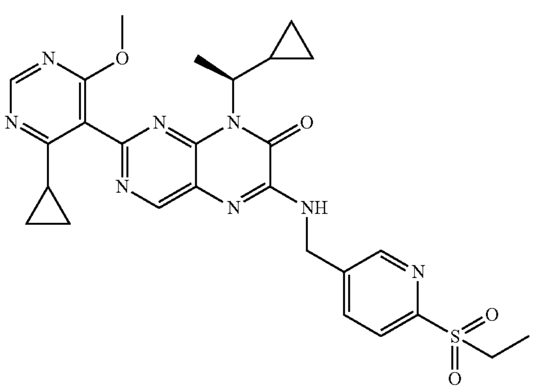 [SMILES: CCS(=O)(=O)c1ccc(CNc2nc3cnc(-c4c(OC)ncnc4C4CC4)nc3n([C@@H](C)C3CC3)c2=O)cn1] | 1.03 | 563.2 | | A |

TABLE 1-continued

| Example | Structure | RT (min) | m/z [M + H]+ | m/z [M − H]− | HPLC Method |
|---|---|---|---|---|---|
| 125 | 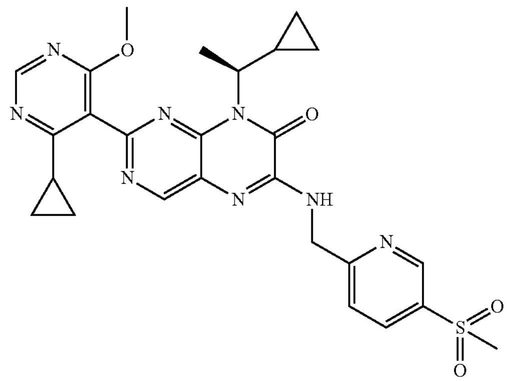 [SMILES: COc1ncnc(C2CC2)c1-c1ncc2nc(NCc3ccc(S(C)(=O)=O)cn3)c(=O)n([C@@H](C)C3CC3)c2n1] | 0.99 | 549.2 | | A |
| 126 | 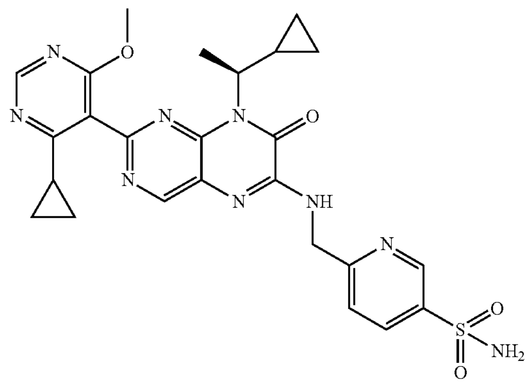 | 0.93 | 550.2 | | A |
| 127 | 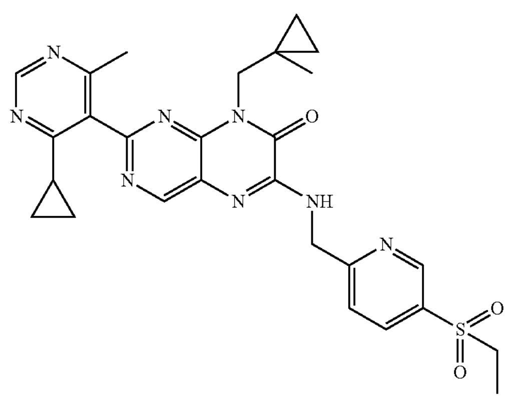 [SMILES: CCS(=O)(=O)c1ccc(CNc2nc3cnc(-c4c(C)ncnc4C4CC4)nc3n(CC3(C)CC3)c2=O)nc1] | 0.96 | 547.5 | | A |
| 128 | 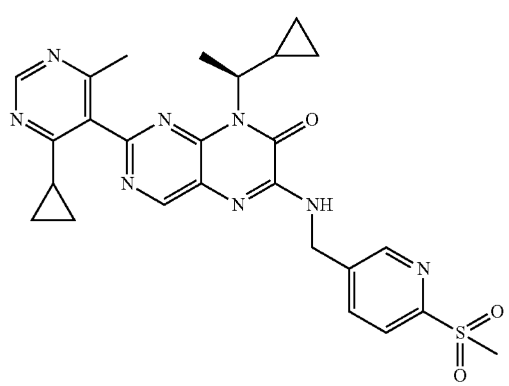 [SMILES: Cc1ncnc(C2CC2)c1-c1ncc2nc(NCc3ccc(S(C)(=O)=O)nc3)c(=O)n([C@@H](C)C3CC3)c2n1] | 0.91 | 533.4 | | A |

TABLE 1-continued

| Example | Structure | RT (min) | m/z [M + H]+ | m/z [M − H]− | HPLC Method |
|---|---|---|---|---|---|
| 129 | 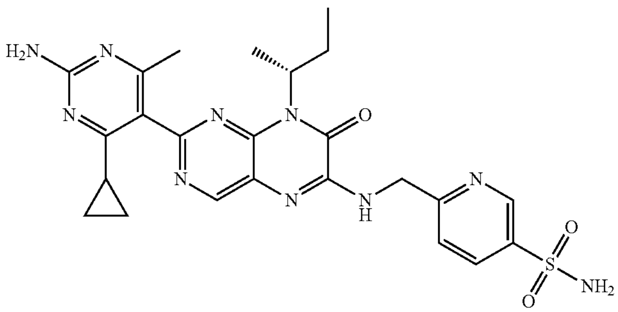 [SMILES: CC[C@@H](C)n1c(=O)c(NCc2ccc(S(N)(=O)=O)cn2)nc2cnc(-c3c(C)nc(N)nc3C3CC3)nc21] | 0.56 | 537.1 | | A |
| 130 | 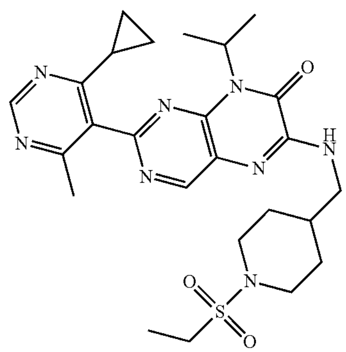 [SMILES: CCS(=O)(=O)N1CCC(CNc2nc3cnc(-c4c(C)ncnc4C4CC4)nc3n(C(C)C)c2=O)CC1] | 0.96 | 526.8 | | A |
| 131 | 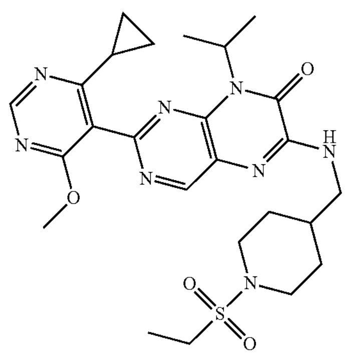 [SMILES: CCS(=O)(=O)N1CCC(CNc2nc3cnc(-c4c(OC)ncnc4C4CC4)nc3n(C(C)C)c2=O)CC1] | 1.01 | 542.7 | | A |
| 132 | 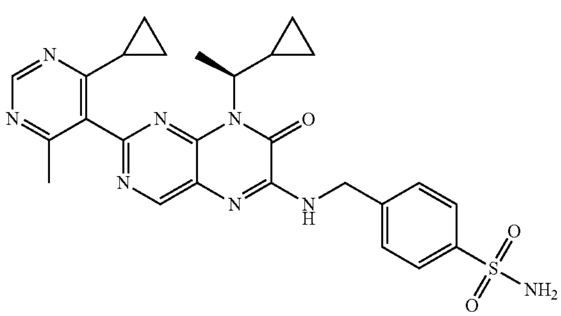 [SMILES: Cc1ncnc(C2CC2)c1-c1ncc2nc(NCc3ccc(S(N)(=O)=O)cc3)c(=O)n([C@@H](C)C3CC3)c2n1] | 0.90 | 532.9 | | A |

TABLE 1-continued

| Example | Structure | RT (min) | m/z [M + H]+ | m/z [M − H]− | HPLC Method |
|---|---|---|---|---|---|
| 133 | 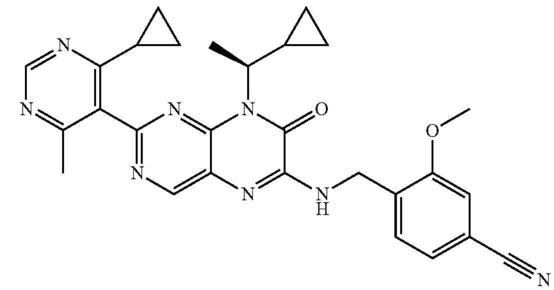 [SMILES: COc1cc(C#N)ccc1CNc1nc2cnc(-c3c(C)ncnc3C3CC3)nc2n([C@@H](C)C2CC2)c1=O] | 1.16 | 509.1 | | A |
| 134 | 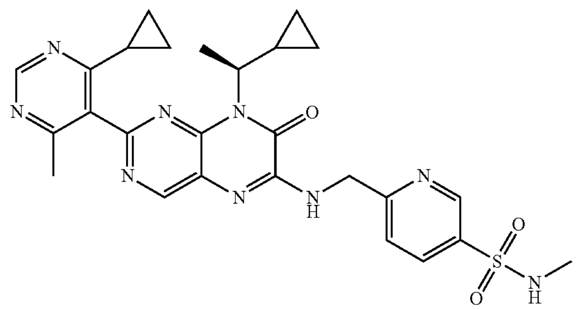 | 0.94 | 547.9 | | A |
| 135 | 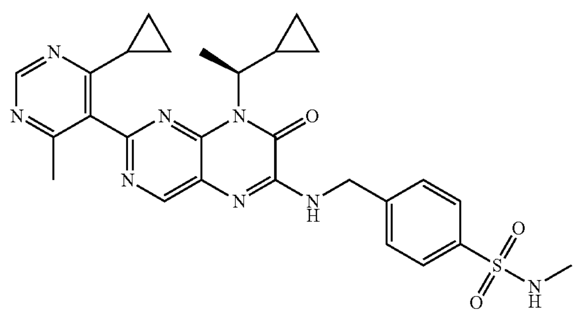 [SMILES: CNS(=O)(=O)c1ccc(CNc2nc3cnc(-c4c(C)ncnc4C4CC4)nc3n([C@@H](C)C3CC3)c2=O)cc1] | 0.99 | 546.9 | | A |
| 136 | 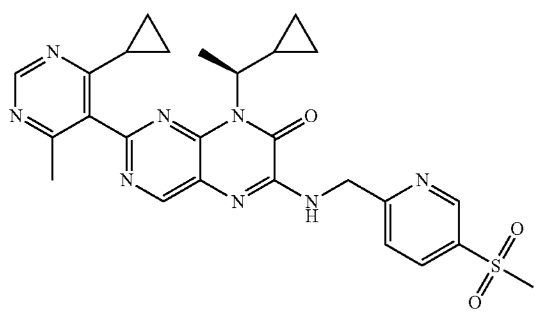 [SMILES: Cc1ncnc(C2CC2)c1-c1ncc2nc(NCc3ccc(S(C)(=O)=O)cn3)c(=O)n([C@@H](C)C3CC3)c2n1] | 0.92 | 533.0 | | A |
| 137 | 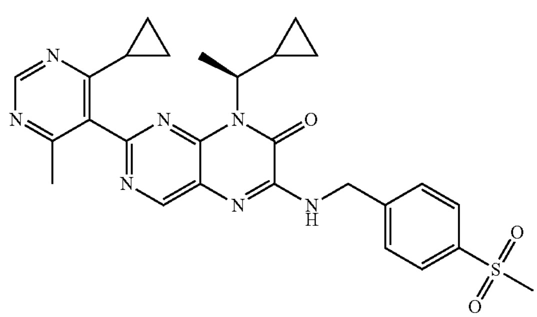 [SMILES: Cc1ncnc(C2CC2)c1-c1ncc2nc(NCc3ccc(S(C)(=O)=O)cc3)c(=O)n([C@@H](C)C3CC3)c2n1] | 0.98 | 531.9 | | A |

TABLE 1-continued
| Example | Structure | RT (min) | m/z [M + H]+ | m/z [M − H]− | HPLC Method |
|---|---|---|---|---|---|
| 138 | 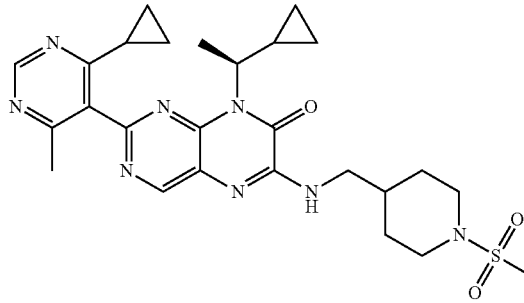 | 1.04 | 552.9 | | A |
| 139 | 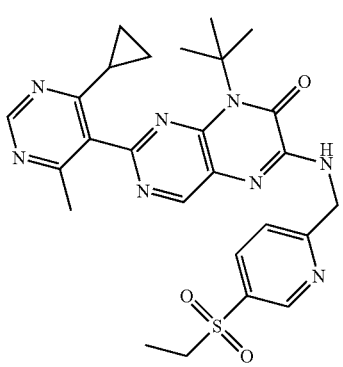 [SMILES: CCS(=O)(=O)c1ccc(CNc2nc3cnc(-c4c(C)ncnc4C4CC4)nc3n(C(C)(C)C)c2=O)nc1] | 0.96 | 534.7 | | A |
| 140 | 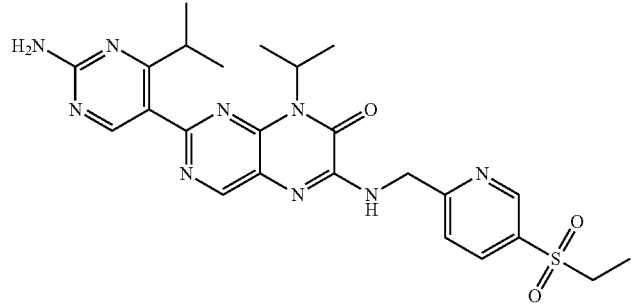 [SMILES: CCS(=O)(=O)c1ccc(CNc2nc3cnc(-c4cnc(N)nc4C(C)C)nc3n(C(C)C)c2=O)nc1] | 1.77 | 524.0 | | B |
| 141 | 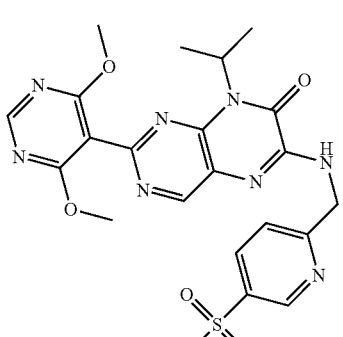 | 0.89 | 527.1 | | A |

TABLE 1-continued

| Example | Structure | RT (min) | m/z [M + H]+ | m/z [M − H]− | HPLC Method |
|---|---|---|---|---|---|
| 142 | 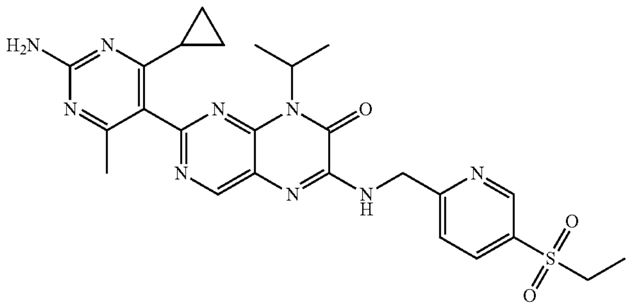 [SMILES: CCS(=O)(=O)c1ccc(CNc2nc3cnc(-c4c(C)nc(N)nc4C4CC4)nc3n(C(C)C)c2=O)nc1] | 1.26 | 536.1 | | B |
| 143 | 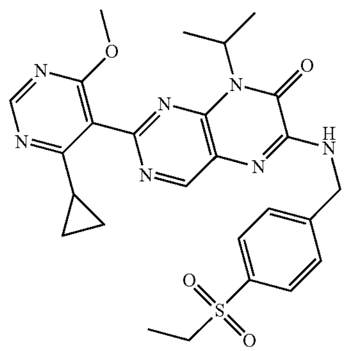 [SMILES: CCS(=O)(=O)c1ccc(CNc2nc3cnc(-c4c(OC)ncnc4C4CC4)nc3n(C(C)C)c2=O)cc1] | 1.01 | 535.9 | | A |
| 144 | 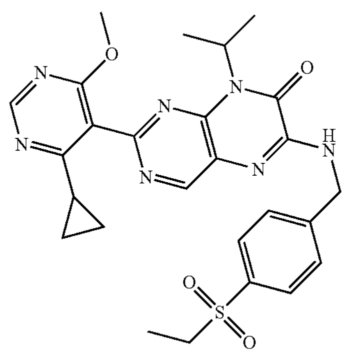 [SMILES: CCS(=O)(=O)c1ccc(CNc2nc3cnc(-c4c(OC)ncnc4C4CC4)nc3n(C(C)C)c2=O)cc1] | 0.97 | 520.0 | | A |
| 145 | 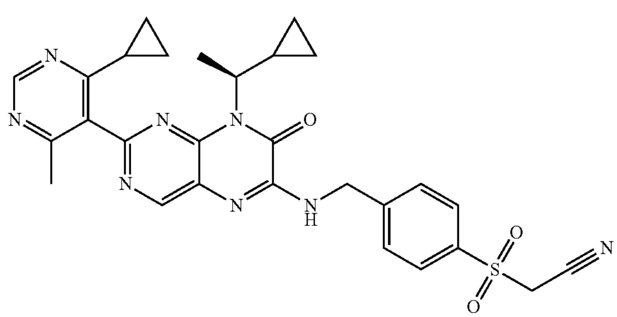 [SMILES: Cc1ncnc(C2CC2)c1-c1ncc2nc(NCc3ccc(S(=O)(=O)CC#N)cc3)c(=O)n([C@@H](C)C3CC3)c2n1] | 1.04 | 557.1 | | A |

TABLE 1-continued

| Example | Structure | RT (min) | m/z [M + H]+ | m/z [M − H]− | HPLC Method |
|---|---|---|---|---|---|
| 146 | 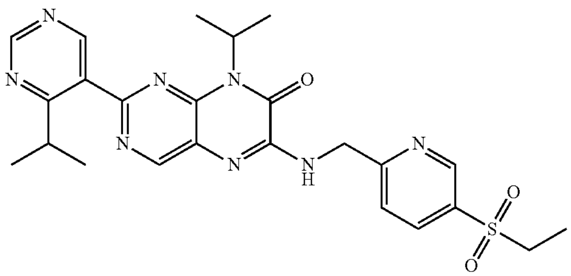 [SMILES: CCS(=O)(=O)c1ccc(CNc2nc3cnc(-c4cncnc4C(C)C)nc3n(C(C)C)c2=O)nc1] | 2.18 | 509.0 | | B |
| 147 | 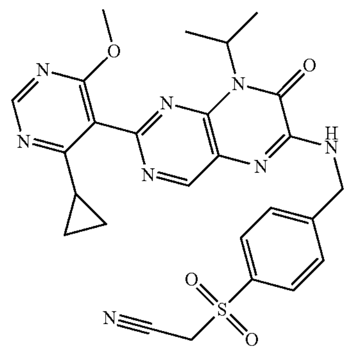 [SMILES: COc1ncnc(C2CC2)c1-c1ncc2nc(NCc3ccc(S(=O)(=O)CC#N)cc3)c(=O)n(C(C)C)c2n1] | 1.02 | 546.9 | | A |
| 148 | 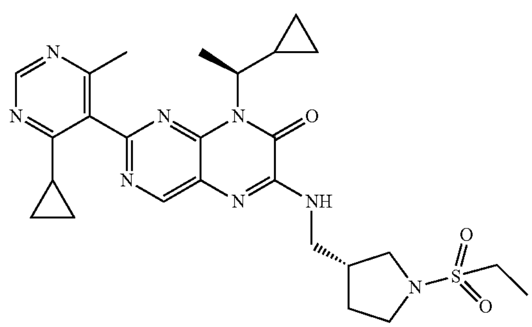 [SMILES: CCS(=O)(=O)N1CC[C@H](CNc2nc3cnc(-c4c(C)ncnc4C4CC4)nc3n([C@@H](C)C3CC3)c2=O)C1] | 0.99 | 540.5 | | A |
| 149 | 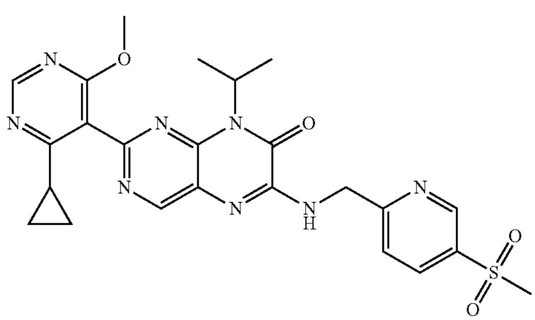 | 0.90 | 522.9 | | A |
| 150 | 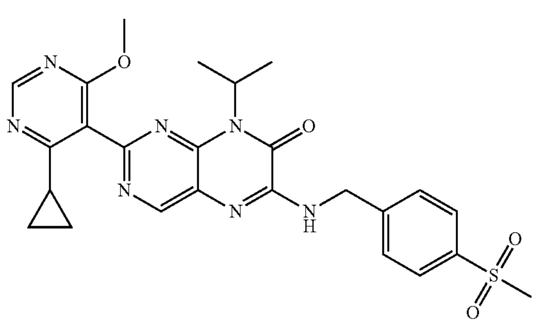 | 0.96 | 522.0 | | A |

TABLE 1-continued
| Example | Structure | RT (min) | m/z [M + H]+ | m/z [M − H]− | HPLC Method |
|---|---|---|---|---|---|
| 151 | 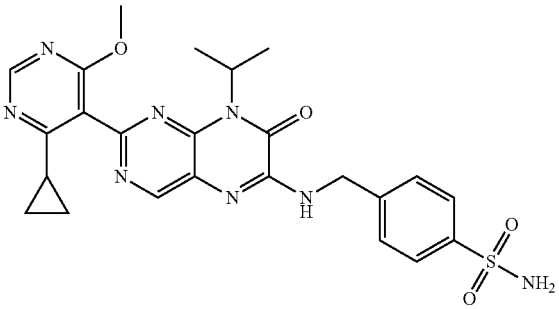 [SMILES: COc1ncnc(C2CC2)c1-c1ncc2nc(NCc3ccc(S(N)(=O)=O)cc3)c(=O)n(C(C)C)c2n1] | 0.90 | 522.9 | | A |
| 152 | 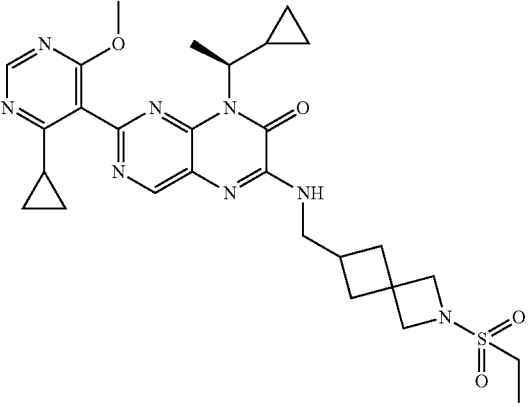 [SMILES: CCS(=O)(=O)N1CC2(CC(CNc3nc4cnc(-c5c(OC)ncnc5C5CC5)nc4n([C@@H](C)C4CC4)c3=O)C2)C1] | 2.57 | 580.9 | | B |
| 153 | 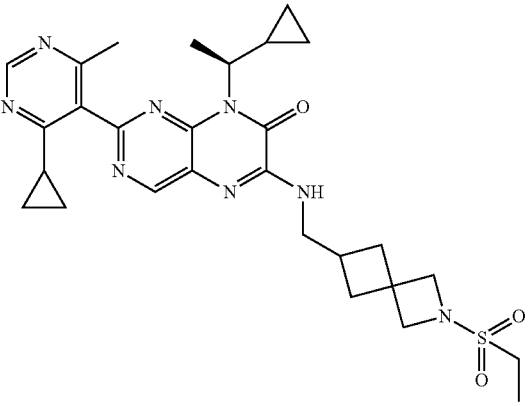 [SMILES: CCS(=O)(=O)N1CC2(CC(CNc3nc4cnc(-c5c(C)ncnc5C5CC5)nc4n([C@@H](C)C4CC4)c3=O)C2)C1] | 1.07 | 564.9 | | A |
| 154 | 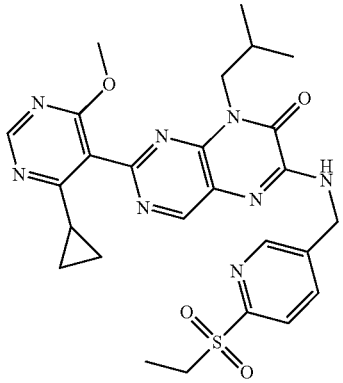 [SMILES: CCS(=O)(=O)c1ccc(CNc2nc3cnc(-c4c(OC)ncnc4C4CC4)nc3n(CC(C)C)c2=O)cn1] | 0.98 | 550.9 | | A |

TABLE 1-continued

| Example | Structure | RT (min) | m/z [M + H]+ | m/z [M − H]− | HPLC Method |
|---|---|---|---|---|---|
| 155 | 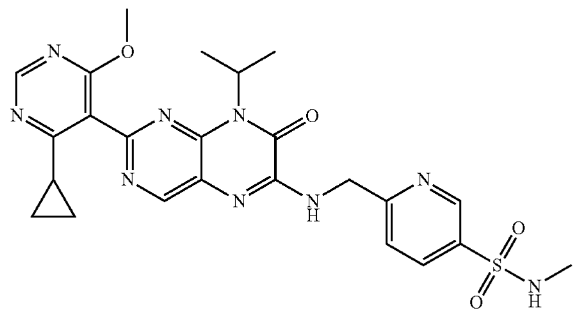 [SMILES: CNS(=O)(=O)c1ccc(CNc2nc3cnc(-c4c(OC)ncnc4C4CC4)nc3n(C(C)C)c2=O)nc1] | 0.90 | 537.9 | | A |
| 156 | 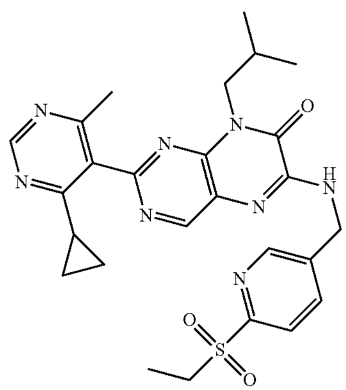 [SMILES: CCS(=O)(=O)c1ccc(CNc2nc3cnc(-c4c(C)ncnc4C4CC4)nc3n(CC(C)C)c2=O)cn1] | 1.00 | 536.1 | | A |
| 157 | 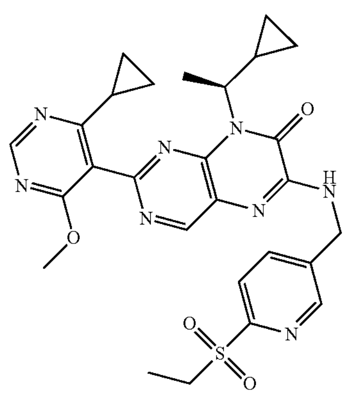 [SMILES: CCS(=O)(=O)c1ccc(CNc2nc3cnc(-c4c(OC)ncnc4C4CC4)nc3n([C@@H](C)C3CC3)c2=O)cn1] | 0.95 | 546.9 | | A |
| 158 | 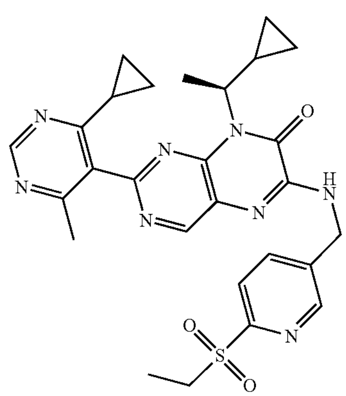 [SMILES: CCS(=O)(=O)c1ccc(CNc2nc3cnc(-c4c(C)ncnc4C4CC4)nc3n([C@@H](C)C3CC3)c2=O)cn1] | 0.98 | 539.3 | | A |

TABLE 1-continued

| Example | Structure | RT (min) | m/z [M + H]+ | m/z [M − H]− | HPLC Method |
|---|---|---|---|---|---|
| 159 | 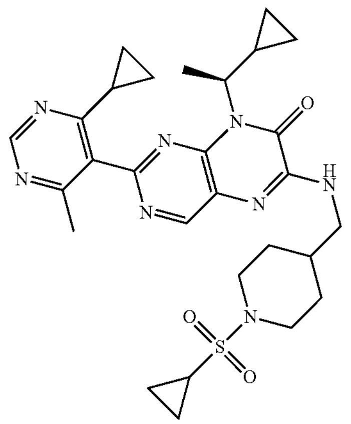 [SMILES: Cc1ncnc(C2CC2)c1-c1ncc2nc(NCC3CCN(S(=O)(=O)C4CC4)CC3)c(=O)n([C@@H](C)C3CC3)c2n1] | 1.05 | 564.8 | | A |
| 160 | 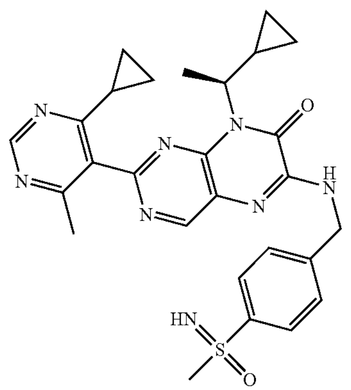 [SMILES: Cc1ncnc(C2CC2)c1-c1ncc2nc(NCc3ccc(S(C)(=N)=O)cc3)c(=O)n([C@@H](C)C3CC3)c2n1] | 0.84 | 531.0 | | A |
| 161 | 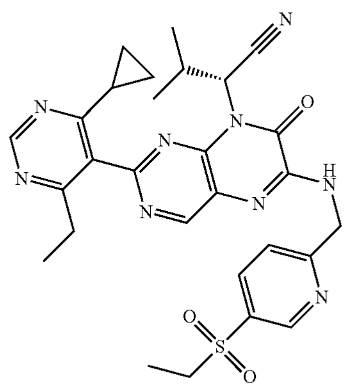 [SMILES: CCc1ncnc(C2CC2)c1-c1ncc2nc(NCc3ccc(S(=O)(=O)CC)cn3)c(=O)n([C@@H](C#N)C(C)C)c2n1] | 0.96 | 575.3 | | A |
| 162 | 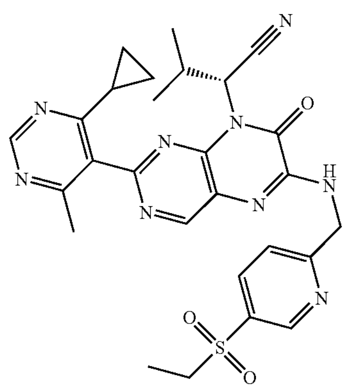 [SMILES: CCS(=O)(=O)c1ccc(CNc2nc3cnc(-c4c(C)ncnc4C4CC4)nc3n([C@@H](C#N)C(C)C)c2=O)nc1] | 0.89 | 561.2 | | A |

TABLE 1-continued

| Example | Structure | RT (min) | m/z [M + H]+ | m/z [M − H]− | HPLC Method |
|---|---|---|---|---|---|
| 163 | 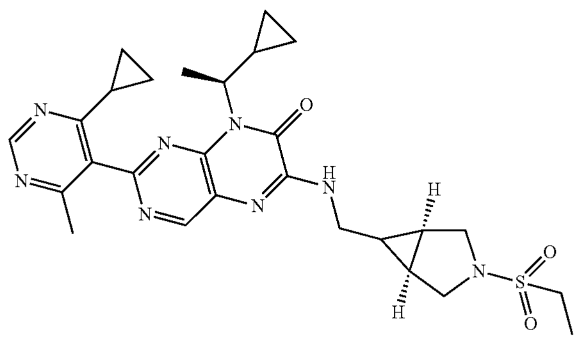 [SMILES: CCS(=O)(=O)N1C[C@@H]2C(CNc3nc4cnc(-c5c(C)ncnc5C5CC5)nc4n([C@@H](C)C4CC4)c3=O)[C@@H]2C1] | 1.01 | 550.7 | | A |
| 164 | 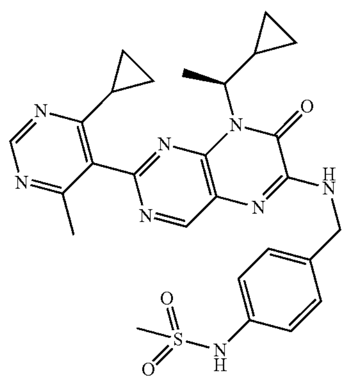 [SMILES: Cc1ncnc(C2CC2)c1-c1ncc2nc(NCc3ccc(NS(C)(=O)=O)cc3)c(=O)n([C@@H](C)C3CC3)c2n1] | 0.97 | 547.0 | | A |
| 165 | 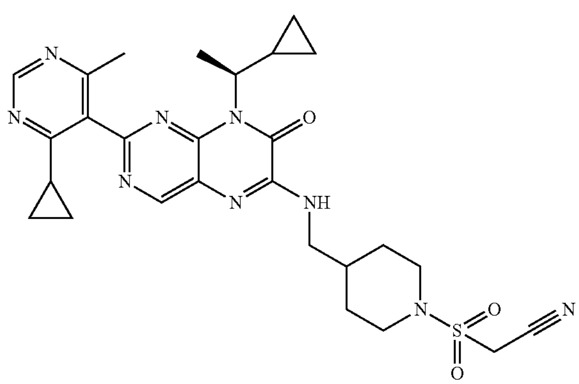 [SMILES: Cc1ncnc(C2CC2)c1-c1ncc2nc(NCC3CCN(S(=O)(=O)CC#N)CC3)c(=O)n([C@@H](C)C3CC3)c2n1] | 1.03 | 563.8 | | A |
| 166 | 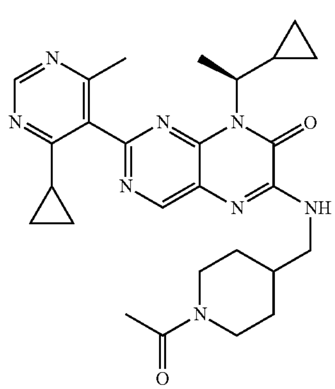 [SMILES: CC(=O)N1CCC(CNc2nc3cnc(-c4c(C)ncnc4C4CC4)nc3n([C@@H](C)C3CC3)c2=O)CC1] | 0.93 | 504.0 | | A |

TABLE 1-continued
| Example | Structure | RT (min) | m/z [M + H]+ | m/z [M − H]− | HPLC Method |
|---|---|---|---|---|---|
| 167 | 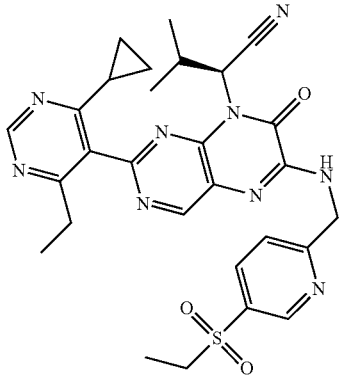 [SMILES: CCc1ncnc(C2CC2)c1-c1ncc2nc(NCc3ccc(S(=O)(=O)CC)cn3)c(=O)n([C@H](C#N)C(C)C)c2n1] | 0.93 | 574.0 | | A |
| 168 | 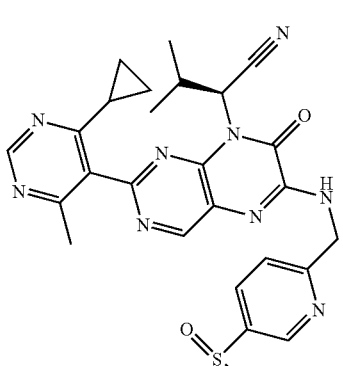 | 0.87 | 559.7 | | A |
| 169 | 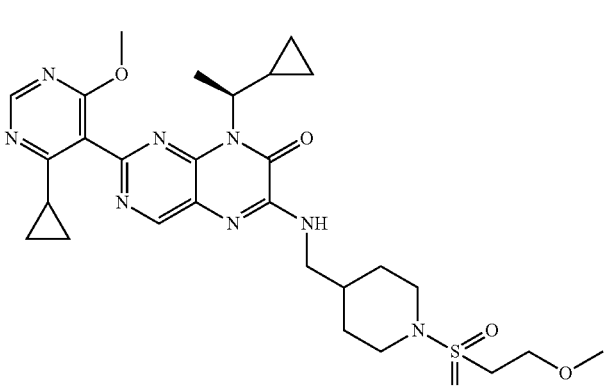 | 1.09 | 599.8 | | A |
| 170 | 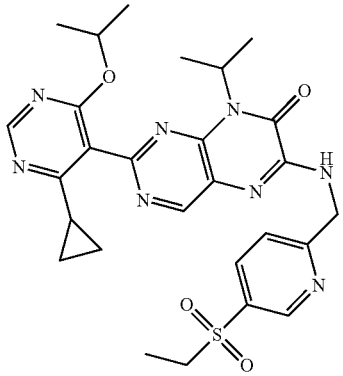 [SMILES: CCS(=O)(=O)c1ccc(CNc2nc3cnc(-c4c(OC(C)C)ncnc4C4CC4)nc3n(C(C)C)c2=O)nc1] | 1.10 | 565.1 | | A |

TABLE 1-continued
| Example | Structure | RT (min) | m/z [M + H]+ | m/z [M − H]− | HPLC Method |
|---|---|---|---|---|---|
| 171 | 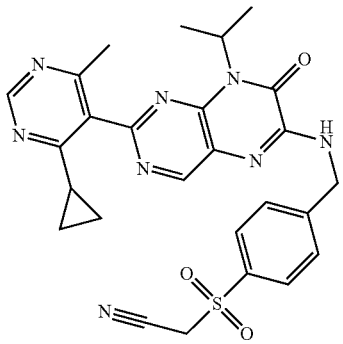 [SMILES: Cc1ncnc(C2CC2)c1-c1ncc2nc(NCc3ccc(S(=O)(=O)CC#N)cc3)c(=O)n(C(C)C)c2n1] | 0.97 | 531.1 | | A |
| 172 | 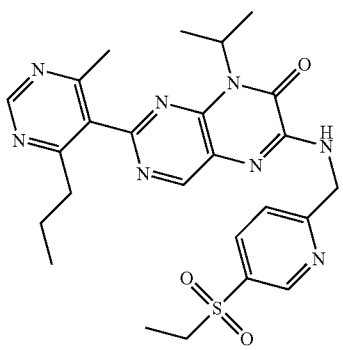 [SMILES: CCCc1ncnc(C)c1-c1ncc2nc(NCc3ccc(S(=O)(=O)CC)cn3)c(=O)n(C(C)C)c2n1] | 0.91 | 524 | | A |
| 173 | 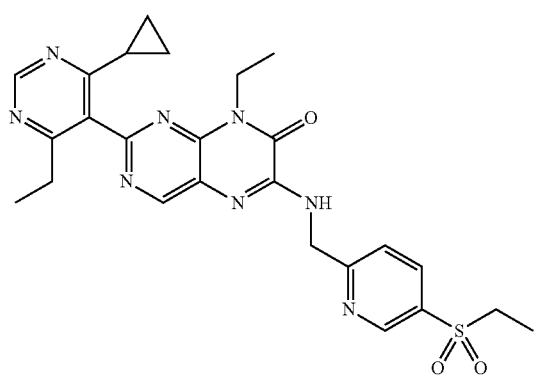 [SMILES: CCc1ncnc(C2CC2)c1-c1ncc2nc(NCc3ccc(S(=O)(=O)CC)cn3)c(=O)n(CC)c2n1] | 1.90 | 520.9 | | B |
| 174 | 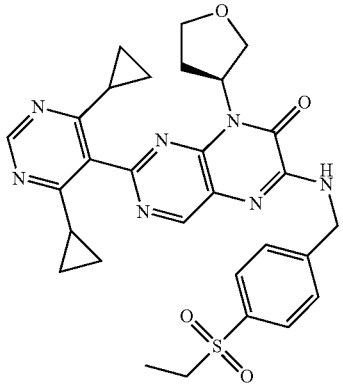 [SMILES: CCS(=O)(=O)c1ccc(CNc2nc3cnc(-c4c(C5CC5)ncnc4C4CC4)nc3n([C@H]3CCOC3)c2=O)cc1] | 0.96 | 574 | | A |

TABLE 1-continued

| Example | Structure | RT (min) | m/z [M + H]+ | m/z [M − H]− | HPLC Method |
|---|---|---|---|---|---|
| 175 | 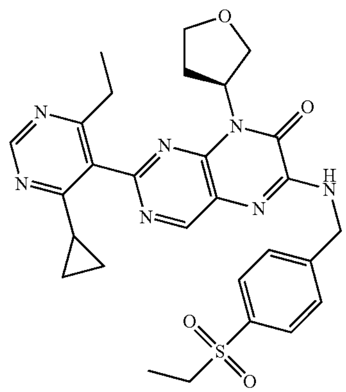 | 0.87 | 561.9 | | A |
| 176 | 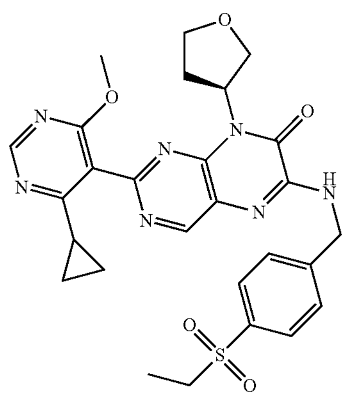 [SMILES: CCS(=O)(=O)c1ccc(CNc2nc3cnc(-c4c(OC)ncnc4C4CC4)nc3n([C@H]3CCOC3)c2=O)cc1] | 0.86 | 563.9 | | A |
| 177 | 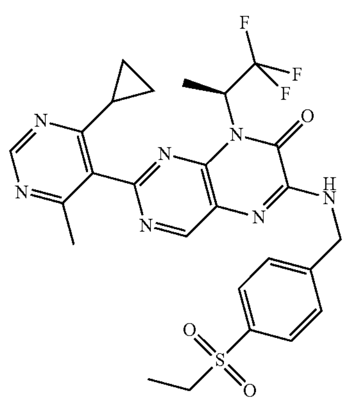 [SMILES: CCS(=O)(=O)c1ccc(CNc2nc3cnc(-c4c(C)ncnc4C4CC4)nc3n([C@@H](C)C(F)(F)F)c2=O)cc1] | 1.00 | 573.0 | | A |
| 178 | 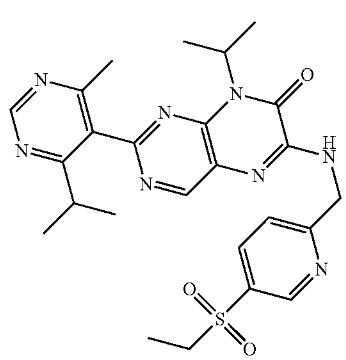 [SMILES: CCS(=O)(=O)c1ccc(CNc2nc3cnc(-c4c(C)ncnc4C(C)C)nc3n(C(C)C)c2=O)nc1] | 0.91 | 523.0 | | A |

TABLE 1-continued

| Example | Structure | RT (min) | m/z [M + H]+ | m/z [M − H]− | HPLC Method |
|---------|-----------|----------|--------------|--------------|-------------|
| 179 | 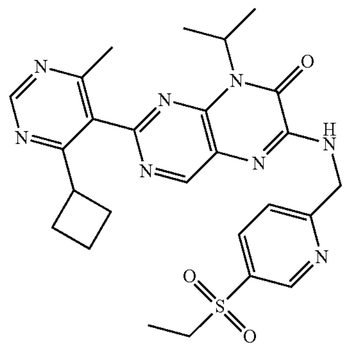 [SMILES: CCS(=O)(=O)c1ccc(CNc2nc3cnc(-c4c(C)ncnc4C4CCC4)nc3n(C(C)C)c2=O)nc1] | 0.96 | 535.1 | | A |
| 180 | 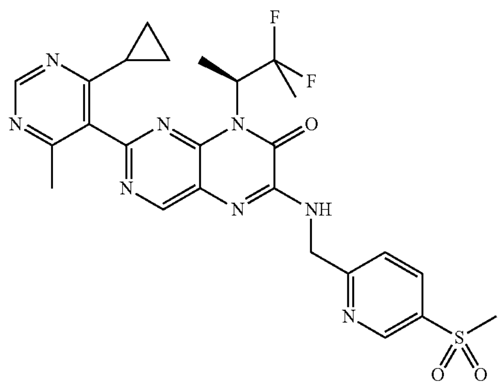 | 1.90 | 560.8 | | B |
| 181 | 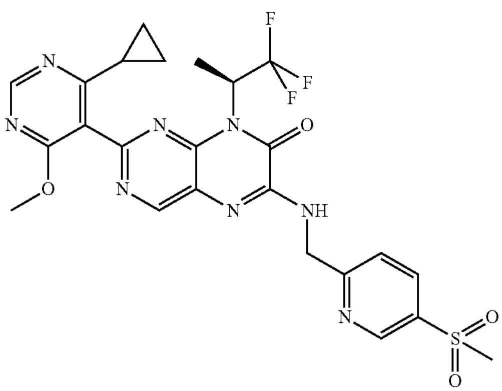 [SMILES: COc1ncnc(C2CC2)c1-c1ncc2nc(NCc3ccc(S(C)(=O)=O)cn3)c(=O)n([C@@H](C)C(F)(F)F)c2n1] | 2.16 | 577.1 | | B |
| 182 | 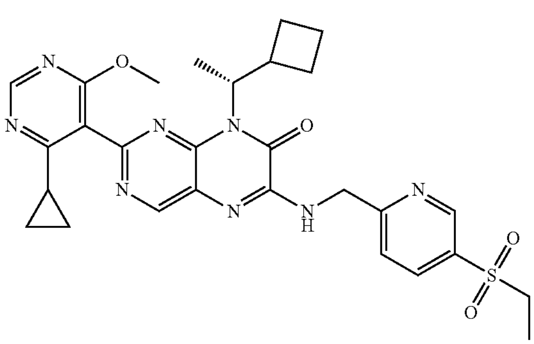 [SMILES: CCS(=O)(=O)c1ccc(CNc2nc3cnc(-c4c(OC)ncnc4C4CC4)nc3n([C@H](C)C3CCC3)c2=O)nc1] | 1.11 | 577.2 | | A |

TABLE 1-continued

| Example | Structure | RT (min) | m/z [M + H]+ | m/z [M − H]− | HPLC Method |
|---|---|---|---|---|---|
| 183 | 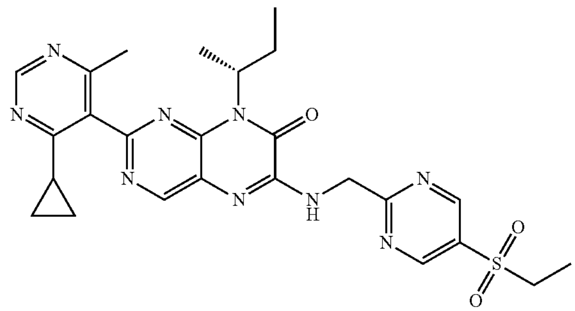 | 0.95 | 536.0 | | A |
| 184 | 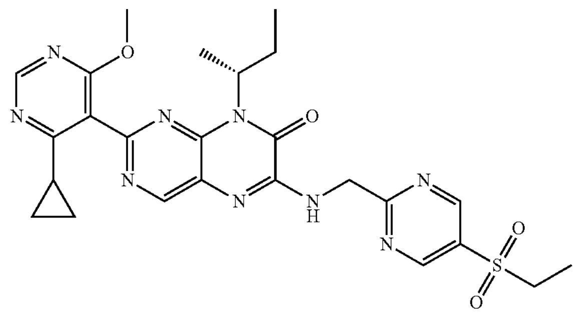 | 1.01 | 552.2 | | A |
| 185 | 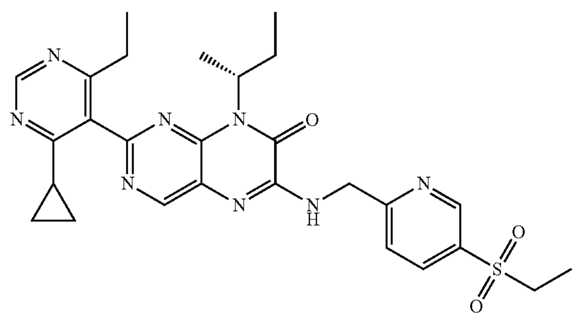 | 1.08 | 550.1 | | A |
| 186 | 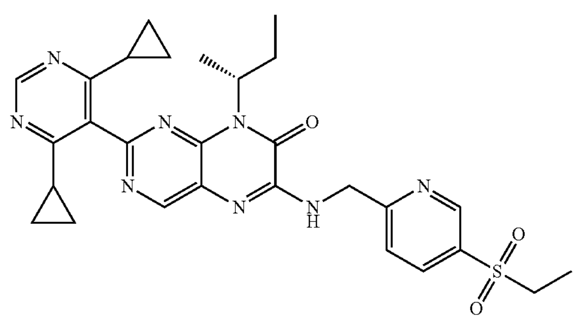 | 1.08 | 561.9 | | A |
| 187 | 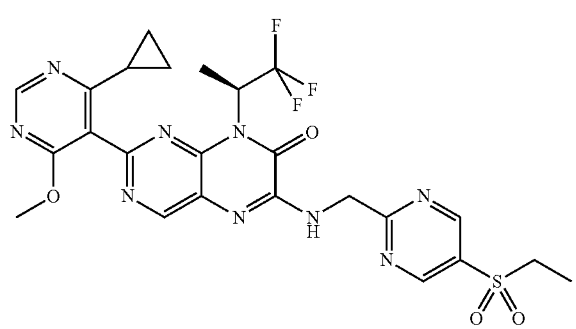 [SMILES: CCS(=O)(=O)c1cnc(CNc2nc3cnc(-c4c(OC)ncnc4C4CC4)nc3n([C@@H](C)C(F)(F)F)c2=O)nc1] | 2.28 | 592.1 | | B |

TABLE 1-continued

| Example | Structure | RT (min) | m/z [M + H]+ | m/z [M − H]− | HPLC Method |
|---------|-----------|----------|--------------|--------------|-------------|
| 188 | 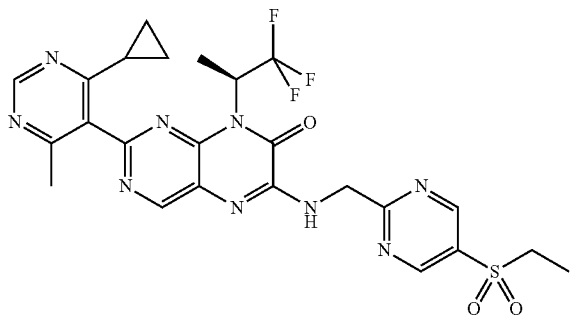 [SMILES: CCS(=O)(=O)c1cnc(CNc2nc3cnc(-c4c(C)ncnc4C4CC4)nc3n([C@@H](C)C(F)(F)F)c2=O)nc1] | 2.08 | 576.0 | | B |
| 189 | 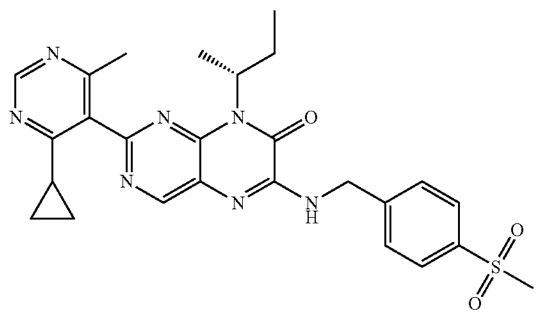 | 0.95 | 519.9 | | A |
| 190 | 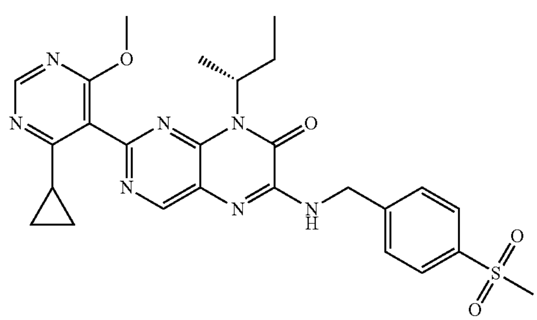 | 1.02 | 536.0 | | A |
| 191 | 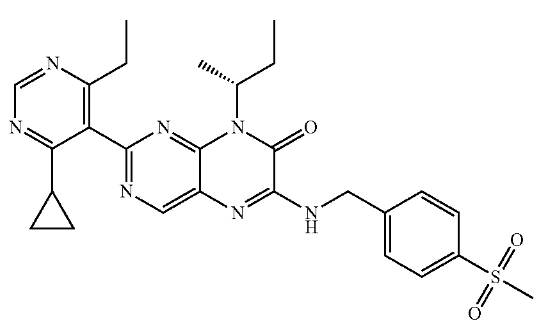 | 1.00 | 533.2 | | A |

TABLE 1-continued

| Example | Structure | RT (min) | m/z [M + H]+ | m/z [M − H]− | HPLC Method |
|---|---|---|---|---|---|
| 192 | 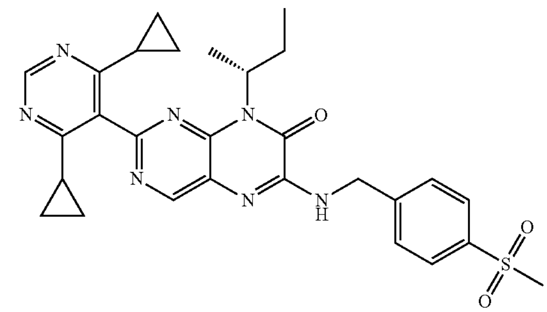 [SMILES: CC[C@@H](C)n1c(=O)c(NCc2ccc(S(C)(=O)=O)cc2)nc2cnc(-c3c(C4CC4)ncnc3C3CC3)nc21] | 1.09 | 545.2 | | A |
| 193 | 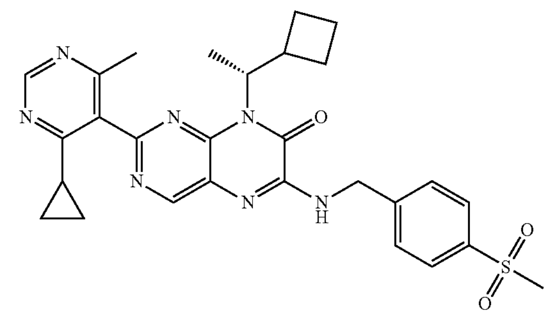 [SMILES: Cc1ncnc(C2CC2)c1-c1ncc2nc(NCc3ccc(S(C)(=O)=O)cc3)c(=O)n([C@H](C)C3CCC3)c2n1] | 1.06 | 546.4 | | A |
| 194 | 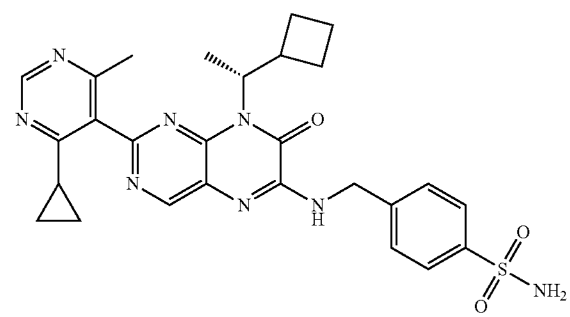 [SMILES: Cc1ncnc(C2CC2)c1-c1ncc2nc(NCc3ccc(S(N)(=O)=O)cc3)c(=O)n([C@H](C)C3CCC3)c2n1] | 0.99 | 547.4 | | A |
| 195 | 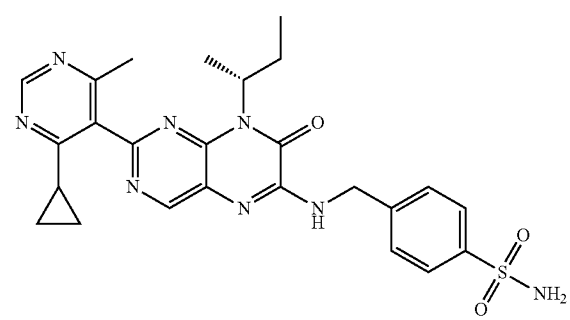 [SMILES: CC[C@@H](C)n1c(=O)c(NCc2ccc(S(N)(=O)=O)cc2)nc2cnc(-c3c(C)ncnc3C3CC3)nc21] | 0.89 | 521.0 | | A |
| 196 | 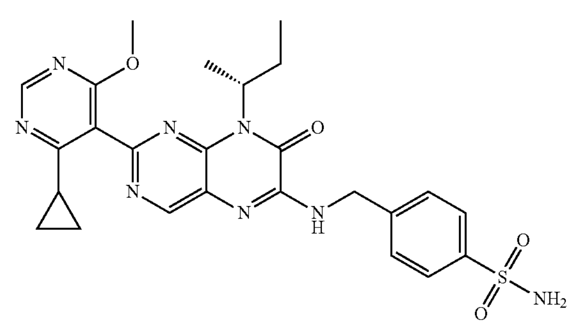 [SMILES: CC[C@@H](C)n1c(=O)c(NCc2ccc(S(N)(=O)=O)cc2)nc2cnc(-c3c(OC)ncnc3C3CC3)nc21] | 0.95 | 537.0 | | A |

TABLE 1-continued

| Example | Structure | RT (min) | m/z [M + H]+ | m/z [M − H]− | HPLC Method |
|---|---|---|---|---|---|
| 197 | 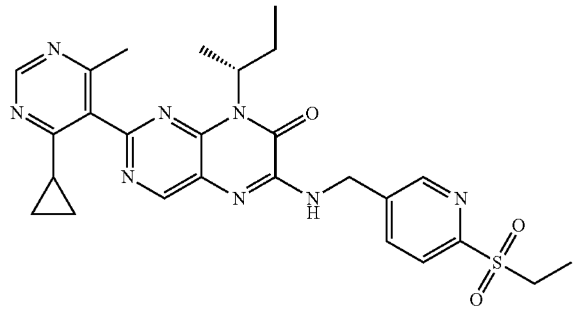 [SMILES: CC[C@@H](C)n1c(=O)c(NCc2ccc(S(=O)(=O)CC)nc2)nc2cnc(-c3c(C)ncnc3C3CC3)nc21] | 0.95 | 535.4 | | A |
| 198 | 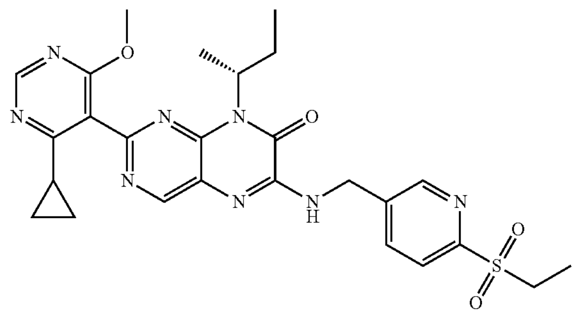 | 1.00 | 551.4 | | A |
| 199 | 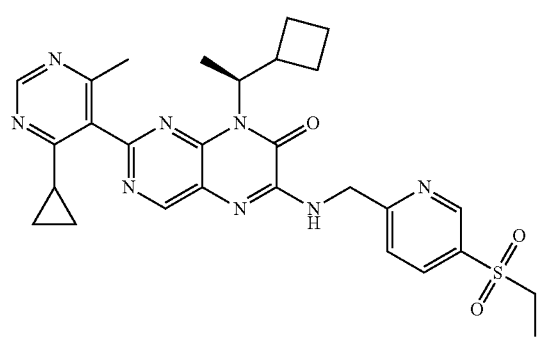 [SMILES: CCS(=O)(=O)c1ccc(CNc2nc3cnc(-c4c(C)ncnc4C4CC4)nc3n([C@@H](C)C3CCC3)c2=O)nc1] | 1.04 | 561.4 | | A |
| 200 | 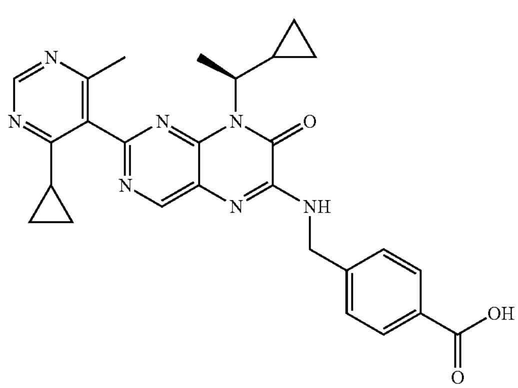 [SMILES: Cc1ncnc(C2CC2)c1-c1ncc2nc(NCc3ccc(C(=O)O)cc3)c(=O)n([C@@H](C)C3CC3)c2n1] | 1.09 | 498.3 | | A |

TABLE 1-continued

| Example | Structure | RT (min) | m/z [M + H]+ | m/z [M − H]− | HPLC Method |
|---|---|---|---|---|---|
| 201 | 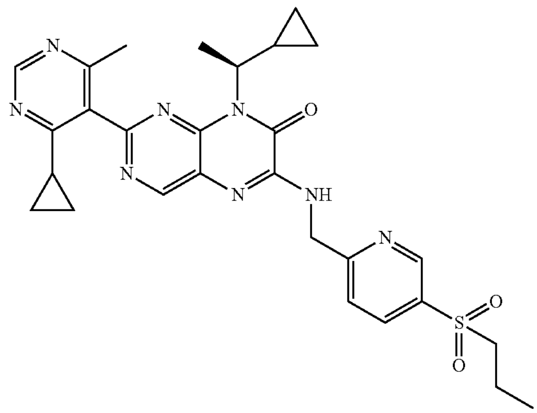 [SMILES: CCCS(=O)(=O)c1ccc(CNc2nc3cnc(-c4c(C)ncnc4C4CC4)nc3n([C@@H](C)C3CC3)c2=O)nc1] | 1.05 | 561.1 | | A |
| 202 | 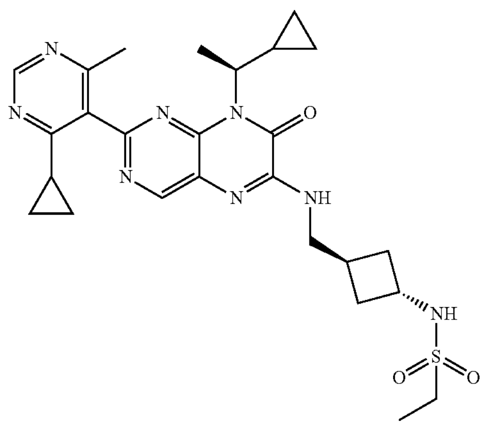 [SMILES: CCS(=O)(=O)N[C@H]1C[C@H](CNc2nc3cnc(-c4c(C)ncnc4C4CC4)nc3n([C@@H](C)C3CC3)c2=O)C1] | 1.01 | 539.3 | | A |
| 203 | 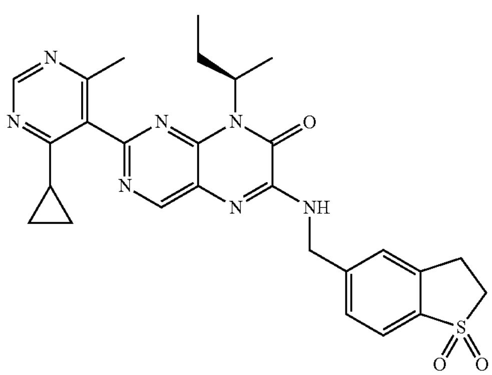 [SMILES: CC[C@@H](C)n1c(=O)c(NCc2ccc3c(c2)CCS3(=O)=O)nc2cnc(-c3c(C)ncnc3C3CC3)nc21] | 0.95 | 532.4 | | A |
| 204 | 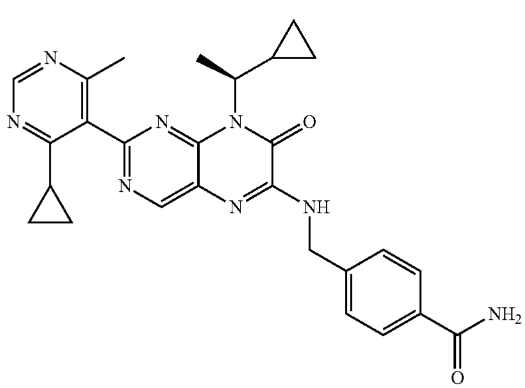 [SMILES: Cc1ncnc(C2CC2)c1-c1ncc2nc(NCc3ccc(C(N)=O)cc3)c(=O)n([C@@H](C)C3CC3)c2n1] | 0.89 | 497.4 | | A |

TABLE 1-continued
| Example | Structure | RT (min) | m/z [M + H]+ | m/z [M − H]− | HPLC Method |
|---|---|---|---|---|---|
| 205 | 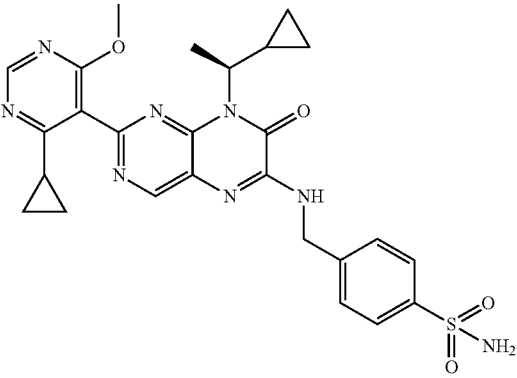 | 1.01 | 549.0 | | A |
| 206 | 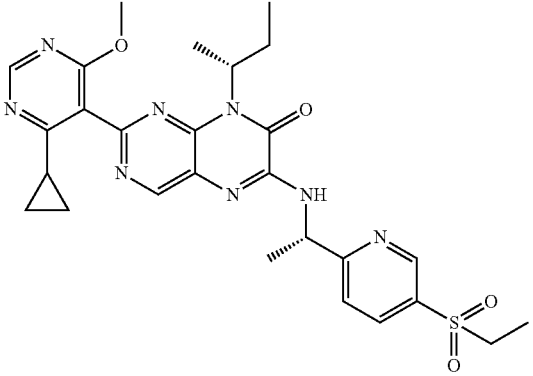 [SMILES: CC[C@@H](C)n1c(=O)c(N[C@@H](C)c2ccc(S(=O)(=O)CC)cn2)nc2cnc(-c3c(OC)ncnc3C3CC3)nc21] | 1.01 | 565.3 | | A |
| 207 | 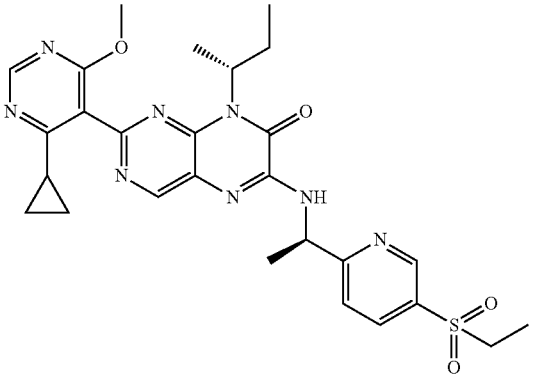 [SMILES: CC[C@@H](C)n1c(=O)c(N[C@H](C)c2ccc(S(=O)(=O)CC)cn2)nc2cnc(-c3c(OC)ncnc3C3CC3)nc21] | 1.20 | 565.3 | | A |
| 208 | 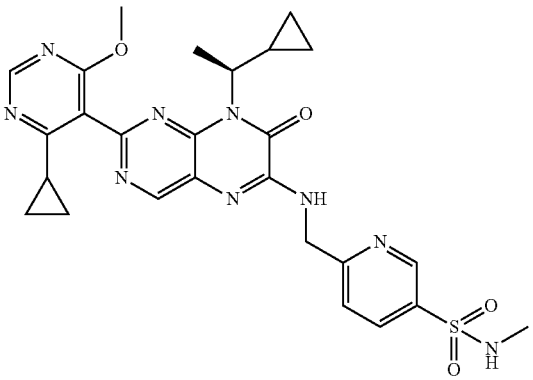 [SMILES: CNS(=O)(=O)c1ccc(CNc2nc3cnc(-c4c(OC)ncnc4C4CC4)nc3n([C@@H](C)C3CC3)c2=O)nc1] | 1.07 | 564 | | A |

TABLE 1-continued

| Example | Structure | RT (min) | m/z [M + H]+ | m/z [M − H]− | HPLC Method |
|---|---|---|---|---|---|
| 209 | 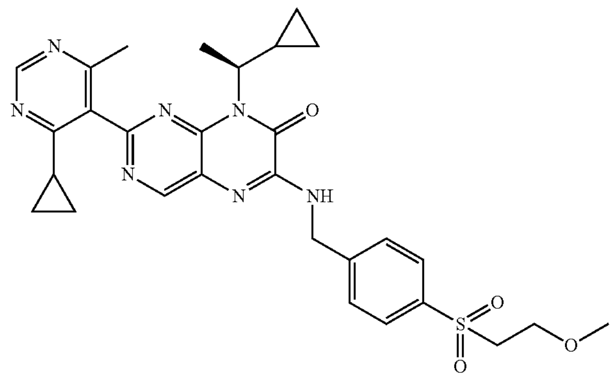 [SMILES: COCCS(=O)(=O)c1ccc(CNc2nc3cnc(-c4c(C)ncnc4C4CC4)nc3n([C@@H](C)C3CC3)c2=O)cc1] | 1.07 | 575.8 | | A |
| 210 | 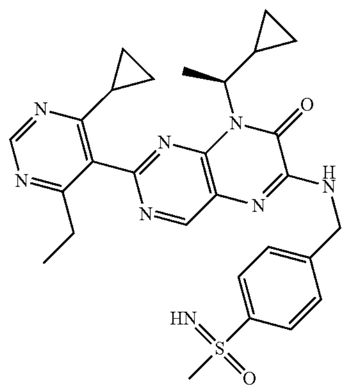 [SMILES: CCc1ncnc(C2CC2)c1-c1ncc2nc(NCc3ccc(S(C)(=N)=O)cc3)c(=O)n([C@@H](C)C3CC3)c2n1] | 0.91 | 545.0 | | A |
| 211 | 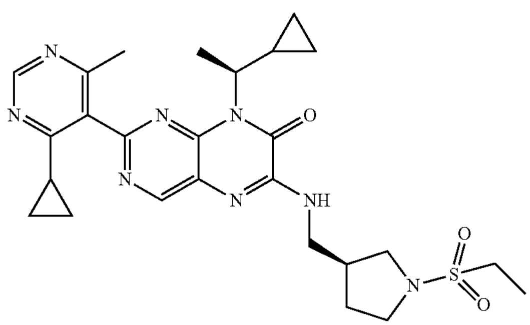 [SMILES: CCS(=O)(=O)N1CC[C@@H](CNc2nc3cnc(-c4c(C)ncnc4C4CC4)nc3n([C@@H](C)C3CC3)c2=O)C1] | 0.98 | 539.0 | | A |
| 212 | 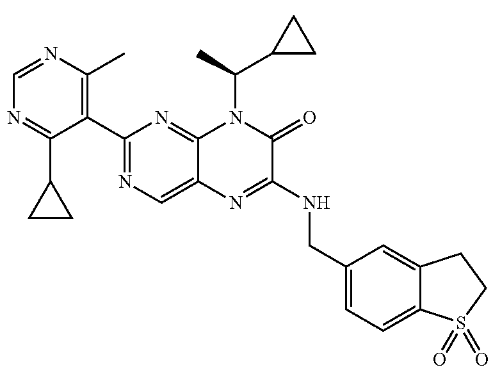 [SMILES: Cc1ncnc(C2CC2)c1-c1ncc2nc(NCc3ccc4c(c3)CCS4(=O)=O)c(=O)n([C@@H](C)C3CC3)c2n1] | 1.05 | 543.8 | | A |

TABLE 1-continued

| Example | Structure | RT (min) | m/z [M + H]+ | m/z [M − H]− | HPLC Method |
|---|---|---|---|---|---|
| 213 | 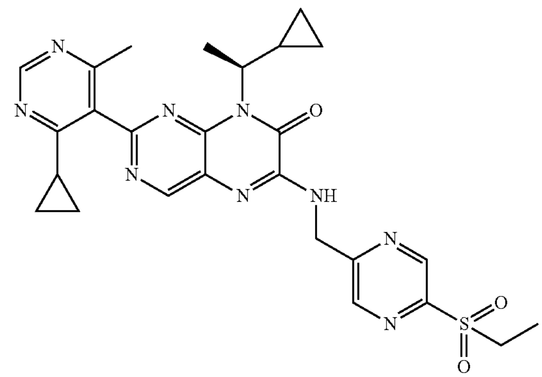 [SMILES: CCS(=O)(=O)c1cnc(CNc2nc3cnc(-c4c(C)ncnc4C4CC4)nc3n([C@@H](C)C3CC3)c2=O)cn1] | 1.03 | 547.9 | | A |
| 214 | 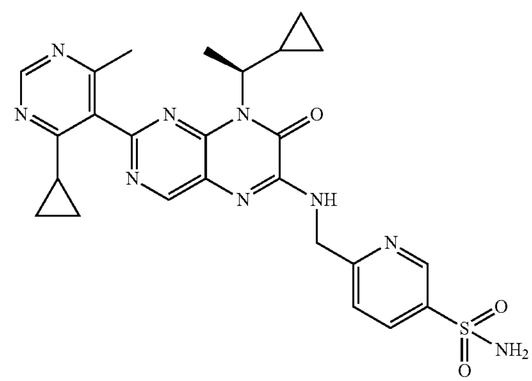 [SMILES: Cc1ncnc(C2CC2)c1-c1ncc2nc(NCc3ccc(S(N)(=O)=O)cn3)c(=O)n([C@@H](C)C3CC3)c2n1] | 0.91 | 533.9 | | A |
| 215 | 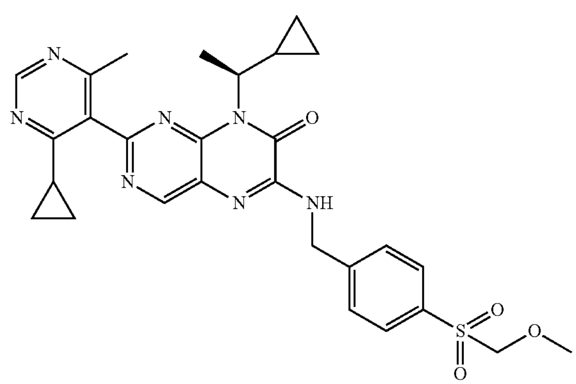 [SMILES: COCS(=O)(=O)c1ccc(CNc2nc3cnc(-c4c(C)ncnc4C4CC4)nc3n([C@@H](C)C3CC3)c2=O)cc1] | 1.10 | 561.8 | | A |
| 216 | 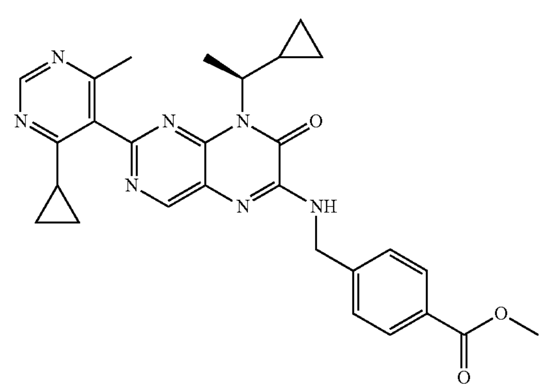 [SMILES: COC(=O)c1ccc(CNc2nc3cnc(-c4c(C)ncnc4C4CC4)nc3n([C@@H](C)C3CC3)c2=O)cc1] | 1.22 | 511.9 | | A |

TABLE 1-continued
| Example | Structure | RT (min) | m/z [M + H]+ | m/z [M − H]− | HPLC Method |
|---|---|---|---|---|---|
| 217 | 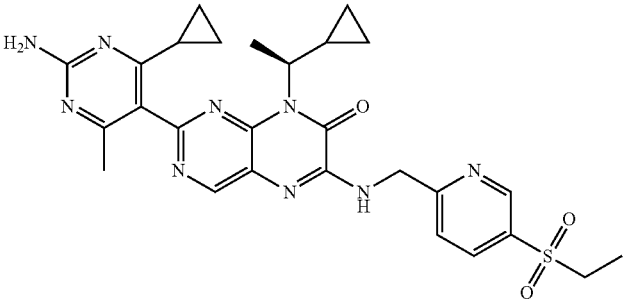 [SMILES: CCS(=O)(=O)c1ccc(CNc2nc3cnc(-c4c(C)nc(N)nc4C4CC4)nc3n([C@@H](C)C3CC3)c2=O)nc1] | 1.49 | 562.4 | | B |
| 218 | 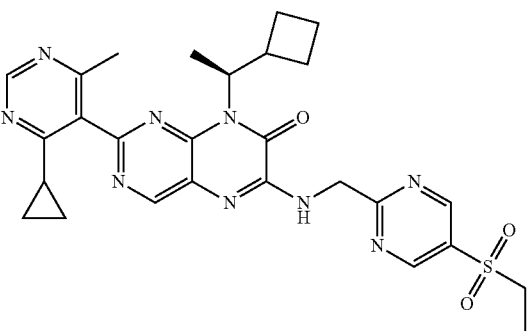 | 2.40 | 562.4 | | B |
| 219 | 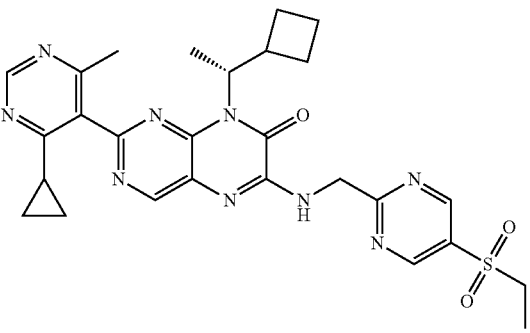 [SMILES: CCS(=O)(=O)c1cnc(CNc2nc3cnc(-c4c(C)ncnc4C4CC4)nc3n([C@H](C)C3CCC3)c2=O)nc1] | 1.04 | 563.4 | | A |
| 220 | 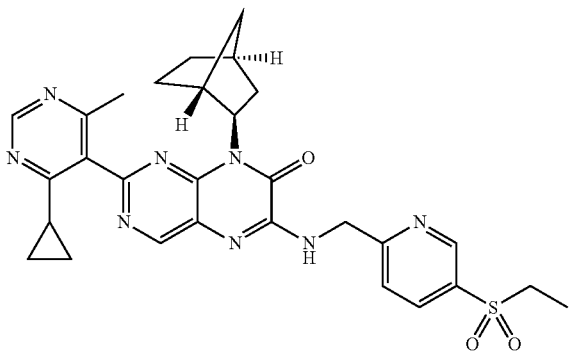 [SMILES: CCS(=O)(=O)c1ccc(CNc2nc3cnc(-c4c(C)ncnc4C4CC4)nc3n([C@@H]3C[C@H]4CC[C@@H]3C4)c2=O)nc1] | 1.97 | 573.5 | | B |

TABLE 1-continued

| Example | Structure | RT (min) | m/z [M + H]+ | m/z [M − H]− | HPLC Method |
|---|---|---|---|---|---|
| 221 | 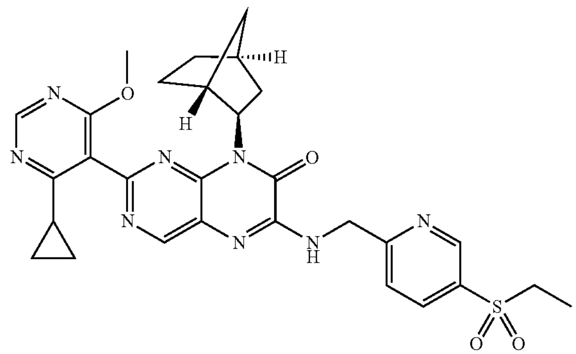 [SMILES: CCS(=O)(=O)c1ccc(CNc2nc3cnc(-c4c(OC)ncnc4C4CC4)nc3n([C@@H]3C[C@H]4CC[C@@H]3C4)c2=O)nc1] | 1.13 | 589.5 | | A |
| 222 | 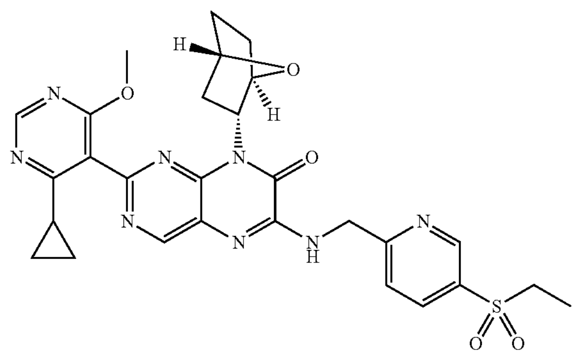 [SMILES: CCS(=O)(=O)c1ccc(CNc2nc3cnc(-c4c(OC)ncnc4C4CC4)nc3n([C@@H]3C[C@@H]4CC[C@H]3O4)c2=O)nc1] | 0.88 | 591.4 | | A |
| 223 | 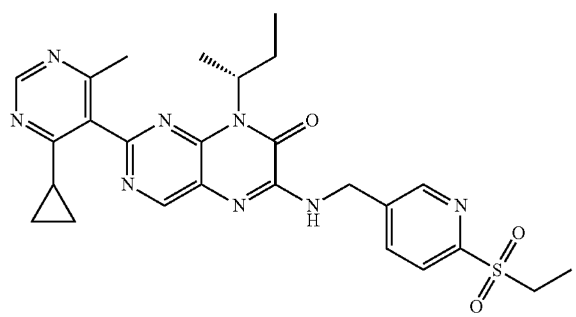 [SMILES: CC[C@@H](C)n1c(=O)c(NCc2ccc(S(=O)(=O)CC)nc2)nc2cnc(-c3c(C)ncnc3C3CC3)nc21] | 1.01 | 549.4 | | A |
| 224 | 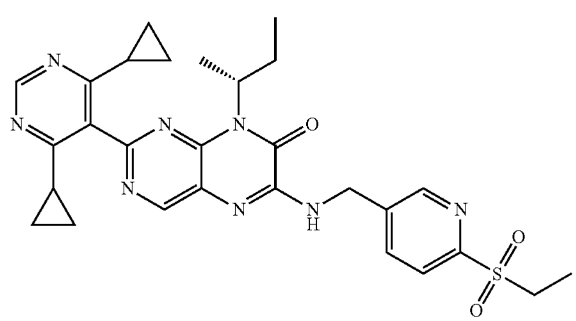 [SMILES: CC[C@@H](C)n1c(=O)c(NCc2ccc(S(=O)(=O)CC)nc2)nc2cnc(-c3c(C4CC4)ncnc3C3CC3)nc21] | 1.08 | 561.4 | | A |

TABLE 1-continued

| Example | Structure | RT (min) | m/z [M + H]+ | m/z [M − H]− | HPLC Method |
|---|---|---|---|---|---|
| 225 | 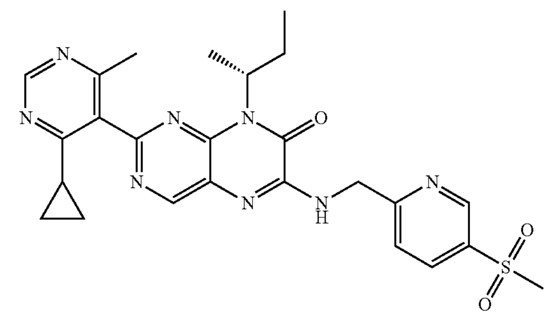 | 0.90 | 521.1 | | A |
| 226 | 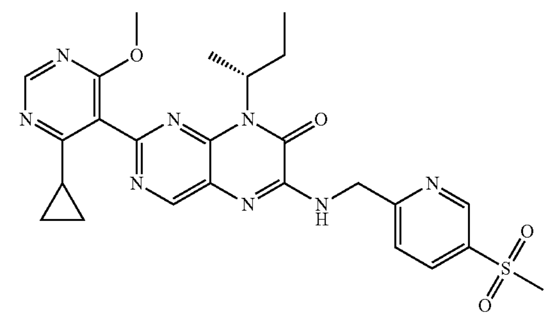 | 0.96 | 537.2 | | A |
| 227 | 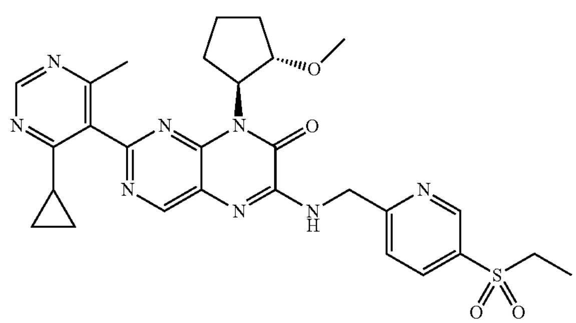 | 0.88 | 577.3 | | A |
| 228 | 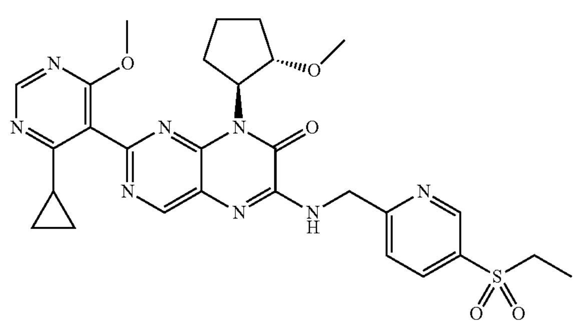 [SMILES: CCS(=O)(=O)c1ccc(CNc2nc3cnc(-c4c(OC)ncnc4C4CC4)nc3n([C@H]3CCC[C@@H]3OC)c2=O)nc1] | 0.95 | 593.4 | | A |
| 229 | 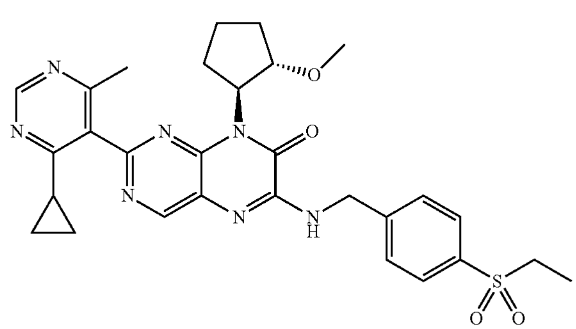 | 0.91 | 562.2 | | A |

TABLE 1-continued

| Example | Structure | RT (min) | m/z [M + H]+ | m/z [M − H]− | HPLC Method |
|---|---|---|---|---|---|
| 230 | 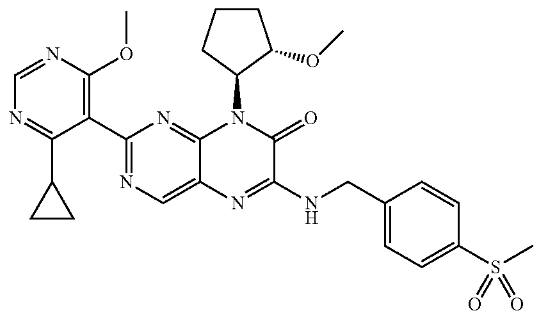 [SMILES: COc1ncnc(C2CC2)c1-c1ncc2nc(NCc3ccc(S(C)(=O)=O)cc3)c(=O)n([C@H]3CCC[C@@H]3OC)c2n1] | 0.96 | 578.1 | | A |
| 231 | 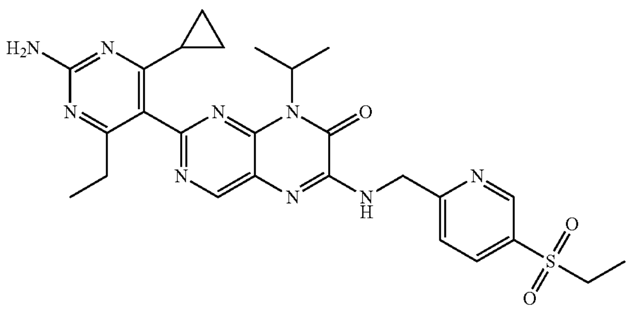 [SMILES: CCc1nc(N)nc(C2CC2)c1-c1ncc2nc(NCc3ccc(S(=O)(=O)CC)cn3)c(=O)n(C(C)C)c2n1] | 1.41 | 550.2 | | B |
| 232 | 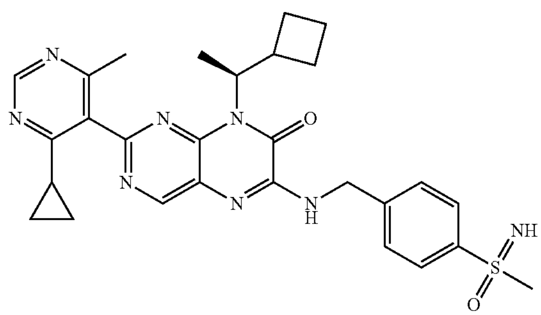 [SMILES: Cc1ncnc(C2CC2)c1-c1ncc2nc(NCc3ccc(S(C)(=N)=O)cc3)c(=O)n([C@@H](C)C3CCC3)c2n1] | 2.14 | 545 | | B |
| 233 | 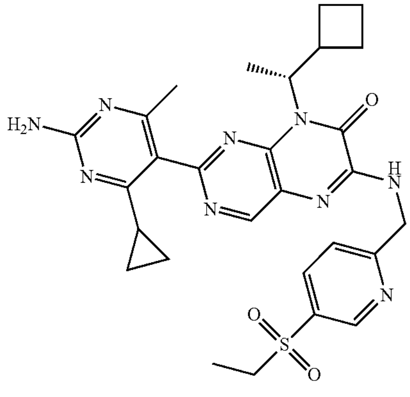 [SMILES: CCS(=O)(=O)c1ccc(CNc2nc3cnc(-c4c(C)nc(N)nc4C4CC4)nc3n([C@H](C)C3CCC3)c2=O)nc1] | 1.76 | 576 | | B |

TABLE 1-continued

| Example | Structure | RT (min) | m/z [M + H]+ | m/z [M − H]− | HPLC Method |
|---|---|---|---|---|---|
| 234 | 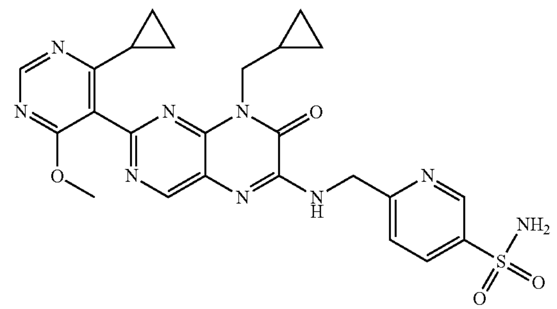 [SMILES: COc1ncnc(C2CC2)c1-c1ncc2nc(NCc3ccc(S(N)(=O)=O)cn3)c(=O)n(CC3CC3)c2n1] | 0.85 | 536.4 | | A |
| 235 | 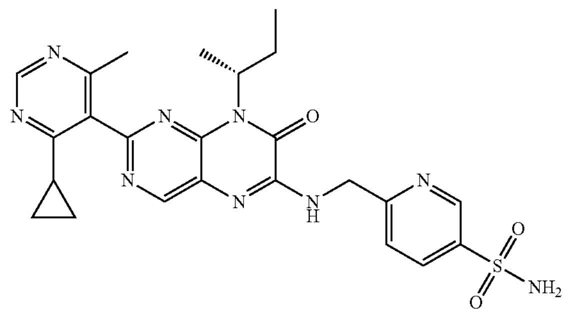 | 0.80 | 522.2 | | A |
| 236 | 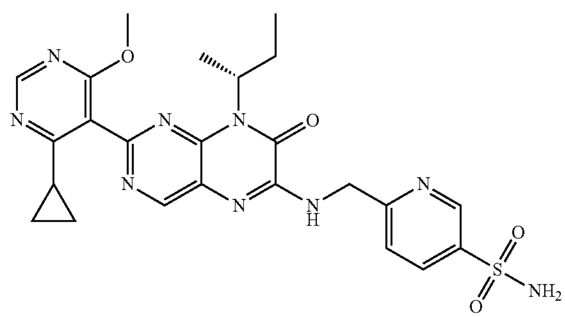 | 0.88 | 538.3 | | A |
| 237 | 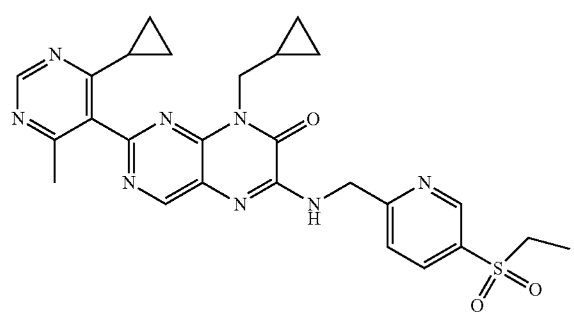 [SMILES: CCS(=O)(=O)c1ccc(CNc2nc3cnc(-c4c(C)ncnc4C4CC4)nc3n(CC3CC3)c2=O)nc1] | 0.90 | 533.4 | | A |
| 238 | 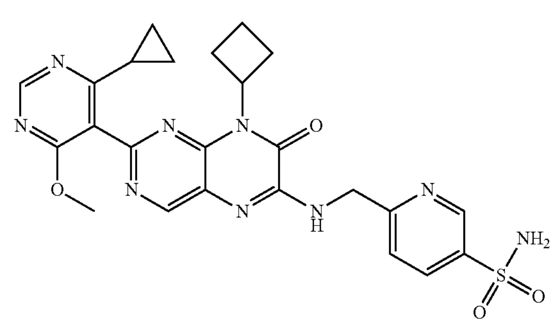 [SMILES: COc1ncnc(C2CC2)c1-c1ncc2nc(NCc3ccc(S(N)(=O)=O)cn3)c(=O)n(C3CCC3)c2n1] | 0.88 | 536.4 | | A |

TABLE 1-continued

| Example | Structure | RT (min) | m/z [M + H]+ | m/z [M − H]− | HPLC Method |
|---|---|---|---|---|---|
| 239 | 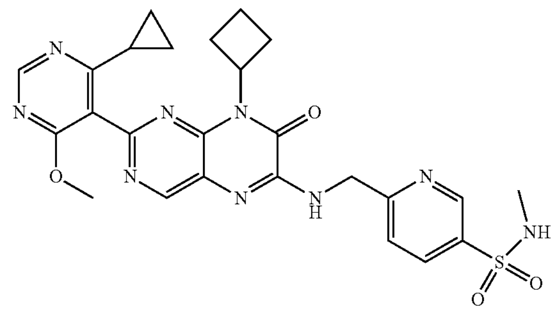 [SMILES: CNS(=O)(=O)c1ccc(CNc2nc3cnc(-c4c(OC)ncnc4C4CC4)nc3n(C3CCC3)c2=O)nc1] | 0.96 | 550.4 | | A |
| 240 | 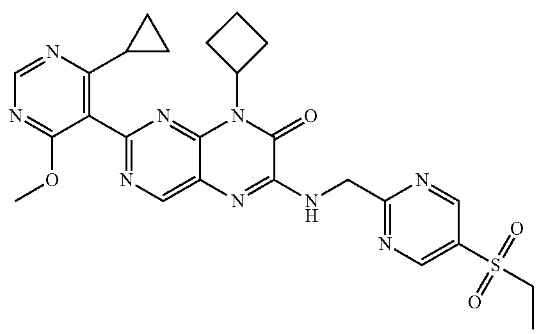 [SMILES: CCS(=O)(=O)c1cnc(CNc2nc3cnc(-c4c(OC)ncnc4C4CC4)nc3n(C3CCC3)c2=O)nc1] | 0.98 | 550.5 | | A |
| 241 | 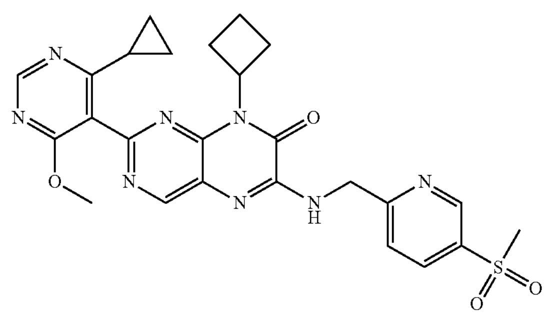 [SMILES: COc1ncnc(C2CC2)c1-c1ncc2nc(NCc3ccc(S(C)(=O)=O)cn3)c(=O)n(C3CCC3)c2n1] | 0.94 | 535.4 | | A |
| 242 | 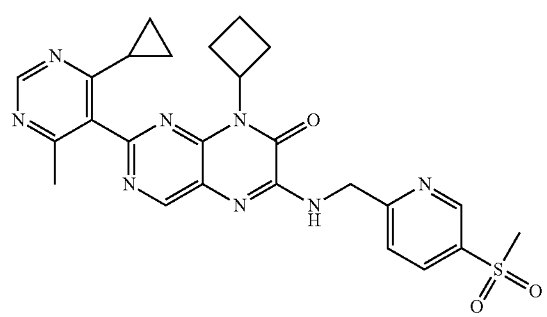 [SMILES: Cc1ncnc(C2CC2)c1-c1ncc2nc(NCc3ccc(S(C)(=O)=O)cn3)c(=O)n(C3CCC3)c2n1] | 0.88 | 519.4 | | A |
| 243 | 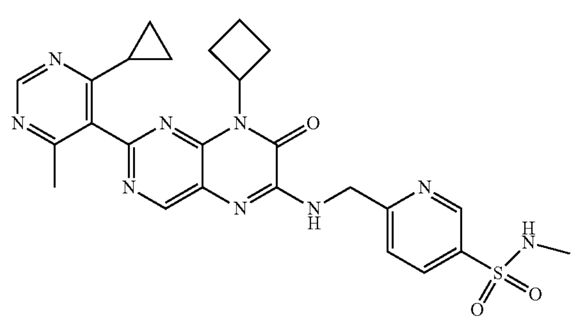 [SMILES: CNS(=O)(=O)c1ccc(CNc2nc3cnc(-c4c(C)ncnc4C4CC4)nc3n(C3CCC3)c2=O)nc1] | 0.89 | 534.5 | | A |

TABLE 1-continued

| Example | Structure | RT (min) | m/z [M + H]+ | m/z [M − H]− | HPLC Method |
|---|---|---|---|---|---|
| 244 | 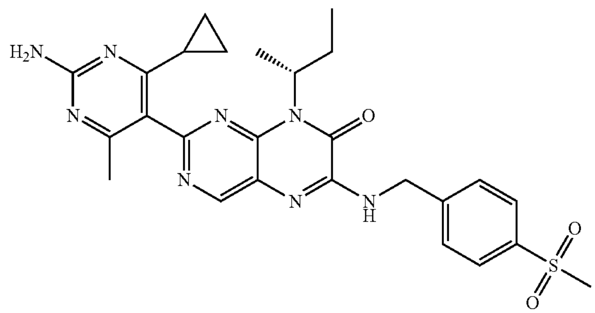 [SMILES: CC[C@@H](C)n1c(=O)c(NCc2ccc(S(C)(=O)=O)cc2)nc2cnc(-c3c(C)nc(N)nc3C3CC3)nc21] | 0.70 | 535.3 | | A |
| 245 | 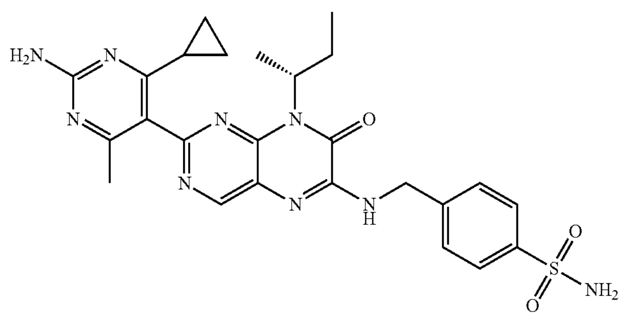 [SMILES: CC[C@@H](C)n1c(=O)c(NCc2ccc(S(N)(=O)=O)cc2)nc2cnc(-c3c(C)nc(N)nc3C3CC3)nc21] | 0.65 | 536.3 | | A |
| 246 | 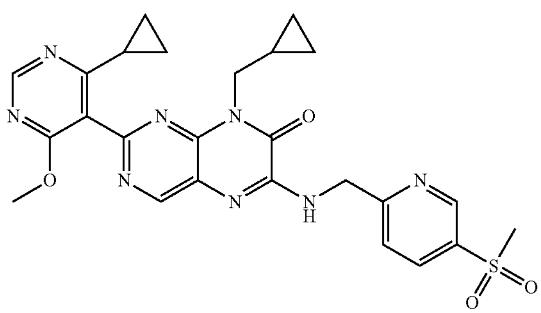 [SMILES: COc1ncnc(C2CC2)c1-c1ncc2nc(NCc3ccc(S(C)(=O)=O)cn3)c(=O)n(CC3CC3)c2n1] | 0.91 | 535.5 | | A |
| 247 | 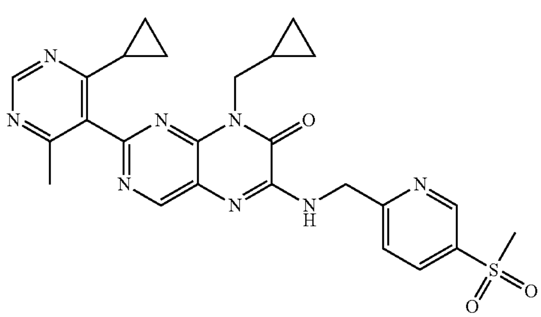 [SMILES: Cc1ncnc(C2CC2)c1-c1ncc2nc(NCc3ccc(S(C)(=O)=O)cn3)c(=O)n(CC3CC3)c2n1] | 0.84 | 519.4 | | A |
| 248 | 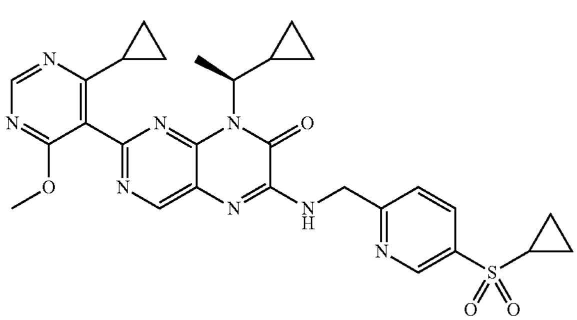 [SMILES: COc1ncnc(C2CC2)c1-c1ncc2nc(NCc3ccc(S(=O)(=O)C4CC4)cn3)c(=O)n([C@@H](C)C3CC3)c2n1] | 2.44 | 575.5 | | B |

TABLE 1-continued

| Example | Structure | RT (min) | m/z [M + H]+ | m/z [M − H]− | HPLC Method |
|---|---|---|---|---|---|
| 249 | 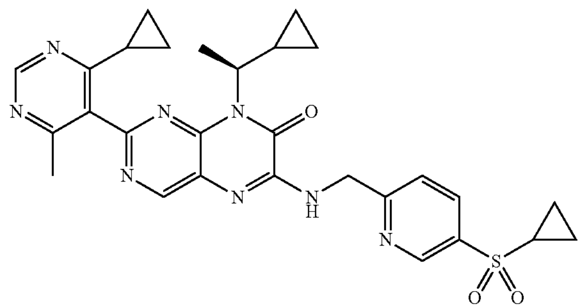 [SMILES: Cc1ncnc(C2CC2)c1-c1ncc2nc(NCc3ccc(S(=O)(=O)C4CC4)cn3)c(=O)n([C@@H](C)C3CC3)c2n1] | 2.25 | 559.5 | | B |
| 250 | 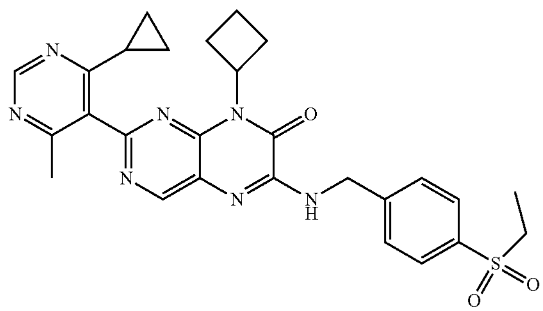 [SMILES: CCS(=O)(=O)c1ccc(CNc2nc3cnc(-c4c(C)ncnc4C4CC4)nc3n(C3CCC3)c2=O)cc1] | 0.99 | 532.5 | | A |
| 251 | 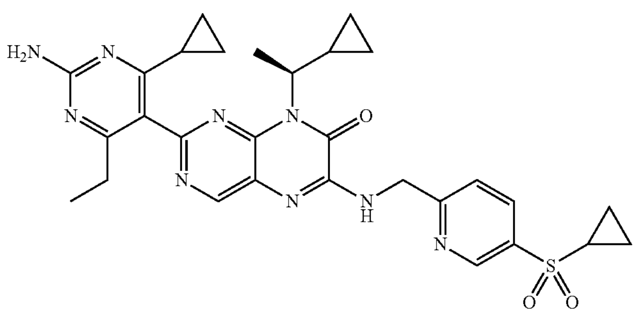 [SMILES: CCc1nc(N)nc(C2CC2)c1-c1ncc2nc(NCc3ccc(S(=O)(=O)C4CC4)cn3)c(=O)n([C@@H](C)C3CC3)c2n1] | 1.74 | 588.5 | | B |
| 252 | 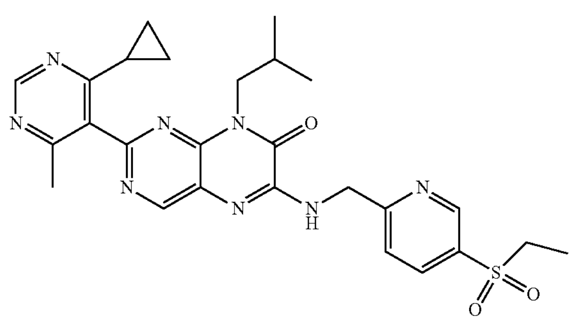 [SMILES: CCS(=O)(=O)c1ccc(CNc2nc3cnc(-c4c(C)ncnc4C4CC4)nc3n(CC(C)C)c2=O)nc1] | 0.93 | 535.5 | | A |
| 253 | 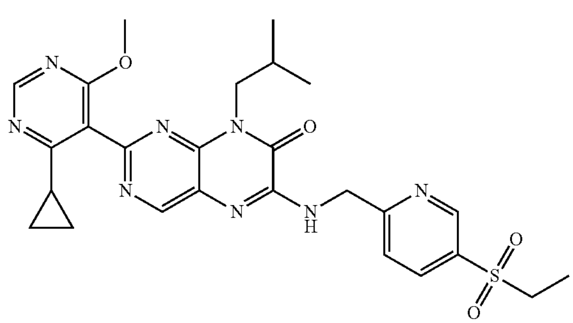 [SMILES: CCS(=O)(=O)c1ccc(CNc2nc3cnc(-c4c(OC)ncnc4C4CC4)nc3n(CC(C)C)c2=O)nc1] | 0.99 | 551.5 | | A |

TABLE 1-continued
| Example | Structure | RT (min) | m/z [M + H]+ | m/z [M − H]− | HPLC Method |
|---|---|---|---|---|---|
| 254 | 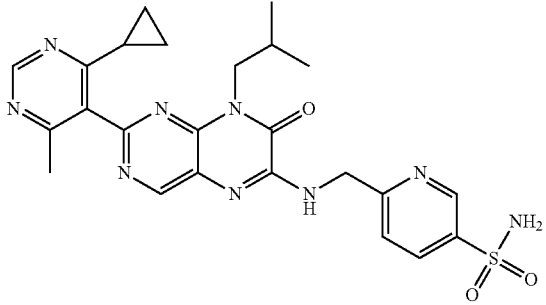 [SMILES: Cc1ncnc(C2CC2)c1-c1ncc2nc(NCc3ccc(S(N)(=O)=O)cn3)c(=O)n(CC(C)C)c2n1] | 0.90 | 522.3 | | A |
| 255 | 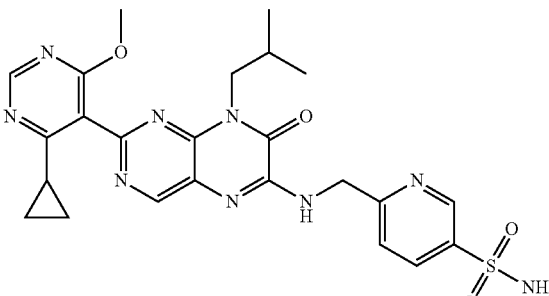 | 0.97 | 538.3 | | A |
| 256 | 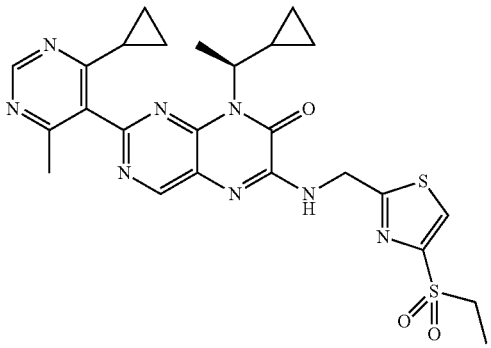 [SMILES: CCS(=O)(=O)c1csc(CNc2nc3cnc(-c4c(C)ncnc4C4CC4)nc3n([C@@H](C)C3CC3)c2=O)n1] | 2.13 | 553.4 | | B |
| 257 | 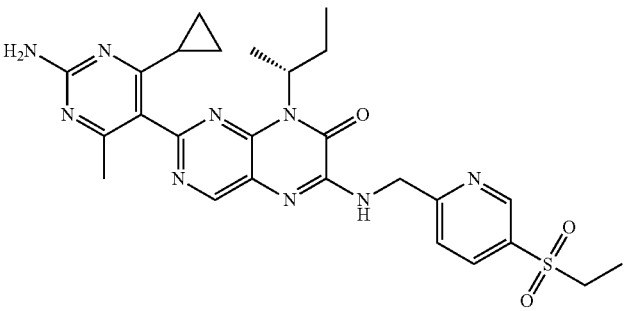 [SMILES: CC[C@@H](C)n1c(=O)c(NCc2ccc(S(=O)(=O)CC)cn2)nc2cnc(-c3c(C)nc(N)nc3C3CC3)nc21] | 1.42 | 550.5 | | B |

TABLE 1-continued

| Example | Structure | RT (min) | m/z [M + H]+ | m/z [M − H]− | HPLC Method |
|---|---|---|---|---|---|
| 258 | 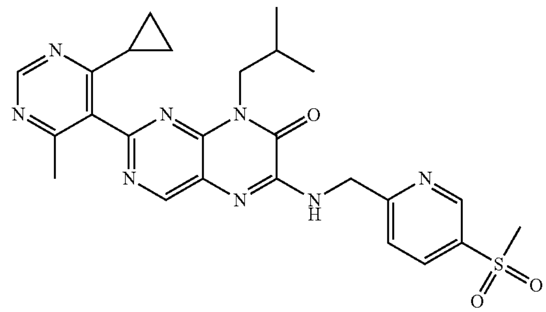 [SMILES: Cc1ncnc(C2CC2)c1-c1ncc2nc(NCc3ccc(S(C)(=O)=O)cn3)c(=O)n(CC(C)C)c2n1] | 1.92 | 521.5 | | B |
| 259 | 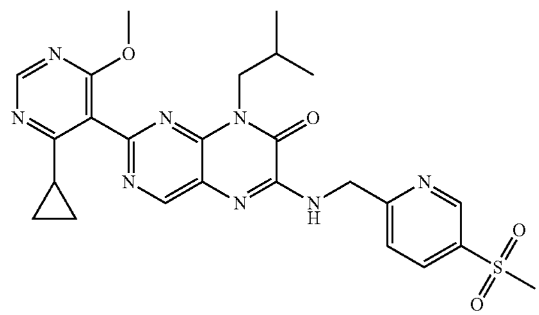 [SMILES: COc1ncnc(C2CC2)c1-c1ncc2nc(NCc3ccc(S(C)(=O)=O)cn3)c(=O)n(CC(C)C)c2n1] | 0.95 | 537.5 | | A |
| 260 | 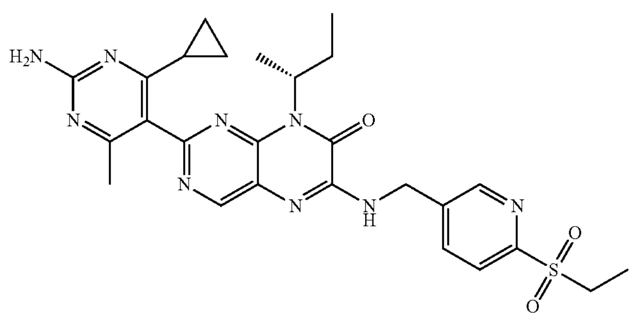 [SMILES: CC[C@@H](C)n1c(=O)c(NCc2ccc(S(=O)(=O)CC)nc2)nc2cnc(-c3c(C)nc(N)nc3C3CC3)nc21] | 0.69 | 550.3 | | A |
| 261 | 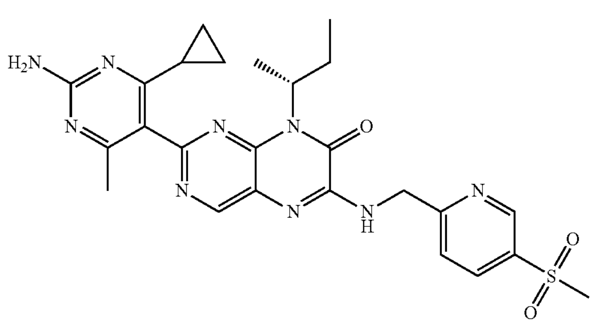 [SMILES: CC[C@@H](C)n1c(=O)c(NCc2ccc(S(C)(=O)=O)cn2)nc2cnc(-c3c(C)nc(N)nc3C3CC3)nc21] | 0.64 | 536.2 | | A |

TABLE 1-continued
| Example | Structure | RT (min) | m/z [M + H]+ | m/z [M − H]− | HPLC Method |
|---|---|---|---|---|---|
| 262 | 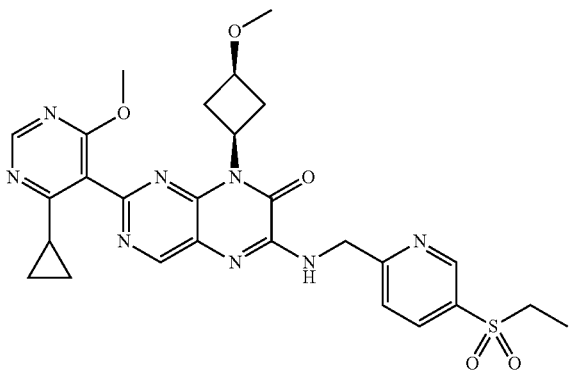 | 0.86 | 579.3 | | A |
| 263 | 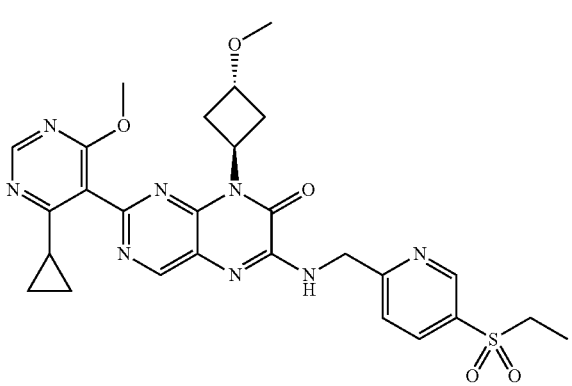 [SMILES: CCS(=O)(=O)c1ccc(CNc2nc3cnc(-c4c(OC)ncnc4C4CC4)nc3n([C@H]3C[C@H](OC)C3)c2=O)nc1] | 0.86 | 579.3 | | A |
| 264 | 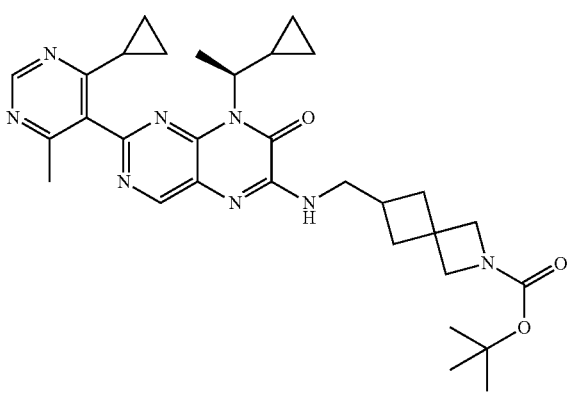 [SMILES: Cc1ncnc(C2CC2)c1-c1ncc2nc(NCC3CC4(C3)CN(C(=O)OC(C)(C)C)C4)c(=O)n([C@@H](C)C3CC3)c2n1] | 0.89 | 607.3 | | A |
| 265 | 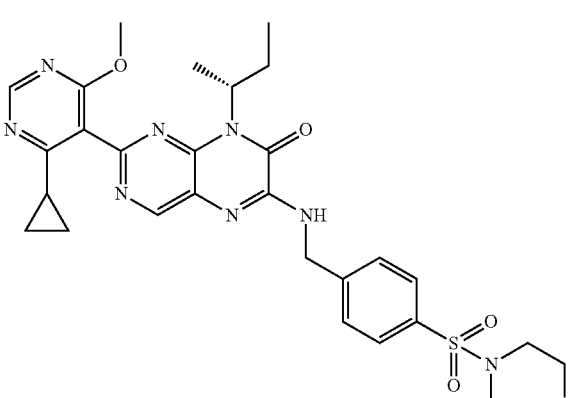 | 0.89 | 521.5 | | A |

Table I also provides physicochemical data (i.e., HPLC retention time and mass spec data) for all the prepared compounds. The HPLC methods are defined below in the Synthetic Examples section.

The present invention further relates to a pharmaceutically acceptable salt of a compound of the formula (I) with inorganic or organic acids or bases.

In another aspect, the invention relates to compounds of formula (I)—or the pharmaceutically acceptable salts thereof—as medicaments.

In another aspect, the invention relates to compounds of formula (I)—or the pharmaceutically acceptable salts thereof—for use in a method for treatment of a patient.

In another aspect, the invention relates to compounds of formula (I)—or the pharmaceutically acceptable salts thereof—for use in the treatment of autoimmune diseases and allergic disorders.

In another aspect, the invention relates to the use of compounds of formula (I)—or the pharmaceutically acceptable salts thereof—for preparing a pharmaceutical composition for the treatment of autoimmune diseases and allergic disorders.

In another aspect, the invention relates to a method for the treatment of autoimmune diseases and allergic disorders comprising administering a therapeutically effective amount of a compound of formula (I)—or one of the pharmaceutically acceptable salts thereof—to a patient.

In another aspect, the invention relates to a pharmaceutical composition containing as active substance one or more compounds of formula (I)—or the pharmaceutically acceptable salts thereof—optionally in combination with conventional excipients and/or carriers.

The compounds of formula (I) may be made using the general synthetic methods described below, which also constitute part of the invention.

General Synthetic Methods

The compounds according to the invention may be prepared by the methods of synthesis, synthetic examples, methods known to those of ordinary skill in the art and methods reported in the chemical literature. In the methods of synthesis and examples described hereinafter, the substituents $R^1$, $R^2$, $R^3$, $R^4$, $R^5$, and W shall have the meanings defined hereinbefore in the detailed description of the compounds of formula I. These methods that are described here are intended as an illustration and for the enablement of the instant invention without restricting the scope of its subject matter, the claimed compounds, and the examples. Where the preparation of starting compounds is not described, they are commercially obtainable, may be prepared analogously to compounds or methods described herein, or are described in the chemical literature. Unless otherwise specified, solvents, temperatures, pressures, and other reaction conditions may be readily selected by one of ordinary skill in the art.

Amine intermediates of formula $R^1$—W—$C(R^2)(R^3)$—$NH_2$ are either commercially available, may be prepared according to the general procedures or references described in U.S. Pat. No. 7,879,873 and WO 2011/049917, or may be prepared by one skilled in the art using methods described in the chemical literature.

Compounds of formula (I) may be prepared from intermediate A' according to Scheme I.

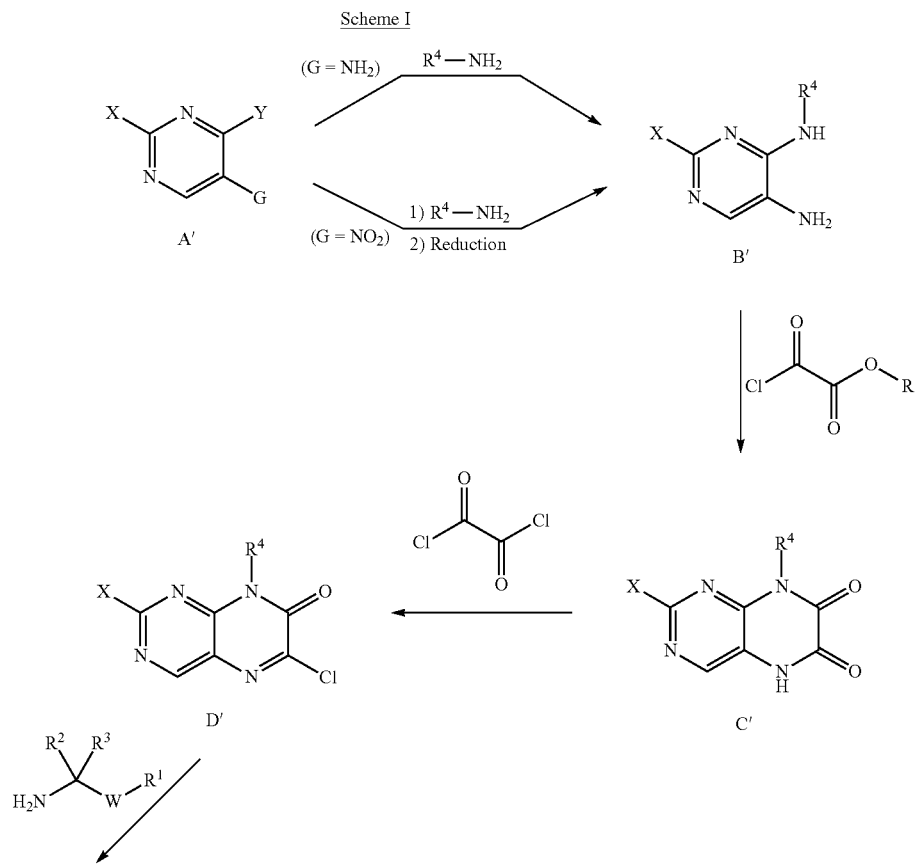

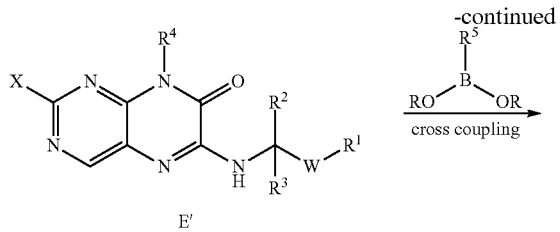 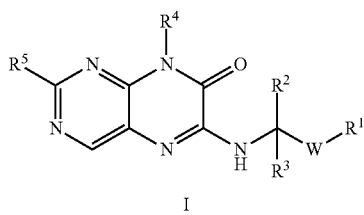

As illustrated in Scheme I, a suitable pyrimidine of formula A', wherein G is $NH_2$, X is a suitable group for palladium-mediated cross coupling reactions (e.g., I, Br, Cl, or $OSO_2CF_3$), and Y is a suitable leaving group (e.g., Cl), may be reacted with a suitable amine or amine salt (e.g., hydrochloride salt) of formula $R^4NH_2$ such as isopropyl amine in the presence of a suitable base (e.g., i-$Pr_2EtN$, or $Et_3N$) in a suitable solvent (e.g., n-butanol) and under a suitable reaction conditions such as an appropriate temperature (e.g., about 120° C.) to provide a compound of formula B'. Alternatively, the said pyrimidine of formula A' wherein G is a suitable synthetic precursor for $NH_2$ (e.g., a nitro group) may be reacted with a suitable amine or amine salt (e.g., hydrochloride salt) of formula $R^4NH_2$ such as 1-methyl cyclopropylamine in the presence of a suitable reagent and solvent (e.g., i-$Pr_2EtN$ and THF, respectively), and under a suitable reaction conditions such as an appropriate temperature (e.g., about −78° C. to about 25° C.) to afford an intermediate, which may be converted to a compound of formula B' upon further reaction with suitable reagents (e.g., a $NO_2$ group that may be reduced with a suitable reagent such as $SnCl_2$). The selection of a suitable amine of formula $R^4NH_2$ and pyrimidine of formula A' for the aforementioned reaction by a person skilled in the art may be based on criteria such as steric and electronic nature of the amine and the pyrimidine. A diaminopyrimidine of formula B' may be reacted with a suitable reagent such as chloro-oxo-acetic acid ethyl ester in a suitable solvent (e.g., acetone) and in the presence of a suitable base (e.g., $K_2CO_3$) to furnish a compound of formula C'. A dicarbonyl compound of formula C' may be reacted with a suitable dehydrochlorinating reagent such as oxalyl chloride in the presence of a suitable additive (e.g., a catalytic amount of DMF) in a suitable solvent (e.g., $CH_2Cl_2$), and under a suitable reaction conditions such as an appropriate temperature (e.g., about ambient temperature) to provide a compound of formula D'. A chloro-pteridinone of formula D' may be reacted with a suitable amine or amine salt of formula $R^1$—W—$C(R^2)(R^3)$—$NH_2$ such as 4-ethanesulfonyl benzyl amine in the presence of a suitable base (e.g., $Et_3N$) in a suitable solvent (e.g., THF) and under a suitable reaction conditions such as an appropriate temperature (e.g., about ambient temperature) to yields a compound of formula E'. A pyrimidine of formula E' may be heated with a suitable cross-coupling partner (e.g., a boronic acid) and a suitable base (e.g., $K_3PO_4$), in a suitable solvent (e.g., 1,4-dioxane), in the presence of a suitable cross-coupling catalyst (e.g., Pd(dppf)$Cl_2$), under suitable reaction conditions such as a suitable atmosphere (e.g., argon) and at a suitable temperature (e.g., about 100° C.) to provide a compound of formula (I).

Synthetic Examples

Non-limiting examples demonstrating the preparation of the compounds of the invention are provided below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:
   a) Waters Sunfire OBD C18 5 μM 30×150 mm column
   b) Waters XBridge OBD C18 5 μM 30×150 mm column
   c) Waters ODB C8 5 μM 19×150 mm column.
   d) Waters Atlantis ODB C18 5 μM 19×50 mm column.
   e) Waters Atlantis T3 OBD 5 μM 30×100 mm column
   f) Phenomenex Gemini Axia C18 5 μM 30×100 mm column HPLC Methods:
Analytical LC/MS Analysis Method A:
Column: Waters BEH 2.1×50 mm C18 1.7 um column
Gradient:

| Time (min) | 0.05% Formic Acid in Water | 0.05% Formic Acid in ACN | Flow (mL/min) |
|---|---|---|---|
| 0 | 90 | 10 | 0.8 |
| 1.19 | 0 | 100 | 0.8 |
| 1.77 | 0 | 100 | 0.8 |

Analytical LC/MS Analysis Method B:
Column: Waters BEH 2.1×50 mm C18 1.7 um column
Gradient:

| Time (min) | 0.05% Formic Acid in Water | 0.05% Formic Acid in ACN | Flow (mL/min) |
|---|---|---|---|
| 0 | 90 | 10 | 0.8 |
| 4.45 | 0 | 100 | 0.8 |
| 4.58 | 0 | 100 | 0.8 |

List of Abbreviations Used in Synthetic Examples:

| | |
|---|---|
| Ac | Acetyl |
| ACN | Acetonitrile |
| AcOH | Acetic acid |
| AIBN | Azobisisobutyronitrile |
| aq | Aqueous |
| Bu | Butyl |
| $Boc_2O$ | Di-tert-butyl dicarbonate |
| dba | Dibenzylideneacetone |
| DCM | Dichloromethane |
| DMA | N,N-dimethylacetamide |
| DIEA | N,N-diisopropylethylamine |
| DME | 1,2-Dimethoxyethane |

| | |
|---|---|
| DMAP | 4-Dimethylaminopyridine |
| DMF | N,N-Dimethylformamide |
| dppe | (Diphenylphosphine)ethane |
| dppf | 1,1'-bis(diphenylphosphino)ferrocene |
| ee | Enantiomeric excess |
| ES+ | Electron spray positive ionization |
| Et | Ethyl |
| EtOAc | Ethyl acetate |
| EtOH | Ethanol |
| Josiphos | (S)-1-[($R_p$)-2-(Dicyclohexylphosphino)ferroceyl]ethyl-di-t-butylphosphine |
| h | hour(s) |
| HPLC | High performance liquid chromatography |
| i | Iso |
| LC | Liquid chromatography |
| Me | Methyl |
| MeOH | Methanol |
| min | Minutes |
| MPLC | Medium Pressure Liquid Chromatography |
| MS | Mass spectrometry |
| NBS | N-Bromo-succinimide |
| NCS | N-Chloro-succinimide |
| NMP | N-Methylpyrrolidinone |
| Oxone | Potassium peroxymonosulfate |
| Pd/C | Palladium on carbon |
| Ph | Phenyl |
| PPh3 | Triphenylphosphine |
| Pr | Propyl |
| RaNi | Raney Nickel |
| RT | Retention time (HPLC) |
| rt | Ambient temperature |
| SFC | Supercritical Fluid Chromatography |
| t | Tertiary |
| tert | Tertiary |
| Tf | Triflate |
| TBAF | Tetrabutylammonium fluoride |
| TEA | Triethylamine |
| TFA | Trifluoroacetic acid |
| THF | Tetrahydrofuran |
| Xanphos | 4,5-Bis(diphenylphosphino)-9,9-dimethylxanthene |

Method 1:

Synthesis of Intermediate A

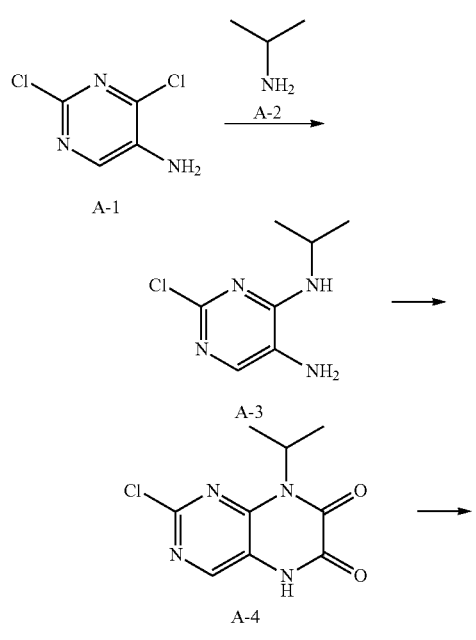

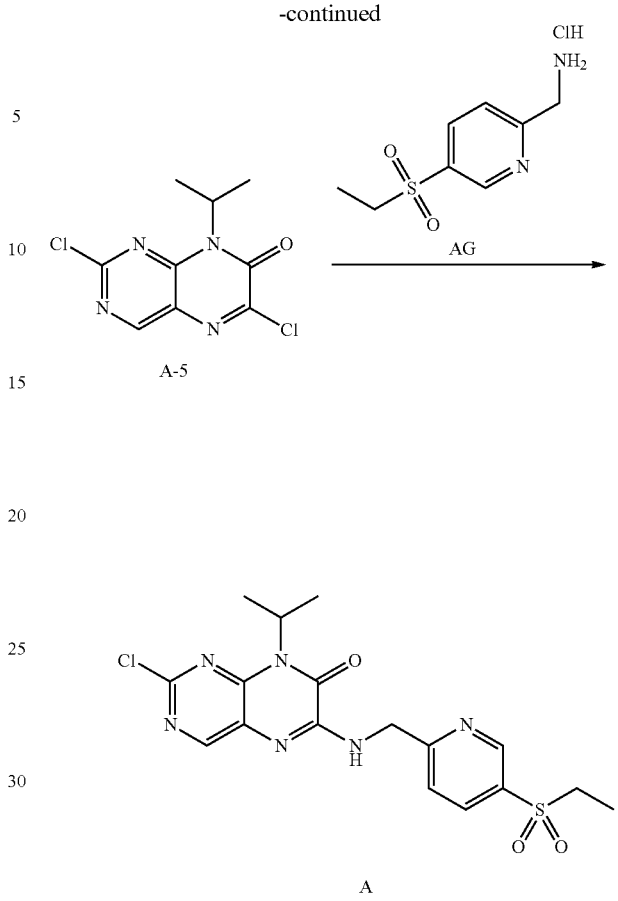

To a stirred suspension of A-1 (3.00 g, 18.18 mmol) in n-butanol (10 mL) is added A-2 (10.80 g, 18.18 mmol) followed by DIEA (6.46 mL, 36.58 mmol). The mixture is stirred for 17 h at 120° C. The reaction is cooled to rt and quenched by the addition of saturated aqueous $NH_4Cl$ solution. The reaction is then diluted with EtOAc. The organic layer is separated and washed with water, followed by brine. The organic layer is dried ($Na_2SO_4$), decanted and concentrated. The resultant residue is purified by $SiO_2$ flash chromatography to yield A-3.

To a stirred suspension of A-3 (1.00 g, 5.00 mmol) in acetone (100 mL) is added ethyl chlorooxoacetate (0.88 g, 6.43 mmol) followed by $K_2CO_3$ (1.85 g, 13.39 mmol). The mixture is stirred at rt for 18 h and the solid precipitate is isolated to yield A-4.

To a stirred suspension of A-4 (1.14 g, 5.00 mmol) in $CH_2Cl_2$ (250 mL) is added oxalyl chloride (1 mL) followed by 5 drops of DMF. The mixture is stirred for 5 h at rt. The mixture is then concentrated at reduced pressure to yield A-5.

To a stirred suspension of A-5 (0.1 g, 0.39 mmol) in THF (4 mL) is added TEA (0.16 mL, 1.16 mmol) (or DIEA), followed by AG (91 mg, 0.38 mmol). The reaction is allowed to stir for 18 h at rt. The reaction is quenched by the addition of saturated aqueous $NH_4Cl$ solution and the organics are extracted with EtOAc. The organic layer is washed with water and brine, dried ($Na_2SO_4$), decanted and concentrated under vacuum. The resultant residue is purified by $SiO_2$ flash chromatography to yield intermediate A. MS (ES+): m/z 423.0 $[M+H]^+$.

Method 2:
Synthesis of Intermediate B

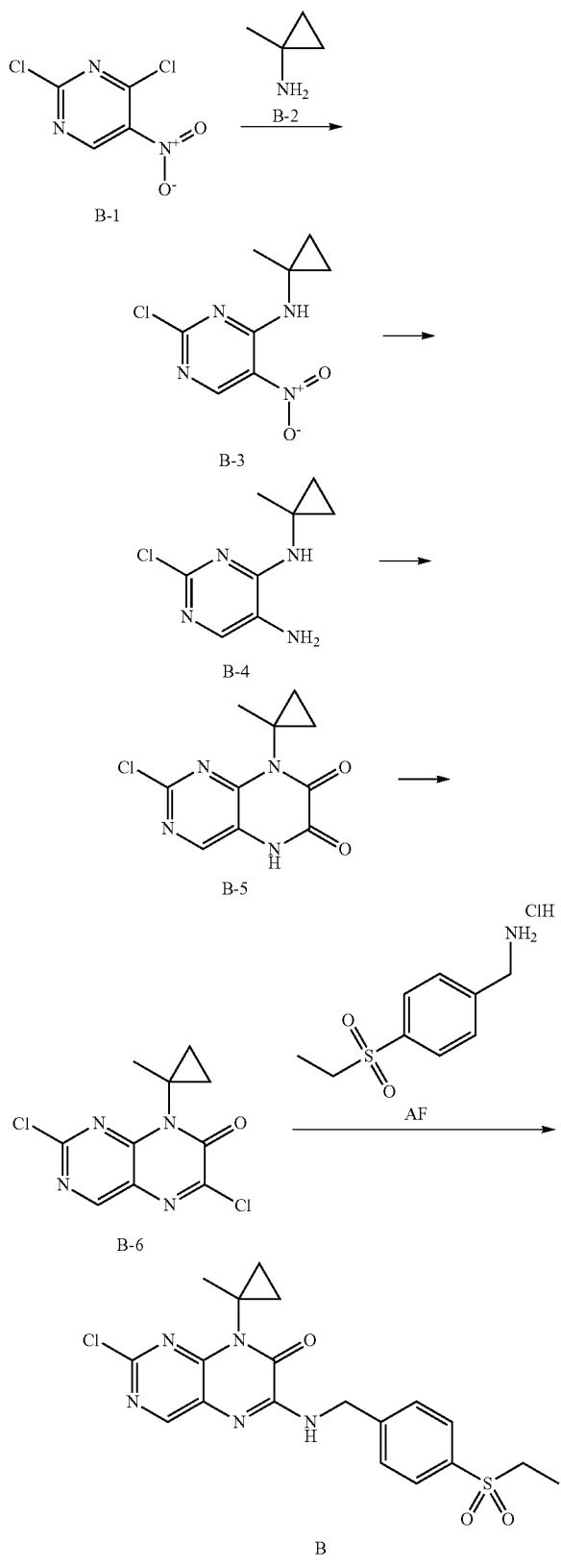

To a stirred suspension of B-1 (1.80 g, 9.30 mmol) and B-2 (1.00 g, 9.30 mmol) in THF (10 mL) at −78° C. is added DIEA (3.29 mL, 18.59 mmol) and the reaction is allowed to slowly warm to 25° C. The volatiles are removed under reduced pressure and the crude is redissolved in EtOAc and washed with $H_2O$. The organic layer is separated and washed two more times with $H_2O$. The organic layer is washed with brine, dried ($Na_2SO_4$), decanted and concentrated. The resultant residue is purified by $SiO_2$ flash chromatography to yield B-3.

To a solution of B-3 (1.78 g, 7.79 mmol) in EtOH (50 mL) is added $SnCl_2$ (1.48 g, 7.79 mmol) and heated to reflux for 4 h. The reaction is allowed to cool to rt then poured over ice. The solution is treated with 1N $NaOH_{(aq)}$ to bring the pH to ~9 then filtered through a pad of diatomaceous earth. The organic phase is separated and washed with $H_2O$ followed by brine. The organic layer is dried ($Na_2SO_4$), decanted and concentrated. The crude product is purified by $SiO_2$ flash chromatography to yield B-4.

As an alternative procedure for the reduction of nitropyrimidine to the corresponding amino pyrimidine the following general procedure has been utilized for analogous intermediates: To a solution of the nitropyrimidine in EtOH is added catalytic RaNi. The reaction vessel is evacuated and purged with $N_2(g)$, then evacuated and filled with $H_2(g)$. The reaction is maintained under $H_2(g)$ atmosphere for 15 h. The vessel is evacuated and purged with $N_2(g)$. The reaction is filtered through a pad of diatomaceous earth to remove the Ni catalyst and the filtrate is concentrated. The resultant residue is purified by $SiO_2$ flash chromatography to afford the corresponding aminopyrimidine.

To a stirred solution of B-4 (0.40 g, 2.01 mmol) in acetone (10 mL) is $K_2CO_3$ (0.70 g, 5.06 mmol) followed by ethyl chlorooxoacetate (0.27 mL, 2.43 mmol). The reaction is stirred at rt for 24 h. The reaction is then filtered, redissolved in $H_2O$ and extracted with EtOAc. The aqueous phase is separated and extracted two more times with EtOAc. The organic layers are combined, dried ($Na_2SO_4$), decanted and concentrated to yield B-5.

To a solution of B-5 (0.70 g, 2.77 mmol) in $CH_2Cl_2$ (50 mL) is added oxalyl chloride (0.47 mL, 5.54 mmol) followed by 5 drops of DMF. The reaction is allowed to stir at rt for 18 h. The volatiles are removed in vacuo. The crude is redissolved in DCM and poured into $H_2O$. The organic layer is separated, washed with brine, dried ($Na_2SO_4$), decanted and concentrated. The resultant residue is purified by $SiO_2$ flash chromatography to yield B-6.

To a stirred solution of the B-6 (0.83 g, 3.06 mmol) in THF (10 mL) is added DIEA (1.07 mL, 6.12 mmol) followed by AF (0.72 g, 3.06 mmol). The reaction is stirred at rt for 18 h. The volatiles are removed in vacuo, the crude residue is re-suspended in DCM and poured into $H_2O$. The aqueous phase is separated and extracted two more times with DCM. The organic layers are combined, washed with brine, dried ($Na_2SO_4$), decanted and concentrated. The resultant residue is purified by $SiO_2$ flash to yield intermediate B. MS (ES+): m/z 434.1 $[M+H]^+$.

The following intermediates are prepared in analogous fashion:

(Note: As described in Method 34, the oxalamic acid ethyl ester intermediates generated from the reactions of A-3 (Method 1) and B-4 (Method 2) with ethyl chlorooxoacetate may be isolated and heated at a suitable temperature (e.g., 130° C.) with a suitable base, such as TEA, in a suitable solvent, such as EtOH, to afford the corresponding intermediates A-3 and B-5, respectively.)

| Intermediate | Structure | Synthetic Method | m/z[M + H]+ |
|---|---|---|---|
| C | 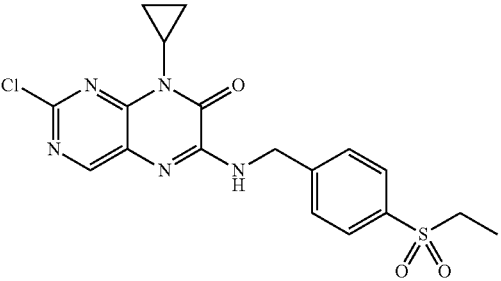 [SMILES: CCS(=O)(=O)c1ccc(CNc2nc3cnc(Cl)nc3n(C3CC3)c2=O)cc1] | 1 | 420.1 |
| D | 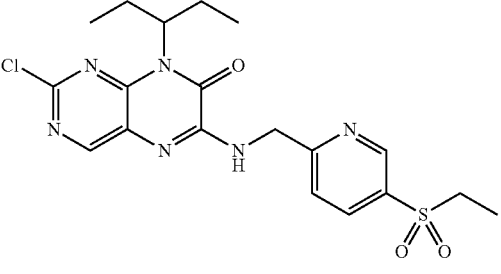 [SMILES: CCC(CC)n1c(=O)c(NCc2ccc(S(=O)(=O)CC)cn2)nc2cnc(Cl)nc21] | 1 | 451.2 |
| E | 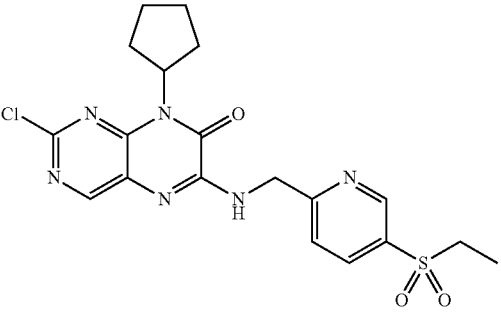 [SMILES: CCS(=O)(=O)c1ccc(CNc2nc3cnc(Cl)nc3n(C3CCCC3)c2=O)nc1] | 2 | 449.3 |
| F | 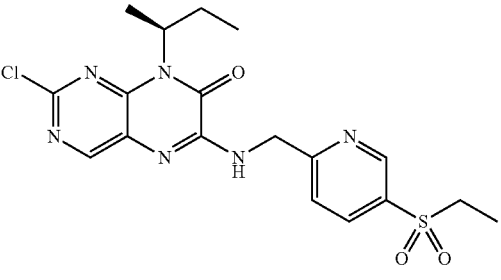 [SMILES: CC[C@H](C)n1c(=O)c(NCc2ccc(S(=O)(=O)CC)cn2)nc2cnc(Cl)nc21] | 1 | 437.2 |
| G | 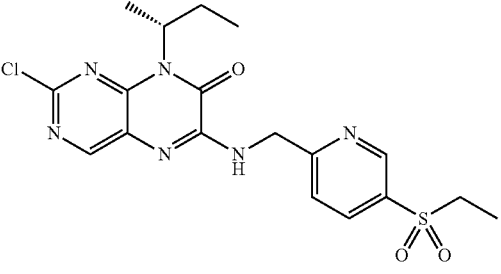 [SMILES: CC[C@@H](C)n1c(=O)c(NCc2ccc(S(=O)(=O)CC)cn2)nc2cnc(Cl)nc21] | 1 | 437.2 |

-continued

| Intermediate | Structure | Synthetic Method | m/z[M + H]⁺ |
|---|---|---|---|
| H | 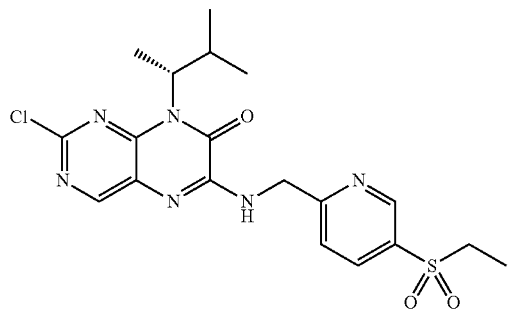 [SMILES: CCS(=O)(=O)c1ccc(CNc2nc3cnc(Cl)nc3n([C@H](C)C(C)C)c2=O)nc1] | 1 | 451.2 |
| I | 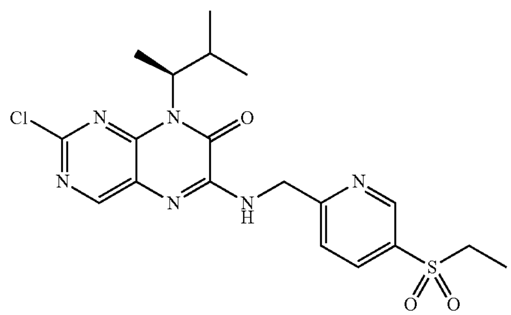 [SMILES: CCS(=O)(=O)c1ccc(CNc2nc3cnc(Cl)nc3n([C@@H](C)C(C)C)c2=O)nc1] | 1 | 451.2 |
| J | 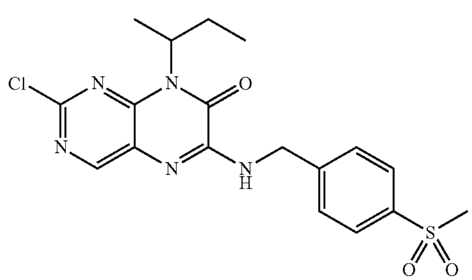 [SMILES: CCC(C)n1c(=O)c(NCc2ccc(S(C)(=O)=O)cc2)nc2cnc(Cl)nc21] | 1 | 422.5 |
| K | 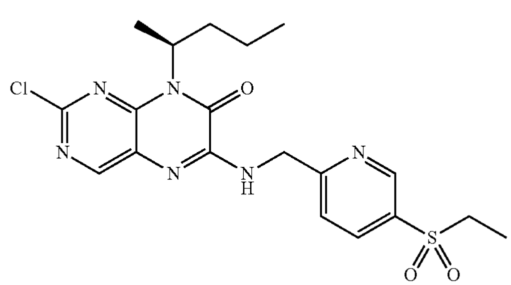 [SMILES: CCC[C@H](C)n1c(=O)c(NCc2ccc(S(=O)(=O)CC)cn2)nc2cnc(Cl)nc21] | 2 | 451.1 |
| L | 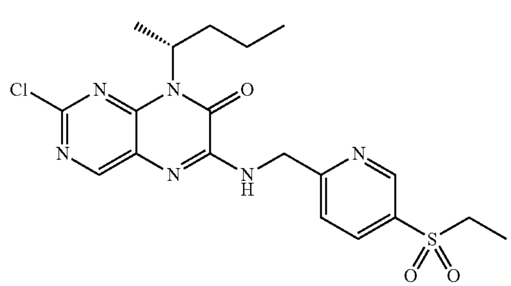 [SMILES: CCC[C@@H](C)n1c(=O)c(NCc2ccc(S(=O)(=O)CC)cn2)nc2cnc(Cl)nc21] | 2 | 451.1 |

| Intermediate | Structure | Synthetic Method | m/z[M + H]+ |
|---|---|---|---|
| M | 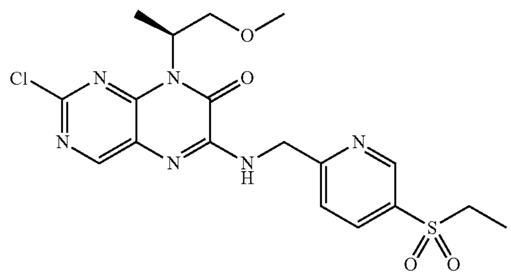 [SMILES: CCS(=O)(=O)c1ccc(CNc2nc3cnc(Cl)nc3n([C@@H](C)COC)c2=O)nc1] | 1 | 453.2 |
| N | 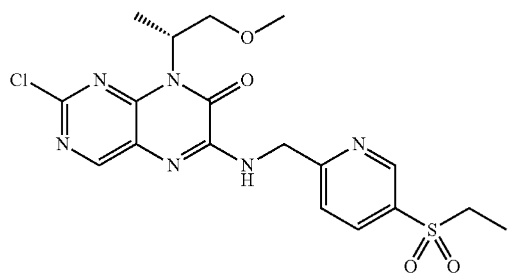 [SMILES: CCS(=O)(=O)c1ccc(CNc2nc3cnc(Cl)nc3n([C@H](C)COC)c2=O)nc1] | 1 | 453.2 |
| O | 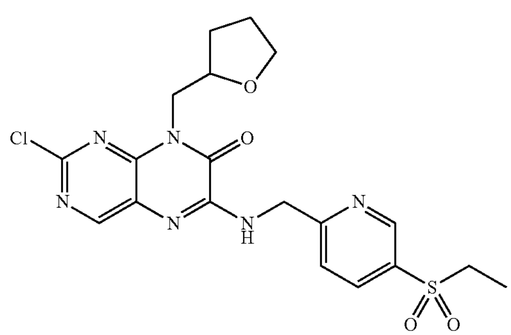 [SMILES: CCS(=O)(=O)c1ccc(CNc2nc3cnc(Cl)nc3n(CC3CCCO3)c2=O)nc1] | 1 | 465.2 |
| P | 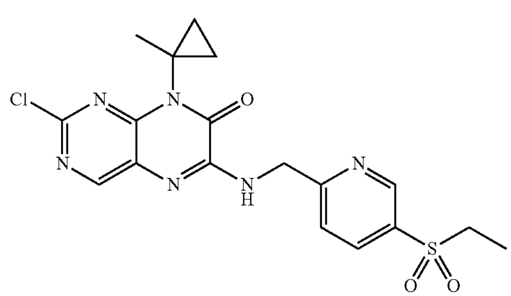 [SMILES: CCS(=O)(=O)c1ccc(CNc2nc3cnc(Cl)nc3n(C3(C)CC3)c2=O)nc1] | 2 | 435.2 |
| Q | 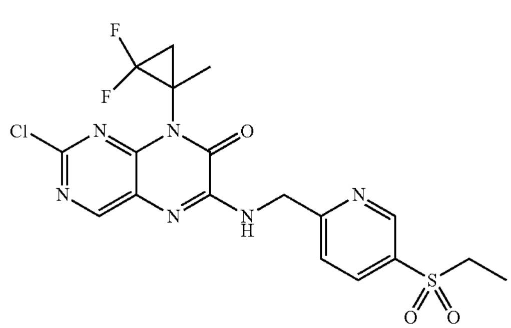 [SMILES: CCS(=O)(=O)c1ccc(CNc2nc3cnc(Cl)nc3n(C3(C)CC3(F)F)c2=O)nc1] | 2 | 471.1 |

| Intermediate | Structure | Synthetic Method | m/z[M + H]+ |
|---|---|---|---|
| R | 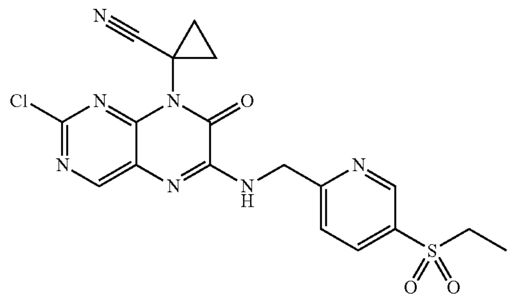 | 2 | 466.2 |
| S | 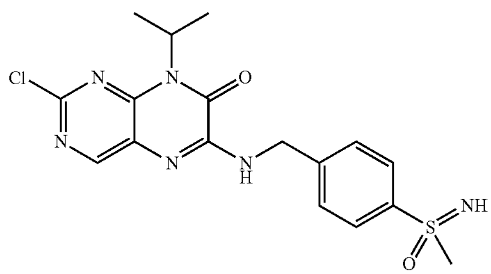 [SMILES: CC(C)n1c(=O)c(NCc2ccc(S(C)(=N)=O)cc2)nc2cnc(Cl)nc21] | 1 | 409.1 |
| T | 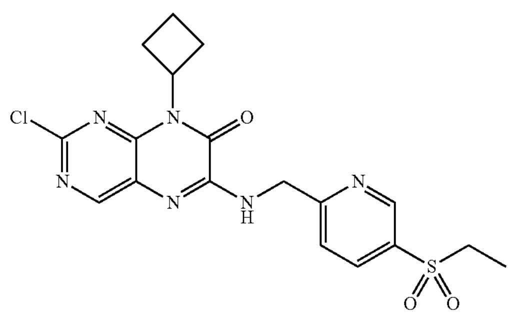 [SMILES: CCS(=O)(=O)c1ccc(CNc2nc3cnc(Cl)nc3n(C3CCC3)c2=O)nc1] | 1 | 434.9 |
| U | 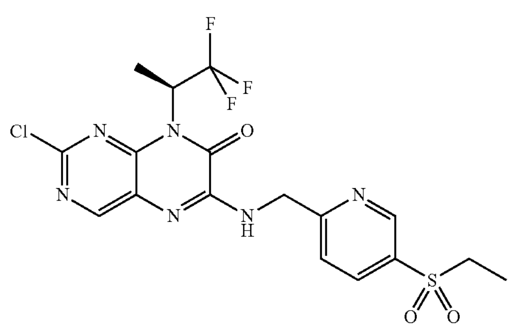 [SMILES: CCS(=O)(=O)c1ccc(CNc2nc3cnc(Cl)nc3n([C@@H](C)C(F)(F)F)c2=O)nc1] | 2 | 477.0 |
| V | 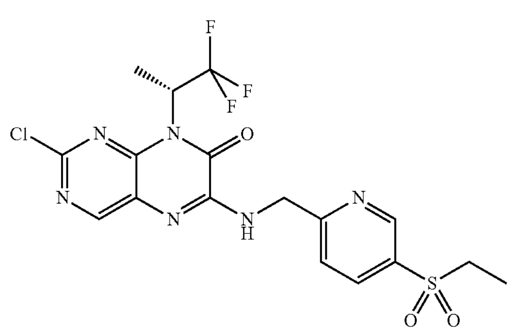 [SMILES: CCS(=O)(=O)c1ccc(CNc2nc3cnc(Cl)nc3n([C@H](C)C(F)(F)F)c2=O)nc1] | 2 | 476.9 |

| Intermediate | Structure | Synthetic Method | m/z[M + H]+ |
|---|---|---|---|
| W | 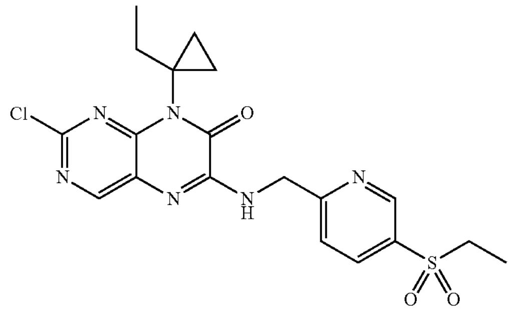 [SMILES: CCC1(n2c(=O)c(NCc3ccc(S(=O)(=O)CC)cn3)nc3cnc(Cl)nc32)CC1] | 2 | 449.1 |
| X | 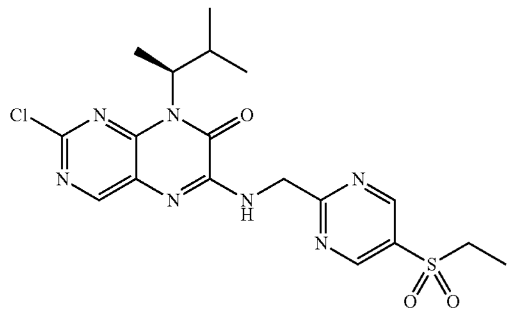 [SMILES: CCS(=O)(=O)c1cnc(CNc2nc3cnc(Cl)nc3n([C@@H](C)C(C)C)c2=O)nc1] | 1 | 451.9 |
| Y | 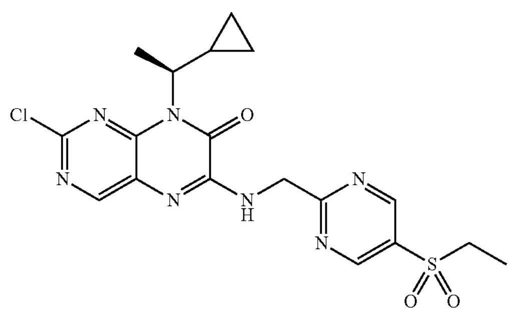 [SMILES: CCS(=O)(=O)c1cnc(CNc2nc3cnc(Cl)nc3n([C@@H](C)C3CC3)c2=O)nc1] | 1 | 449.9 |
| Z | 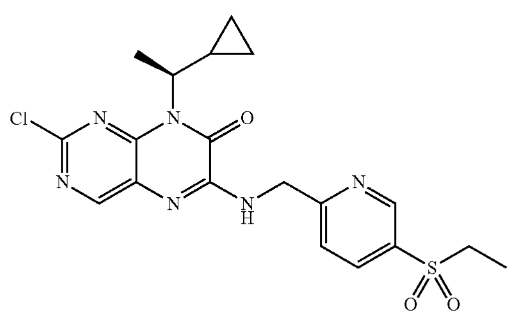 [SMILES: CCS(=O)(=O)c1ccc(CNc2nc3cnc(Cl)nc3n([C@@H](C)C3CC3)c2=O)nc1] | 1 | 448.9 |
| AA | 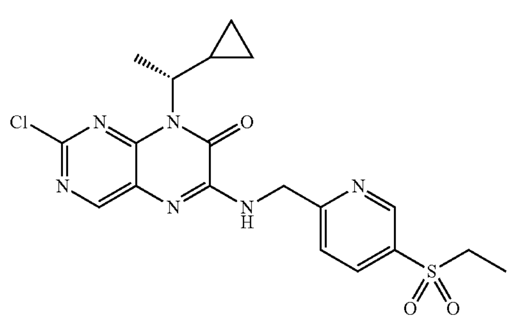 [SMILES: CCS(=O)(=O)c1ccc(CNc2nc3cnc(Cl)nc3n([C@H](C)C3CC3)c2=O)nc1] | 1 | 449.0 |

-continued

| Intermediate | Structure | Synthetic Method | m/z[M + H]+ |
|---|---|---|---|
| BB | 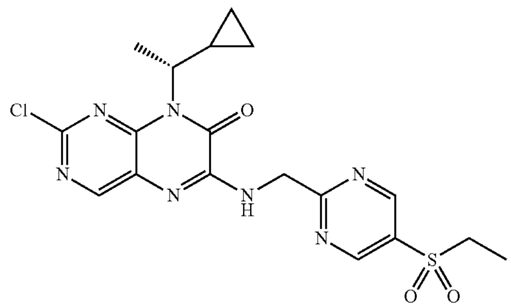 [SMILES: CCS(=O)(=O)c1cnc(CNc2nc3cnc(Cl)nc3n([C@H](C)C3CC3)c2=O)nc1] | 1 | 449.9 |
| CC | 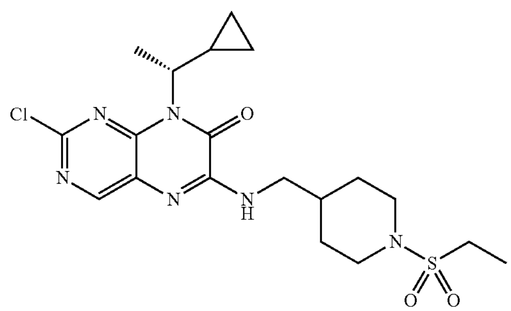 [SMILES: CCS(=O)(=O)N1CCC(CNc2nc3cnc(Cl)nc3n([C@H](C)C3CC3)c2=O)CC1] | 1 | 455.0 |
| DD | 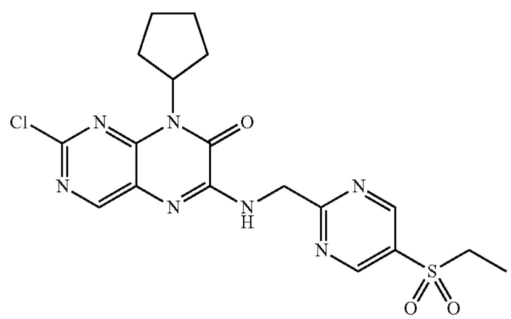 [SMILES: CCS(=O)(=O)c1cnc(CNc2nc3cnc(Cl)nc3n(C3CCCC3)c2=O)nc1] | 1 | 449.9 |
| EE | 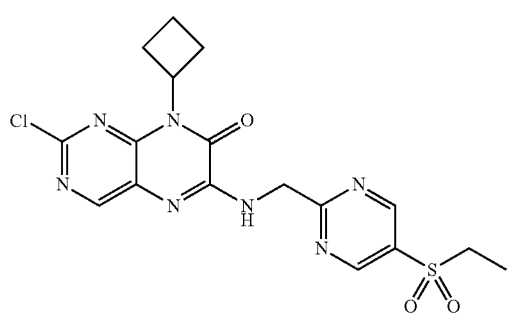 [SMILES: CCS(=O)(=O)c1cnc(CNc2nc3cnc(Cl)nc3n(C3CCC3)c2=O)nc1] | 1 | 435.9 |
| FF | 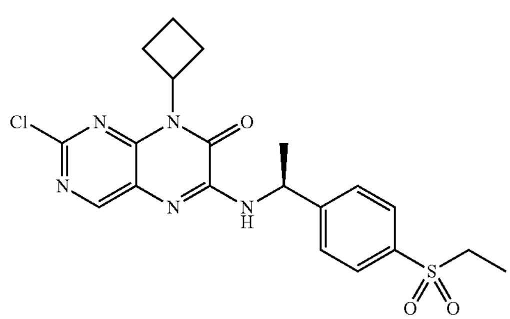 [SMILES: CCS(=O)(=O)c1ccc([C@H](C)Nc2nc3cnc(Cl)nc3n(C3CCC3)c2=O)cc1] | 1 | 447.9 |

-continued
| Intermediate | Structure | Synthetic Method | m/z[M + H]+ |
|---|---|---|---|
| GG | 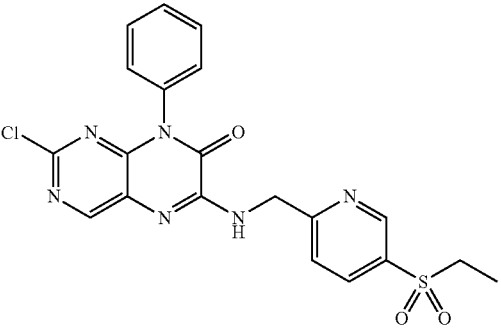 [SMILES: CCS(=O)(=O)c1ccc(CNc2nc3cnc(Cl)nc3n(-c3ccccc3)c2=O)nc1] | 1 | 457.1 |
| HH | 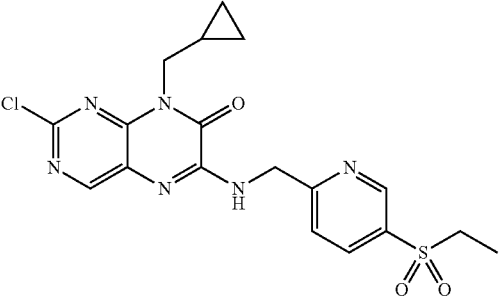 [SMILES: CCS(=O)(=O)c1ccc(CNc2nc3cnc(Cl)nc3n(CC3CC3)c2=O)nc1] | 1 | 434.9 |
| II | 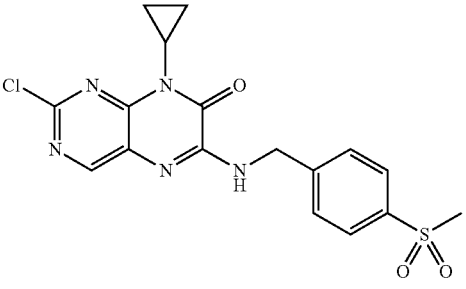 [SMILES: CS(=O)(=O)c1ccc(CNc2nc3cnc(Cl)nc3n(C3CC3)c2=O)cc1] | 1 | 406.0 |
| JJ | 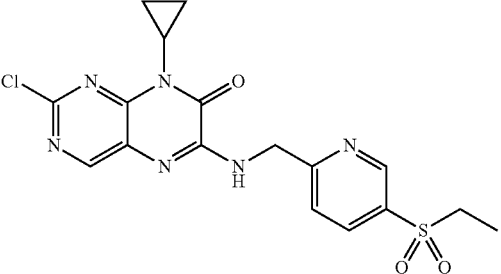 [SMILES: CCS(=O)(=O)c1ccc(CNc2nc3cnc(Cl)nc3n(C3CC3)c2=O)nc1] | 1 | 421.0 |
| KK | 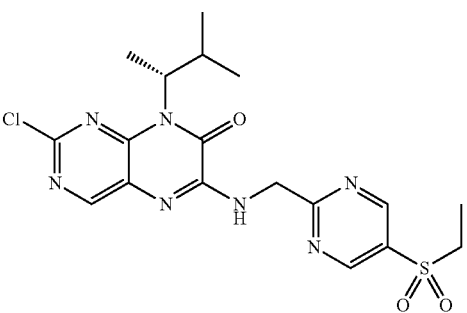 [SMILES: CCS(=O)(=O)c1cnc(CNc2nc3cnc(Cl)nc3n([C@H](C)C(C)C)c2=O)nc1] | 1 | 451.2 |

-continued

| Intermediate | Structure | Synthetic Method | m/z[M + H]+ |
|---|---|---|---|
| LL | 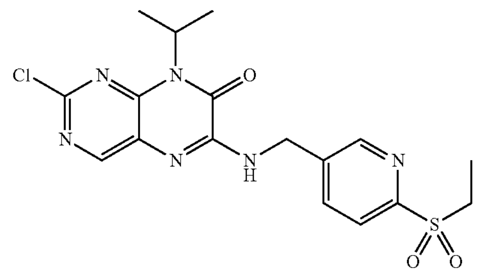 [SMILES: CCS(=O)(=O)c1ccc(CNc2nc3cnc(Cl)nc3n(C(C)C)c2=O)cn1] | 1 | 423.1 |
| MM | 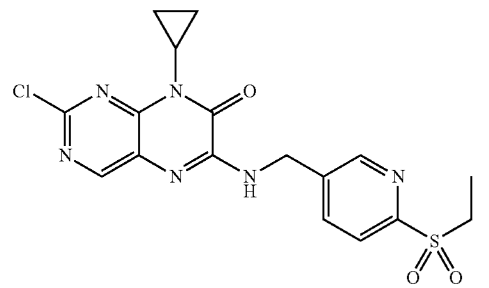 [SMILES: CCS(=O)(=O)c1ccc(CNc2nc3cnc(Cl)nc3n(C3CC3)c2=O)cn1] | 1 | 421.0 |
| NN | 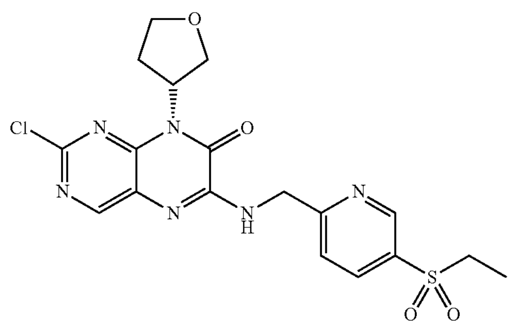 | 1 | 451.0 |
| OO | 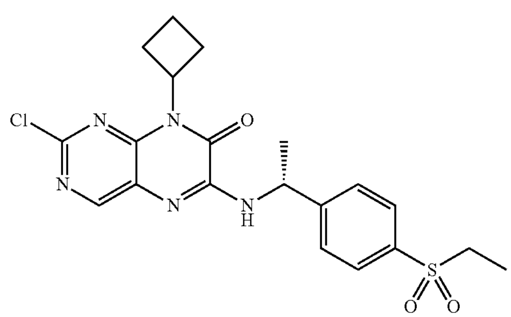 [SMILES: CCS(=O)(=O)c1ccc([C@@H](C)Nc2nc3cnc(Cl)nc3n(C3CCC3)c2=O)cc1] | 1 | 447.9 |
| PP | 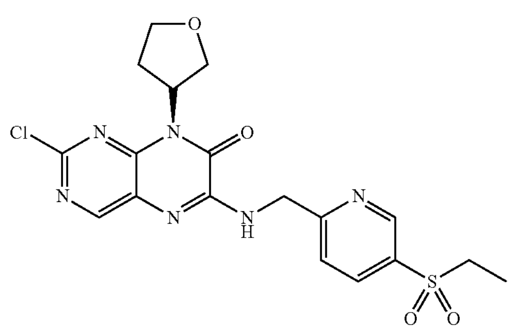 | 1 | 451.0 |

-continued

| Intermediate | Structure | Synthetic Method | m/z[M + H]+ |
|---|---|---|---|
| QQ | 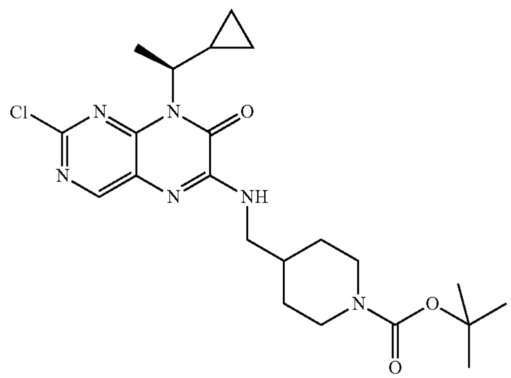 [SMILES: C[C@@H](C1CC1)n1c(=O)c(NCC2CCN(C(=O)OC(C)(C)C)CC2)nc2cnc(Cl)nc21] | 1 | 451.0 |
| RR | 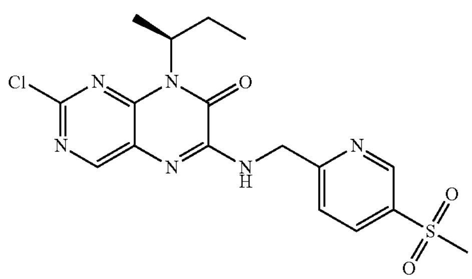 | 1 | 423.3 |
| SS | 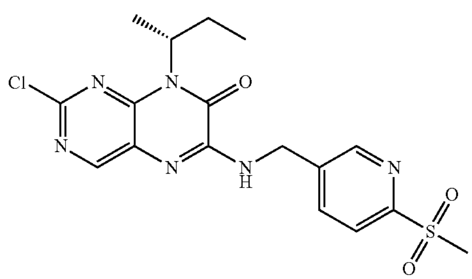 [SMILES: CC[C@@H](C)n1c(=O)c(NCc2ccc(S(C)(=O)=O)nc2)nc2cnc(Cl)nc21] | 1 | 423.3 |
| TT | 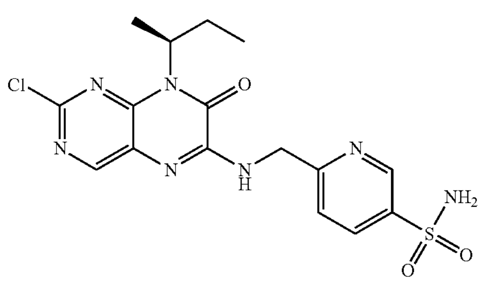 [SMILES: CC[C@H](C)n1c(=O)c(NCc2ccc(S(N)(=O)=O)cn2)nc2cnc(Cl)nc21] | 1 | 424.3 |
| UU | 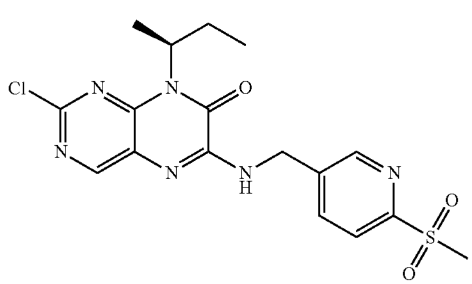 [SMILES: CC[C@H](C)n1c(=O)c(NCc2ccc(S(C)(=O)=O)nc2)nc2cnc(Cl)nc21] | 1 | 423.3 |

-continued

| Intermediate | Structure | Synthetic Method | m/z[M + H]+ |
|---|---|---|---|
| VV | 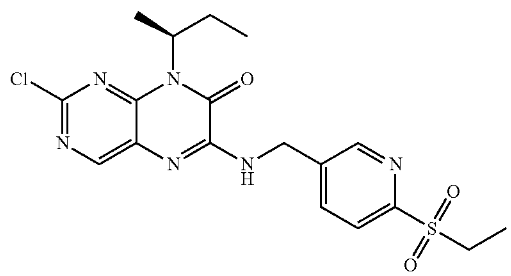 [SMILES: CC[C@H](C)n1c(=O)c(NCc2ccc(S(=O)(=O)CC)nc2)nc2cnc(Cl)nc21] | 1 | 437.3 |
| WW | 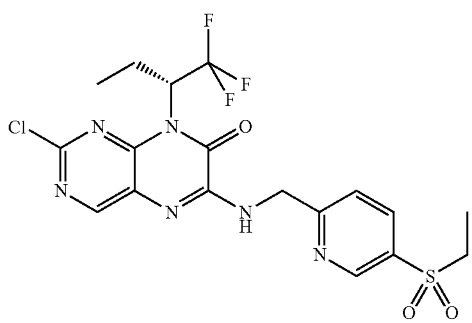 [SMILES: CC[C@@H](n1c(=O)c(NCc2ccc(S(=O)(=O)CC)cn2)nc2cnc(Cl)nc21)C(F)(F)F] | 2 | 491.3 |
| XX | 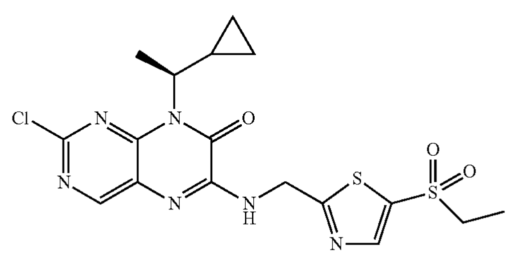 [SMILES: CCS(=O)(=O)c1cnc(CNc2nc3cnc(Cl)nc3n([C@@H](C)C3CC3)c2=O)s1] | 1 | 455.3 |
| YY | 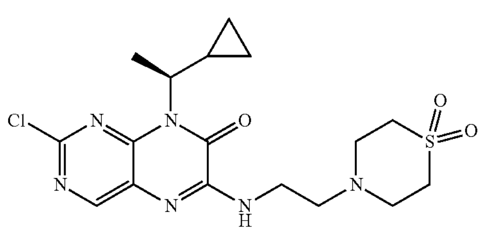 [SMILES: C[C@@H](C1CC1)n1c(=O)c(NCCN2CCS(=O)(=O)CC2)nc2cnc(Cl)nc21] | 2 | 427.3 |
| ZZ | 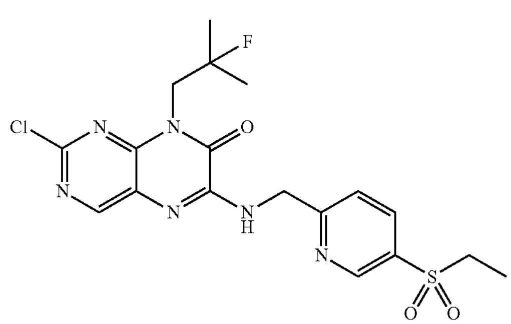 [SMILES: CCS(=O)(=O)c1ccc(CNc2nc3cnc(Cl)nc3n(CC(C)(C)F)c2=O)nc1] | 1 | 455.4 |

-continued

| Intermediate | Structure | Synthetic Method | m/z[M + H]+ |
|---|---|---|---|
| AAA | 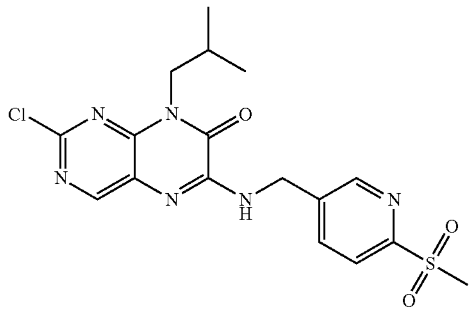 [SMILES: CC(C)Cn1c(=O)c(NCc2ccc(S(C)(=O)=O)nc2)nc2cnc(Cl)nc21] | 1 | 423.3 |
| BBB | 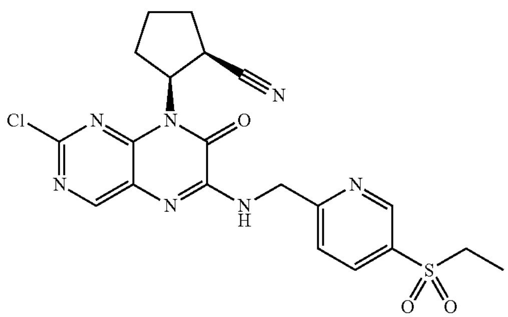 [SMILES: CCS(=O)(=O)c1ccc(CNc2nc3cnc(Cl)nc3n([C@H]3CCC[C@H]3C#N)c2=O)nc1] | 1 | 474.1 |
| CCC | 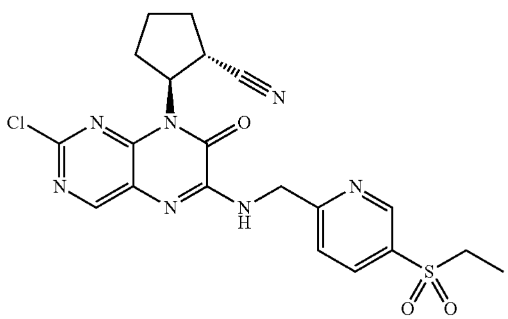 [SMILES: CCS(=O)(=O)c1ccc(CNc2nc3cnc(Cl)nc3n([C@H]3CCC[C@@H]3C#N)c2=O)nc1] | 1 | 474.1 |
| DDD | 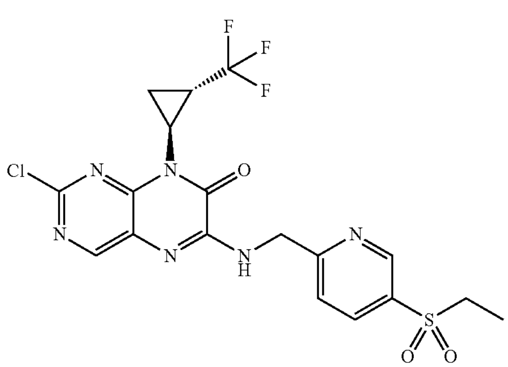 [SMILES: CCS(=O)(=O)c1ccc(CNc2nc3cnc(Cl)nc3n([C@H]3C[C@@H]3C(F)(F)F)c2=O)nc1] | 2 | 489.1 |

-continued

| Intermediate | Structure | Synthetic Method | m/z[M + H]+ |
|---|---|---|---|
| EEE | 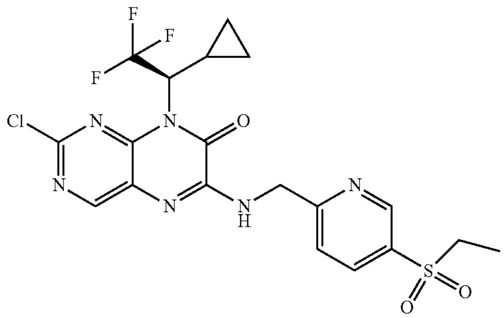 [SMILES: CCS(=O)(=O)c1ccc(CNc2nc3cnc(Cl)nc3n([C@H](C3CC3)C(F)(F)F)c2=O)nc1] | 2 | 503.3 |
| FFF | 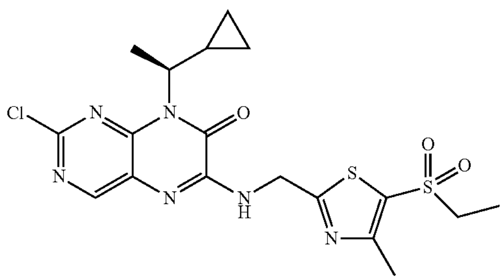 [SMILES: CCS(=O)(=O)c1sc(CNc2nc3cnc(Cl)nc3n([C@@H](C)C3CC3)c2=O)nc1C] | 1 | 469.3 |
| GGG | 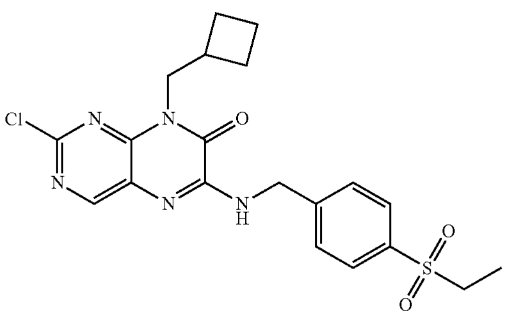 [SMILES: CCS(=O)(=O)c1ccc(CNc2nc3cnc(Cl)nc3n(CC3CCC3)c2=O)cc1] | 1 | 448.1 |
| HHH | 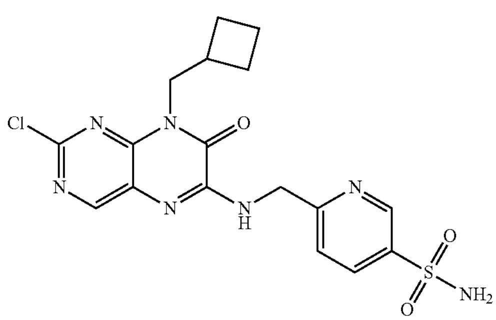 [SMILES: NS(=O)(=O)c1ccc(CNc2nc3cnc(Cl)nc3n(CC3CCC3)c2=O)nc1] | 1 | 436.3 |
| III | 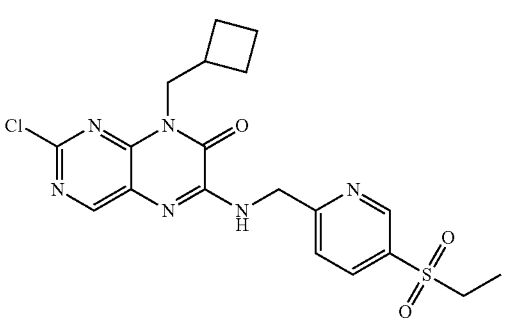 [SMILES: CCS(=O)(=O)c1ccc(CNc2nc3cnc(Cl)nc3n(CC3CCC3)c2=O)nc1] | 1 | 449.3 |

-continued

| Intermediate | Structure | Synthetic Method | m/z[M + H]⁺ |
|---|---|---|---|
| JJJ | 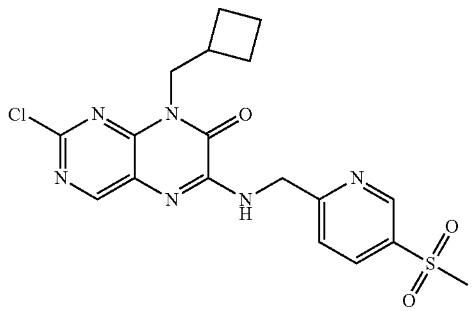 [SMILES: CS(=O)(=O)c1ccc(CNc2nc3cnc(Cl)nc3n(CC3CCC3)c2=O)nc1] | 1 | 435.3 |
| KKK | 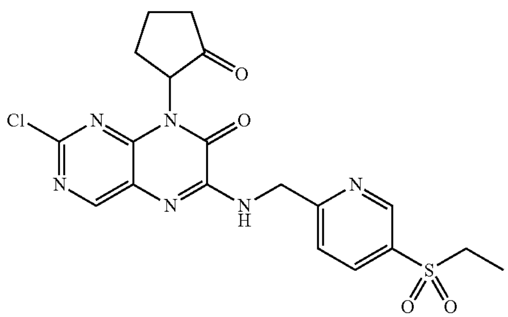 [SMILES: CCS(=O)(=O)c1ccc(CNc2nc3cnc(Cl)nc3n(C3CCCC3=O)c2=O)nc1] | 1 | 463.1 |
| LLL | 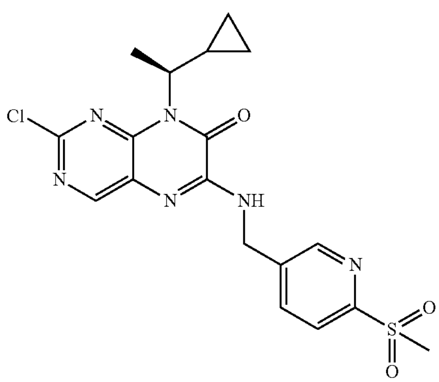 [SMILES: C[C@@H](C1CC1)n1c(=O)c(NCc2ccc(S(C)(=O)=O)nc2)nc2cnc(Cl)nc21] | 1 | 435.2 |
| MMM | 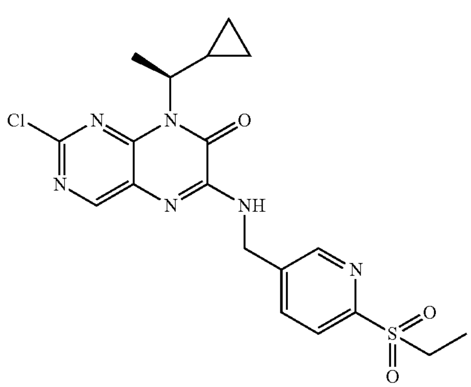 [SMILES: CCS(=O)(=O)c1ccc(CNc2nc3cnc(Cl)nc3n([C@@H](C)C3CC3)c2=O)cn1] | 1 | 448.9 |

-continued
| Intermediate | Structure | Synthetic Method | m/z[M + H]+ |
|---|---|---|---|
| NNN | 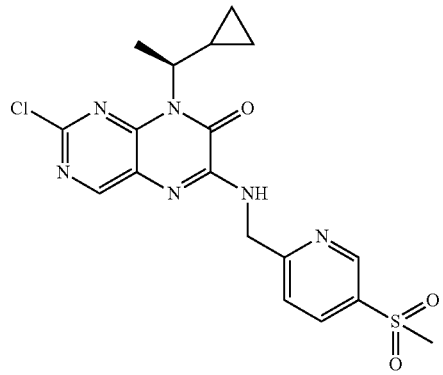 [SMILES: C[C@@H](C1CC1)n1c(=O)c(NCc2ccc(S(C)(=O)=O)cn2)nc2cnc(Cl)nc21] | 1 | 435.2 |
| OOO | 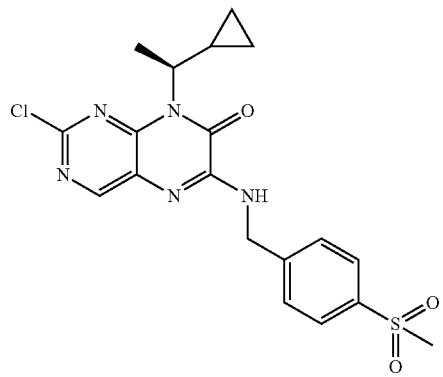 [SMILES: C[C@@H](C1CC1)n1c(=O)c(NCc2ccc(S(C)(=O)=O)cc2)nc2cnc(Cl)nc21] | 1 | 434.9 |
| PPP | 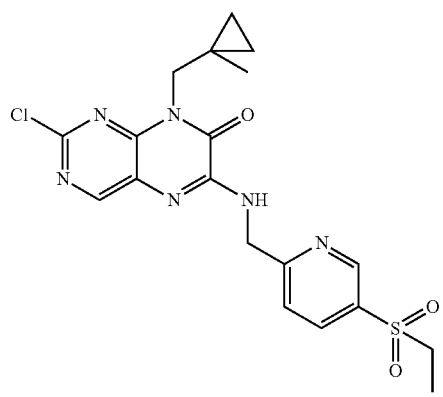 [SMILES: CCS(=O)(=O)c1ccc(CNc2nc3cnc(Cl)nc3n(CC3(C)CC3)c2=O)nc1] | 1 | 449.2 |

-continued
| Intermediate | Structure | Synthetic Method | m/z[M + H]+ |
|---|---|---|---|
| QQQ | 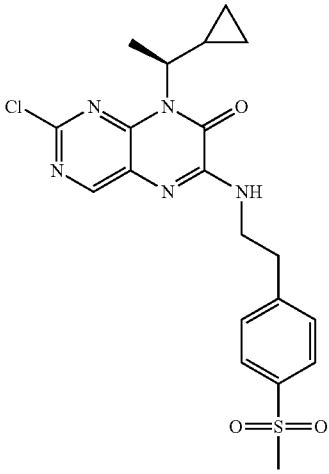 [SMILES: C[C@@H](C1CC1)n1c(=O)c(NCCc2ccc(S(C)(=O)=O)cc2)nc2cnc(Cl)nc21] | 1 | 448.2 |
| RRR | 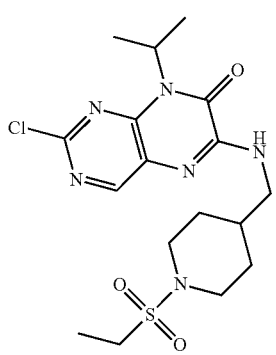 | 1 | 429.0 |
| SSS | 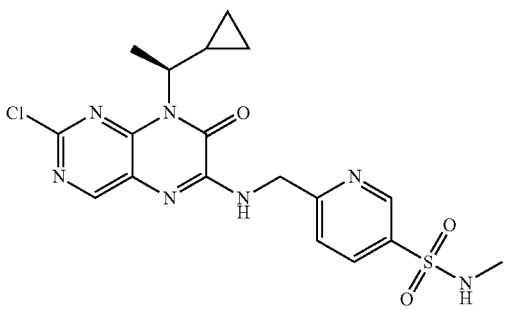 [SMILES: CNS(=O)(=O)c1ccc(CNc2nc3cnc(Cl)nc3n([C@@H](C)C3CC3)c2=O)nc1] | 1 | 450.0 |
| TTT | 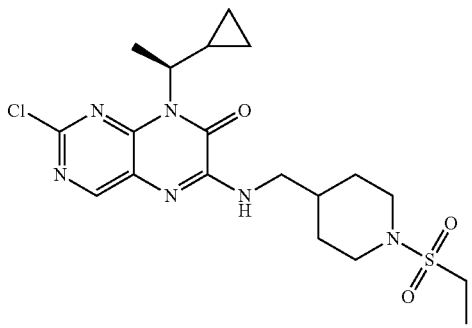 [SMILES: CCS(=O)(=O)N1CCC(CNc2nc3cnc(Cl)nc3n([C@@H](C)C3CC3)c2=O)CC1] | 1 | 441.2 |

-continued

| Intermediate | Structure | Synthetic Method | m/z[M + H]+ |
|---|---|---|---|
| UUU | 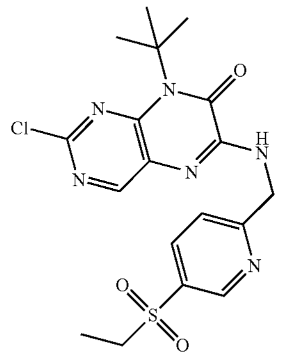 [SMILES: CCS(=O)(=O)c1ccc(CNc2nc3cnc(Cl)nc3n(C(C)(C)C)c2=O)nc1] | 1 | 436.9 |
| VVV | 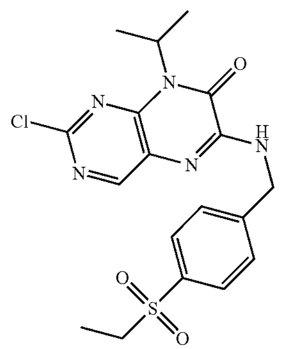 [SMILES: CCS(=O)(=O)c1ccc(CNc2nc3cnc(Cl)nc3n(C(C)C)c2=O)cc1] | 1 | 422.0 |
| WWW | 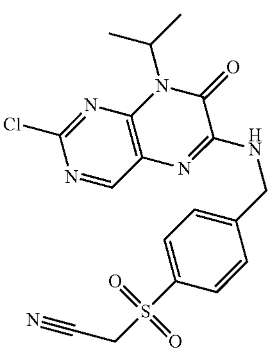 [SMILES: CC(C)n1c(=O)c(NCc2ccc(S(=O)(=O)CC#N)cc2)nc2cnc(Cl)nc21] | 1 | 432.9 |
| XXX | 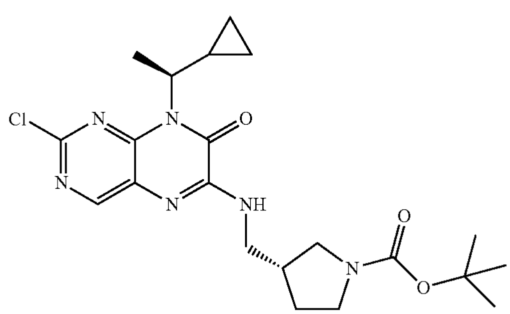 [SMILES: C[C@@H](C1CC1)n1c(=O)c(NC[C@H]2CCN(C(=O)OC(C)(C)C)C2)nc2cnc(Cl)nc21] | 1 | 449.0 |

| Intermediate | Structure | Synthetic Method | m/z[M + H]+ |
|---|---|---|---|
| YYY | 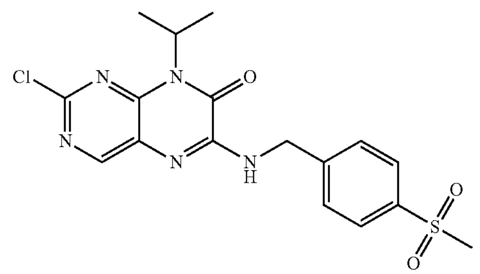 [SMILES: CC(C)n1c(=O)c(NCc2ccc(S(C)(=O)=O)cc2)nc2cnc(Cl)nc21] | 1 | 407.8 |
| ZZZ | 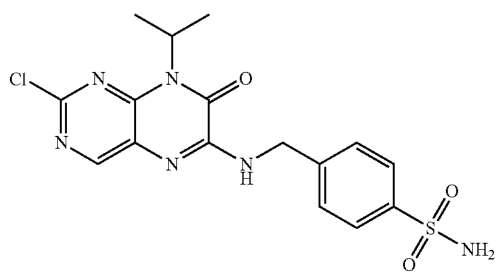 [SMILES: CC(C)n1c(=O)c(NCc2ccc(S(N)(=O)=O)cc2)nc2cnc(Cl)nc21] | 1 | 408.8 |
| AAAA | 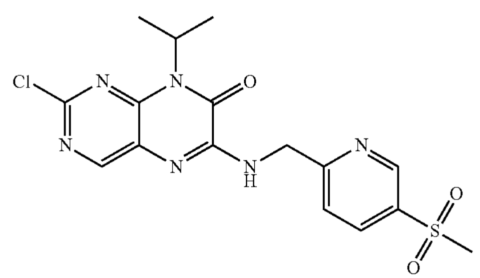 [SMILES: CC(C)n1c(=O)c(NCc2ccc(S(C)(=O)=O)cn2)nc2cnc(Cl)nc21] | 1 | 408.9 |
| BBBB | 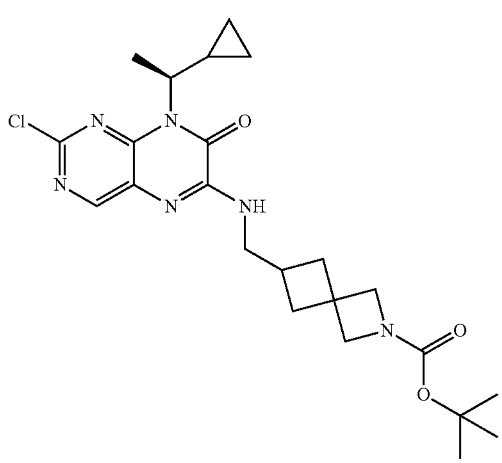 [SMILES: C[C@@H](C1CC1)n1c(=O)c(NCC2CC3(C2)CN(C(=O)OC(C)(C)C)C3)nc2cnc(Cl)nc21] | 1 | 475.0 |
| CCCC | 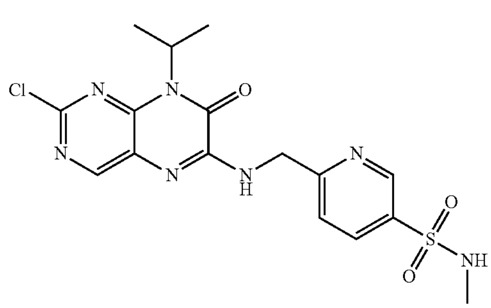 [SMILES: CNS(=O)(=O)c1ccc(CNc2nc3cnc(Cl)nc3n(C(C)C)c2=O)nc1] | 1 | 423.9 |

-continued

| Intermediate | Structure | Synthetic Method | m/z[M + H]+ |
|---|---|---|---|
| DDDD | 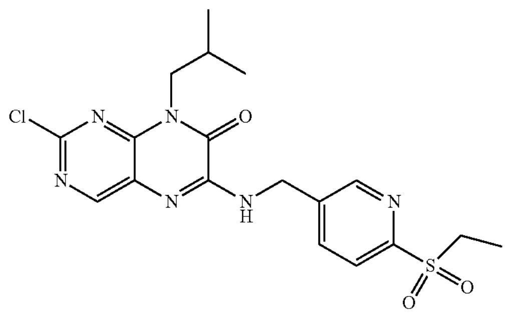 [SMILES: CCS(=O)(=O)c1ccc(CNc2nc3cnc(Cl)nc3n(CC(C)C)c2=O)cn1] | 1 | 436.9 |
| EEEE | 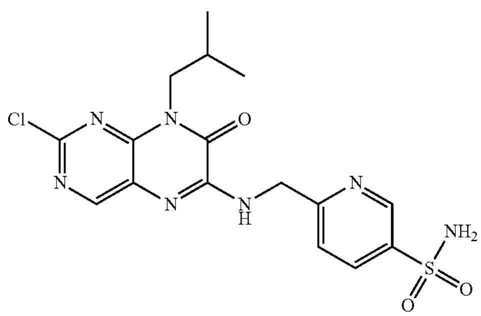 [SMILES: CC(C)Cn1c(=O)c(NCc2ccc(S(N)(=O)=O)cn2)nc2cnc(Cl)nc21] | 1 | 424.3 |
| FFFF | 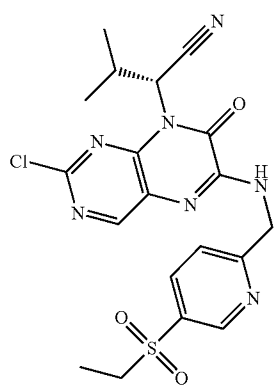 [SMILES: CCS(=O)(=O)c1ccc(CNc2nc3cnc(Cl)nc3n([C@@H](C#N)C(C)C)c2=O)nc1] | 2 | 461.9 |
| GGGG | 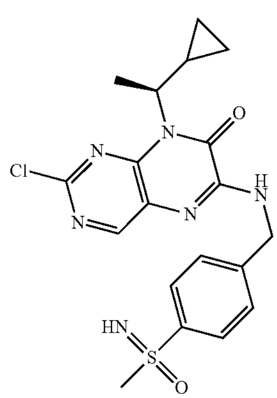 [SMILES: C[C@@H](C1CC1)n1c(=O)c(NCc2ccc(S(C)(=N)=O)cc2)nc2cnc(Cl)nc21] | 1 | 433.0 |

| Intermediate | Structure | Synthetic Method | m/z[M + H]+ |
|---|---|---|---|
| HHHH | 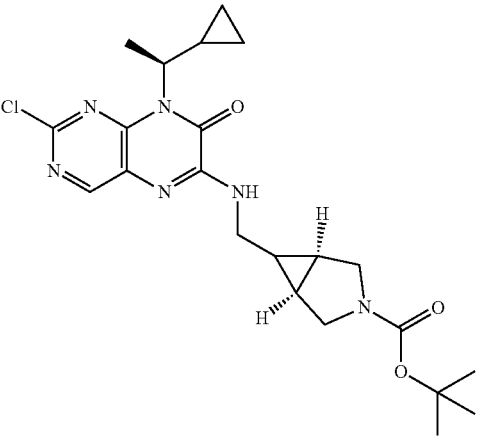 [SMILES: C[C@@H](C1CC1)n1c(=O)c(NCC2[C@H]3CN(C(=O)OC(C)(C)C)C[C@@H]23)nc2cnc(Cl)nc21] | 1 | 461.0 |
| IIII | 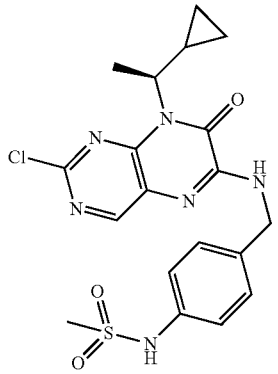 [SMILES: C[C@@H](C1CC1)n1c(=O)c(NCc2ccc(NS(C)(=O)=O)cc2)nc2cnc(Cl)nc21] | 1 | 448.9 |
| JJJJ | 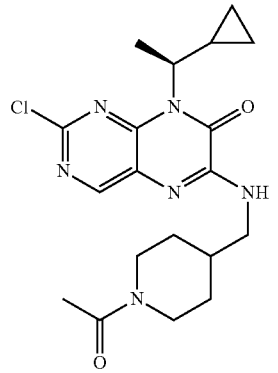 [SMILES: CC(=O)N1CCC(CNc2nc3cnc(Cl)nc3n([C@@H](C)C3CC3)c2=O)CC1] | 1 | 405.0 |
| KKKK | 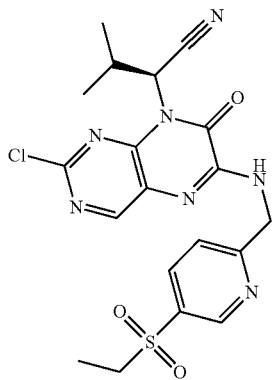 [SMILES: CCS(=O)(=O)c1ccc(CNc2nc3cnc(Cl)nc3n([C@H](C#N)C(C)C)c2=O)nc1] | 2 | 461.9 |

-continued

| Intermediate | Structure | Synthetic Method | m/z[M + H]⁺ |
|---|---|---|---|
| LLLL | 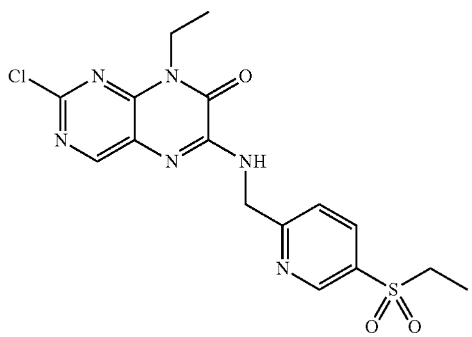 [SMILES: CCn1c(=O)c(NCc2ccc(S(=O)(=O)CC)cn2)nc2cnc(Cl)nc21] | 1 | 409.2 |
| MMMM | 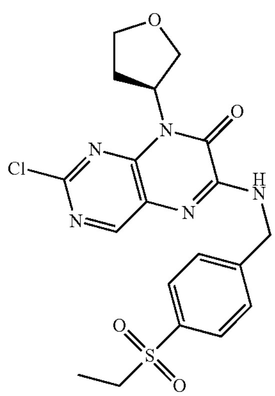 [SMILES: CCS(=O)(=O)c1ccc(CNc2nc3cnc(Cl)nc3n([C@H]3CCOC3)c2=O)cc1] | 1 | 449.9 |
| NNNN | 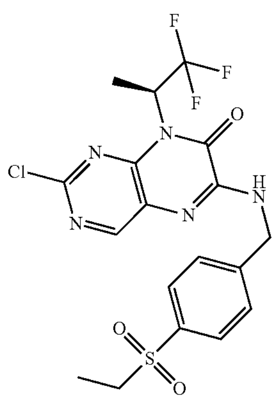 [SMILES: CCS(=O)(=O)c1ccc(CNc2nc3cnc(Cl)nc3n([C@@H](C)C(F)(F)F)c2=O)cc1] | 2 | 475.9 |
| OOOO | 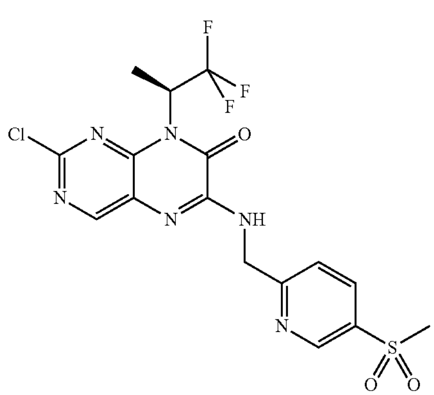 [SMILES: C[C@H](n1c(=O)c(NCc2ccc(S(C)(=O)=O)cn2)nc2cnc(Cl)nc21)C(F)(F)F] | 2 | 463.2 |

-continued

| Intermediate | Structure | Synthetic Method | m/z[M + H]+ |
|---|---|---|---|
| PPPP | 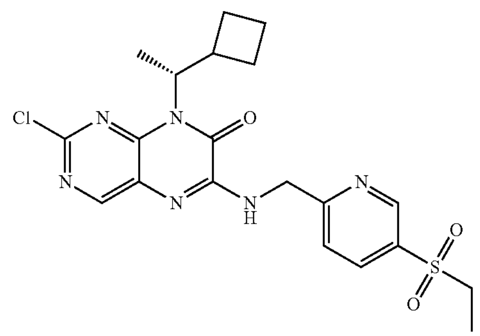 [SMILES: CCS(=O)(=O)c1ccc(CNc2nc3cnc(Cl)nc3n([C@H](C)C3CCC3)c2=O)nc1] | 1 | 463.2 |
| QQQQ | 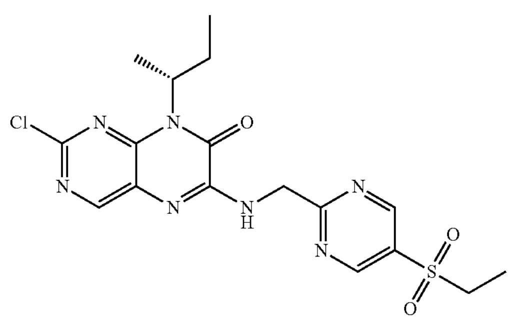 [SMILES: CC[C@@H](C)n1c(=O)c(NCc2ncc(S(=O)(=O)CC)cn2)nc2cnc(Cl)nc21] | 1 | 438.1 |
| RRRR | 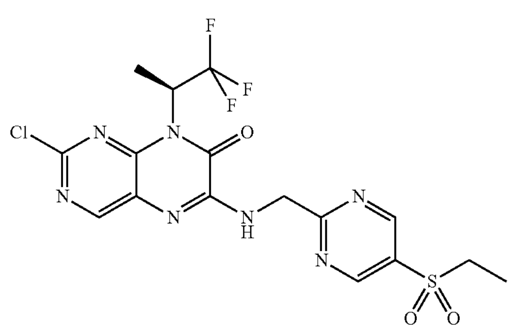 | 2 | 477.9 |
| SSSS | 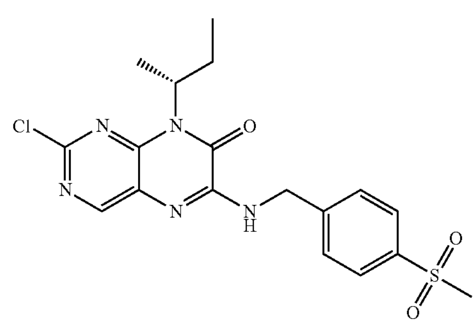 [SMILES: CC[C@@H](C)n1c(=O)c(NCc2ccc(S(C)(=O)=O)cc2)nc2cnc(Cl)nc21] | 1 | 422.1 |

-continued
| Intermediate | Structure | Synthetic Method | m/z[M + H]+ |
|---|---|---|---|
| TTTT | 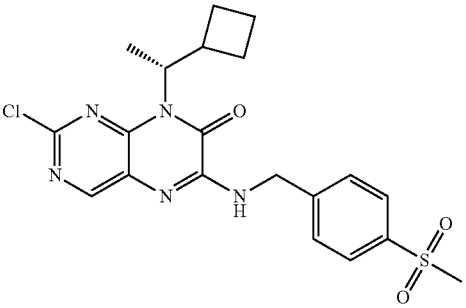 [SMILES: C[C@H](C1CCC1)n1c(=O)c(NCc2ccc(S(C)(=O)=O)cc2)nc2cnc(Cl)nc21] | 1 | 448.2 |
| UUUU | 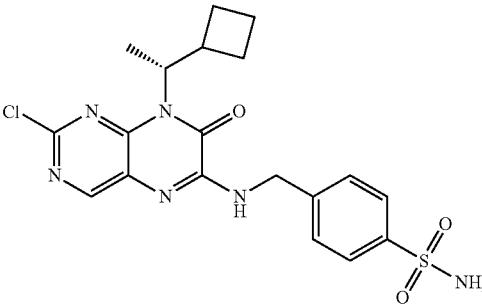 | 1 | 449.2 |
| VVVV | 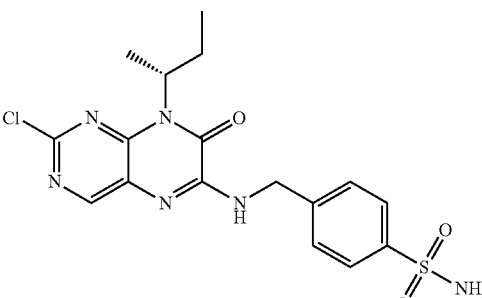 | 1 | 423.1 |
| WWWW | 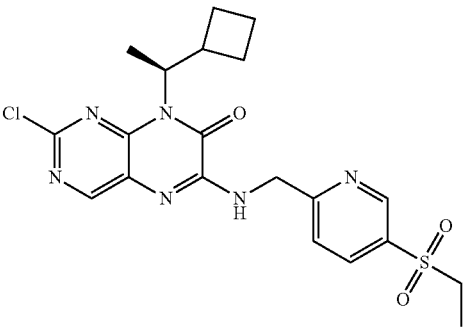 [SMILES: CCS(=O)(=O)c1ccc(CNc2nc3cnc(Cl)nc3n([C@@H](C)C3CCC3)c2=O)nc1] | 1 | 463.2 |

| Intermediate | Structure | Synthetic Method | m/z[M + H]⁺ |
|---|---|---|---|
| XXXX | 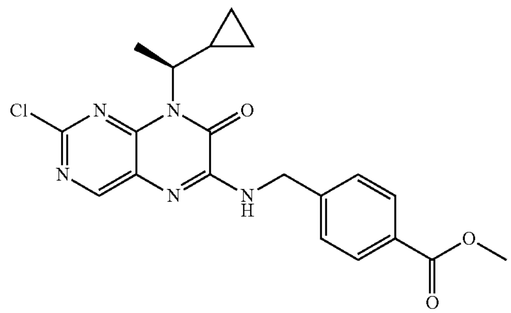 [SMILES: COC(=O)c1ccc(CNc2nc3cnc(Cl)nc3n([C@@H](C)C3CC3)c2=O)cc1] | 1 | 414.0 |
| YYYY | 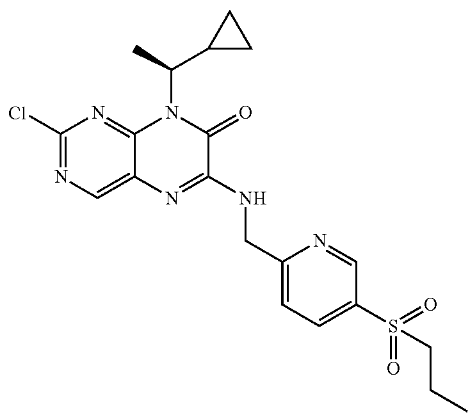 [SMILES: CCCS(=O)(=O)c1ccc(CNc2nc3cnc(Cl)nc3n([C@@H](C)C3CC3)c2=O)nc1] | 1 | 463.2 |
| ZZZZ | 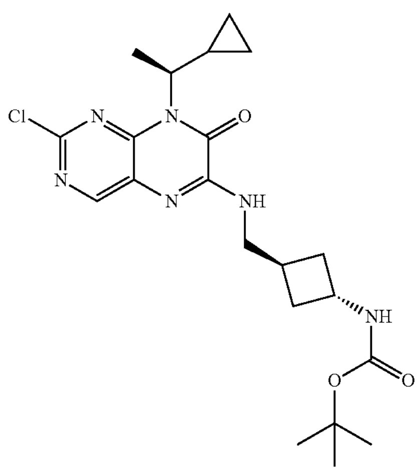 [SMILES: C[C@@H](C1CC1)n1c(=O)c(NC[C@H]2C[C@H](NC(=O)OC(C)(C)C)C2)nc2cnc(Cl)nc21] | 1 | 449.3 |
| AAAAA | 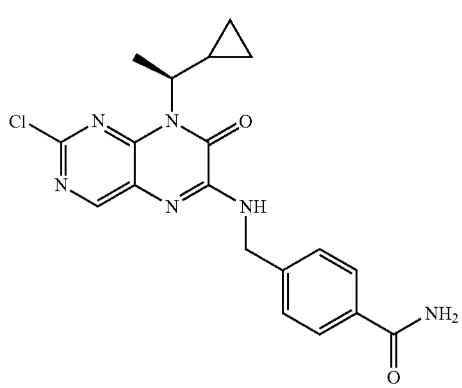 [SMILES: C[C@@H](C1CC1)n1c(=O)c(NCc2ccc(C(N)=O)cc2)nc2cnc(Cl)nc21] | 1 | 399.3 |

| Intermediate | Structure | Synthetic Method | m/z[M + H]+ |
|---|---|---|---|
| BBBBB | 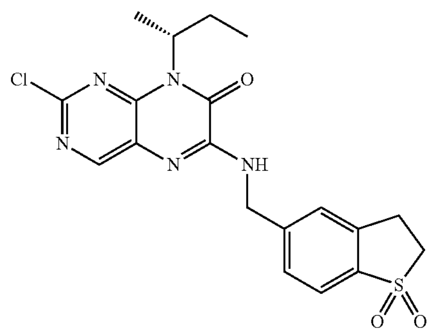 [SMILES: CC[C@@H](C)n1c(=O)c(NCc2ccc3c(c2)CCS3(=O)=O)nc2cnc(Cl)nc21] | 1 | 433.9 |
| CCCCC | 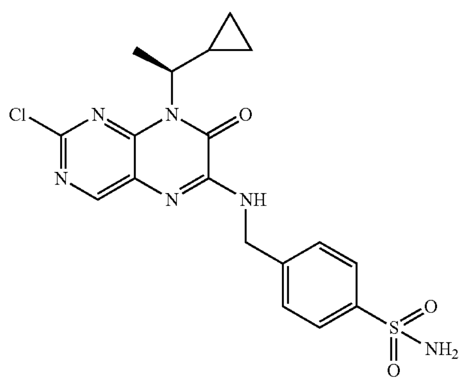 [SMILES: C[C@@H](C1CC1)n1c(=O)c(NCc2ccc(S(N)(=O)=O)cc2)nc2cnc(Cl)nc21] | 1 | 435.9 |
| DDDDD | 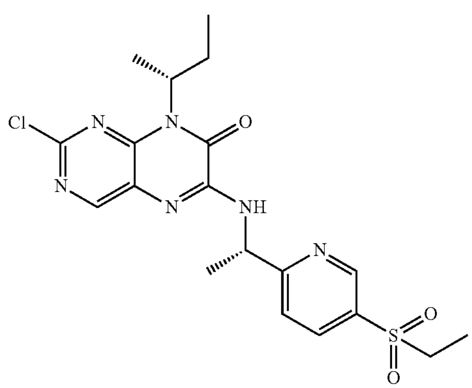 [SMILES: CC[C@@H](C)n1c(=O)c(N[C@@H](C)c2ccc(S(=O)(=O)CC)cn2)nc2cnc(Cl)nc21] | 1 | 451.0 |
| EEEEE | 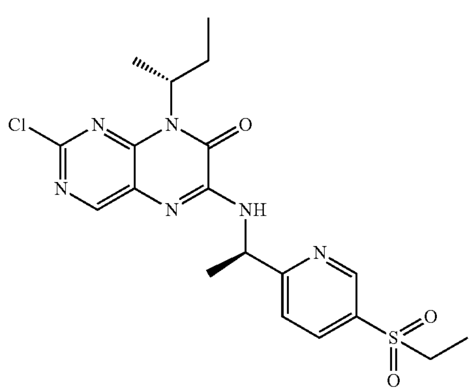 [SMILES: CC[C@@H](C)n1c(=O)c(N[C@H](C)c2ccc(S(=O)(=O)CC)cn2)nc2cnc(Cl)nc21] | 1 | 451.0 |

| Intermediate | Structure | Synthetic Method | m/z[M + H]+ |
|---|---|---|---|
| FFFFF | 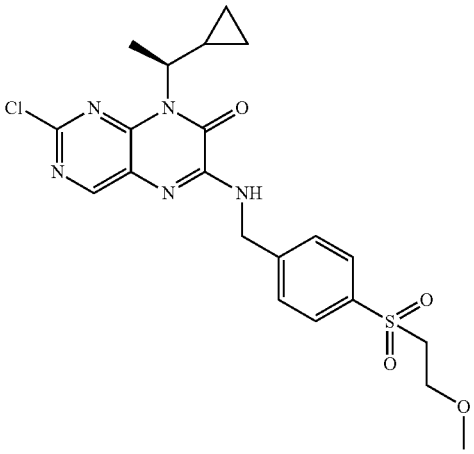 [SMILES: COCCS(=O)(=O)c1ccc(CNc2nc3cnc(Cl)nc3n([C@@H](C)C3CC3)c2=O)cc1] | 1 | 477.9 |
| GGGGG | 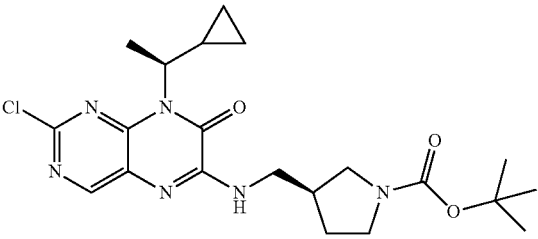 [SMILES: C[C@@H](C1CC1)n1c(=O)c(NC[C@@H]2CCN(C(=O)OC(C)(C)C)C2)nc2cnc(Cl)nc21] | 1 | 449.0 |
| HHHHH | 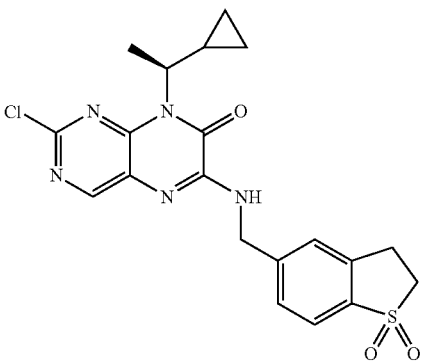 [SMILES: C[C@@H](C1CC1)n1c(=O)c(NCc2ccc3c(c2)CCS3(=O)=O)nc2cnc(Cl)nc21] | 1 | 446.0 |
| IIIII | 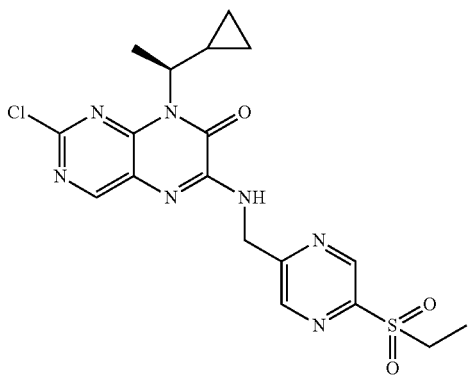 [SMILES: CCS(=O)(=O)c1cnc(CNc2nc3cnc(Cl)nc3n([C@@H](C)C3CC3)c2=O)cn1] | 1 | 450.0 |

| Intermediate | Structure | Synthetic Method | m/z[M + H]+ |
|---|---|---|---|
| JJJJJ | 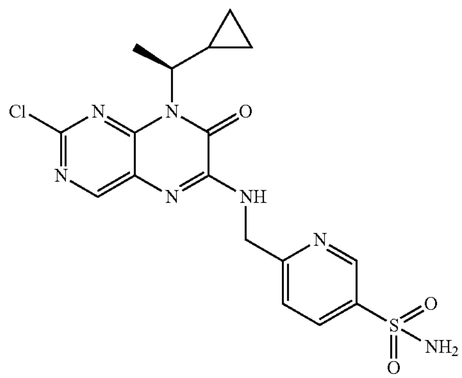 [SMILES: C[C@@H](C1CC1)n1c(=O)c(NCc2ccc(S(N)(=O)=O)cn2)nc2cnc(Cl)nc21] | 1 | 435.9 |
| KKKKK | 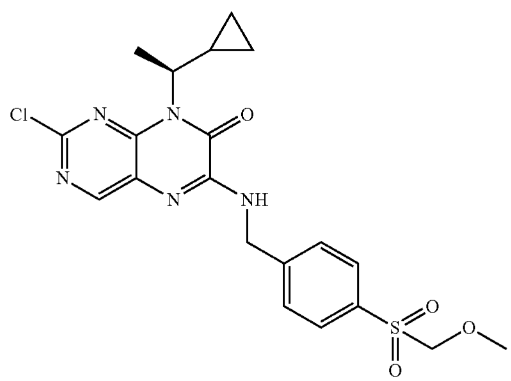 [SMILES: COCS(=O)(=O)c1ccc(CNc2nc3cnc(Cl)nc3n([C@@H](C)C3CC3)c2=O)cc1] | 1 | 464.0 |
| LLLLL | 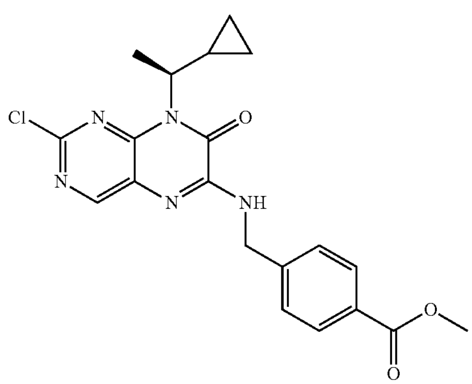 [SMILES: COC(=O)c1ccc(CNc2nc3cnc(Cl)nc3n([C@@H](C)C3CC3)c2=O)cc1] | 1 | 414.0 |
| MMMMM | 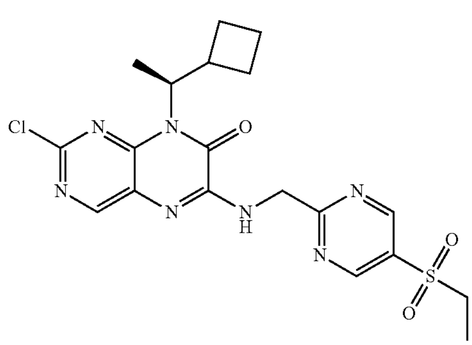 [SMILES: CCS(=O)(=O)c1cnc(CNc2nc3cnc(Cl)nc3n([C@@H](C)C3CCC3)c2=O)nc1] | 1 | 464.3 |

-continued

| Intermediate | Structure | Synthetic Method | m/z[M + H]⁺ |
|---|---|---|---|
| NNNNN | 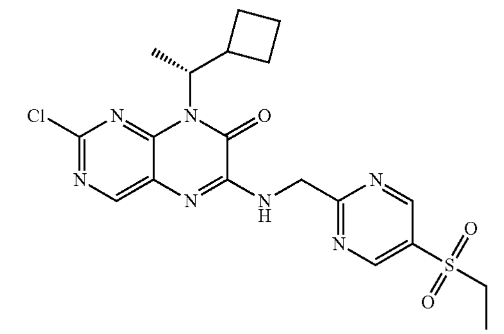 [SMILES: CCS(=O)(=O)c1cnc(CNc2nc3cnc(Cl)nc3n([C@H](C)C3CCC3)c2=O)nc1] | 1 | 464.3 |
| OOOOO | 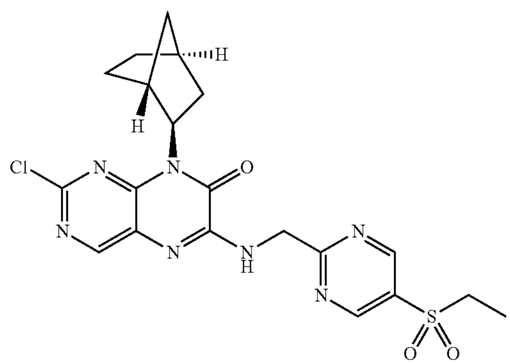 [SMILES: CCS(=O)(=O)c1cnc(CNc2nc3cnc(Cl)nc3n([C@@H]3C[C@H]4CC[C@@H]3C4)c2=O)nc1] | 1 | 475.2 |
| PPPPP | 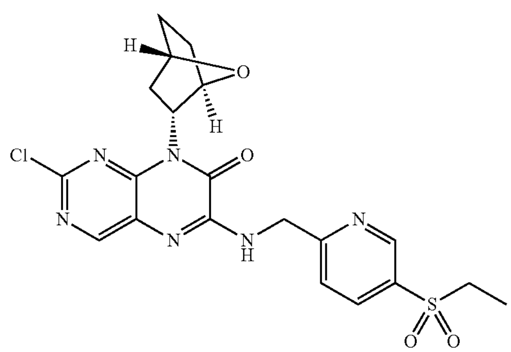 [SMILES: CCS(=O)(=O)c1ccc(CNc2nc3cnc(Cl)nc3n([C@@H]3C[C@@H]4CC[C@H]3O4)c2=O)nc1] | 1 | 477.3 |
| QQQQQ | 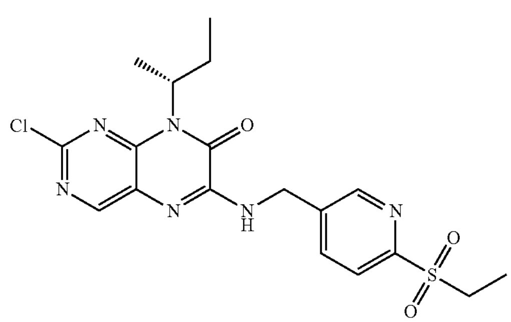 [SMILES: CC[C@@H](C)n1c(=O)c(NCc2ccc(S(=O)(=O)CC)nc2)nc2cnc(Cl)nc21] | 1 | 437.2 |

-continued

| Intermediate | Structure | Synthetic Method | m/z[M + H]+ |
|---|---|---|---|
| RRRRR | 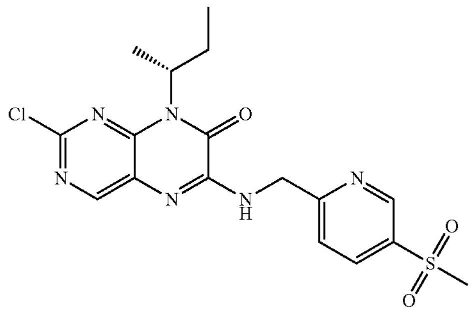 [SMILES: CC[C@@H](C)n1c(=O)c(NCc2ccc(S(C)(=O)=O)cn2)nc2cnc(Cl)nc21] | 1 | 423.2 |
| SSSSS | 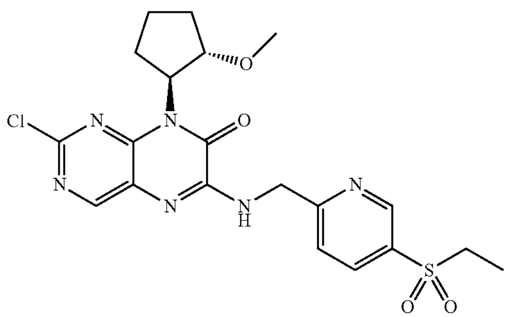 [SMILES: CCS(=O)(=O)c1ccc(CNc2nc3cnc(Cl)nc3n([C@H]3CCC[C@@H]3OC)c2=O)nc1] | 1 | 479.3 |
| TTTTT | 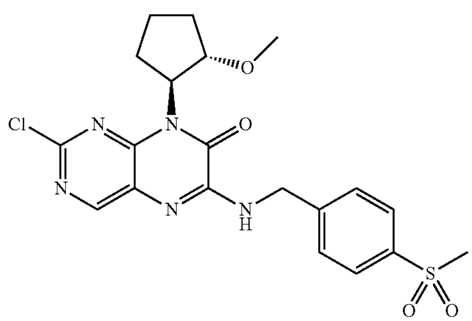 [SMILES: CO[C@H]1CCC[C@@H]1n1c(=O)c(NCc2ccc(S(C)(=O)=O)cc2)nc2cnc(Cl)nc21] | 1 | 464.1 |
| UUUUU | 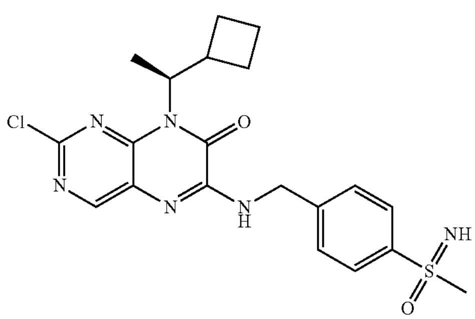 [SMILES: C[C@@H](C1CCC1)n1c(=O)c(NCc2ccc(S(C)(=N)=O)cc2)nc2cnc(Cl)nc21] | 1 | 447.3 |
| VVVVV | 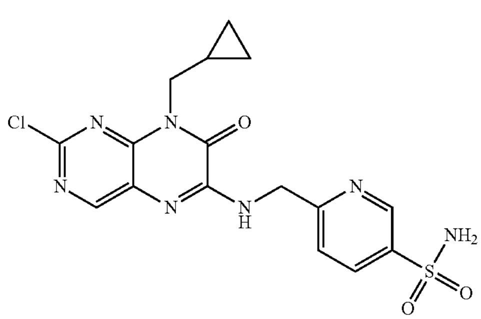 [SMILES: NS(=O)(=O)c1ccc(CNc2nc3cnc(Cl)nc3n(CC3CC3)c2=O)nc1] | 1 | 422.2 |

| Intermediate | Structure | Synthetic Method | m/z[M + H]+ |
|---|---|---|---|
| WWWWW | 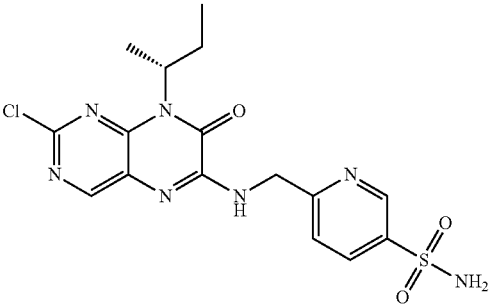 [SMILES: CC[C@@H](C)n1c(=O)c(NCc2ccc(S(N)(=O)=O)cn2)nc2cnc(Cl)nc21] | 1 | 424.1 |
| XXXXX | 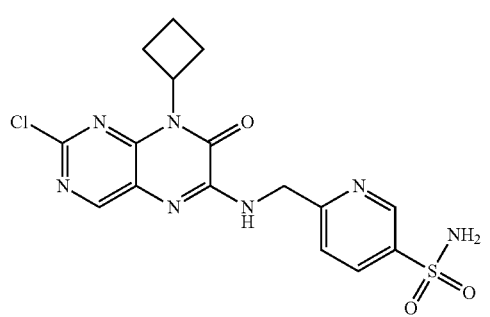 [SMILES: NS(=O)(=O)c1ccc(CNc2nc3cnc(Cl)nc3n(C3CCC3)c2=O)nc1] | 1 | 422.2 |
| YYYYY | 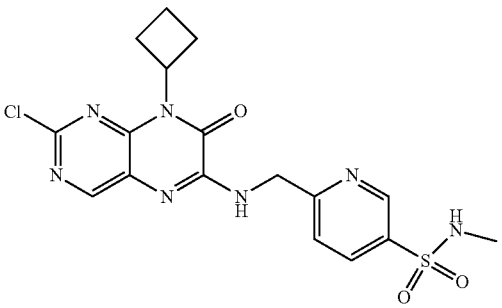 [SMILES: CNS(=O)(=O)c1ccc(CNc2nc3cnc(Cl)nc3n(C3CCC3)c2=O)nc1] | 1 | 436.3 |
| ZZZZZ | 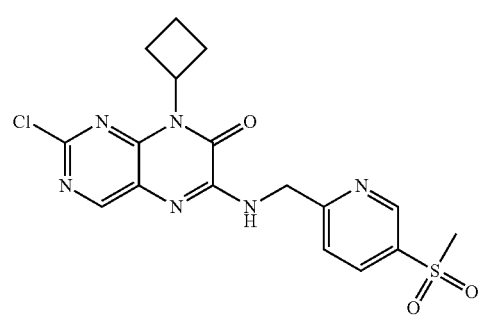 [SMILES: CS(=O)(=O)c1ccc(CNc2nc3cnc(Cl)nc3n(C3CCC3)c2=O)nc1] | 1 | 421.2 |
| AAAAAA | 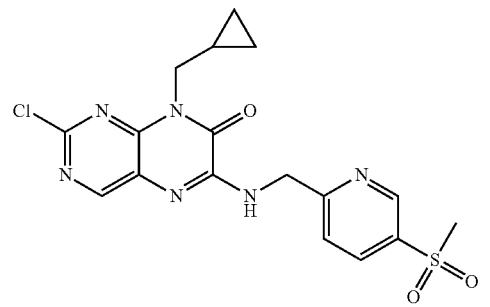 [SMILES: CS(=O)(=O)c1ccc(CNc2nc3cnc(Cl)nc3n(CC3CC3)c2=O)nc1] | 1 | 421.2 |

-continued
| Intermediate | Structure | Synthetic Method | m/z[M + H]+ |
|---|---|---|---|
| BBBBBB | 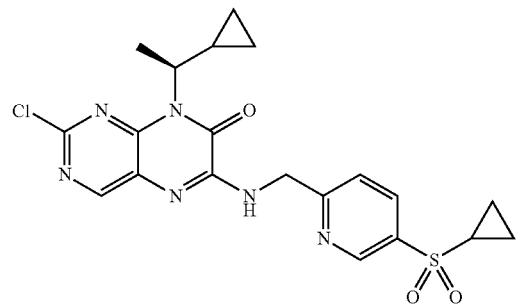 [SMILES: C[C@@H](C1CC1)n1c(=O)c(NCc2ccc(S(=O)(=O)C3CC3)cn2)nc2cnc(Cl)nc21] | 1 | 461.3 |
| CCCCCC | 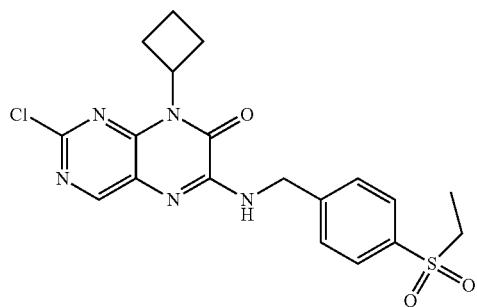 [SMILES: CCS(=O)(=O)c1ccc(CNc2nc3cnc(Cl)nc3n(C3CCC3)c2=O)cc1] | 1 | 434.3 |
| DDDDDD | 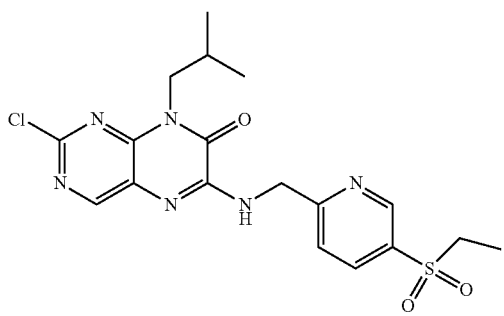 [SMILES: CCS(=O)(=O)c1ccc(CNc2nc3cnc(Cl)nc3n(CC(C)C)c2=O)nc1] | 1 | 437.3 |
| EEEEEE | 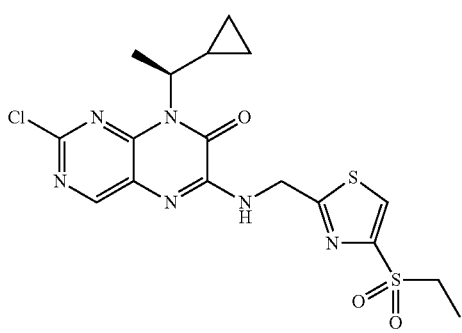 [SMILES: CCS(=O)(=O)c1csc(CNc2nc3cnc(Cl)nc3n([C@@H](C)C3CC3)c2=O)n1] | 1 | 455.3 |

| Intermediate | Structure | Synthetic Method | m/z[M + H]+ |
|---|---|---|---|
| FFFFFF | 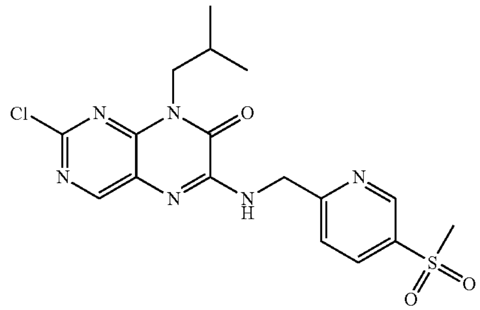 [SMILES: CC(C)Cn1c(=O)c(NCc2ccc(S(C)(=O)=O)cn2)nc2cnc(Cl)nc21] | 1 | 423.3 |
| GGGGGG | 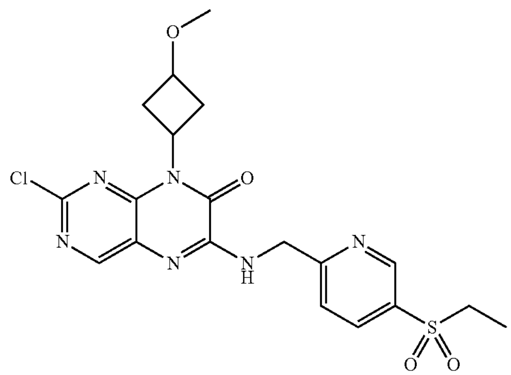 [SMILES: CCS(=O)(=O)c1ccc(CNc2nc3cnc(Cl)nc3n(C3CC(OC)C3)c2=O)nc1] | 1 | 465.1 |
| HHHHHH | 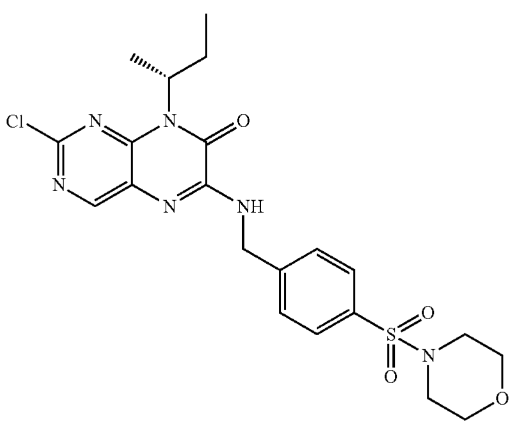 [SMILES: CC[C@@H](C)n1c(=O)c(NCc2ccc(S(=O)(=O)N3CCOCC3)cc2)nc2cnc(Cl)nc21] | 1 | 493.2 |

Method 3:

Synthesis of Intermediate AB

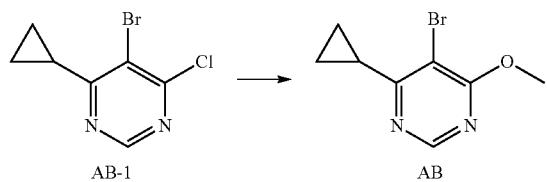

To a solution of AB-1 (300 mg, 1.29 mmol) in anhydrous MeOH (15 mL) is added NaOMe (208 mg, 3.86 mmol). The mixture is stirred at rt for 1 h. The solution is filtered and concentrated. The residue is purified by $SiO_2$ flash chromatography to yield intermediate AB. MS (ES+): m/z 230.8 $[M+H]^+$.

Method 4:

Synthesis of Intermediate AC

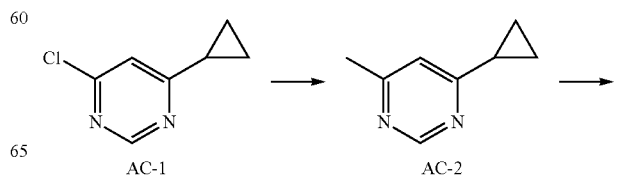

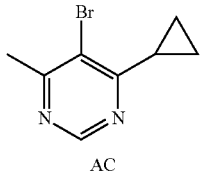

AC

To a solution of AC-1 (320 mg, 2.07 mmol), 2,4,6-trimethyl-1,3,5,2,4,6-trioxatriborinane (520 mg, 4.14 mmol), and aq Na$_2$CO$_3$ (2M, 3.1 mL, 6.21 mmol) in dioxane (10 mL) is added dichloropalladium 4-ditert-butylphosphanyl-N,N-dimethyl-aniline (73 mg, 0.10 mmol). The mixture is heated to 130° C. for 40 min in a microwave reactor. The mixture is diluted with MeOH (5 mL), filtered and concentrated. The residue is purified by SiO$_2$ flash chromatography to yield AC-2.

To a solution of AC-2 (363 mg, 2.71 mmol) in EtOH (10 mL) at −10° C. is added Br$_2$ (432 mg, 2.71 mmol). The reaction mixture is stirred at rt for 18 h. The solution is concentrated and the residue is purified by SiO$_2$ flash chromatography to yield intermediate AC. MS (ES+): m/z 214.3 [M+H]$^+$.

Method 5:
Synthesis of Intermediate AD

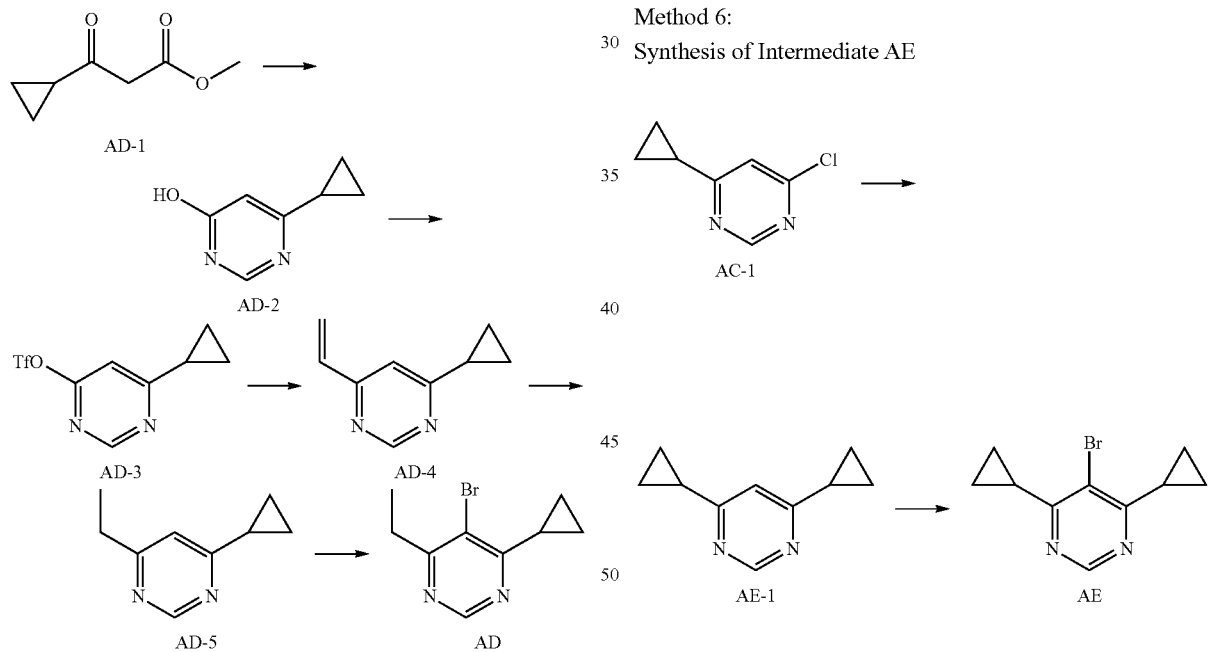

A mixture of AD-1 (100.0 g, 0.70 mol), formamidine acetate (146 g, 1.4 mol) and NaOMe (266.0 g, 4.9 mol) in MeOH (2 L) is stirred at 16° C. for 2 days. The reaction mixture is neutralized to pH 7 with acetic acid and filtered. The filtrate is concentrated under reduced pressure and the crude product is purified by SiO$_2$ flash chromatography to yield AD-2.

To a stirred solution of AD-2 (66.0 g, 0.48 mol) and TEA (145.1 g, 1.44 mol) in DCM (1.5 L) at 0° C. is added, dropwise, a solution of Tf$_2$O (164.2 g, 0.58 mol) in DCM (500 mL) and stirred for 3 h. The reaction mixture is quenched by the addition of H$_2$O (200 mL) and extracted with DCM (3×500 mL). The combined organic phase is washed with saturated aq NaHCO$_3$, dried (Na$_2$SO$_4$), decanted and concentrated. The resultant residue is purified by SiO$_2$ flash chromatography to yield AD-3.

A mixture of AD-3 (17.0 g, 0.06 mol), vinylboronic acid pinacolester (29.3 g, 0.09 mol), K$_2$CO$_3$ (26.3 g, 0.19 mol), Ag$_2$O (1.7 g, 10% wt) and Pd(dppf)Cl$_2$ (1.7 g, 10% wt) in anhydrous THF (400 mL) is stirred at reflux under N$_2$ atmosphere for 18 h. The mixture is cooled to rt and filtered. The filtrate is concentrated under reduced pressure and the resultant residue is purified by SiO$_2$ flash chromatography to yield AD-4.

A mixture of AD-4 (27.3 g, 0.28 mol) and RaNi (30.0 g, 10% wt) in EtOH (500 mL) is stirred under an H$_2$ atmosphere for 16 h. The vessel is purged with N$_2$ and the contents filtered. The filtrate is concentrated under reduced pressure and the resultant AD-5 (19.6 g) is used directly.

To a stirred solution of AD-5 (19.6 g, 0.13 mol) in EtOH (300 mL) at −10° C. is added Br$_2$ (52.9 g, 0.33 mol). Following the addition, the mixture is stirred at rt for 30 min. The reaction mixture is quenched by the addition of 10% Na$_2$S$_2$O$_{3(aq)}$ solution and basified by the addition of 10% Na$_2$CO$_{3(aq)}$ solution to adjust to ~pH 8. The mixture is extracted with EtOAc (3×200 mL). The organic layers are combined, dried (Na$_2$SO$_4$), decanted and concentrated. The resultant residue is purified by SiO$_2$ flash chromatography to yield intermediate AD. MS (ES+): m/z 228.9 [M+H]$^+$.

Method 6:
Synthesis of Intermediate AE

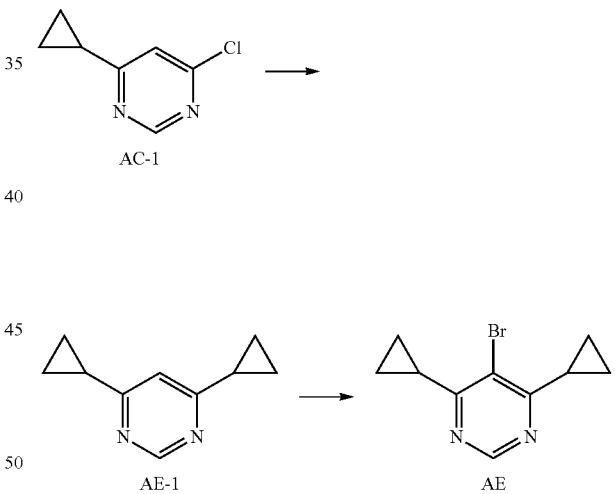

To a solution of AC-1 (2.50 g, 16.17 mmol), cyclopropylboronic acid (4.17 g, 48.51 mmol) and Na$_2$CO$_3$ (aq) (2M, 24.26 mL, 48.51 mmol) in dioxane (30 mL) is added bis(di-tert-butyl(4-dimethylaminophenyl)phosphine)dichloropalladium(II) (572.5 mg, 0.81 mmol). The vessel is sealed and heated to 130° C. for 2 h. The vessel is cooled to rt, diluted with MeOH and filtered. The filtrate is concentrated and purified by SiO$_2$ flash chromatography to yield AE-1.

To a solution of AE-1 (660 mg, 4.12 mmol) in EtOH (15 mL) at −10° C. is added Br$_2$ (658 mg, 4.12 mmol). The reaction is stirred at rt for 3 h. NH$_3$ in MeOH solution (2N, 1 mL) is added to neutralize. The mixture is concentrated and purified by SiO$_2$ flash chromatography to yield intermediate AE. MS (ES+): m/z 240.9 [M+H]$^+$.

Method 7:
Synthesis of Intermediate AF

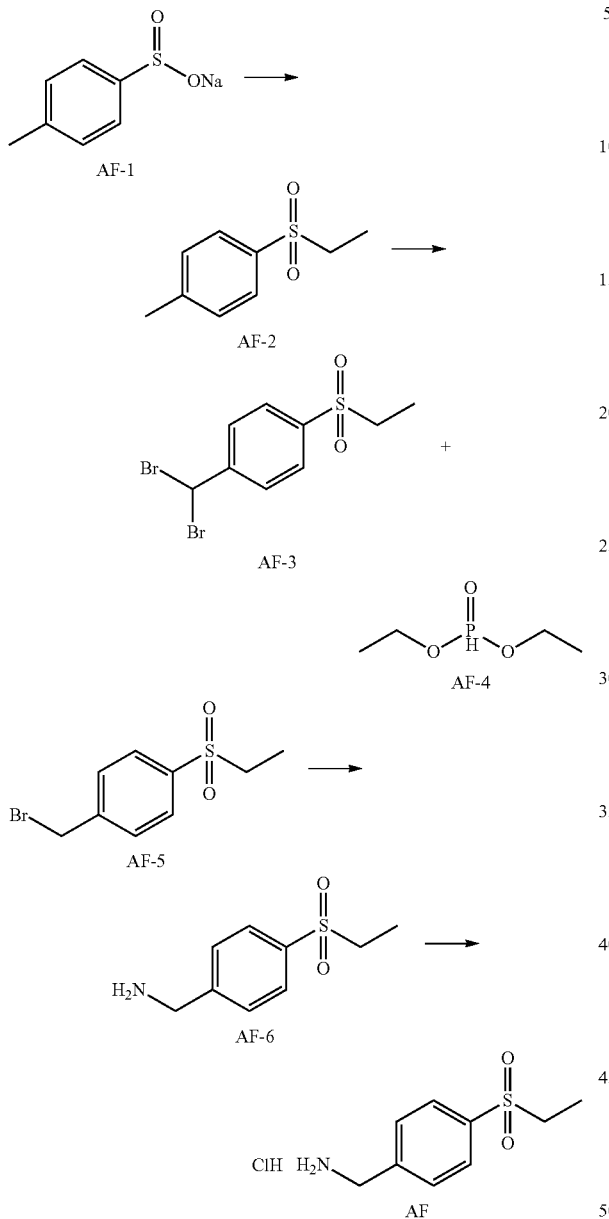

Method 8:
Synthesis of Intermediate AG

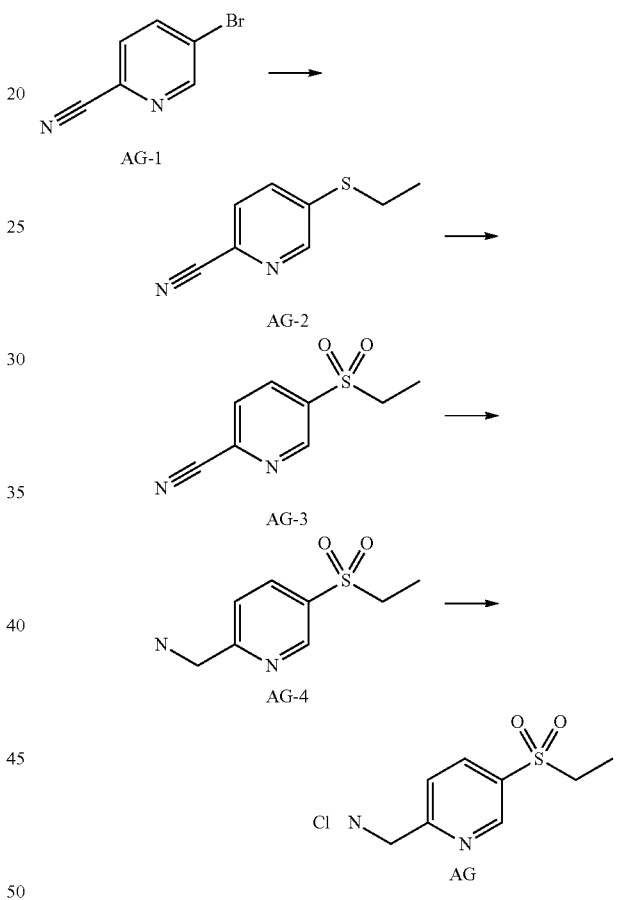

A mixture of AF-1 (100 g, 561 mmol), EtI (131 g, 842 mmol) and TBAB (18 g, 56 mmol) in H₂O (200 mL), acetone (150 mL) and toluene (150 mL) is stirred in a sealed vessel at 80° C. for 18 h. The mixture is partitioned between H₂O and EtOAc. The organic layer is dried and concentrated. The residue is purified by SiO₂ flash chromatography to yield AF-2.

A mixture of AF-2 (200 g, 1.09 mol), NBS (425.02 g, 2.39 mol) and AIBN (17.82 g, 108.54 mmol) in CCl₄ (1.40 L) is refluxed for 18 h. The mixture is partitioned between H₂O and DCM. The organic layer is dried (Na₂SO₄), decanted and concentrated to yield AF-3.

To a solution of AF-3 (333 g, 974 mmol) and DIEA (129 g, 1 mol) in ACN (500 mL) at 0° C. is added AF-4 (138 g, 1 mol) in ACN (150 mL) dropwise. The mixture is stirred for 5 h then concentrated. The resultant residue is crystallized from MeOH to yield AF-5.

A solution of AF-5 (50 g, 190 mmol) in MeOH (200 mL) is added into a solution of NH₃ in MeOH (2N, 800 mL) at −78° C. The reaction mixture is stirred at rt for 18 h then concentrated. The resultant residue is crystallized from EtOAc to afford AF-6.

A solution of AF-6 (50 g, 250 mmol) in HCl in MeOH (1N, 250 mL) is stirred at rt for 12 h then concentrated to yield intermediate AF as the HCl salt. MS (ES+): m/z 200.4 [M+H]⁺.

A mixture of AG-1 (8.0 g, 43.96 mmol), K₂CO₃ (7.88 g, 57.1 mmol) and sodium ethanethiolate (4.06 g, 48.3 mmol) in NMP (60.0 mL) under N₂ is stirred at rt for 18 h. The reaction mixture is poured into H₂O and filtered. The solids are washed with H₂O and dried under vacuum to yield AG-2.

To a suspension of AG-2 (6.0 g, 36.6 mmol) in AcOH (2.63 g, 43.8 mmol) is added a solution of KMnO₄ (5.78 g, 36.6 mmol) in H₂O (20.0 mL) dropwise. The reaction mixture is stirred at rt for 15 h. The mixture is diluted with water and extracted with EtOAc. The organic layer is dried (Na₂SO₄), decanted and concentrated. The resultant residue is purified by SiO₂ flash chromatography to yield AG-3.

A solution of AG-3 (3.3 g, 16.8 mmol) and Pd/C (500 mg, 10% on carbon catalyst) in MeOH (30 mL) is stirred at rt under H₂ (50 psi) for 8 h. The vessel is purged with N₂, filtered and the filtrate concentrated to yield AG-4.

To a stirred solution of AG-4 (2.5 g, 12.5 mmol) in EtOAc (30 mL) is added HCl in EtOAc (2N, 20.0 mL). The solution is stirred at rt for 5 h and then filtered to yield intermediate AG. MS (ES+): m/z 201.2 [M+H]$^+$.

Method 9:
Synthesis of Intermediate AH

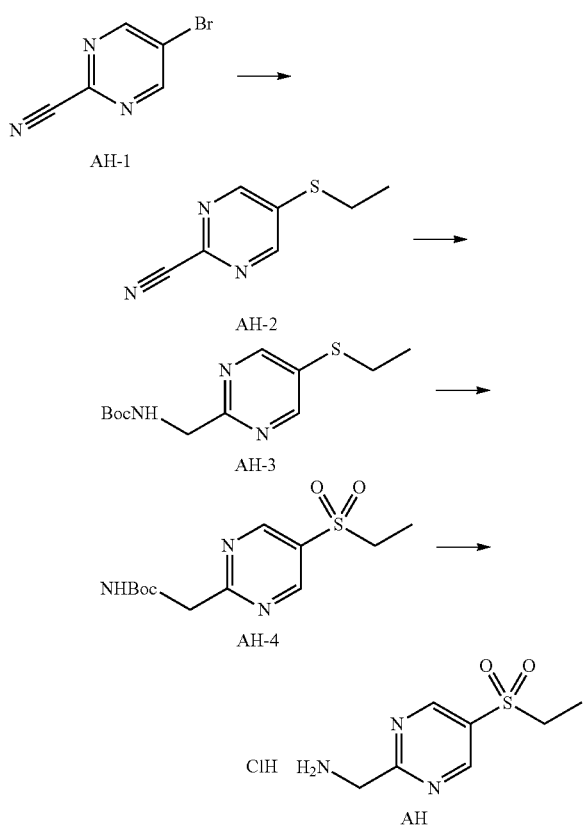

A mixture of AH-1 (113 g, 0.62 mol), $K_2CO_3$ (171 g, 1.24 mol) and sodium ethanethiolate (67 g, 0.80 mol) in DMF (2 L) is stirred at rt under $N_2$ for 18 h. The mixture is diluted with $H_2O$ and extracted with EtOAc. The organic layers are dried ($Na_2SO_4$), decanted and concentrated. The resultant residue is purified by $SiO_2$ flash chromatography to yield AH-2.

A solution of AH-2 (20.0 g, 0.12 mol), RaNi (40 g), $Boc_2O$ (31.7 g, 0.14 mol) and TEA (24.5 g, 0.24 mol) in THF (600 mL) is stirred at rt under $H_2$ (50 psi) for 12 h. The mixture is filtered and the filtrate concentrated under reduced pressure. The resultant residue is purified by $SiO_2$ flash chromatography to yield AH-3.

To a suspension of AH-3 (65 g, 0.24 mol) in AcOH (200 mL) at $-10°$ C. is added dropwise a solution of $KMnO_4$ (45.8 g, 0.29 mL) in water (500 mL). Following complete addition, the reaction mixture is stirred at rt for 30 min. The mixture is diluted with $H_2O$ and basified by addition of aqueous $Na_2CO_3$ to ~pH 8 and extracted with EtOAc. The combined organic layers are dried ($Na_2SO_4$), decanted, and concentrated. The resultant residue is purified by crystallization to yield AH-4.

To a stirred solution of compound AH-4 (46.5 g, 0.15 mol) in MeOH (300 mL) is added 4M HCl in MeOH (300 mL) at rt and stirred for 15 h. The mixture is concentrated under reduced pressure. The resultant residue is purified by crystallization to yield intermediate AH. MS (ES+): m/z 202.1 [M+H]$^+$.

Method 10:
Synthesis of Intermediate AI

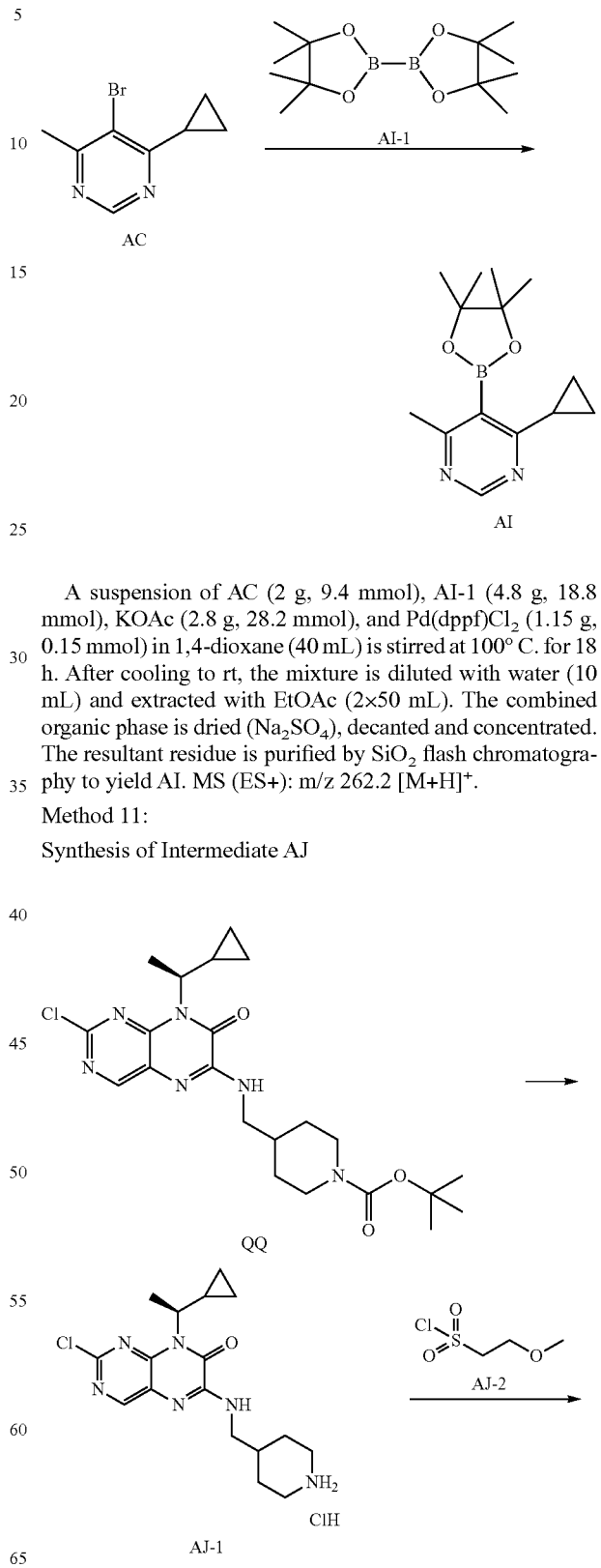

A suspension of AC (2 g, 9.4 mmol), AI-1 (4.8 g, 18.8 mmol), KOAc (2.8 g, 28.2 mmol), and Pd(dppf)Cl$_2$ (1.15 g, 0.15 mmol) in 1,4-dioxane (40 mL) is stirred at 100° C. for 18 h. After cooling to rt, the mixture is diluted with water (10 mL) and extracted with EtOAc (2×50 mL). The combined organic phase is dried ($Na_2SO_4$), decanted and concentrated. The resultant residue is purified by $SiO_2$ flash chromatography to yield AI. MS (ES+): m/z 262.2 [M+H]$^+$.

Method 11:
Synthesis of Intermediate AJ

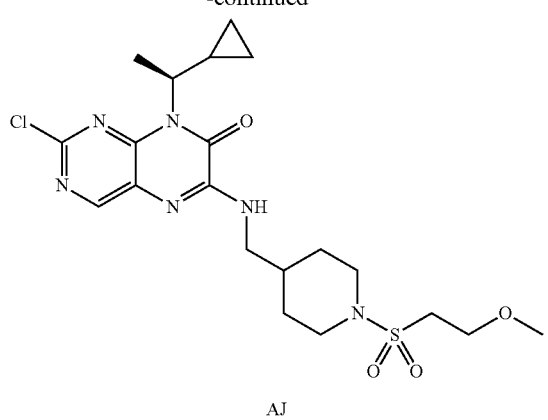

AJ

To a solution of QQ (509 mg, 1.1 mmol) in MeOH (4 mL) is added HCl in dioxane (4N, 1.1 mL, 4.4 mmol). The reaction mixture is stirred at rt for 18 h. The mixture is concentrated under reduced pressure. The resultant residue is triturated with diethyl ether and filtered to yield intermediate AJ-1.

To a solution of AJ-1 (200 mg, 0.55 mmol) in DCM (3 mL) is added TEA (0.77 mL, 5.51 mmol), followed by AJ-2 (175 mg, 1.10 mmol). The reaction mixture is stirred at rt for 1 h, then diluted with water (5 mL) and extracted with EtOAc (20 mL). The organic layer is dried ($Na_2SO_4$), decanted and concentrated. The resultant residue is purified by $SiO_2$ flash chromatography to yield intermediate AJ. MS (ES+): m/z 485.0 $[M+H]^+$.

Method 12:
Synthesis of Intermediate AK

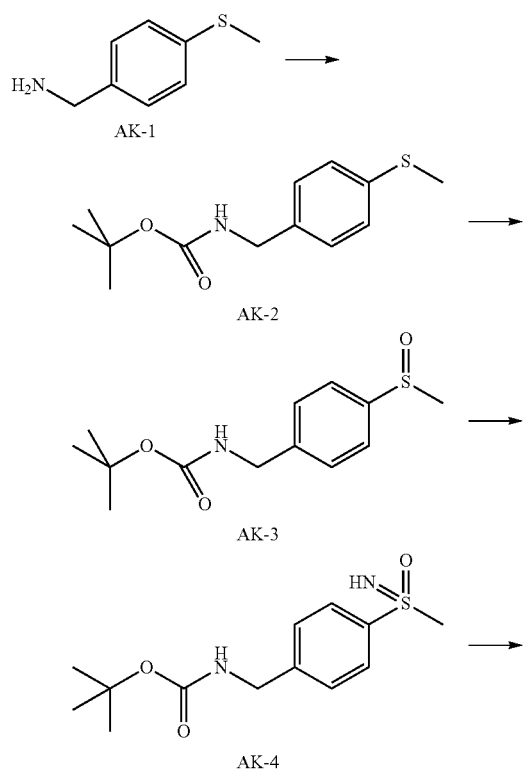

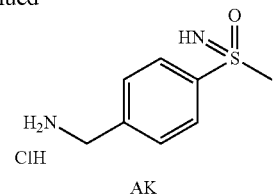

AK

To a solution of AK-1 (2.00 g, 13.1 mmol) in THF (25 mL) is added $Boc_2O$ (3.45 mL, 15.0 mmol) and TEA (3.64 mL, 26.1 mmol). The reaction mixture is stirred at rt for 18 h and then diluted with $H_2O$ and extracted with EtOAc. The organic layers are concentrated to yield AK-2.

To solution of AK-2 (3.3 g, 13.1 mmol) in AcOH (10 mL) is slowly added $H_2O_2$ (1.37 mL, 13.7 mmol). The reaction mixture is stirred at rt for 3 h and is then quenched with saturated $Na_2SO_{3(aq)}$ and neutralized with 1N $NaOH_{(aq)}$. The mixture is extracted with EtOAc and concentrated to yield AK-3.

A mixture of AK-3 (1.0 g, 3.7 mmol), MgO (600 mg, 14.9 mmol), trifluoroacetamide (839 mg, 7.4 mmol), and Rh(II) acetate dimer (115 mg, 0.26 mmol) in DCM (10 mL) is added (diacetoxyiodo)benzene (1.79 g, 5.6 mmol). The mixture is stirred at rt for 18 h and then concentrated under reduced pressure. The resultant residue is dissolved in MeOH, filtered through a pad of diatomaceous earth and to it, $K_2CO_3$ (2.55 g, 18.6 mmol) is added. The mixture is stirred at rt for 18 h and is concentrated under reduced pressure. The resultant residue is purified by $SiO_2$ flash chromatography to yield AK-4.

To a stirred solution of compound AK-4 (585 mg, 2.1 mmol) in DCM (2 mL) is added HCl in dioxane (4N, 2 mL). The reaction mixture is stirred at rt for 15 h and then concentrated under reduced pressure to yield intermediate AK. MS (ES+): m/z 185.0 $[M+H]^+$.

Method 13:
Synthesis of Intermediate AL

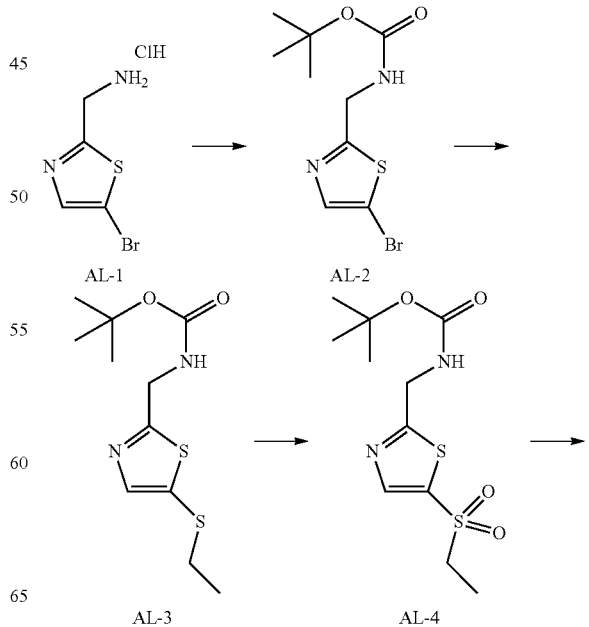

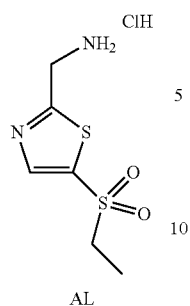

To a solution of AL-1 (500 mg, 2.18 mmol) in ACN (12 mL) is added DIEA (0.46 mL, 2.61 mmol), Boc$_2$O (1.02 g, 4.68 mmol), followed by DMAP (13.3 mg, 0.11 mmol). The reaction mixture is stirred at rt for 2.5 h. The reaction mixture is concentrated and the residue is diluted with EtOAc and washed with H$_2$O then brine, dried over Na$_2$SO$_4$, filtered and concentrated. The residue is purified by SiO$_2$ flash chromatography to yield AL-2.

A mixture of AL-2 (250 mg, 0.85 mmol), Pd$_2$(dba)$_3$ (39 mg, 0.043 mmol) Xanphos (41 mg, 0.071 mmol), Josiphos (13 mg, 0.024 mmol) and TEA (0.83 mL, 0.97 mmol) in toluene (17 mL) is degassed and heated to 115° C. for 1 h. The reaction mixture is then cooled to rt and ethanethiol (0.076 mL, 1.02 mmol) is added. The reaction mixture is heated to 115° C. for 3 h. The reaction mixture is concentrated and the residue is purified by SiO$_2$ flash chromatography to yield AL-3.

To a solution of AL-3 (200 mg, 0.71 mmol) in acetone (14 mL) is added a solution of oxone (961 mg, 1.56 mmol) in water (7 mL). The reaction mixture is stirred at rt ofor 18 h.

The mixture is concentrated then diluted with H$_2$O and extracted with DCM twice. The organics are combined and washed with brine, dried over Na$_2$SO$_4$, filtered and concentrated to yield AL-4.

To a solution of AL-4 (206 mg, 0.67 mmol) in DCM (4 mL) is added HCl in dioxane (4N, 1.68 mL, 6.73 mmol). The reaction mixture is stirred at rt for 2 h. The reaction mixture is concentrated to yield AL as the HCl salt. MS (ES+): m/z 207.1 [M+H]$^+$.

Method 14:
Synthesis of Intermediate AM

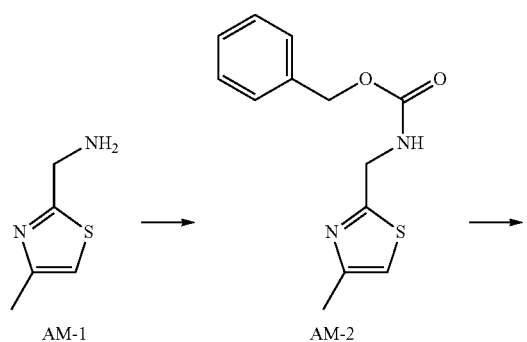

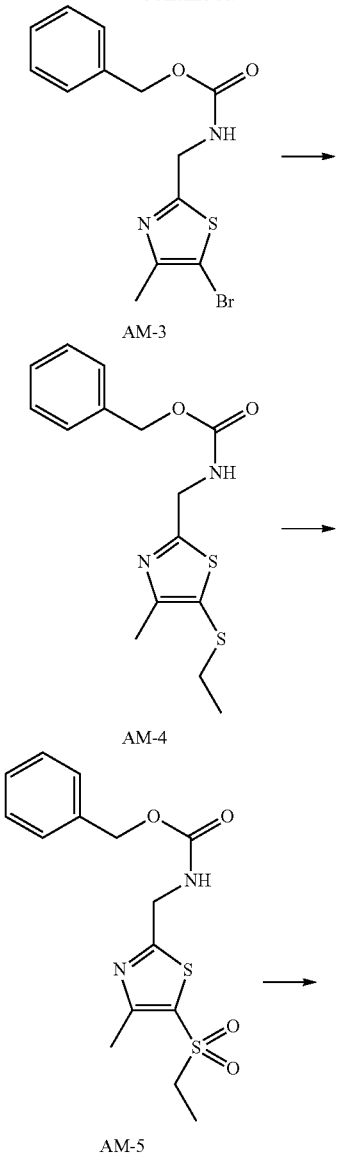

To a solution of AM-1 (1 g, 7.80 mmol) in THF (40 mL) at 0° C. is added DIEA (4.08 mL, 23.40 mmol) followed by dropwise addition of benzylchloroformate (1.52 mL, 10.14 mmol). The reaction mixture is warmed to rt and stirred overnight. The reaction mixture is then concentrated, diluted with water and then extracted with EtOAc. The organic layer is then washed with sat. aq NaHCO$_3$ (2×), H$_2$O (2×), and brine, dried over MgSO$_4$, filtered and concentrated. The residue is purified by SiO$_2$ flash chromatography to yield AM-2.

To a solution of AM-2 (1 g, 3.81 mmol) in THF (20 mL) at 0° C. is added dropwise Br$_2$ (0.30 mL, 5.91 mmol). The reaction mixture is warmed to rt and stirred overnight. The reaction mixture is diluted with water then extracted with EtOAc. The organic layer is then washed with sat. aq NaHCO$_3$ (2×), water (2×) and brine, dried over MgSO$_4$, filtered and concentrated. The residue is purified by SiO$_2$ flash chromatography to yield AM-3.

AM-4 is synthesized in a fashion analogous to intermediate AL-3.

AM-5 is synthesized in a fashion analogous to intermediate AL-4.

To a solution of AM-5 (146 mg, 0.41 mmol) in EtOH (10 mL) is added 10% Pd/C (150 mg) and the mixture is stirred at rt under an H₂ atmosphere for 18 h. The reaction mixture is filtered through celite and washed with EtOAc. The filtrate is concentrated then HBr in acetic acid (1.5 mL, 33 wt %) is added. The mixture is stirred at rt for 2.5 h then filtered to yield AM as the HCl salt. MS (ES+): m/z 221.1 [M+H]⁺.

Method 15:
Synthesis of Intermediate AN

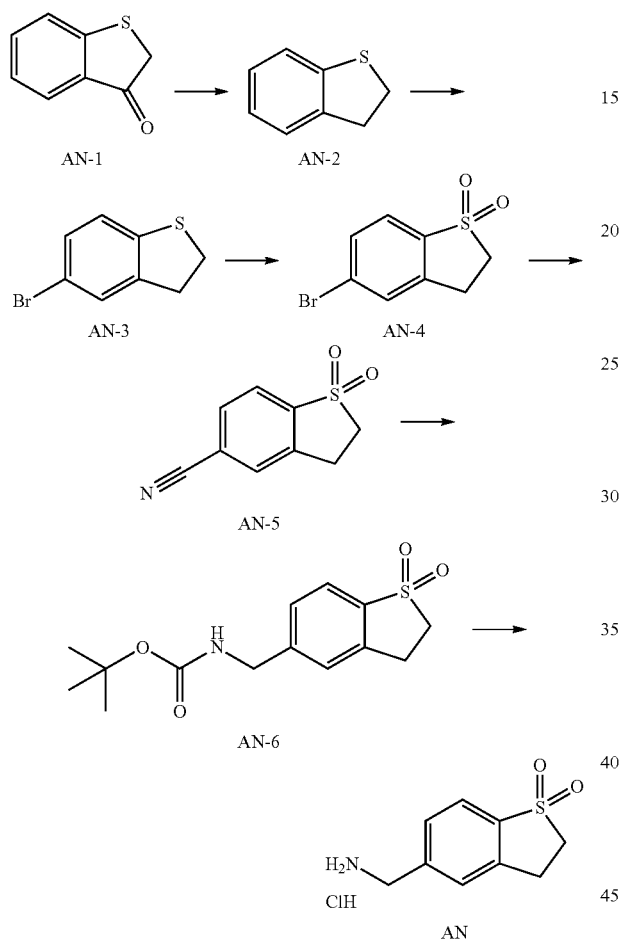

To a solution of AN-4 (800 mg, 3.24 mmol) in NMP (10 mL) is added CuI (920 mg, 4.83 mmol) and CuCN (397 mg, 4.43 mmol). The microwave reaction is heated at 200° C. for 3 h. The mixture is poured into H₂O, extracted with EtOAc. The organic layer is washed with brine, dried over Na₂SO₄ and concentrated. The residue is purified by recrystallization to yield AN-5.

AN-6 is synthesized in a fashion analogous to intermediate AH-3.

AN is synthesized in a fashion analogous to intermediate AH. MS (ES+): m/z 198.0 [M+H]⁺.

Method 16:
Synthesis of Intermediate AO

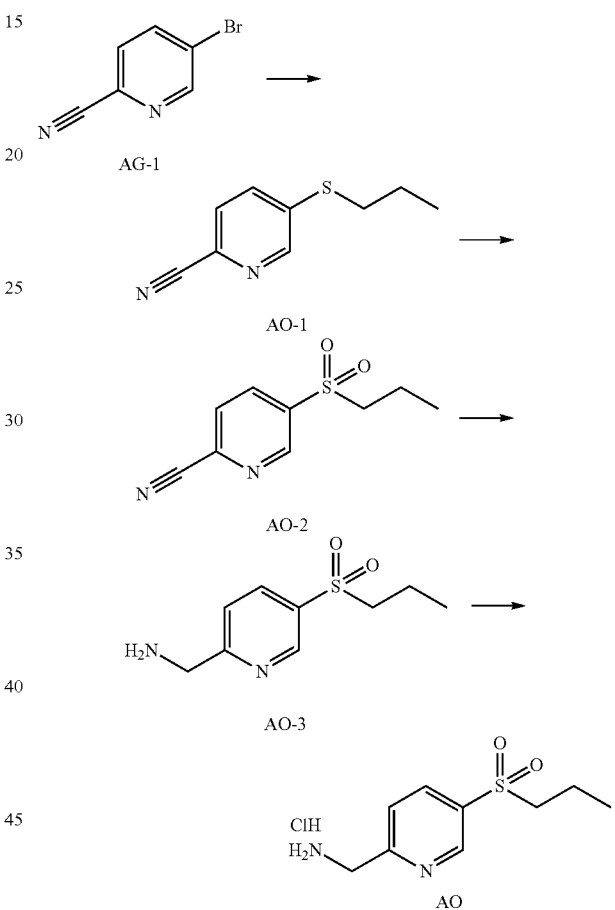

To a solution of AN-1 (6 g, 3.99 mmol) in EtOH (60 mL) is added N₂H₄ hydrate (31.1 ml). The mixture is heated to reflux for 45 min. The mixture is cooled to rt and then concentrated. The residue is dissolved in diethylene glycol (20 mL) and KOH (6.72 g, 120 mmol) is added. The mixture is stirred at 120° C. for 18 h. The mixture is cooled to rt, diluted with EtOAc and the pH is adjusted with 1N HCl to pH<4. The organic layers are washed with brine, dried over Na₂SO₄ and concentrated. The residue is purified by SiO₂ flash chromatography to yield AN-2.

To a solution of AN-2 (1.3 g, 9.54 mmol) in DCM (20 mL) is added dropwise Br₂ (1.53 g, 9.57 mmol) at 0° C. The mixture is stirred at rt for 12 h. The mixture is quenched with aq NaHSO₃ and extracted with DCM twice. The organic layers are combined and washed with brine, dried over Na₂SO₄ and concentrated. The residue is purified by SiO₂ flash chromatography to yield AN-3.

AN-4 is synthesized in a fashion analogous to intermediate AH-4.

To a solution of sodium 1-propanethiolate (12.8 g, 130 mmol) in ACN (150 mL) kept below 20° C. is added portionwise AG-1 (19.8 g, 108 mmol). The mixture is then stirred at rt for 16 h, poured into water (300 mL) and extracted with EtOAc (300 mL). The combined organic phase is dried (Na₂SO₄), filtered and concentrated. The residue is purified by SiO₂ flash chromatography to yield AO-1.

To a stirred solution of AO-1 (16.5 g, 83.0 mmol) in AcOH (150 mL) kept below 10° C. is added a solution of KMnO₄ (14.5 g, 92.0 mmol) in H₂O (150 mL) dropwise. The reaction mixture is stirred for 30 min. The mixture is diluted with water, basified by addition of saturated aq Na₂CO₃ and extracted with EtOAc. The solution is concentrated and the residue is purified by SFC to yield AO-2.

A mixture of AO-2 (7.80 g, 37.0 mmol) and Ra Ni (8.00 g) in MeOH (100 mL) is stirred at rt under H₂ for 18 h. After filtration and concentration the residue is purified by MPLC to yield AO-3.

To solid AO-3 (7.40 g, 35.0 mmol) is added acetic acid ethyl ester (2 mL) and HCl in EtOAc (100 mL). The solution is stirred at rt for 5 h and the solids are filtered to yield intermediate AO.

Method 17:

Synthesis of Intermediate AP

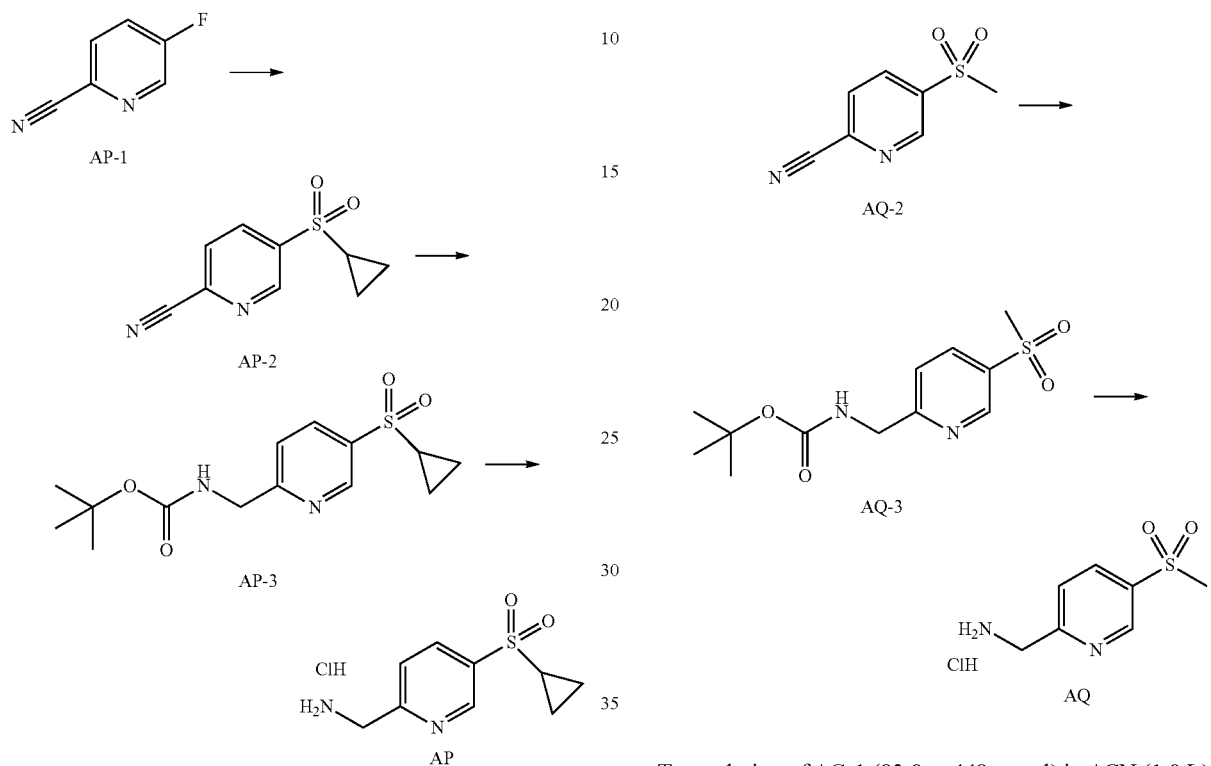

A mixture of AP-1 (12.8 g, 130 mmol), sodium cyclopropanesulfonate (53.1 g, 369 mmol) and CuI (23.3 g, 123 mmol) in DMSO (150 mL) is stirred at 110° C. for 2 h. After cooling to rt, the solution is poured into water and extracted with EtOAc. The combined organic phase is dried over $Na_2SO_4$, filtered and concentrated. The resulting residue is purified by MPLC to yield AP-2.

A mixture of AP-2 (10.3 g, 49 mmol), Ra Ni (25.0 g), $Boc_2O$ (16.2 g, 74 mmol) and TEA (10.0 g, 99 mmol) in MeOH (250 mL) is stirred under a $H_2$ atmosphere at rt for 18 h. After filtration and concentration the residue is purified by MPLC to AP-3.

To a solution of AP-3 (6.90 g, 22 mmol) in MeOH (60 mL) is added HCl in EtOH (60 mL). The solution is stirred at rt for 3 h and is concentrated and recrystallized to yield intermediate AP.

Method 18:

Synthesis of Intermediate AQ

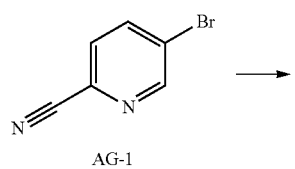

To a solution of AG-1 (82.0 g, 448 mmol) in ACN (1.0 L) is added sodium t-butoxide (64.5 g). The mixture is cooled to 0° C. and sodium methanethiolate (172.5 g, 20% in $H_2O$) is added dropwise. The reaction mixture is then allowed to stir at rt for 16 h. Water (800 mL) is added and the mixture is extracted with DCM. The combined organic phases are washed with brine, dried ($Na_2SO_4$) and concentrated. The residue is purified by $SiO_2$ flash chromatography to yield AQ-1.

To a suspension of AQ-1 (51.5 g, 343 mmol) in AcOH (500 mL) is added a solution of $KMnO_4$ (59.7 g, 36.6 mmol) in $H_2O$ (500.0 mL) dropwise at 5° C. The reaction mixture is then stirred at rt for 1 h. The mixture is extracted with EtOAc, washed with aq. $NaHCO_3$, dried ($Na_2SO_4$) and concentrated. The resultant residue is purified by recrystallization to yield AQ-2.

To a solution of AQ-2 (15.0 g, 82 mmol) in MeOH (200 mL) is added Ra Ni (10.0 g), TEA (34.4 mL) and $Boc_2O$ (17.8 g). The mixture is stirred at rt under $H_2$ (50 psi) for 12 h. The vessel is purged with $N_2$, filtered and the filtrate concentrated. The residue is purified by $SiO_2$ flash chromatography to yield AQ-3.

A solution of AQ-3 (30.0 g, 105 mmol) in HCl in MeOH (500 mL) is stirred at rt for 12 h. The mixture is concentrated and recrystallized to yield intermediate AQ. MS (ES+): m/z 187 [M+H]+.

Intermediate AR and Intermediate AS (as the HCl salt. MS (ES+): m/z 202.1 [M+H]+) is synthesized in a fashion analogous to intermediate AQ.

AR

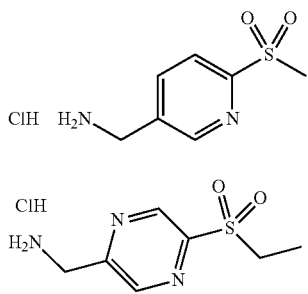

Method 19:
Synthesis of Intermediate AT

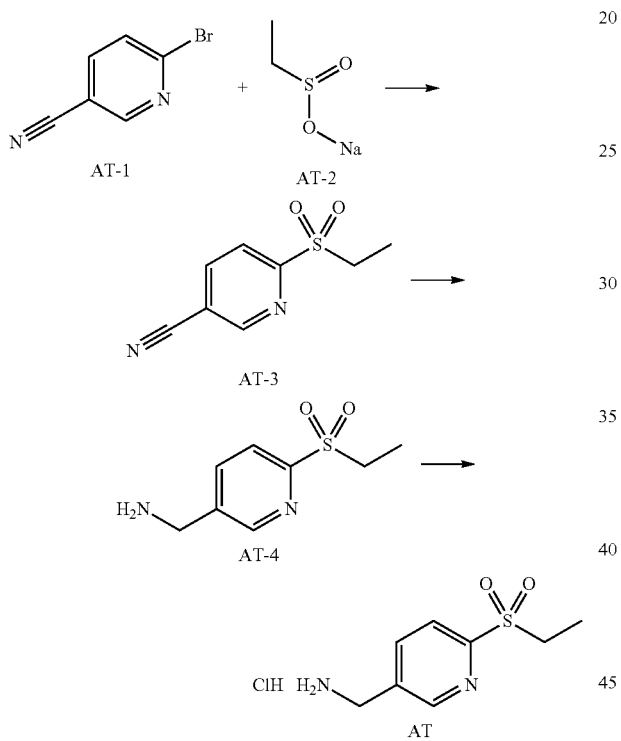

To a mixture of AT-1 (10.0 g, 55 mmol), N,N-dimethyl-ethane-1,2-diamine (0.96 g, 11 mmol) and Copper(II) trifluoromethanesulfonate (1.98, 5 mmol) in DMSO (100 mL) is added AT-2 (8.27 g, 98 mmol) at rt. The mixture is then heated to 120° C. for 30 min, quenched with $H_2O$ and extracted with EtOAc. The organic layer is dried, concentrated and purified by $SiO_2$ flash chromatography to yield AT-3.

A mixture of AT-3 (32.3 g, 165 mmol) and Pd (3.50 g, 33 mmol) in $NH_4OH$ (30 mL)/EtOH (200 mL) is stirred at rt under $H_2$ (15 psi) for 15 h. The mixture is filtered, concentrated and purified by $SiO_2$ flash chromatography to yield AT-4.

To a stirred solution of AT-4 (17.5 g, 87 mmol) in EtOH (100 mL) is added HCl in EtOH (100 mL). The solution is stirred at rt for 3 h and then concentrated and recrystallized to yield intermediate AT. MS (ES+): m/z 201 [M+H]$^+$.

Method 20:
Synthesis of Intermediate AU

AS

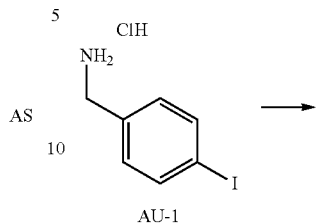

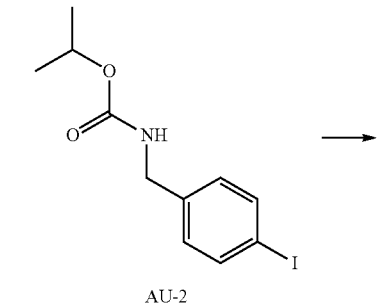

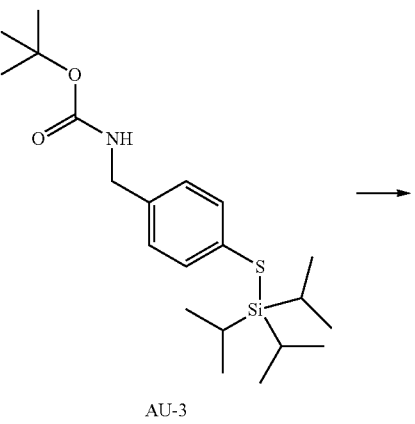

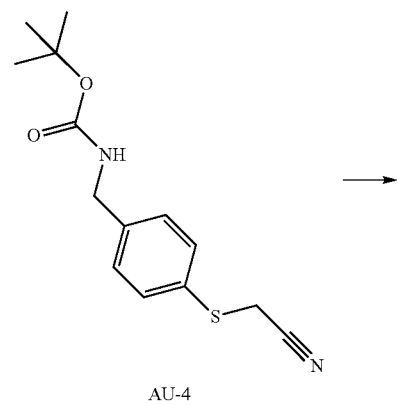

Method 21:
Synthesis of Intermediate AV

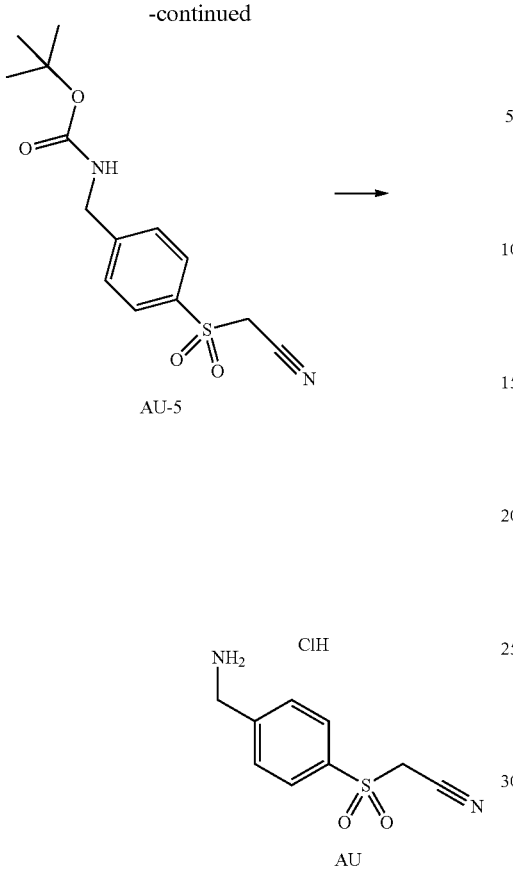

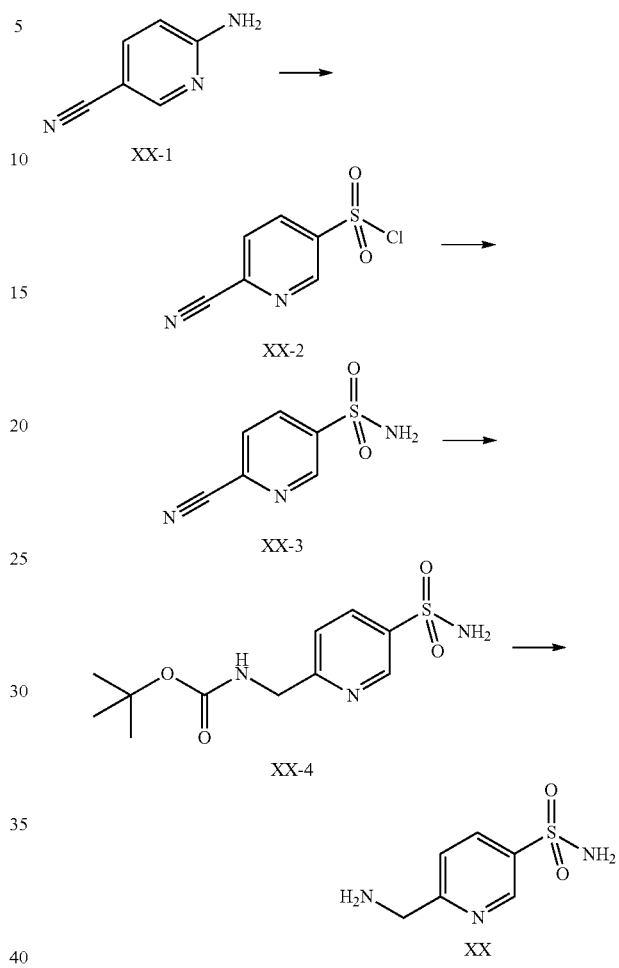

To a solution of AU-1 (7.15 g, 26.5 mmol) in THF (50 mL) is added Boc$_2$O (6.70 mL, 29.2 mmol) and TEA (7.40 mL, 53.1 mmol). The reaction is allowed to stir at rt for 72 h. The solution is concentrated to yield AU-2.

A mixture of AU-2 (5.25 g, 15.8 mmol), sodium t-butoxide (1.82 g, 18.9 mmol), Pd(OAc)$_2$ (177 mg, 0.79 mmol), and 1,1'-Bis(diisopropylphosphino)ferrocene (396 mg, 0.95 mmol) are added to a sealed vessel which is purged with argon. Dioxane (35 mL) is added and the mixture is stirred at rt for 1 h. Triisopropylsilanethiol (3.72 mL, 17.3 mmol) is added and the solution is heated to 100° C. for 1 h. The reaction is then poured into EtOAc and water. The organic layer is concentrated and the residue is purified by SiO$_2$ flash chromatography to yield AU-3.

A solution of AU-3 (2.50 g, 6.32 mmol) in THF (25 mL) is cooled to 0° C. and degassed with argon. Terabutylammoniumbromide (2.12 g, 7.58 mmol) is then added and the solution is stirred at 0° C. for 1 h. Bromoacetonitrile (660 uL, 9.48 mmol) is then added and the solution is stirred at 0° C. for 5 min. The solution is concentrated and partitioned between diethyl ether and water. The organic layer is concentrated to yield AU-4 which is carried forward without further manipulation.

To a solution of AU-4 (1.80 g, 6.47 mmol) in ACN/H$_2$O (10 mL) is added sodium periodate (4.18 g, 19.5 mmol) followed by ruthenium(III) chloride (7.87 mg, 0.038 mmol). The reaction mixture is stirred at rt for 30 min and is then concentrated. The residue is purified by SiO$_2$ flash chromatography to yield AU-5.

To a stirred solution of AU-5 (470 mg, 1.51 mmol) in DCM (3 mL) is added HCl in dioxane (2.00 mL, 8.00 mmol). The solution is stirred at rt for 1 h and concentrated to yield intermediate AU. MS (ES+): m/z 211.1 [M+H]$^+$.

AV-1 (20.0 g, 168 mmol) is added to conc. HCl (200 mL) at 0° C. followed by dropwise addition of aq NaNO$_2$ (25.5 g in 25 mL H$_2$O) maintaining an internal temperature of <5° C. The solution is allowed to stir at 0° C. for 15 min and then is slowly added to a mixture of SO$_2$ (108 g) and CuCl (84 mg) in AcOH (200 mL, >5 eq) at 5° C. The solution is stirred 90 min at 5° C. The reaction mixture is extracted with DCM (2×500 mL), dried (Na$_2$SO$_4$), and the organic solution of AV-2 used directly in the next step.

To a solution of AV-2 (20.0 g, 99 mmol) in DCM (200 mL) is added a solution of ammonia in MeOH (100 mL) at 0 C and stirred at rt for 30 min. The mixture is concentrated to dryness and the resultant residue is purified by SiO$_2$ flash chromatography to yield AV-3.

To a solution of AV-3 (15.0 g, 82 mmol) in MeOH (200 mL) is added Ra Ni (10.0 g), TEA (34.4 mL) and Boc$_2$O (17.8 g). The mixture is stirred at rt under H$_2$ (50 psi) for 12 h. The vessel is purged with N$_2$, filtered and the filtrate concentrated. The residue is purified by SiO$_2$ flash chromatography to yield AV-4.

A solution of AV-4 (30.0 g, 105 mmol) in HCl in MeOH (500 mL) is stirred at rt for 12 h. The mixture is concentrated and recrystallized to yield intermediate AV. MS (ES+): m/z 188.1 [M+H]$^+$.

Intermediate AW is synthesized in a fashion analogous to Intermediate AV.

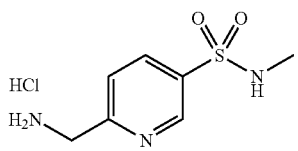

AW

Method 22:
Synthesis of Intermediates (S)-AX and (R)-AX

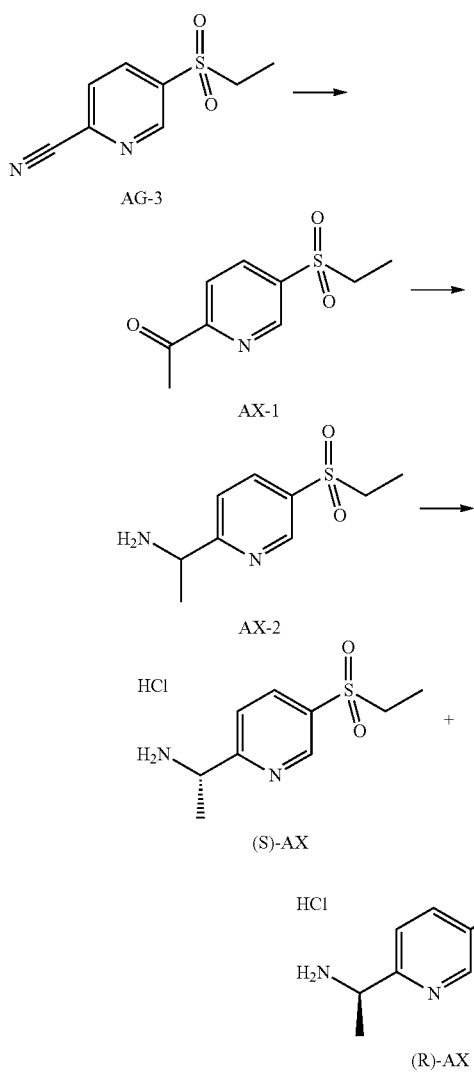

To a solution of AG-3 (2.40 g, 12 mmol) in THF (30 mL) is added dropwise MeMgBr (30 mL) at −30° C. After the addition, the mixture is stirred at rt for 4 h. The reaction mixture is quenched by addition of sat. aq NH$_4$Cl (100 mL) and extracted with EtOAc (3×100 mL). The organic phase is washed with brine, dried over Na$_2$SO$_4$ and concentrated under reduced pressure. The residue is purified by SiO$_2$ flash chromatography to yield AX-1.

To a solution of AX-1 (200 mg, 1.0 mmol) in MeOH (2 mL) is added NH$_4$OAc (723 mg) and NaBH$_3$CN (41 mg) at 0° C. The mixture is stirred at rt for 16 h. The solvent is removed under reduced pressure, water (50 mL) is added and the mixture is adjusted to pH>12 and then extracted with DCM (50 mL). The organic phase is dried over Na$_2$SO$_4$ and concentrated. The residue is purified by prep-TLC to yield AX-2.

AX-2 is separated by SFC to give (S)-AX (67.9% ee) and (R)-AX (95.5% ee).

Method 23:
Synthesis of Intermediates AY

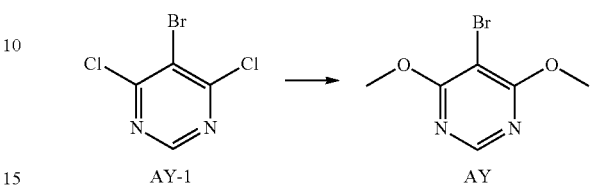

To a solution of AY-1 (1.25 g, 5.49 mmol) in anhydrous MeOH (15 mL) is added NaOMe (2.37 g, 43.89 mmol). The mixture is stirred at rt for 1 h. The solution is filtered and concentrated. The residue is purified by SiO$_2$ flash chromatography to yield intermediate AY. MS (ES+): m/z 218.9 [M+H]$^+$.

Method 24:
Synthesis of Intermediates AZ

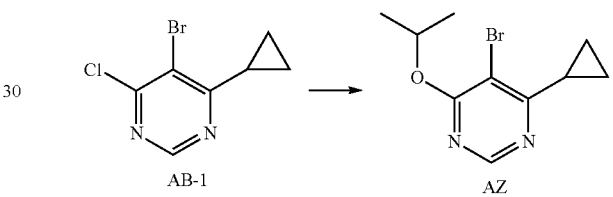

To a solution of sodium hydride (342 mg, (60%), 8.57 mmol) in DMF (10 mL) is added anhydrous isopropanol (360 uL, 4.71 mmol). The mixture is stirred at rt for 1 h. AB-1 (1.00 g, 4.28 mmol) is then added and the mixture is stirred for an additional 1 h before being poured onto ice. The mixture is then extracted with EtOAc and concentrated. The residue is purified by SiO$_2$ flash chromatography to yield intermediate AZ. MS (ES+): m/z 258.8 [M+H]$^+$.

Method 25:
Synthesis of Intermediates BA

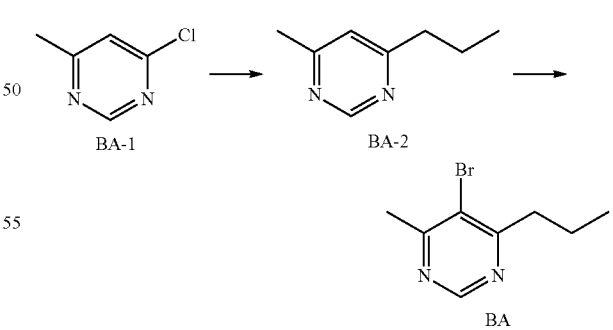

A solution of BA-1 (1.00 g, 7.78 mmol), and Ni(dppe)Cl$_2$ (82 mg, 0.16 mmol) in anhydrous Et$_2$O (5 mL) is cooled to −10° C. Then, n-propyl magnesium bromide is added dropwise and the mixture is stirred for 2 h at −10° C. The mixture is quenched with saturated NH$_4$Cl, extracted with DCM and concentrated. The crude BA-2 is carried forward without further manipulation.

To a solution of BA-2 (1.0 g, 7.34 mmol) in EtOH (10 mL) at 0° C. is added Br₂ (379 uL, 7.34 mmol). The reaction mixture is stirred at rt for 2 h. The solution is concentrated and the residue is purified by SiO₂ flash chromatography to yield intermediate BA. MS (ES+): m/z 217.4 [M+H]⁺.

Method 26:
Synthesis of Intermediates BC

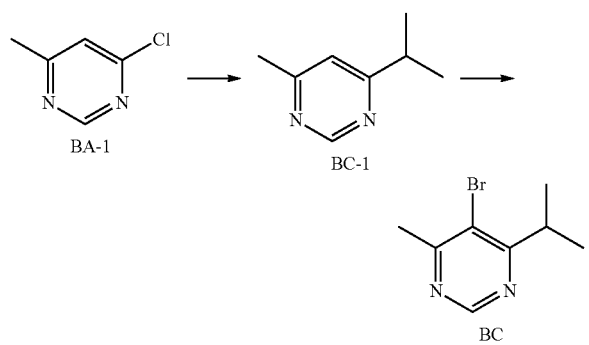

A solution of BA-1 (1.00 g, 7.78 mmol), and Ni(dppe)Cl₂ (82 mg, 0.16 mmol) in anhydrous Et₂O (5 mL) is cooled to −10° C. A solution of isopropyl magnesium bromide (3.22 mL, 9.33 mmol) is added dropwise and the mixture is stirred for 1 h at −10° C. The mixture is quenched with sat. NH₄Cl, extracted with DCM and concentrated. The crude BC-1 is carried on as is.

To a solution of BC-1 (1.0 g, 7.34 mmol) in EtOH (10 mL) at 0° C. is added Br₂ (378 uL, 7.34 mmol). The reaction mixture is stirred at rt for 2 h. The solution is concentrated and the residue is purified by SiO₂ flash chromatography to yield intermediate BC. MS (ES+): m/z 216.4 [M+H]⁺.

Method 27:
Synthesis of Intermediates BD

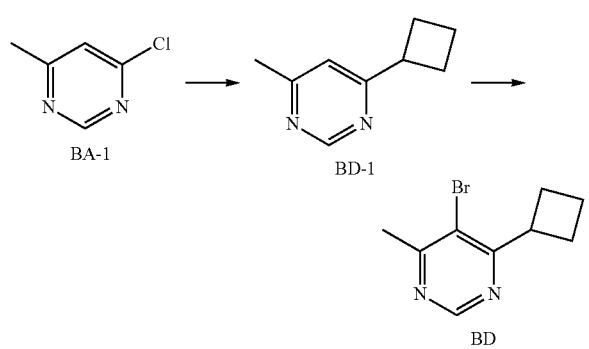

A solution of BA-1 (1.00 g, 7.78 mmol), and Ni(dppe)Cl₂ (82 mg, 0.16 mmol) in anhydrous Et₂O (5 mL) is cooled to −10° C. A solution of cyclopropyl magnesium bromide (1.36 g, 8.56 mmol) is added dropwise and the mixture is stirred for 2 h at −10° C. The mixture is quenched with saturated aqueous NH₄Cl, extracted with DCM and concentrated. The crude BD-1 is carried forward without further manipulation.

To a solution of BD-1 (1.0 g, 6.74 mmol) in EtOH (10 mL) at 0° C. is added Br₂ (347 uL, 6.74 mmol). The reaction mixture is stirred at rt for 18 h. The solution is concentrated and the residue is purified by SiO₂ flash chromatography to yield intermediate BD. MS (ES+): m/z 229.2 [M+H]⁺.

Method 28:
Synthesis of Intermediate BE

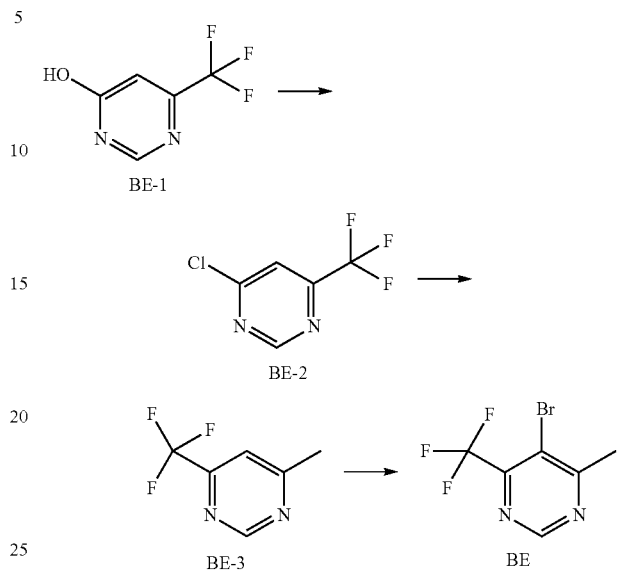

To a solution of BE-1 (40.0 g, 244 mmol) in THF (800 mL) is added PPh₃ (98.0 g) and NCS (160.0 g). The reaction mixture is stirred at 80° C. for 10 h. The mixture is then quenched with water and extracted with EtOAc. The solution is concentrated and the residue is purified by SiO₂ flash chromatography to yield BE-2.

To a stirred solution of BE-2 (3.00 g, 14.79 mmol) in toluene and DMF is added Pd(PPh₃)₄ (600 mg), Pd(dppf)Cl₂ (600 mg) and Na₂CO₃ (6.27 g, 59.17 mmol). The mixture is stirred at 90° C. for 5 h. The mixture is quenched with water, extracted with EtOAc. The solution is concentrated and the residue is purified by SiO₂ flash chromatography to yield BE-3.

To a solution of BE-3 (860 mg, 5.0 mmol) in EtOH (5 mL) at −10° C. is added Br₂ (347 uL, 6.74 mmol). The reaction mixture is stirred at rt for 18 h. The solution is concentrated and the residue is purified by SiO₂ flash chromatography to yield intermediate BE. MS (ES+): m/z 267 [M+H]⁺.

Method 29:
Synthesis of Intermediate BF

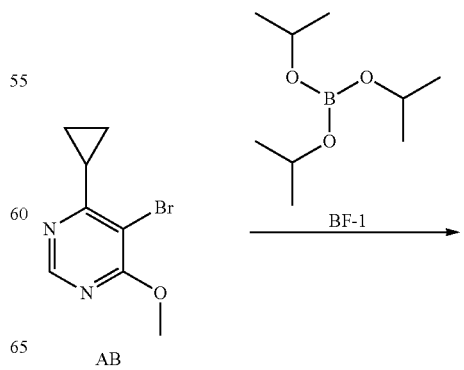

-continued

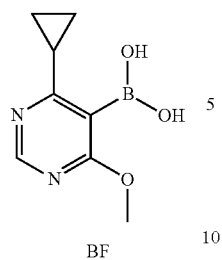

BF

To a solution of AB (6.00 g, 26.2 mmol) and BF-1 (7.86 mL, 34.1 mmol) in toluene (60 mL) and THF (18 mL) at −78° C. is added n-butyl lithium (12.6 mL, 31.4 mmol), dropwise, over 30 min. The solution is the stirred at −78° C. for 30 min and is then slowly warmed to −20° C. The solution is the quenched with 1 N HCl (40 mL). The layers are then separated and the aqueous layer is adjusted to pH~8 with 2M NaOH. A white solid begins to precipitate and the mixture is cooled in the refrigerator for 1 h. The solids are filtered to yield intermediate BF. The aqueous layer is extracted with MeTHF and concentrated to give additional intermediate BF. MS (ES+): m/z 195.1 [M+H]$^+$.

Intermediate BG is synthesized in a fashion analogous to Intermediate BF.

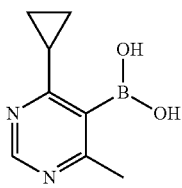

BG

Method 30:
Synthesis of Intermediate BH

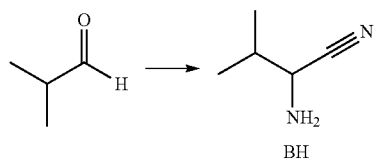

BH

To a mixture of 2-methyl-propionaldehyde (5 g, 69.34 mmol) and NH$_4$Cl (7.42 g, 138.69 mmol) in water (50 mL) is added NaCN (4.08 g, 83.2 mmol). The mixture is stirred at rt for 18 h. The mixture is extracted with EtOAc (3×). The organics are combined, dried over Na$_2$SO$_4$, concentrated to give crude intermediate BH, which is carried forward without further manipulation.

Method 31:
Synthesis of Intermediate BI

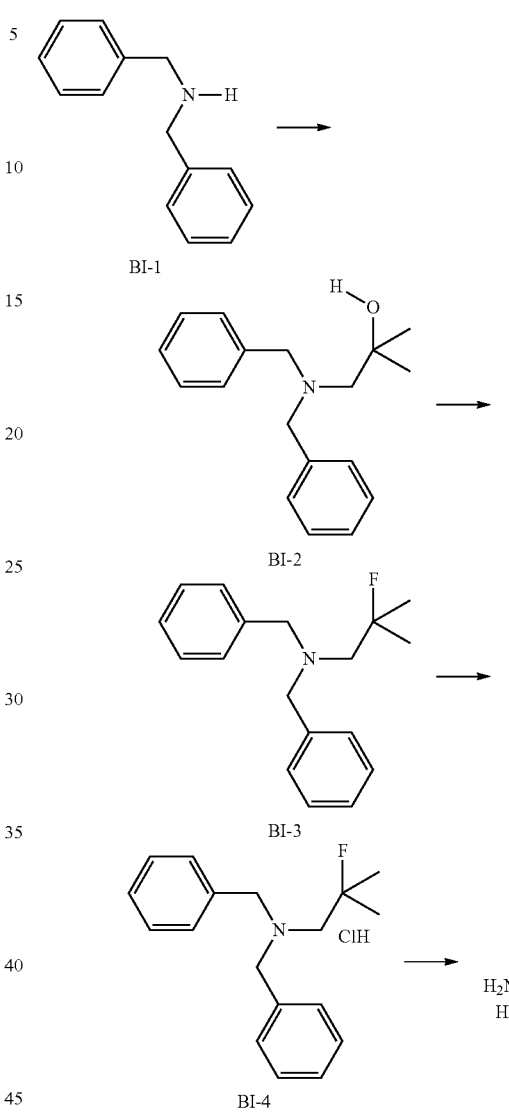

To a mixture of BI-1 (20 mL, 104 mmol) and 2,2-dimethyl oxirane (15 mL, 17 mmol) is added LiBr (1.86 g, 21.4 mmol) in one portion. The reaction mixture is stirred at rt for 16 h. Additional 2,2-dimethyl oxirane (2.0 mL, 23 mmol) is added and the mixture is heated at 60° C. for 2 h. The reaction mixture is quenched with water then extracted with EtOAc twice. The organics are combined and washed with brine, dried over Na$_2$SO$_4$, filtered and concentrated to yield BI-2.

To a solution of BI-2 (2.0 g, 7.4 mmol) in DCM (20 mL) at −21° C. is added Deoxo-Fluor (1.51 mL, 8.17 mmol). After the addition, the reaction mixture is stirred at −21° C. for 5 mins then quenched with sat. aq NaHCO$_3$ until pH~8. The layers are separated and the aq layer is extracted with DCM. The combined organics are washed with sat. aq NaHCO$_3$, dried over Na$_2$SO$_4$, filtered and concentrated to yield BI-3.

To a solution of BI-3 (1.5 g, 5.5 mmol) in toluene (30 mL) is added dropwise HCl in dioxane (4N, 1.45 mL, 5.80 mmol). The reaction mixture is stirred at rt for 2 h then filtered to yield BI-4.

A mixture of BI-4 (500 mg, 1.62 mmol), 5% Pd/C (103 mg) and MeOH (3 mL) is hydrogenated on Endeavor (60° C., 400 psi) for 5 h. The reaction mixture is filtered through celite and rinsed with MeOH. The filtrate is concentrated to yield intermediate BI as the HCl salt. MS (ES+): m/z 92.3 [M+H]⁺.

Method 32:
Synthesis of Intermediate BJ

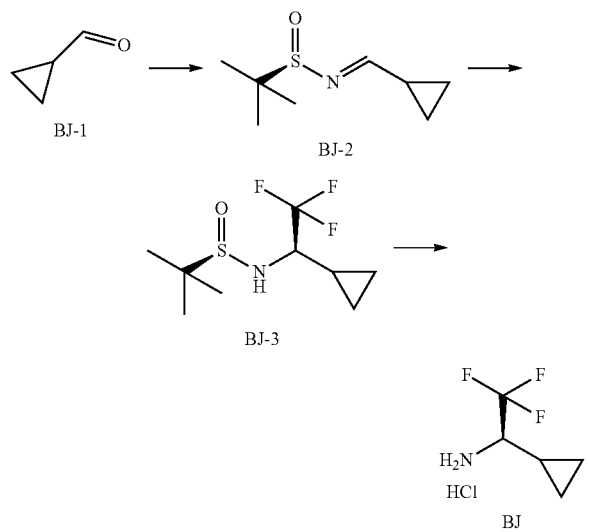

To a solution of BJ-1 (7.40 mL, 99.0 mmol) in DCM (100 mL) is added (R)-2-methyl-2-propanesulfinamide (10.0 g, 82.5 mmol), MgSO₄ (49.66 g, 412 mmol) and pyridinium p-toluenesulfonate (1.04 g, 4.13 mmol). The reaction mixture is allowed to stir at rt for 72 h. The reaction mixture is then filtered and the residue is purified by SiO₂ flash chromatography to yield BJ-2.

To a solution of BJ-2 (9.72 g, 56.1 mmol) in THF (200 mL) is added tetramethylammonium fluoride (6.27 g, 67.3 mmol). The solution is degassed with argon and is then cooled to −55° C. A solution of trifluoromethyltrimethylsilane (12.4 mL, 84.1 mmol) in THF (250 mL) is added dropwise with an additional funnel and the reaction is allowed to stir at −55° C. for 2 h. The reaction mixture is then slowly allowed to warm to −10° C. and is quenched with sat. aqueous NH₄Cl. The aqueous layer is extracted with EtOAc and the combined organic layers are concentrated to yield BJ-3, which is carried forward without further manipulation.

To a solution of BJ-3 (9.00 g, 37.0 mmol) in MeOH (30 mL) is added 4M HCl in dioxane (18.5 mL, 74.0 mmol). The solution is allowed to stir at rt for 1 h. The reaction mixture is then concentrated to half volume and diluted with diethyl ether until a white precipitate is formed. The solid is then filtered to yield intermediate BJ.

Method 33:
Synthesis of Intermediate BK

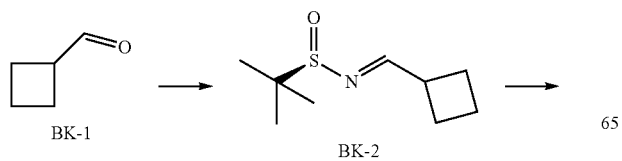

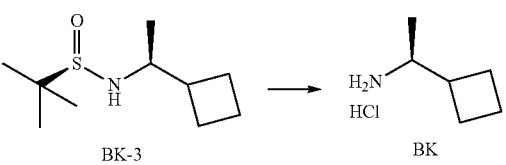

To a solution of BK-1 (9.47 g, 113 mmol) in DCM (100 mL) is added (R)-2-methyl-2-propanesulfinamide (10.5 g, 86.6 mmol), MgSO₄ (52.1 g, 433 mmol) and pyridinium p-toluenesulfonate (1.09 g, 4.33 mmol). The reaction mixture is allowed to stir at rt for 18 h. The reaction mixture is then filtered and the residue is purified by SiO₂ flash chromatography to yield BK-2.

To a solution of BK-2 (8.60 g, 45.9 mmol) in DCM (350 mL) at −50° C., is added methylmagnesium bromide (36.0 mL, 108 mmol). The solution is stirred at −50° C. for 3 h. The reaction is then allowed to warm to rt and stirred for 18 h. The solution is quenched with sat. aqueous NH₄Cl and extracted with EtOAc (2×). The organic layer is concentrated to yield BK-3, which is carried forward without further manipulation.

To a solution of BK-3 (5.00 g, 24.6 mmol) in MeOH (20 mL) is added 4M HCl in dioxane (12.3 mL, 49.2 mmol). The solution is allowed to stir at rt for 1 h. The reaction mixture is then concentrated and the residue is purified by SiO₂ flash chromatography to yield intermediate BK.

Intermediate BL is synthesized in a fashion analogous to Intermediate BK

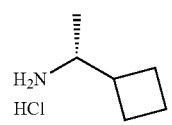

Intermediates BM, BN, BO, BP, BQ, BR, BS are synthesized in a fashion analogous to Intermediate AJ

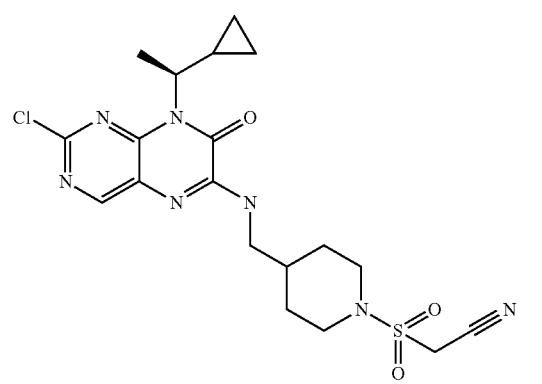

229
-continued
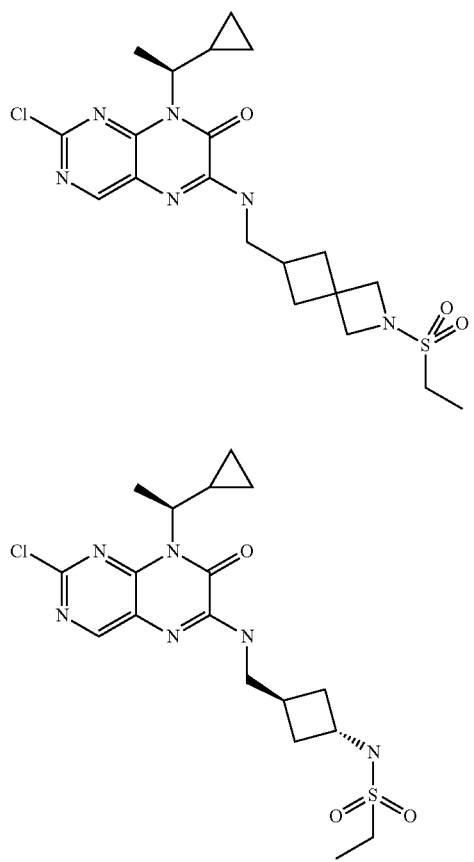
BN
BO
BP
BQ
230
-continued
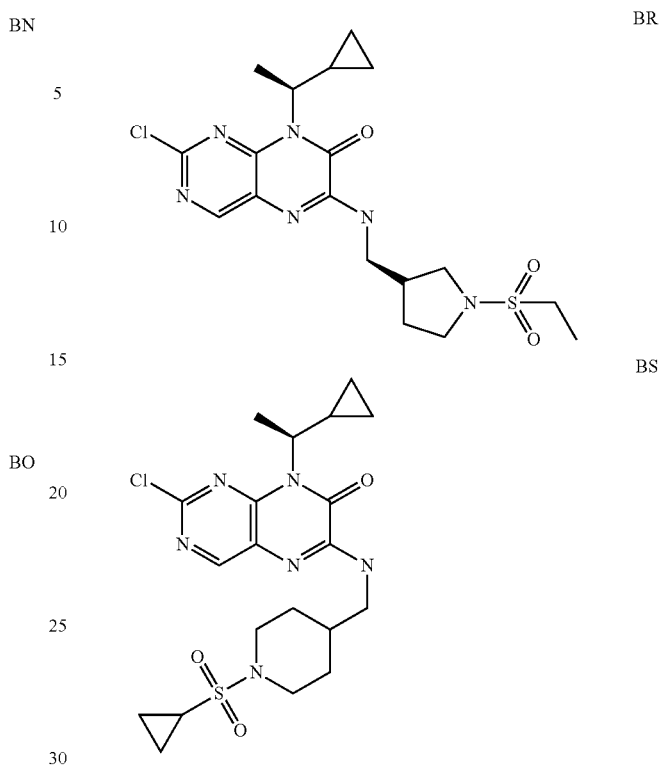
BR
BS
Method 34:
Synthesis of Intermediates BT
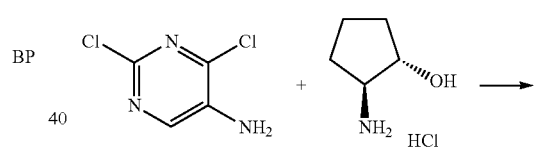
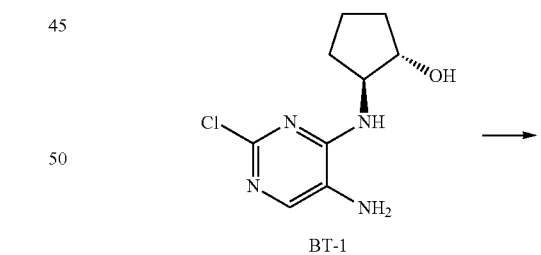
BT-1
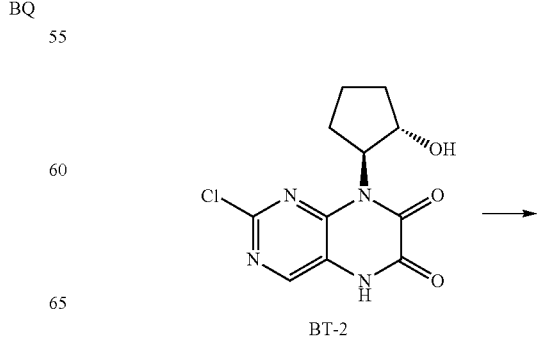
BT-2

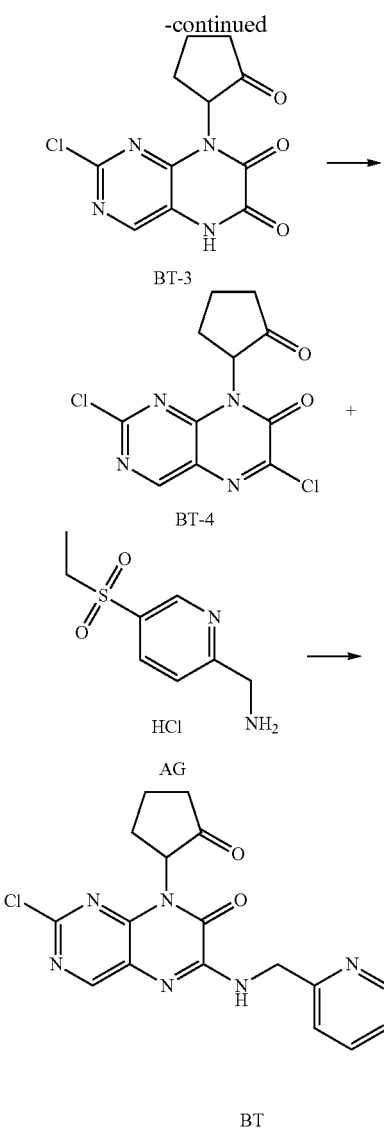

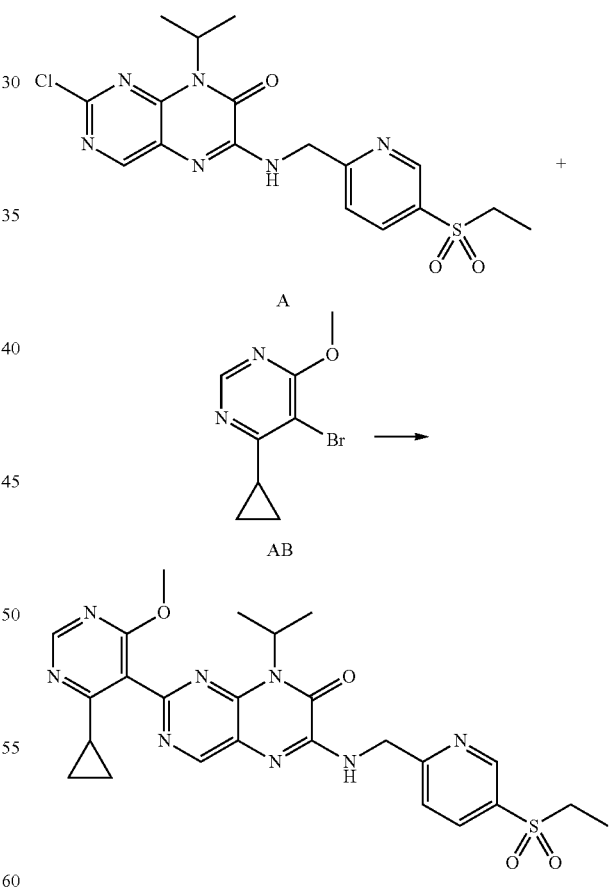

with sat. NaHCO$_3$ (50 mL) and the organic layer dried (Na$_2$SO4) and concentrated under reduced pressure. The solid residue is twice suspended in DCM (50 mL), sonicated, and filtered. The resulting solid is re-suspended in EtOAc (20 mL) and sonicated. The solid product is filtered to yield BT-3.

To a mixture of BT-3 (124 mg, 0.442 mmol) in DCM (6 mL) at rt is added oxalyl chloride (0.076 mL, 0.88 mmol) followed dropwise by dry DMF (0.30 mL, 3.9 mmol) until dissolution of the solid. The mixture is stirred at rt for 30 min, whereupon LCMS indicates unreacted starting material. To the mixture is added more oxalyl chloride (0.048 mL, 0.55 mmol) and the mixture stirred an additional 10 min. The reaction is concentrated under a stream of nitrogen at 35° C. for 1 h and the resultant residue BT-4 is used directly.

To a stirred solution of BT-4 (132 mg, 0.442 mmol) and AG (105 mg, 0.442 mmol) in DMF (2 mL) at rt is added TEA (0.311 mL, 2.21 mmol) and the mixture is stirred at rt for 15 min. To the reaction mixture is added water (50 mL) and this is extracted with EtOAc (3×50 mL). The organic layers are combined, dried (Na$_2$SO$_4$), decanted and concentrated. The resultant residue is purified by SiO$_2$ flash chromatography to yield intermediate BT. MS (ES+): m/z 463.1 [M+H]$^+$.

Method 35:
Synthesis of Example 9.

To a stirring suspension of 2,4-Dichloro-pyrimidin-5-ylamine (3.03 g, 18.1 mmol) in n-BuOH (40 mL) is added (1S,2S)-2-Amino-cyclopentanol hydrochloride (2.50 g, 17.2 mmol) and DIEA (9.20 ml, 51.8 mmol). The mixture is stirred at 130° C. for 4 h. The reaction mixture is then concentrated under reduced pressure and the crude product is triturated to a solid in EtOAc and heptane and filtered to yield BT-1.

To a stirred solution of BT-1 (3.61 g, 15.5 mol) in acetone (200 mL) is added K$_2$CO$_3$ (5.34 g, 38.6 mmol) and chloro-oxo-acetic acid ethyl ester (1.94 mL, 17.0 mmol). The mixture is stirred at rt for 1 h. The reaction mixture is filtered and the filtrate is concentrated under reduced pressure. The crude ketoester is dissolved in absolute EtOH (50 mL), placed in a pressure flask, and TEA (5.43 mL, 38.6 mmol) is added. This is heated to 130° C. for 1 h. The reaction mixture is concentrated under reduced pressure and dissolved in EtOAc (100 mL). The organic layer is washed with water (2×20 mL) then brine (20 mL) and dried (Na$_2$SO$_4$), decanted and concentrated. The resultant residue is triturated to a solid in EtOAc and heptane to yield BT-2.

To a mixture of BT-2 (500 mg, 1.73 mmol) in DCM (100 mL) is added Dess-Martin periodinane (2.25 g, 5.20 mmol) and the mixture is stirred at rt for 96 h. The mixture is washed Intermediate AB (27 mg, 0.12 mmol), bis(pinacolato)diboron (30 mg, 0.12 mmol), potassium acetate (35 mg, 0.36 mmol) and [1,1'-bisdiphenylphosphinoferrocene]-palladium (II) dichloride (9 mg, 0.011 mmol) are combined in a solution of degassed toluene/DME/ethanol/water (3:2:2:1, 3 mL). The vessel is heated to 90° C. for 20 min in a microwave reactor. In a separate vessel, intermediate A (50 mg, 0.12 mmol), bis(pinacolato)diboron (30 mg, 0.12 mmol), KOAc (35 mg, 0.36 mmol) and bis(di-tert-butyl(4-dimethylaminophenyl)phosphine)dichloropalladium(II) (8 mg, 0.011 mmol) are combined in degassed 1,4 dioxane (3 mL). The reaction is heated to 90° C. for 20 min in a microwave reactor. The contents of the two vessels are combined and Na$_2$CO$_{3(aq)}$ (2M, 1 mL) is added. The reaction is heated to 120° C. for 30 min in a microwave reactor. The vessel is cooled to rt and the contents filtered and concentrated. The resultant residue is purified by SiO$_2$ flash chromatography to yield Example 9. MS (ES+): m/z 537.2 [M+H]$^+$.

Synthesis of Example 11.

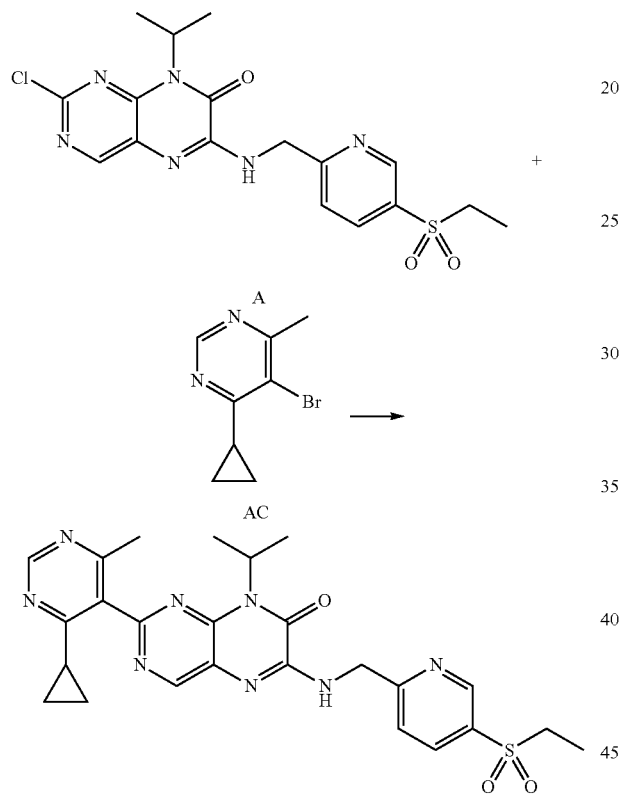

Synthesis of Example 15.

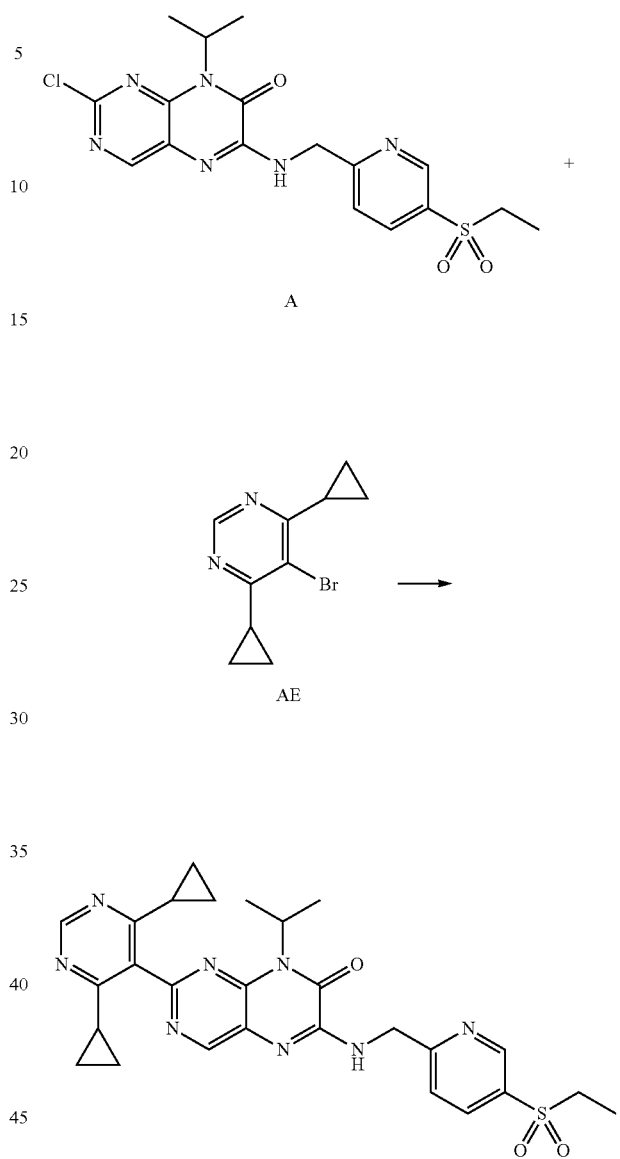

Intermediate AC (252 mg, 1.18 mmol), bis(pinacolato)diboron (600 mg, 2.36 mmol), potassium acetate (348 mg, 2.36 mmol) and [1,1'-bisdiphenylphosphinoferrocene]-palladium(II) dichloride (95 mg, 0.118 mmol) are combined in a solution of degassed toluene/DME/ethanol/water (3:2:2:1, 3 mL). The vessel is heated to 90° C. for 20 min in a microwave reactor. In a separate vessel, intermediate A (500 mg, 1.18 mmol), bis(pinacolato)diboron (600 mg, 2.36 mmol), potassium acetate (348 mg, 2.36 mmol) and bis(di-tert-butyl(4-dimethylaminophenyl)phosphine)dichloropalladium(II) (84 mg, 0.118 mmol) are combined in degassed 1,4 dioxane (3 mL). The reaction is heated to 90° C. for 20 min in a microwave reactor. The contents of the two vessels are combined and Na$_2$CO$_{3(aq)}$ (2M, 1 mL) is added. The reaction is heated to 120° C. for 30 min in a microwave reactor. The vessel is cooled to rt and the contents filtered and concentrated. The resultant residue is purified by SiO$_2$ flash chromatography to yield Example 11. MS (ES+): m/z 521.4 [M+H]$^+$.

Intermediate AE (283 mg, 1.18 mmol), bis(pinacolato)diboron (600 mg, 2.36 mmol), potassium acetate (348 mg, 3.54 mmol) and [1,1'-bisdiphenylphosphinoferrocene]-palladium(II) dichloride (95 mg, 0.12 mmol) are combined in a solution of degassed toluene/DME/ethanol/water (3:2:2:1, 3 mL). The vessel is heated to 90° C. for 20 min in a microwave reactor. In a separate vessel, intermediate A (500 mg, 1.18 mmol), bis(pinacolato)diboron (600 mg, 2.36 mmol), potassium acetate (348 mg, 3.54 mmol) and bis(di-tert-butyl(4-dimethylaminophenyl)phosphine)dichloropalladium(II) (84 mg, 0.12 mmol) are combined in degassed 1,4 dioxane (3 mL). The reaction is heated to 90° C. for 20 min in a microwave reactor. The contents of the two vessels are combined and 2M sodium bicarbonate (1 mL) is added. The reaction is heated to 120° C. for 30 min in a microwave reactor. The vessel is cooled to rt and the contents filtered and concentrated. The resultant residue is purified by SiO$_2$ flash chromatography to yield Example 15. MS (ES+): m/z 547.4 [M+H]$^+$.

Synthesis of Example 17.

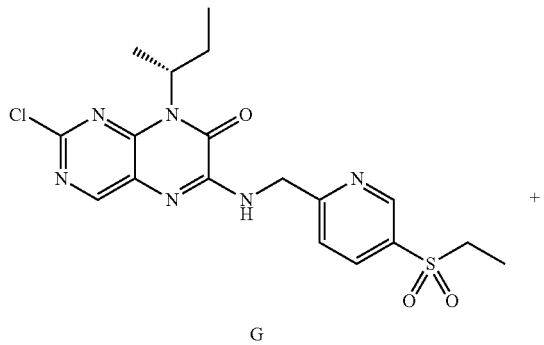

G

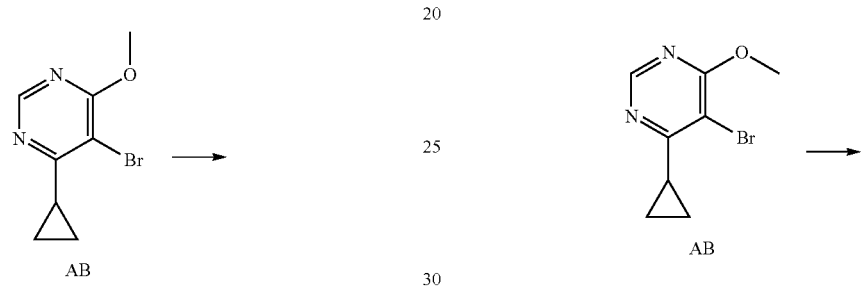

AB

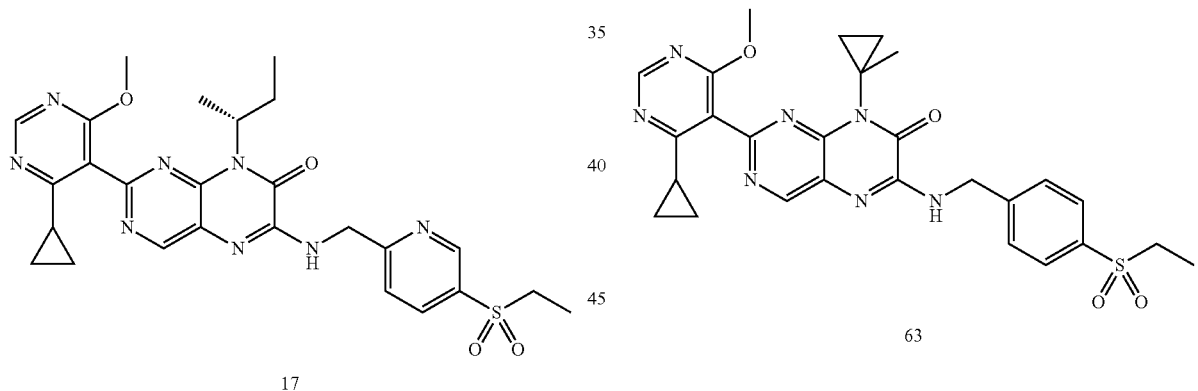

17

Intermediate AB (52 mg, 0.23 mmol), bis(pinacolato)diboron (58 mg, 0.23 mmol), KOAc (67 mg, 0.23 mmol) and [1,1'-bisdiphenylphosphinoferrocene]-palladium(II) dichloride (18 mg, 0.23 mmol) are combined in a solution of degassed toluene/DME/ethanol/water (3:2:2:1, 3 mL). The vessel is heated to 90° C. for 20 min in a microwave reactor. In a separate vessel, intermediate G (100 mg, 0.23 mmol), bis(pinacolato)diboron (58 mg, 0.23 mmol), KOAc (67 mg, 0.69 mmol) and bis(di-tert-butyl(4-dimethylaminophenyl)phosphine)dichloropalladium(II) (16 mg, 0.023 mmol) are combined in degassed 1,4 dioxane (3 mL). The reaction is heated to 90° C. for 20 min in a microwave reactor. The contents of the two vessels are combined and $Na_2CO_{3(aq)}$ (2M, 1 mL) is added. The reaction is heated to 120° C. for 30 min in a microwave reactor. The vessel is cooled to rt and the contents filtered and concentrated. The resultant residue is purified by $SiO_2$ flash chromatography to yield Example 17. MS (ES+): m/z 551.4 $[M+H]^+$.

Synthesis of Example 63.

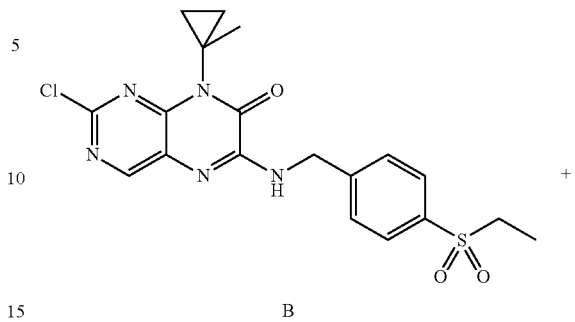

B

AB

63

Intermediate AB (105 mg, 0.46 mmol), bis(pinacolato)diboron (175 mg, 0.69 mmol), potassium acetate (67 mg, 0.69 mmol) and [1,1'-bisdiphenylphosphinoferrocene]-palladium (II) dichloride (18 mg, 0.045 mmol) are combined in a solution of degassed toluene/DME/ethanol/water (3:2:2:1, 3 mL). The vessel is heated to 90° C. for 20 min in a microwave reactor. In a separate vessel, intermediate B (100 mg, 0.23 mmol), bis(pinacolato)diboron (175 mg, 0.69 mmol), KOAc (67 mg, 0.69 mmol) and bis(di-tert-butyl(4-dimethylaminophenyl)phosphine)dichloropalladium(II) (16 mg, 0.045 mmol) are combined in degassed 1,4 dioxane (3 mL). The reaction is heated to 90° C. for 20 min in a microwave reactor. The contents of the two vessels are combined and 2M sodium bicarbonate (1 mL) is added. The reaction is heated to 120° C. for 30 min in a microwave reactor. The vessel is cooled to rt and the contents filtered and concentrated. The resultant residue is purified by $SiO_2$ flash chromatography to yield Example 63. MS (ES+): m/z 548.0 $[M+H]^+$.

Synthesis of Example 65.

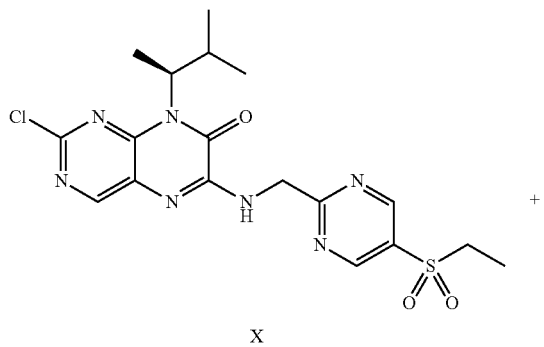

X

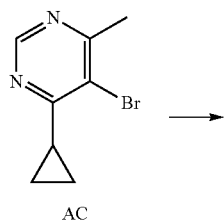

AC

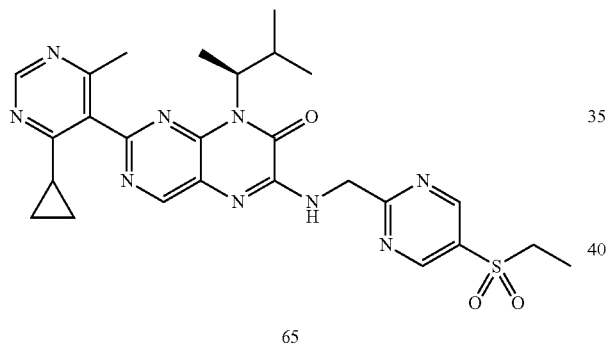

65

Intermediate AC (174 mg, 0.820 mmol), bis(pinacolato)diboron (277 mg, 1.093 mmol), potassium acetate (161 mg, 1.64 mmol) and [1,1'-bisdiphenylphosphinoferrocene]-palladium(II) dichloride (43 mg, 0.055 mmol) are combined in a solution of degassed toluene/DME/ethanol/water (3:2:2:1, 3 mL). The vessel is heated to 90° C. for 20 min in a microwave reactor. In a separate vessel, intermediate X (247 mg, 0.547 mmol), bis(pinacolato)diboron (277 mg, 0.820 mmol), potassium acetate (161 mg, 1.64 mmol) and bis(di-tert-butyl(4-dimethylaminophenyl)phosphine)dichloropalladium(II) (43 mg, 0.055 mmol) are combined in degassed 1,4 dioxane (3 mL). The reaction is heated to 90° C. for 20 min in a microwave reactor. The contents of the two vessels are combined and $Na_2CO_{3(aq)}$ (2M, 1 mL) is added. The reaction is heated to 120° C. for 30 min in a microwave reactor. The vessel is cooled to rt and the contents filtered and concentrated. The resultant residue is purified by $SiO_2$ flash chromatography to yield Example 65. MS (ES+): m/z 550.0 [M+H]$^+$.

The following compounds are prepared in an analogous manner:

Examples 1-8, 10, 12-14, 16, 18-62, 64, 66-92, 129.

Method 14:

Synthesis of Example 93.

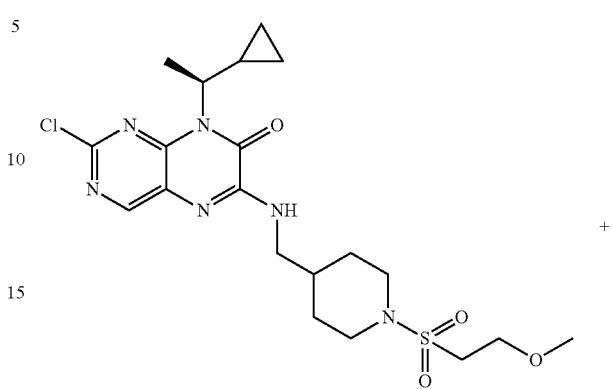

AJ

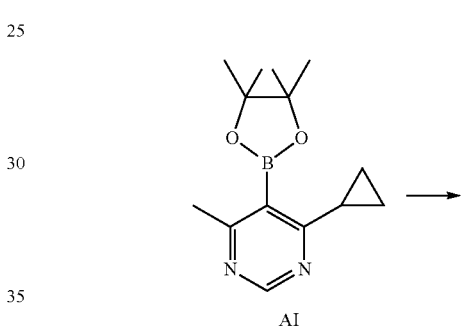

AI

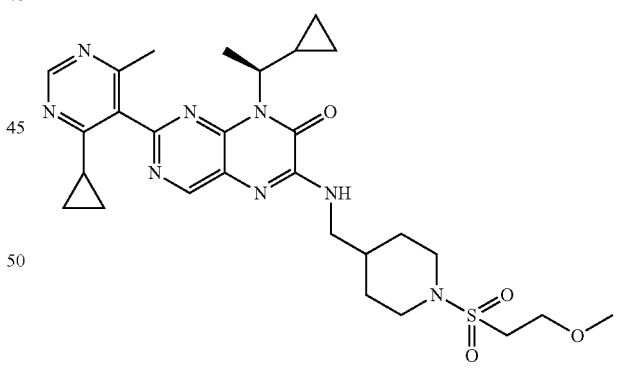

93

A mixture of AJ (100 mg, 0.21 mmol), intermediate AI (83.7 mg, 0.32 mmol), $K_3PO_4$ (91 mg, 0.43 mmol), and Pd(dppf)Cl$_2$ (26 mg, 0.03 mmol) in 1,4-dioxane (2 mL) is purged with argon, and then $H_2O$ (0.25 mL) is added. The mixture is stirred at 100° C. for 18 h. After cooling to rt, the mixture is diluted with water (2 mL) and extracted with EtOAc (2×5 mL). The combined organic phase is dried (Na$_2$SO$_4$), decanted and concentrated. The resultant residue is purified by reversed HPLC to yield Example 93. MS (ES+): m/z 584.0 [M+H]$^+$.

Synthesis of Example 136.

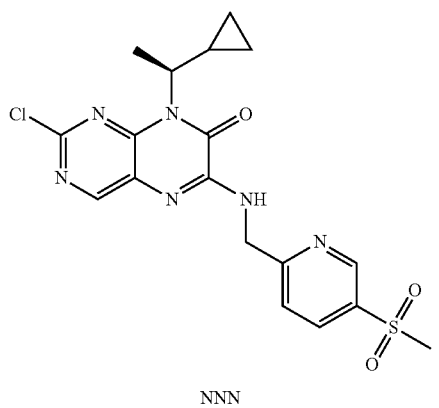

NNN

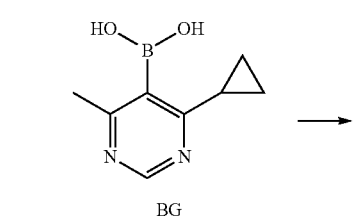

BG

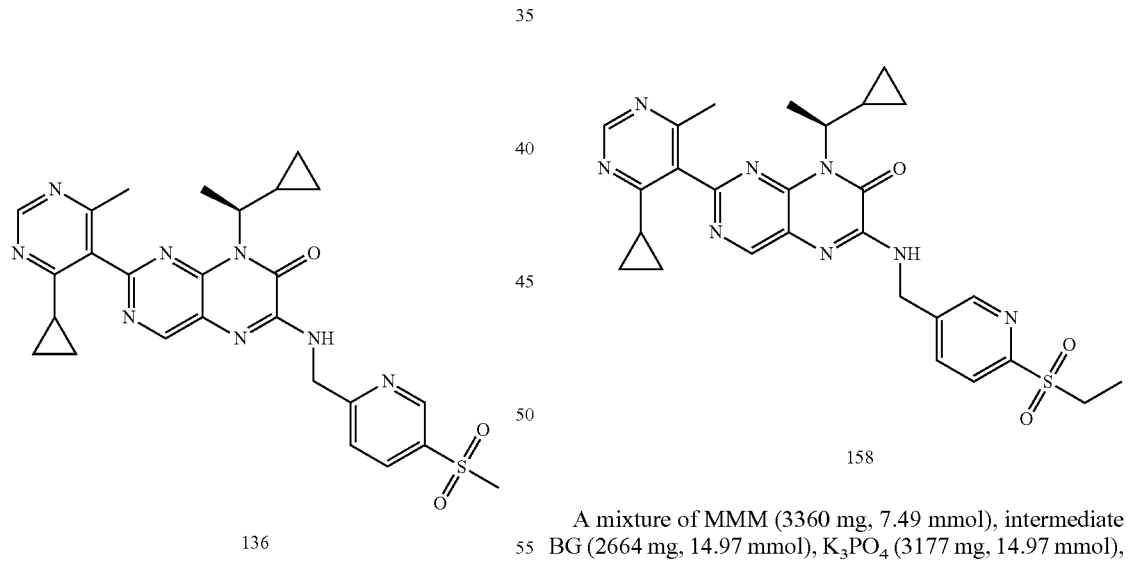

136

A mixture of NNN (3500 mg, 8.05 mmol), intermediate BG (2149 mg, 12.07 mmol), K$_3$PO$_4$ (3417 mg, 16.09 mmol), and Pd(dppf)Cl$_2$ (986 mg, 1.21 mmol) in 1,4-dioxane (60 mL) is purged with argon, and then H$_2$O (6 mL) is added. The mixture is stirred at 100° C. for 18 h. After cooling to rt, the mixture is diluted with water (2 mL) and extracted with EtOAc (2×5 mL). The combined organic phase is dried (Na$_2$SO$_4$), decanted and concentrated. The resultant residue is purified by reversed HPLC to yield Example 136. MS (ES+): m/z 533.0 [M+H]$^+$.

Synthesis of Example 158

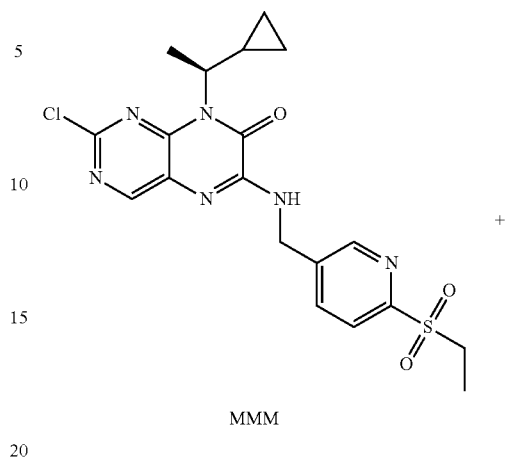

MMM

BG

158

A mixture of MMM (3360 mg, 7.49 mmol), intermediate BG (2664 mg, 14.97 mmol), K$_3$PO$_4$ (3177 mg, 14.97 mmol), and Pd(dppf)Cl$_2$ (916 mg, 1.12 mmol) in 1,4-dioxane (60 mL) is purged with argon, and then H$_2$O (6 mL) is added. The mixture is stirred at 100° C. for 18 h. After cooling to rt, the mixture is diluted with water (2 mL) and extracted with EtOAc (2×5 mL). The combined organic phase is dried (Na$_2$SO$_4$), decanted and concentrated. The resultant residue is purified by reversed HPLC to yield Example 158. MS (ES+): m/z 539.3.0 [M+H]$^+$.

The following compounds are prepared in an analogous manner:

Examples 94-128, 130-132, 134, 137-144, 146-157, 159-199, 201-265.

Synthesis of Example 133:

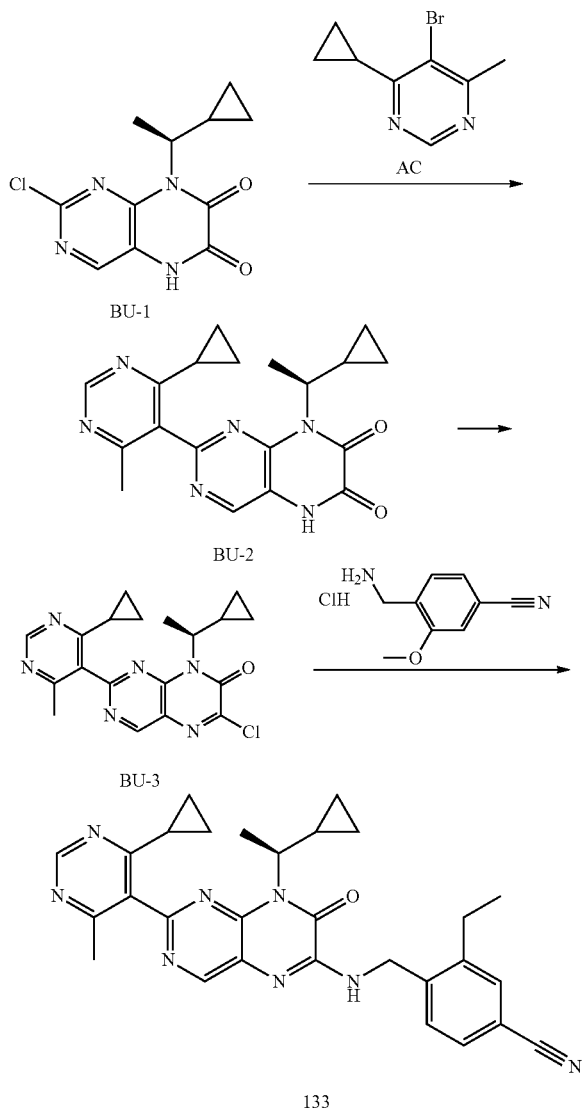

Example 135 and 145 are synthesized in a fashion analogous to Example 133.

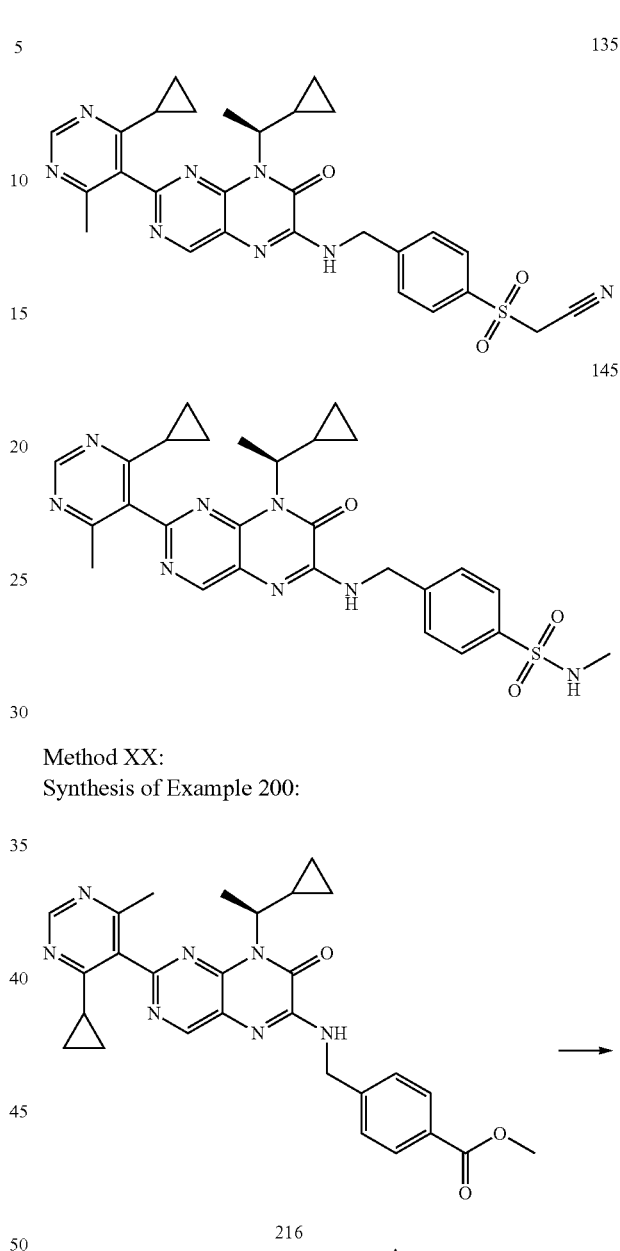

Method XX:
Synthesis of Example 200:

A mixture of AC (5.39 g, 25.3 mmol), bis(pinacolato)diboron (10.4 g, 40.5 mmol), potassium acetate (3.98 g, 40.5 mmol), and Pd(dppf)Cl$_2$ DCM complex (0.83 g, 1.01 mmol) in DME/Tol/EtOH/H$_2$O (10:6:3:1) is purged with argon, sealed, and stirred at 80° C. for 30 min. This is added to an argon purged mixture of BU-1 (2.70 g, 10.1 mmol) and Pd(amphos)Cl$_2$ (0.71 g, 1.01 mmol) and the sealed mixture is heated to 110° C. for 2 h. The mixture is then concentrated, diluted with EtOAc, filtered and then concentrated again. The crude is purified by SiO$_2$ flash chromatography to yield BU-2.

To a solution of the BU-2 (856 mg, 2.35 mmol) in DCM (15 ml) is added oxalyl chloride (596 mg, 4.70 mmol) followed by 5 drops of DMF. The reaction is allowed to stir for 18 h. The reaction is then concentrated and the residue yields BU-3 which is carried on as is.

To a stirred solution of the BU-3 (150 mg, 0.36 mmol) in DMF is added DIEA (196 uL, 1.41 mmol) at rt. After 10 minutes BU-4 (84.1 mg, 0.42 mmol) is added and the reaction is stirred at rt for 10 min. The mixture is then concentrated and purified by reversed HPLC (NH$_4$CO$_3$) to yield Example 133. MS (ES+): m/z 509.1 [M+H]$^+$.

To a solution of 216 (100 mg, 0.195 mmol) in dioxane (2 mL)/water (1 mL) is added LiOH (28.0 mg, 1.17 mmol). The reaction is stirred at rt for 16 h. The mixture is concentrated and dissolved in water, acidified with 1N HCl to pH~5, filtered, washed with water, and dried in vacuum oven to yield 200. MS (ES+): m/z 498.1 [M+H]$^+$ Biological Activity The compounds of the present invention have activity as modulators of RORγ (retinoid acid receptor-related orphan receptor γ).

Reporter Gene Assay (RGA)

A nuclear receptor transactivation assay is performed to quantitate the ability of test compounds to inhibit RORγ transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Ga14DBD hRORC LBD1-3). The positive control is co-transiently transfected with both plasmids, and the negative control contains the pGL4.3 promoter sequence. Assays are assembled in 384 well plates where transiently transfected cells and test compound at varying concentrations are incubated for 20-24 h. The next day, assays plates are taken out and equilibrated at RT for 20-30 minutes. Bright-Glo™ Luciferase Assay System is used to detect Luciferase production. After addition of Bright GLO detection reagent, the plates are incubated at RT for 20 minutes. The plates are read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, 1× Penicillin-Streptomycin-Gibco #15140
Compound Dilution Buffer:
1×HBSS-Invitrogen #14025126
Assay Plates: Greiner #781080-020
Bright Glo Luciferase Assay System: Promega #E2620
Thaw lysis buffer provided in kit, add 100 mL lysis buffer to substrate powder.

The below table presents the results obtained when the compounds of the present invention were tested in the above assay, demonstrating their activity as modulators of RORγ:

TABLE II

Table of Biological Activity in Reporter Gene Assay

| Example | RGA IC$_{50}$ (nM) |
|---|---|
| 1 | 210 |
| 2 | 230 |
| 3 | 230 |
| 4 | 250 |
| 5 | 260 |
| 6 | 260 |
| 7 | 280 |
| 8 | 290 |
| 9 | 300 |
| 10 | 300 |
| 11 | 300 |
| 12 | 300 |
| 13 | 300 |
| 14 | 310 |
| 15 | 310 |
| 16 | 320 |
| 17 | 330 |
| 18 | 330 |
| 19 | 330 |
| 20 | 330 |
| 21 | 360 |
| 22 | 360 |
| 23 | 390 |
| 24 | 390 |
| 25 | 410 |
| 26 | 420 |
| 27 | 420 |
| 28 | 440 |
| 29 | 470 |
| 30 | 550 |
| 31 | 560 |
| 32 | 640 |
| 33 | 670 |
| 34 | 730 |
| 35 | 870 |
| 36 | 880 |
| 37 | 930 |
| 38 | 1100 |
| 39 | 1100 |
| 40 | 1400 |
| 41 | 1400 |
| 42 | 1500 |
| 43 | 2600 |
| 44 | 2800 |
| 45 | 2900 |
| 46 | 3000 |
| 47 | 3200 |
| 48 | 3800 |
| 49 | 4300 |
| 50 | 4400 |
| 51 | 7600 |
| 52 | 420 |
| 53 | 680 |
| 54 | 420 |
| 55 | 1400 |
| 56 | 1400 |
| 57 | 560 |
| 58 | 420 |
| 59 | 850 |
| 60 | 750 |
| 61 | 470 |
| 62 | 990 |
| 63 | 930 |
| 64 | 920 |
| 65 | 590 |
| 66 | 410 |
| 67 | 370 |
| 68 | 330 |
| 69 | 320 |
| 70 | 630 |
| 71 | 480 |
| 72 | 250 |
| 73 | 290 |
| 74 | 410 |
| 75 | 590 |
| 76 | 1600 |
| 77 | 1600 |
| 78 | 2400 |
| 79 | 610 |
| 80 | 1100 |
| 81 | 1700 |
| 82 | 380 |
| 83 | 2200 |
| 84 | 400 |
| 85 | 290 |
| 86 | 550 |
| 87 | 310 |
| 88 | 3400 |
| 89 | 750 |
| 90 | 4100 |
| 91 | 1800 |
| 92 | 850 |
| 93 | 110 |
| 94 | 125 |
| 95 | 355 |
| 96 | 320 |

TABLE II-continued

Table of Biological Activity in Reporter Gene Assay

| Example | RGA IC$_{50}$ (nM) |
|---|---|
| 97 | 101 |
| 98 | 195 |
| 99 | 265 |
| 100 | 130 |
| 101 | 115 |
| 102 | 250 |
| 103 | 82 |
| 104 | 3000 |
| 105 | 1600 |
| 106 | 1150 |
| 107 | 560 |
| 108 | 300 |
| 109 | 790 |
| 110 | 1350 |
| 111 | 460 |
| 112 | 920 |
| 113 | 108 |
| 114 | 107 |
| 115 | 67 |
| 116 | 300 |
| 117 | 155 |
| 118 | 225 |
| 119 | 720 |
| 120 | 420 |
| 121 | 130 |
| 122 | 150 |
| 123 | 135 |
| 124 | 97 |
| 125 | 175 |
| 126 | 119 |
| 127 | 570 |
| 128 | 160 |
| 129 | 2500 |
| 130 | 285 |
| 131 | 205 |
| 132 | 243 |
| 133 | 1035 |
| 134 | 400 |
| 135 | 240 |
| 136 | 255 |
| 137 | 278 |
| 138 | 160 |
| 139 | 700 |
| 140 | 730 |
| 141 | 925 |
| 142 | 333 |
| 143 | 134 |
| 144 | 162 |
| 145 | 95 |
| 146 | 435 |
| 147 | 250 |
| 148 | 505 |
| 149 | 305 |
| 150 | 230 |
| 151 | 255 |
| 152 | 470 |
| 153 | 375 |
| 154 | 295 |
| 155 | 185 |
| 156 | 275 |
| 157 | 92 |
| 158 | 106 |
| 159 | 91 |
| 160 | 285 |
| 161 | 375 |
| 162 | 795 |
| 163 | 160 |
| 164 | 410 |
| 165 | 157 |
| 166 | 1600 |
| 167 | 270 |
| 168 | 435 |
| 169 | 145 |
| 170 | 235 |
| 171 | 200 |
| 172 | 440 |
| 173 | 690 |
| 174 | 275 |
| 175 | 380 |
| 176 | 550 |
| 177 | 73 |
| 178 | 240 |
| 179 | 675 |
| 180 | 235 |
| 181 | 175 |
| 182 | 130 |
| 183 | 325 |
| 184 | 295 |
| 185 | 175 |
| 186 | 150 |
| 187 | 255 |
| 188 | 315 |
| 189 | 120 |
| 190 | 130 |
| 191 | 86 |
| 192 | 83 |
| 193 | 99 |
| 194 | 180 |
| 195 | 183 |
| 196 | 157 |
| 197 | 225 |
| 198 | 225 |
| 199 | 120 |
| 200 | 855 |
| 201 | 75 |
| 202 | 455 |
| 203 | 800 |
| 204 | 665 |
| 205 | 80 |
| 206 | 777 |
| 207 | 1400 |
| 208 | 125 |
| 209 | 75 |
| 210 | 150 |
| 211 | 225 |
| 212 | 120 |
| 213 | 155 |
| 214 | 220 |
| 215 | 330 |
| 216 | 1385 |
| 217 | 160 |
| 218 | 170 |
| 219 | 280 |
| 220 | 390 |
| 221 | 350 |
| 222 | 1250 |
| 223 | 135 |
| 224 | 120 |
| 225 | 230 |
| 226 | 155 |
| 227 | 455 |
| 228 | 595 |
| 229 | 530 |
| 230 | 270 |
| 231 | 195 |
| 232 | 180 |
| 233 | 155 |
| 234 | 590 |
| 235 | 425 |
| 236 | 185 |
| 237 | 265 |
| 238 | 400 |
| 239 | 205 |
| 240 | 600 |
| 241 | 310 |
| 242 | 395 |
| 243 | 230 |
| 244 | 475 |
| 245 | 1700 |
| 246 | 645 |

TABLE II-continued

Table of Biological Activity in Reporter Gene Assay

| Example | RGA IC$_{50}$ (nM) |
|---|---|
| 247 | 385 |
| 248 | 540 |
| 249 | 530 |
| 250 | 190 |
| 251 | 158 |
| 252 | 325 |
| 253 | 340 |
| 254 | 455 |
| 255 | 285 |
| 256 | 1900 |
| 257 | 155 |
| 258 | 210 |
| 259 | 190 |
| 260 | 515 |
| 261 | 470 |
| 262 | 4000 |
| 263 | 4300 |
| 264 | 5900 |
| 265 | 4800 |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORγ.

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of RORγ modulators is of therapeutic benefit, including but not limited to the treatment of autoimmune or allergic disorders.

Such disorders that may be treated by the compounds of the invention include for example: rheumatoid arthritis, psoriasis, systemic lupus erythromatosis, lupus nephritis, systemic sclerosis, vasculitis, scleroderma, asthma, allergic rhinitis, allergic eczema, multiple sclerosis, juvenile rheumatoid arthritis, juvenile idiopathic arthritis, type I diabetes, Crohn's disease, ulcerative colitis, graft versus host desease, psoriatic arthritis, reactive arthritis, ankylosing spondylitis, atherosclerosis, uveitis and non-radiographic spondyloarthropathy.

For treatment of the above-described diseases and conditions, a therapeutically effective dose will generally be in the range of approximately 0.01 mg to about 10 mg/kg of body weight per dosage of a compound of the invention; preferably, from about 0.1 mg to about 5 mg/kg of body weight per dosage. For example, for administration to a 70 kg person, the dosage range would be approximately 0.7 mg to about 750 mg per dosage of a compound of the invention, preferably from about 7.0 mg to about 350 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and generally comprise at least one compound of the invention and at least one pharmaceutically acceptable carrier. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

All patent and non-patent documents or literature cited in this application are herein incorporated by reference in their entirety.

The invention claimed is:
1. A compound of formula (I)

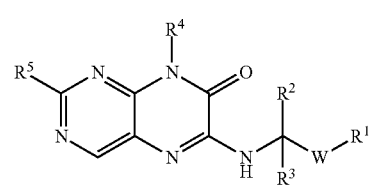

wherein:
R$^1$ is:
  —CN;
  —S(O)$_n$R$^6$;
  —S(O)$_n$NR$^7$R$^8$;

—S(O)(NR$^9$)R$^6$;
—N(R$^9$)C(O)R$^6$;
—N(R$^9$)C(O)OR$^6$;
—N(R$^9$)S(O)$_n$R$^6$;
—C(O)OR$^9$;
—C(O)NR$^7$R$^8$; or
—C(O)R$^9$; or

R$^6$, R$^7$, R$^8$ or R$^9$ of R$^1$ may be cyclized onto W to form a ring; and R$^2$ and R$^3$ are each independently:
  (A) —H;
  (B) C$_{1-3}$ alkyl optionally substituted with one, two or three groups selected from:
    a) C$_{3-6}$ cycloalkyl;
    b) —OR$^9$;
    c) —CN;
    d) —CF$_3$;
    e) -halo;
    f) —C(O)OR$^9$;
    g) —C(O)N(R$^9$)$_2$;
    h) —S(O)$_n$R$^9$; and
    i) —S(O)$_n$NR$^7$R$^8$; or
  (C) C$_{3-6}$ cycloalkyl;
  (D) C$_{3-6}$ heterocyclyl; or
  R$^2$ and R$^3$ are taken together with the carbon to which they are attached to form a C$_{3-6}$ carbocyclic ring; or
  R$^2$ and R$^3$ are taken together with the carbon to which they are attached to form a C$_{3-6}$ heterocyclic ring; or
  R$^2$ or R$^3$ may be cyclized onto W to form a ring;

R$^4$ is:
  (A) C$_{1-6}$ alkyl optionally substituted with one, two or three groups selected from:
    a) C$_{3-6}$ cycloalkyl;
    b) C$_{3-6}$ heterocyclyl;
    c) —OR$^9$;
    d) —CN;
    e) —S(O)$_n$R$^9$;
    f) -halo; and
    g) —CF$_3$; or
  (B) C$_{3-12}$ cycloalkyl optionally substituted with one, two or three groups selected from:
    a) C$_{1-6}$ alkyl;
    b) —OR$^9$;
    c) —CN;
    d) —S(O)$_n$R$^9$;
    e) -halo; and
    f) —CF$_3$; or
  (C) aryl, heteroaryl or heterocyclyl each optionally substituted with one, two or three groups selected from:
    a) C$_{1-6}$ alkyl;
    b) C$_{3-6}$cycloalkyl;
    c) —OR$^9$;
    d) —CN;
    e) —S(O)$_n$R$^9$;
    f) -halo; and
    g) —CF$_3$;

R$^5$ is aryl, heteroaryl, heterocyclyl or C$_{3-12}$ cycloalkyl each optionally substituted with one, two or three groups selected from:
  (A) C$_{1-6}$ alkyl, C$_{3-6}$ cycloalkyl or C$_{3-6}$ heterocyclyl each optionally substituted with one, two or three groups selected from:
    a) C$_{3-6}$ cycloalkyl;
    b) C$_{3-6}$ heterocyclyl;
    c) —OR$^9$;
    d) —CN;
    e) —S(O)$_n$NR$^7$R$^8$
    f) —S(O)$_n$R$^9$;
    g) -halo; and
    h) —CF$_3$; or
  (B) —OR$^9$;
  (C) —CN;
  (D) —CF$_3$;
  (E) -halo;
  (F) —S(O)$_n$NR$^7$R$^8$;
  (G) —S(O)$_n$R$^9$; and
  (H) —NR$^7$R$^8$;

W is aryl, heteroaryl, heterocyclyl, C$_{3-12}$ cycloalkyl, or alkynyl each optionally substituted with one or two groups selected from:
  a) C$_{1-6}$ alkyl;
  b) C$_{3-6}$ cycloalkyl;
  c) —OR$^9$;
  d) —CN;
  e) —CF$_3$;
  f) -halo;
  g) —NR$^7$R$^8$;
  h) —C(O)OR$^9$; and
  i) —C(O)N(R$^9$)$_2$;

R$^6$ is selected from:
  (A) —OH;
  (B) C$_{1-6}$ alkyl optionally substituted with one or two groups selected from:
    a) C$_{3-6}$cycloalkyl;
    b) —OR$^9$;
    c) —CN;
    d) —CF$_3$; and
    e) -halo;
  (C) C$_{3-6}$ cycloalkyl; and
  (D) —CF$_3$;

R$^7$ and R$^8$ are independently selected from:
  (A) —H;
  (B) C$_{1-3}$ alkyl optionally substituted with one or two groups selected from:
    a) C$_{3-6}$cycloalkyl;
    b) —OR$^9$;
    c) —CN; and
    d) -halo; and
  (C) C$_{3-6}$cycloalkyl; or
  R$^7$ and R$^8$, together with the nitrogen to which they are bonded, form a saturated ring with 3-6 carbon atoms wherein one carbon atom in said saturated ring may be optionally replaced by —O—, —NR$^9$— or —S(O)$_n$—;

R$^9$ is selected from;
  (A) —H;
  (B) C$_{1-3}$ alkyl optionally substituted with one or two groups selected from:
    a) C$_{3-6}$cycloalkyl;
    b) —OR$^9$;
    c) —CN;
    d) —CF$_3$
    e) -halo; or
  (C) C$_{3-6}$cycloalkyl; and n is 0, 1 or 2;

or a pharmaceutically acceptable salt thereof.

2. A compound of formula (I) according to claim 1, or a pharmaceutically acceptable salt thereof, wherein:

R$^1$ is:
  —CN,
  —S(O)$_n$R$^6$,
  —S(O)$_n$NR$^7$R$^8$;
  —N(H)S(O)—R$^6$; or
  —S(O)(NH)R$^6$; and wherein:

$R^6$ is:
(A) $C_{1-3}$ alkyl optionally substituted with one or two groups selected from:
a) $C_{3-6}$cycloalkyl;
b) —$OR^9$; and
c) —CN; or
(B) $C_{3-6}$cycloalkyl;

$R^7$ and $R^8$ are each independently:
(A) —H; or
(B) $C_{1-3}$ alkyl; and $R^9$ is selected from;
(A) —H;
(B) $C_{1-3}$ alkyl; or
(C) $C_{3-6}$cycloalkyl; and n is 1 or 2.

3. A compound of formula (I) according to claim 1, or a pharmaceutically acceptable salt thereof, wherein:

$R^1$ is:
—S(O)—$R^6$,
—S(O)$_n$$NR^7R^8$, or
—S(O)(NH)$R^6$; and wherein:

$R^6$ is:
(A) $C_{1-3}$ alkyl optionally substituted with one or two groups selected from:
a) $C_{3-6}$cycloalkyl;
b) —$OR^9$; and
c) —CN; or
(B) $C_{3-6}$cycloalkyl;

$R^7$ and $R^8$ are each independently:
(A) —H; or
(B) $C_{1-3}$ alkyl; and $R^9$ is selected from:
(A) —H;
(B) $C_{1-3}$ alkyl; or
(C) $C_{3-6}$cycloalkyl; and n is 1 or 2.

4. A compound of formula (I) according to claim 1, or a pharmaceutically acceptable salt thereof, wherein:

$R^1$ is —S(O)$_n$$R^6$, —S(O)$_n$$NR^7R^8$ or —S(O)(NH)$R^6$; and
$R^6$ is $C_{1-3}$ alkyl; and
$R^7$ and $R^8$ are each independently:
(A) —H; or
(B) $C_{1-3}$ alkyl; and
n is 2.

5. A compound of formula (I) according to claim 1, or a pharmaceutically acceptable salt thereof, wherein:

$R^2$ and $R^3$ are each independently selected from:
(A) —H;
(B) $C_{1-3}$ alkyl optionally substituted with one, two or three groups selected from:
a) $C_{3-6}$ cycloalkyl;
b) —$OR^9$; or
c) -halo; or $R^2$ and $R^3$ are taken together with the carbon to which they are attached to form a $C_{3-6}$ carbocyclic ring; or
$R^2$ and $R^3$ are taken together with the carbon to which they are attached to form a $C_{3-6}$ heterocyclic ring; and $R^9$ is selected from:
(A) —H; and
(B) $C_{1-3}$ alkyl.

6. A compound of formula (I) according to claim 1, or a pharmaceutically acceptable salt thereof, wherein:

$R^2$ and $R^3$ are each independently selected from H and $C_{1-3}$ alkyl.

7. A compound of formula (I) according to claim 1, or a pharmaceutically acceptable salt thereof, wherein $R^2$ and $R^3$ are H.

8. A compound of formula (I) according to claim 1, or a pharmaceutically acceptable salt thereof, wherein:

$R^4$ is:
(A) $C_{1-6}$ alkyl optionally substituted with one, two or three groups selected from:
a) $C_{3-6}$ cycloalkyl;
b) a 4, 5 or 6-membered heterocyclyl;
c) —$OR_9$;
d) —CN;
e) -halo; and
f) —$CF_3$; or
(B) $C_{3-6}$ cycloalkyl optionally substituted with one, two or three groups selected from:
a) $C_{1-6}$ alkyl;
b) —$OR^9$;
c) —CN;
d) -halo; and
e) —$CF_3$; and
wherein one carbon in said $C_{3-6}$ cycloalkyl may be optionally replaced by —O—;
(C) Phenyl; or
(D) a 4, 5 or 6-membered heterocyclyl; and $R^9$ is selected from:
(A) —H; and
(B) $C_{1-3}$ alkyl.

9. A compound of formula (I) according to claim 1, or a pharmaceutically acceptable salt thereof, wherein:

$R^4$ is:
(A) $C_{1-6}$ alkyl optionally substituted with one or two groups selected from:
a) $C_{3-6}$cycloalkyl;
b) a 4, 5, or 6-membered heterocyclyl;
c) —$OR^9$;
d) —CN;
e) -halo; and
f) —$CF_3$; or
(B) $C_{3-6}$ cycloalkyl optionally substituted with one, two or three groups selected from:
a) $C_{1-6}$ alkyl;
b) —$OR^9$;
c) —CN;
d) -halo; and
e) —$CF_3$; or
(C) Phenyl; or
(D) a 5 or 6-membered heterocyclyl; and $R^9$ is $C_{1-3}$ alkyl.

10. A compound of formula (I) according to claim 1, or a pharmaceutically acceptable salt thereof, wherein:

$R^4$ is:
(A) $C_{1-6}$ alkyl optionally substituted with one or two groups selected from $C_{3-6}$cycloalkyl, halo, —$CF_3$, and $C_{1-3}$ alkoxy; or
(B) $C_{3-6}$ cycloalkyl optionally substituted with one or two groups selected from $C_{1-6}$ alkyl, —$CF_3$, and halo; or
(C) a 5-membered heterocyclyl.

11. A compound of formula (I) according to claim 1, or a pharmaceutically acceptable salt thereof, wherein:

$R^5$ is aryl, heteroaryl or heterocyclyl, each optionally substituted with one, two or three groups selected from:
a) $C_{1-6}$ alkyl;
b) $C_{3-6}$cycloalkyl;
c) —$OR^9$;
d) —CN;

e) —CF$_3$;
f) -halo; and
g) —NR$^7$R$^8$; and
R$^7$, R$^8$ and R$^9$ are each independently selected from:
(A) —H; and
(B) C$_{1-3}$ alkyl.

12. A compound of formula (I) according to claim 1, or a pharmaceutically acceptable salt thereof, wherein:
R$^5$ is:
(A) phenyl optionally substituted with one, two or three groups selected from:
a) C$_{1-6}$ alkyl;
b) C$_{3-6}$ cycloalkyl;
c) —OR$^9$;
d) —CN;
e) —CF$_3$; and
f) -halo; or
(B) a 5 or 6-membered heteroaryl optionally substituted with one, two or three groups selected from:
a) C$_{1-6}$ alkyl;
b) C$_{3-6}$ cycloalkyl;
c) —OR$^9$;
d) —CN;
e) —CF$_3$;
f) -halo; and
g) —NR$^7$R$^8$; and
R$^7$, R$^8$ and R$^9$ are each independently selected from:
(A) —H; and
(B) C$_{1-3}$ alkyl.

13. A compound of formula (I) according to claim 1, or a pharmaceutically acceptable salt thereof, wherein:
R$^5$ is pyridinyl or pyrimidinyl each optionally substituted with one, two or three groups selected from:
a) C$_{1-6}$ alkyl;
b) C$_{3-6}$ cycloalkyl;
c) —OR$^9$;
d) —CF$_3$; and
e) —NR$^7$R$^8$; and
R$^7$ and R$^8$ are each independently selected from:
(A) —H;
(B) C$_{1-3}$ alkyl; and
R$^9$ is C$_{1-3}$ alkyl.

14. A compound of formula (I) according to claim 1, or a pharmaceutically acceptable salt thereof, wherein:
R$^5$ is pyrimidinyl optionally substituted with one or two groups selected from:
a) C$_{1-3}$ alkyl;
b) C$_{3-5}$ cycloalkyl;
c) C$_{1-3}$ alkoxy; and
d) —CF$_3$.

15. A compound of formula (I) according to claim 1, or a pharmaceutically acceptable salt thereof, wherein:
W is phenyl, pyridinyl, pyrimidinyl, piperidinyl, piperizinyl, pyrazinyl or C$_{3-12}$ cycloalkyl, each optionally substituted with one or two groups selected from:
a) C$_{1-6}$ alkyl;
b) C$_{3-6}$ cycloalkyl;
c) —OR$^9$;
d) —CN;
e) —CF$_3$;
f) -halo;
g) —NR$^7$R$^8$;
h) —C(O)OR$^9$; and
i) —C(O)N(R$^9$)$_2$;
R$^7$, R$^8$ and R$^9$ are each selected from:
(A) —H; and
(B) C$_{1-3}$ alkyl.

16. A compound of formula (I) according to claim 1, or a pharmaceutically acceptable salt thereof, wherein W is phenyl, pyridinyl, pyrimidinyl or piperidinyl.

17. A compound of formula (I) according to claim 1, or a pharmaceutically acceptable salt thereof, wherein:
R$^1$ is:
—S(O)nR$^6$,
—S(O)nNR$^7$R$^8$, or
—S(O)(NH)R$^6$;
R$^2$ and R$^3$ are each independently selected from:
(A) —H; and
(B) C$_{1-3}$ alkyl;
R$^4$ is:
(A) C$_{1-6}$ alkyl optionally substituted with one or two groups selected from:
a) C$_{3-6}$ cycloalkyl;
b) a 4, 5, or 6-membered heterocyclyl;
c) —OR$^9$;
d) —CN;
e) -halo; and
f) —CF$_3$;
(B) C$_{3-6}$ cycloalkyl optionally substituted with one, two or three groups selected from:
a) C$_{1-6}$ alkyl;
b) —OR$_9$;
c) —CN;
d) -halo; and
e) —CF$_3$;
(C) Phenyl; or
(D) a 5 or 6-membered heterocyclyl;
R$^5$ is:
(A) phenyl optionally substituted with one or two groups selected from:
a) C$_{1-6}$ alkyl;
b) C$_{3-6}$ cycloalkyl;
c) —OR$^9$;
d) —CN;
e) —CF$_3$; and
f) -halo; or
(B) Pyridinyl or pyrimidinyl each optionally substituted with one, two or three groups selected from:
a) C$_{1-6}$ alkyl;
b) C$_{3-6}$ cycloalkyl;
c) —OR$^9$;
d) —CN;
e) —CF$_3$;
f) -halo; and
g) —NR$^7$R$^8$; and
W is phenyl, pyridinyl, pyrimidinyl, piperidinyl or C$_{3-12}$ cycloalkyl, each optionally substituted with one or two groups selected from:
a) C$_{1-6}$ alkyl;
b) C$_{3-6}$ cycloalkyl;
c) —OR$^9$;
d) —CN;
e) —CF$_3$;
f) -halo;
g) —NR$^7$R$^8$
h) —C(O)OR$^9$; and
i) —C(O)N(R$^9$)$_2$;
R$^6$ is:
(A) C$_{1-3}$ alkyl optionally substituted with one or two groups selected from:
a) C$_{3-6}$ cycloalkyl;
b) —OR$^9$ and
b) —CN; or (B) C$_{3-6}$cycloalkyl;
R$^7$, R$^8$ and R$^9$ are each independently:
(A) —H; or
(B) C$_{1-3}$ alkyl; and
n is 2.

18. A compound of formula (I) according to claim 1, or a pharmaceutically acceptable salt thereof, wherein:
R$^1$ is —S(O)$_n$R$^6$ or —S(O)$_n$NR$^7$R$^8$; and
R$^2$ and R$^3$ are H;
R$^4$ is:
  (A) C$_{1-6}$ alkyl optionally substituted with one or two groups selected from C$_{3-6}$ cycloalkyl, —CF$_3$, and C$_{1-3}$ alkoxy; or
  (B) C$_{3-6}$ cycloalkyl optionally substituted with one or two groups selected from C$_{1-6}$ alkyl, —CN, and halo; or
  (C) 5-membered heterocyclyl;
R$^5$ is pyrimidinyl optionally substituted with one, two or three groups selected from:
  a) C$_{1-6}$ alkyl;
  b) C$_{3-6}$ cycloalkyl;
  c) —OR$^9$;
  d) —CF$_3$; and
  e) —NR$^7$R$^8$;
W is phenyl, pyridinyl, pyrimidinyl or piperidinyl;
R$^6$ is C$_{1-3}$ alkyl;
R$^7$, R$^8$R$^9$ are each independently:
(A) —H; or
(B) C$_{1-3}$ alkyl; and
n is 2.

19. A compound of formula (I) according to claim 18, or a pharmaceutically acceptable salt thereof, wherein:
R$^5$ is pyrimidinyl optionally substituted with one or two groups selected from:
  a) C$_{1-3}$ alkyl;
  b) C$_{3-5}$ cycloalkyl; and
  c) C$_{1-3}$ alkoxy; and
W is phenyl, pyridinyl, pyrimidinyl or piperidinyl.

20. A compound selected from the compounds in the following table:

| Example | Structure |
| --- | --- |
| 1 | 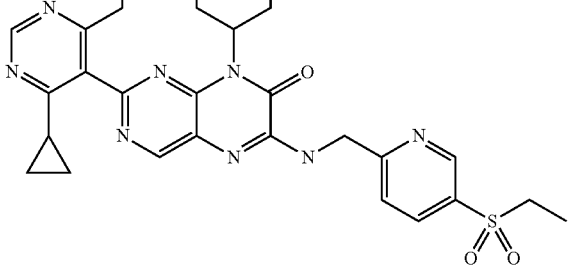 |
| 2 | 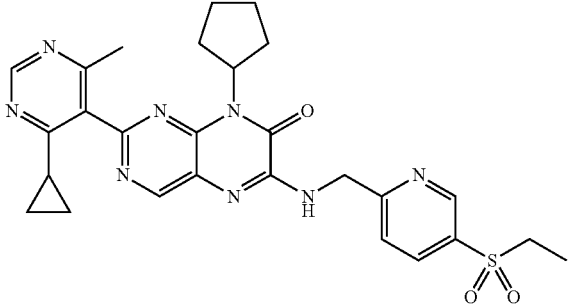 [SMILES: CCS(=O)(=O)c1ccc(CNc2nc3cnc(-c4c(C)ncnc4C4CC4)nc3n(C3CCCC3)c2=O)nc1] |
| 3 | 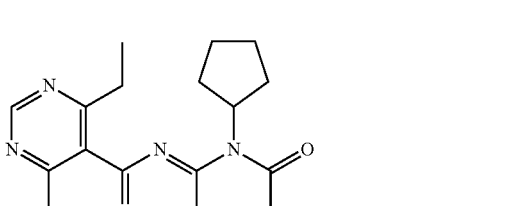 |

-continued

| Example | Structure |
|---------|-----------|
| 4 | 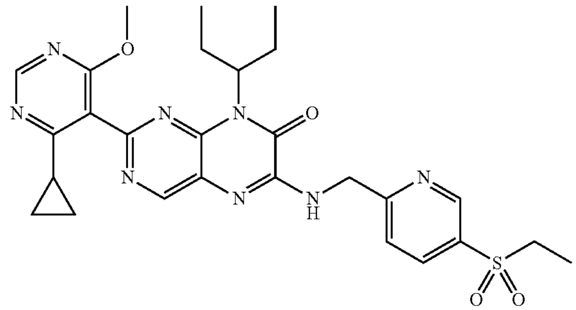 [SMILES: CCC(CC)n1c(=O)c(NCc2ccc(S(=O)(=O)CC)cn2)nc2cnc(-c3c(OC)ncnc3C3CC3)nc21] |
| 5 | 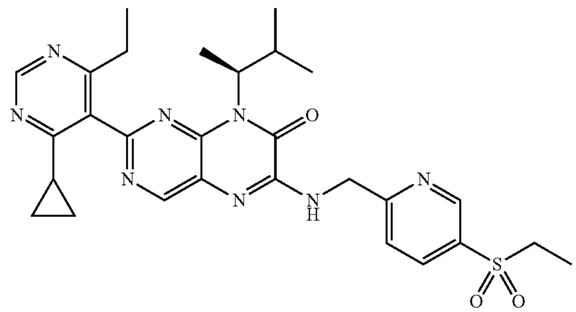 [SMILES: CCc1ncnc(C2CC2)c1-c1ncc2nc(NCc3ccc(S(=O)(=O)CC)cn3)c(=O)n([C@@H](C)C(C)C)c2n1] |
| 6 | 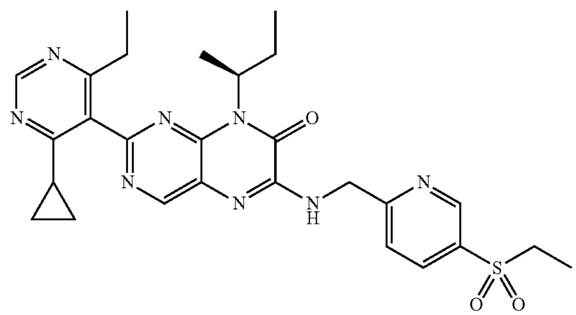 [SMILES: CCc1ncnc(C2CC2)c1-c1ncc2nc(NCc3ccc(S(=O)(=O)CC)cn3)c(=O)n([C@@H](C)CC)c2n1] |
| 7 | 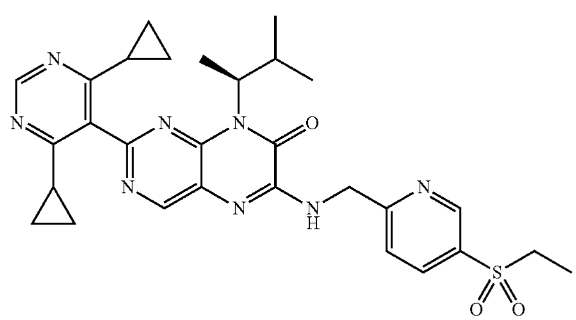 [SMILES: CCS(=O)(=O)c1ccc(CNc2nc3cnc(-c4c(C5CC5)ncnc4C4CC4)nc3n([C@@H](C)C(C)C)c2=O)nc1] |
| 8 | 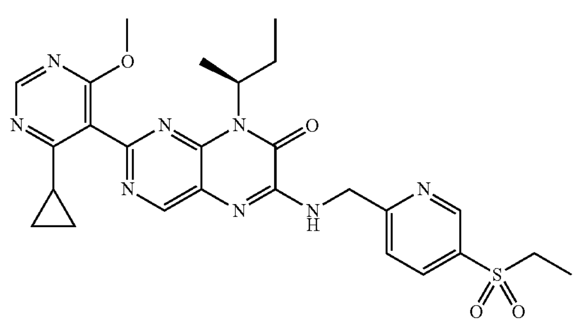 [SMILES: CC[C@H](C)n1c(=O)c(NCc2ccc(S(=O)(=O)CC)cn2)nc2cnc(-c3c(OC)ncnc3C3CC3)nc21] |

| Example | Structure |
|---|---|
| 9 | 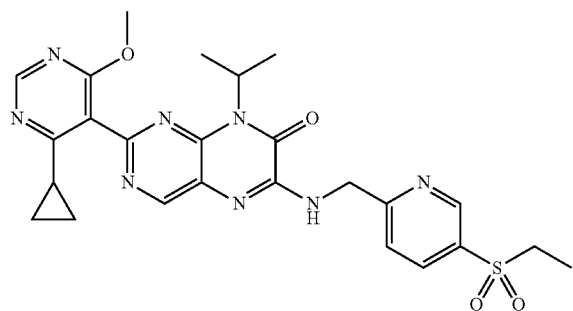 [SMILES: CCS(=O)(=O)c1ccc(CNc2nc3cnc(-c4c(OC)ncnc4C4CC4)nc3n(C(C)C)c2=O)nc1] |
| 10 | 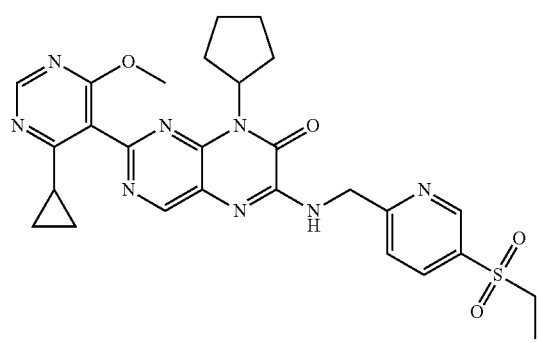 [SMILES: CCS(=O)(=O)c1ccc(CNc2nc3cnc(-c4c(OC)ncnc4C4CC4)nc3n(C3CCCC3)c2=O)nc1] |
| 11 | 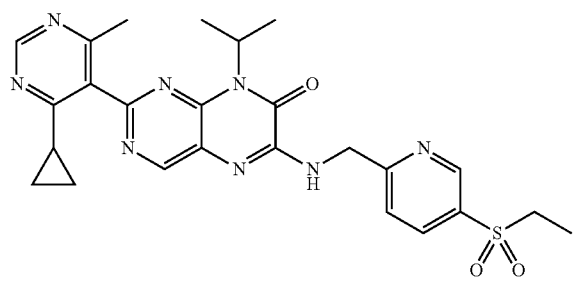 [SMILES: CCS(=O)(=O)c1ccc(CNc2nc3cnc(-c4c(C)ncnc4C4CC4)nc3n(C(C)C)c2=O)nc1] |
| 12 | 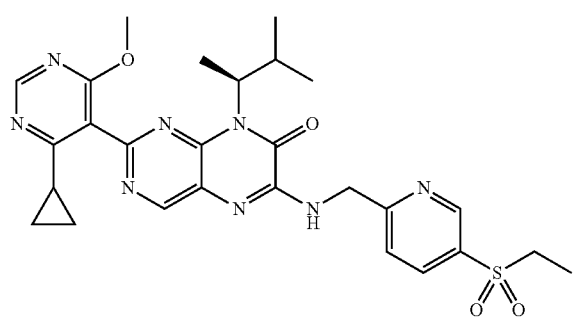 [SMILES: CCS(=O)(=O)c1ccc(CNc2nc3cnc(-c4c(OC)ncnc4C4CC4)nc3n([C@@H](C)C(C)C)c2=O)nc1] |
| 13 | 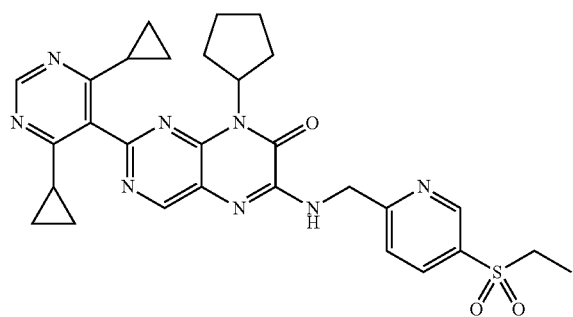 [SMILES: CCS(=O)(=O)c1ccc(CNc2nc3cnc(-c4c(C5CC5)ncnc4C4CC4)nc3n(C3CCCC3)c2=O)nc1] |

| Example | Structure |
|---|---|
| 14 | 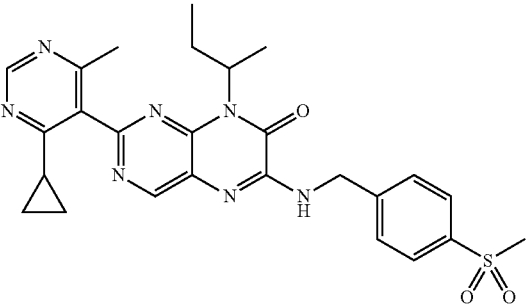 [SMILES: CCC(C)n1c(=O)c(NCc2ccc(S(C)(=O)=O)cc2)nc2cnc(-c3c(C)ncnc3C3CC3)nc21] |
| 15 | 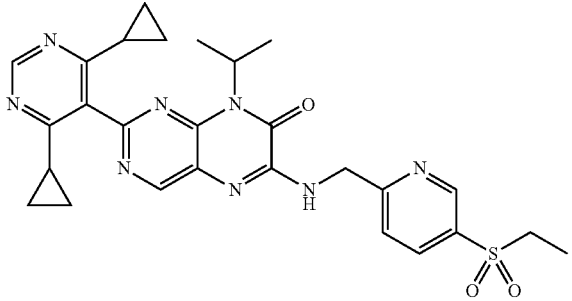 [SMILES: CCS(=O)(=O)c1ccc(CNc2nc3cnc(-c4c(C5CC5)ncnc4C4CC4)nc3n(C(C)C)c2=O)nc1] |
| 16 | 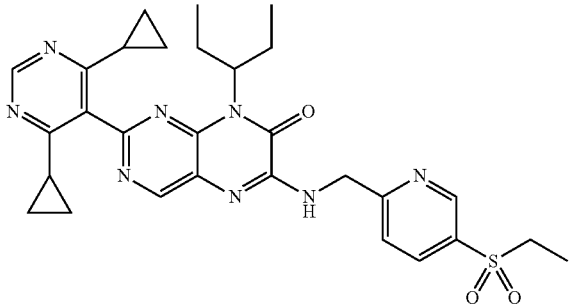 [SMILES: CCC(CC)n1c(=O)c(NCc2ccc(S(=O)(=O)CC)cn2)nc2cnc(-c3c(C4CC4)ncnc3C3CC3)nc21] |
| 17 | 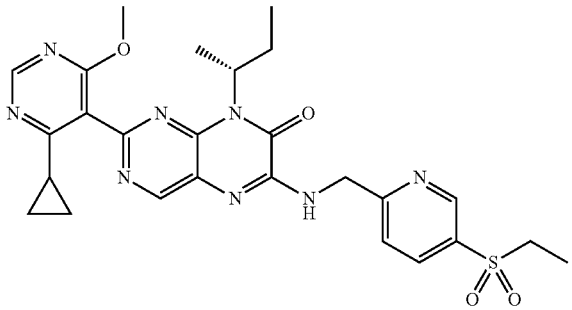 [SMILES: CC[C@@H](C)n1c(=O)c(NCc2ccc(S(=O)(=O)CC)cn2)nc2cnc(-c3c(OC)ncnc3C3CC3)nc21] |
| 18 | 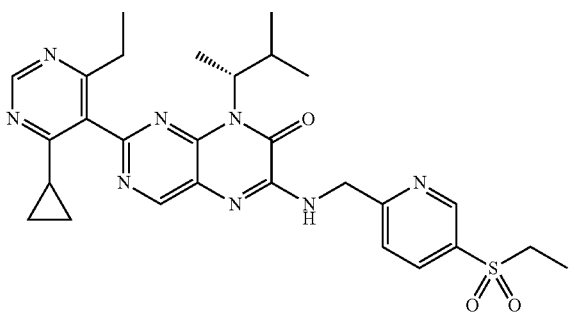 |

| Example | Structure |
|---|---|
| 19 | 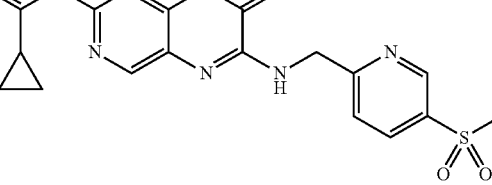 |
| 20 | 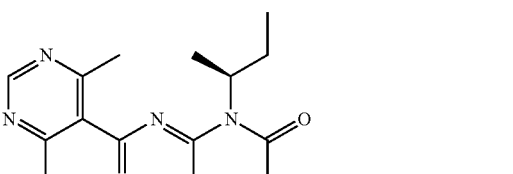 |
| 21 | 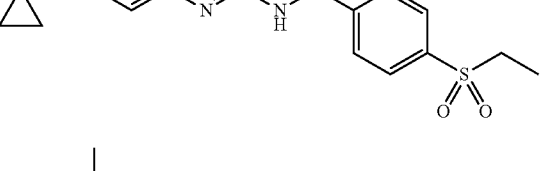 |
| 22 | 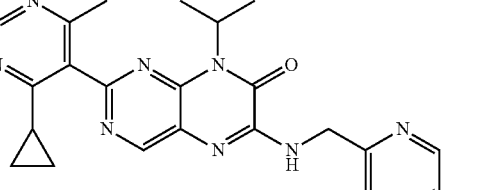 |
| 23 | 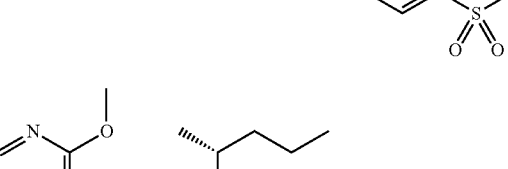 |

-continued
| Example | Structure |
|---|---|
| 24 | 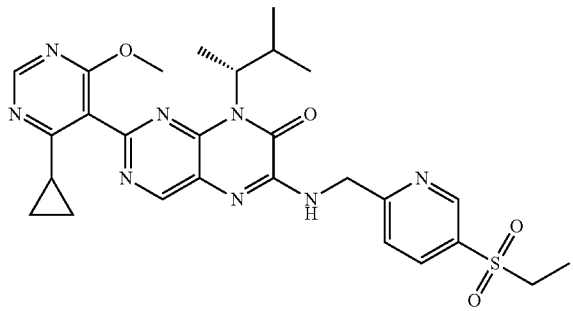 [SMILES: CCS(=O)(=O)c1ccc(CNc2nc3cnc(-c4c(OC)ncnc4C4CC4)nc3n([C@H](C)C(C)C)c2=O)nc1] |
| 25 | 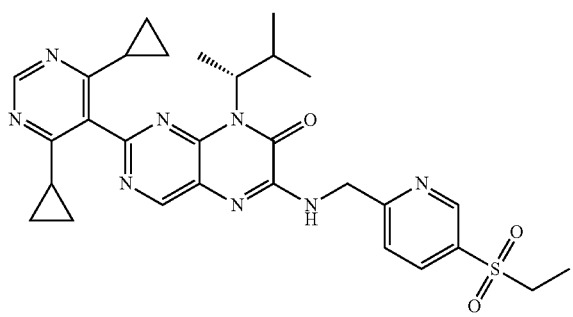 [SMILES: CCS(=O)(=O)c1ccc(CNc2nc3cnc(-c4c(C5CC5)ncnc4C4CC4)nc3n([C@H](C)C(C)C)c2=O)nc1] |
| 26 | 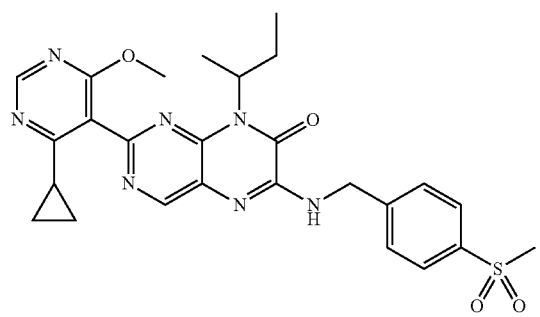 [SMILES: CCC(C)n1c(=O)c(NCc2ccc(S(C)(=O)=O)cc2)nc2cnc(-c3c(OC)ncnc3C3CC3)nc21] |
| 27 | 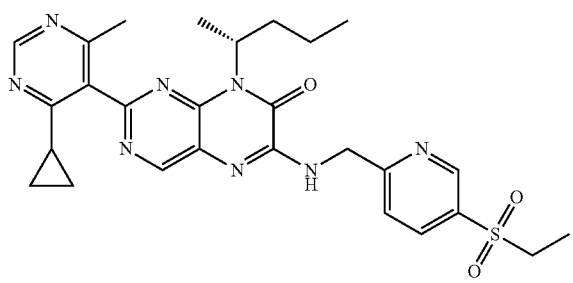 [SMILES: CCC[C@@H](C)n1c(=O)c(NCc2ccc(S(=O)(=O)CC)cn2)nc2cnc(-c3c(C)ncnc3C3CC3)nc21] |
| 28 | 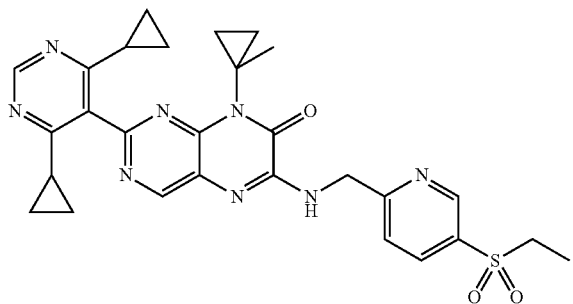 [SMILES: CCS(=O)(=O)c1ccc(CNc2nc3cnc(-c4c(C5CC5)ncnc4C4CC4)nc3n(C3(C)CC3)c2=O)nc1] |

-continued
| Example | Structure |
|---|---|
| 29 | 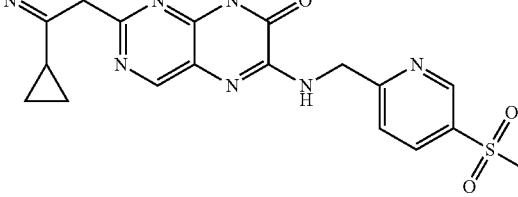 |
| 30 | 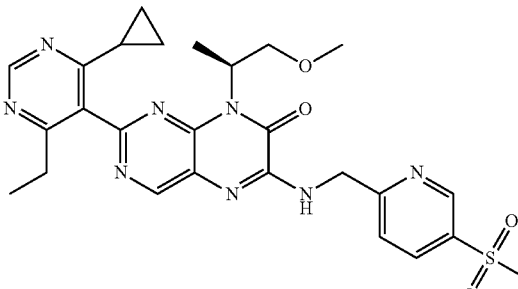 |
| 31 | 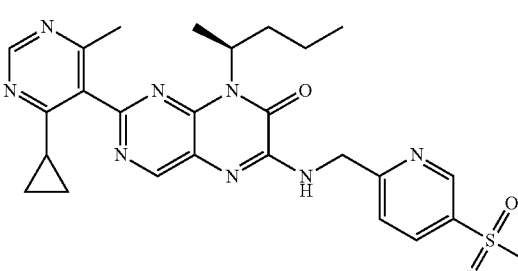 |
| 32 | 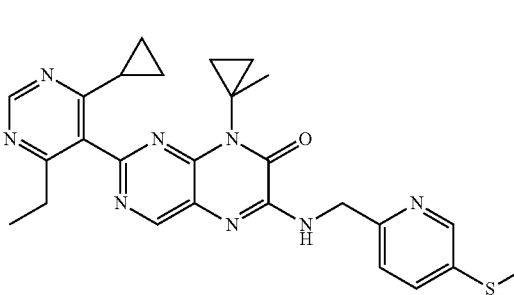 |
| 33 | 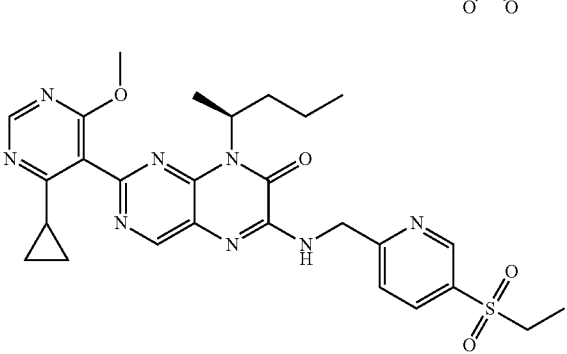 |

| Example | Structure |
|---|---|
| 34 | 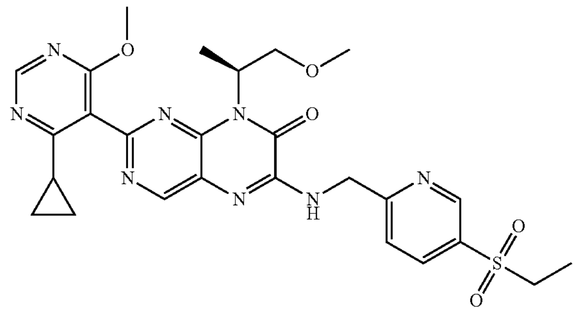 [SMILES: CCS(=O)(=O)c1ccc(CNc2nc3cnc(-c4c(OC)ncnc4C4CC4)nc3n([C@@H](C)COC)c2=O)nc1] |
| 35 | 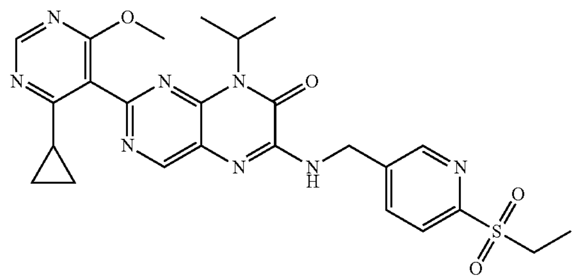 [SMILES: CCS(=O)(=O)c1ccc(CNc2nc3cnc(-c4c(OC)ncnc4C4CC4)nc3n(C(C)C)c2=O)cn1] |
| 36 | 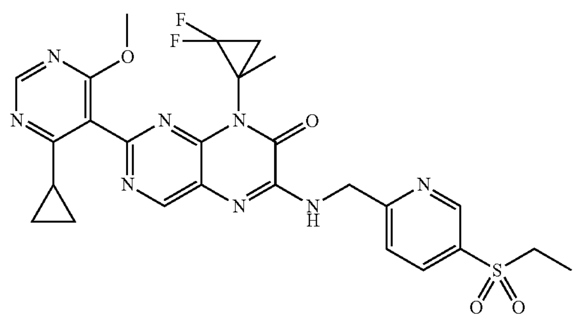 [SMILES: CCS(=O)(=O)c1ccc(CNc2nc3cnc(-c4c(OC)ncnc4C4CC4)nc3n(C3(C)CC3(F)F)c2=O)nc1] |
| 37 | 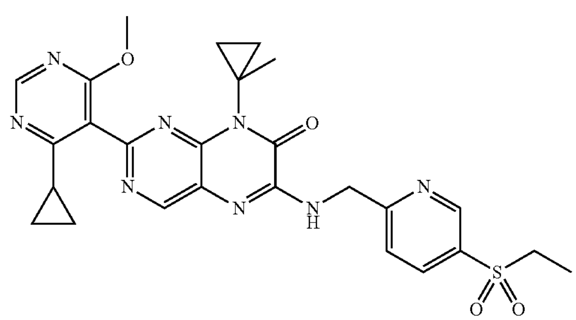 [SMILES: CCS(=O)(=O)c1ccc(CNc2nc3cnc(-c4c(OC)ncnc4C4CC4)nc3n(C3(C)CC3)c2=O)nc1] |
| 38 | 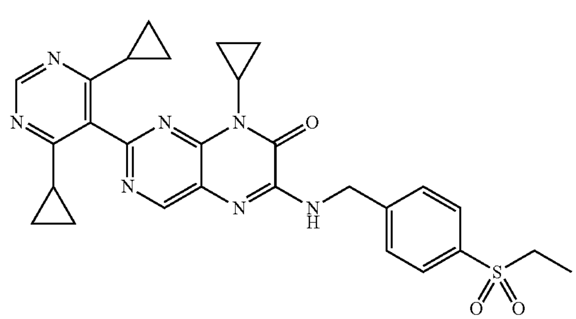 [SMILES: CCS(=O)(=O)c1ccc(CNc2nc3cnc(-c4c(C5CC5)ncnc4C4CC4)nc3n(C3CC3)c2=O)cc1] |

| Example | Structure |
|---|---|
| 39 | 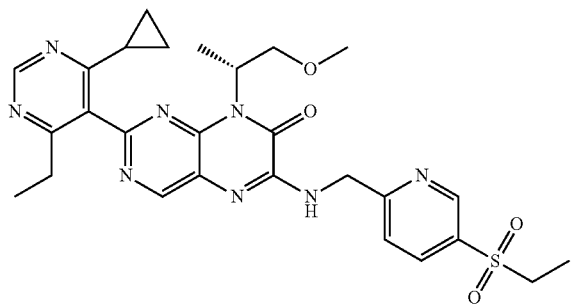 [SMILES: CCc1ncnc(C2CC2)c1-c1ncc2nc(NCc3ccc(S(=O)(=O)CC)cn3)c(=O)n([C@H](C)COC)c2n1] |
| 40 | 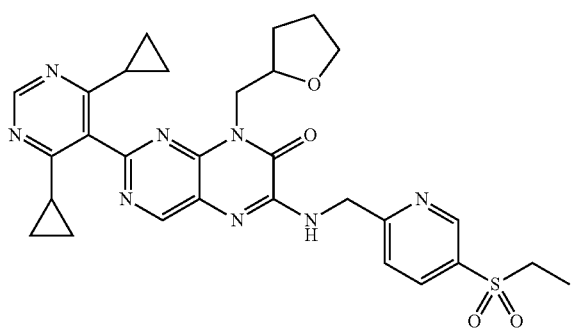 [SMILES: CCS(=O)(=O)c1ccc(CNc2nc3cnc(-c4c(C5CC5)ncnc4C4CC4)nc3n(CC3CCCO3)c2=O)nc1] |
| 41 | 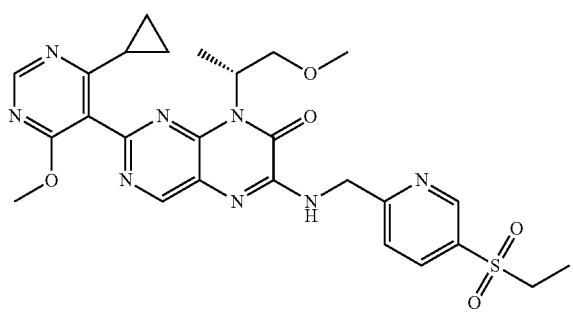 |
| 42 | 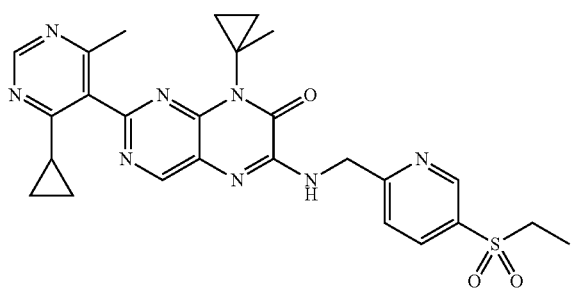 [SMILES: CCS(=O)(=O)c1ccc(CNc2nc3cnc(-c4c(C)ncnc4C4CC4)nc3n(C3(C)CC3)c2=O)nc1] |
| 43 | 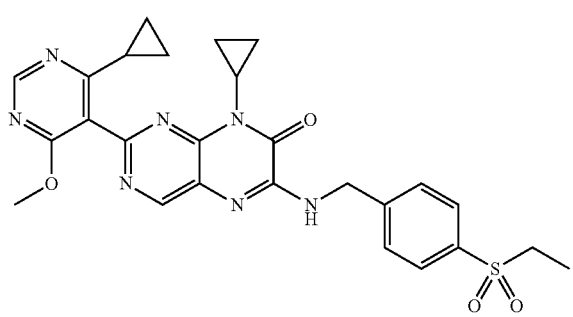 [SMILES: CCS(=O)(=O)c1ccc(CNc2nc3cnc(-c4c(OC)ncnc4C4CC4)nc3n(C3CC3)c2=O)cc1] |

| Example | Structure |
|---|---|
| 44 | 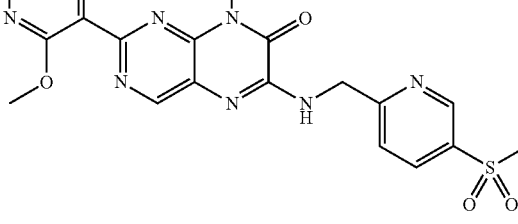 |
| 45 | 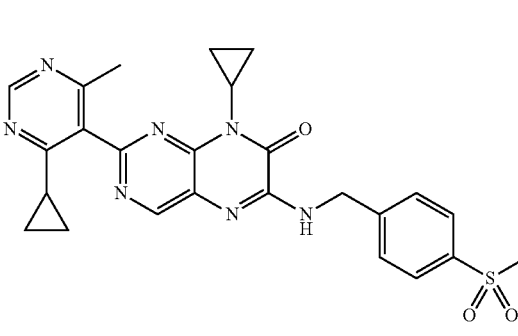 |
| 46 | 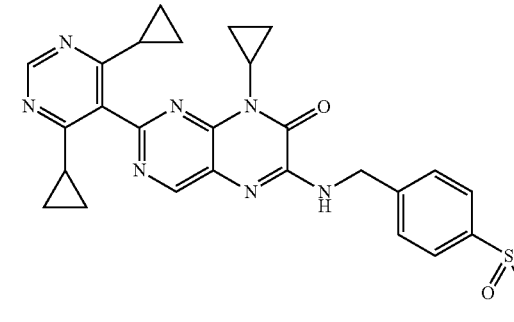 |
| 47 | 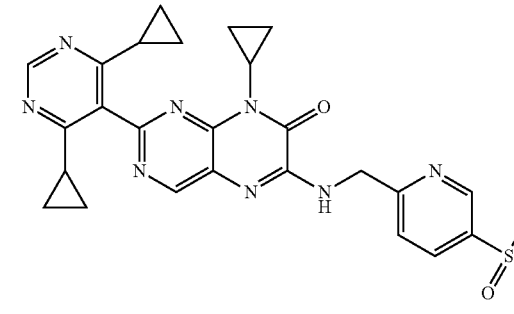 |

| Example | Structure |
|---|---|
| 48 | 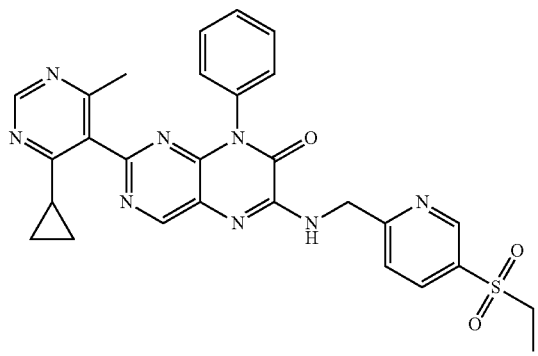 [SMILES: CCS(=O)(=O)c1ccc(CNc2nc3cnc(-c4c(C)ncnc4C4CC4)nc3n(-c3ccccc3)c2=O)nc1] |
| 49 | 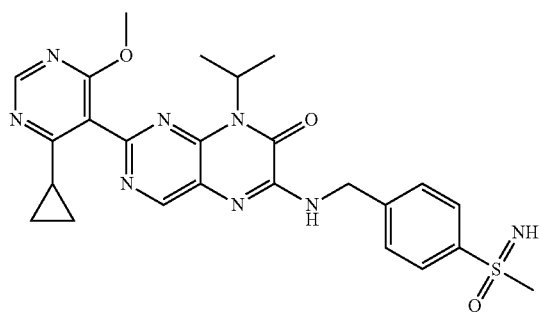 [SMILES: COc1ncnc(C2CC2)c1-c1ncc2nc(NCc3ccc(S(C)(=N)=O)cc3)c(=O)n(C(C)C)c2n1] |
| 50 | 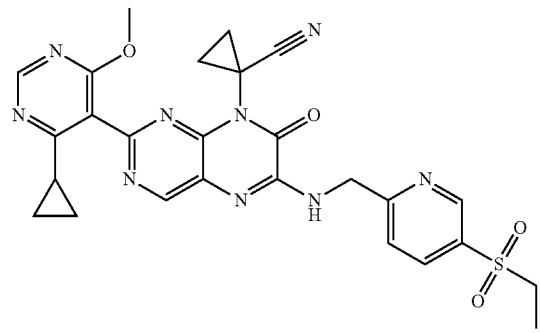 [SMILES: CCS(=O)(=O)c1ccc(CNc2nc3cnc(-c4c(OC)ncnc4C4CC4)nc3n(C3(C#N)CC3)c2=O)nc1] |
| 51 | 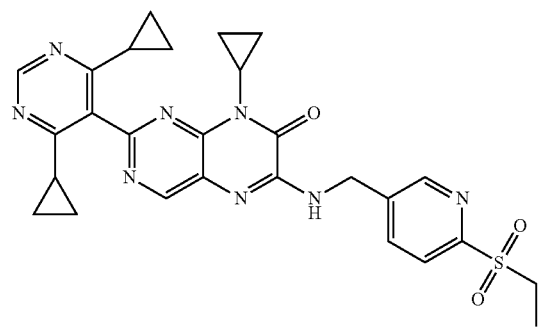 [SMILES: CCS(=O)(=O)c1ccc(CNc2nc3cnc(-c4c(C5CC5)ncnc4C4CC4)nc3n(C3CC3)c2=O)cn1] |

| Example | Structure |
|---|---|
| 52 | 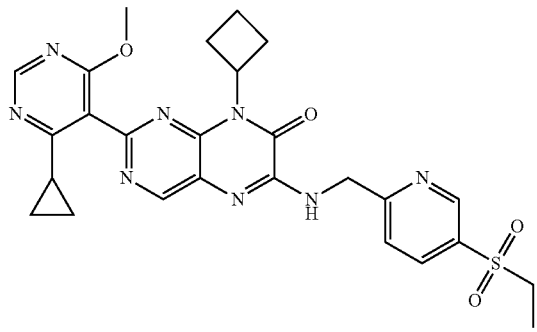 [SMILES: CCS(=O)(=O)c1ccc(CNc2nc3cnc(-c4c(OC)ncnc4C4CC4)nc3n(C3CCC3)c2=O)nc1] |
| 53 | 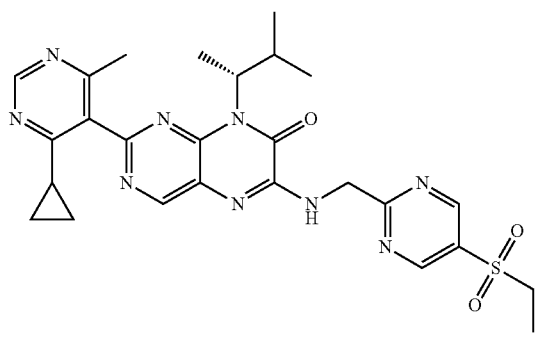 [SMILES: CCS(=O)(=O)c1cnc(CNc2nc3cnc(-c4c(C)ncnc4C4CC4)nc3n([C@H](C)C(C)C)c2=O)nc1] |
| 54 | 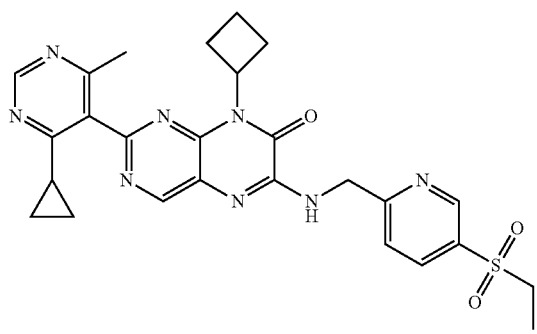 [SMILES: CCS(=O)(=O)c1ccc(CNc2nc3cnc(-c4c(C)ncnc4C4CC4)nc3n(C3CCC3)c2=O)nc1] |
| 55 | 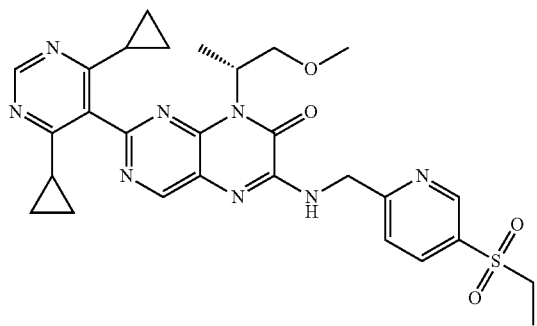 [SMILES: CCS(=O)(=O)c1ccc(CNc2nc3cnc(-c4c(C5CC5)ncnc4C4CC4)nc3n([C@H](C)COC)c2=O)nc1] |

| Example | Structure |
|---|---|
| 56 | 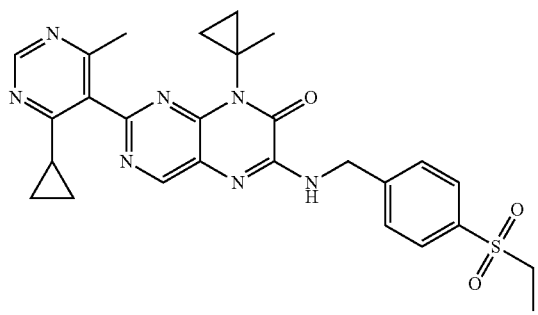 [SMILES: CCS(=O)(=O)c1ccc(CNc2nc3cnc(-c4c(C)ncnc4C4CC4)nc3n(C3(C)CC3)c2=O)cc1] |
| 57 | 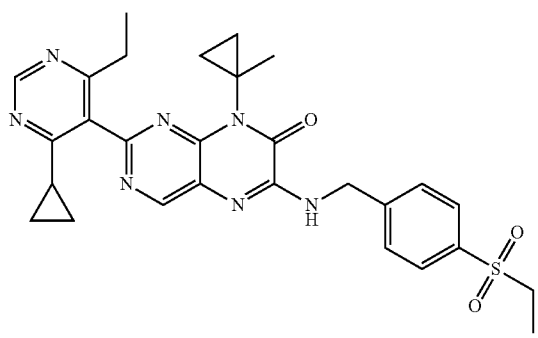 [SMILES: CCc1ncnc(C2CC2)c1-c1ncc2nc(NCc3ccc(S(=O)(=O)CC)cc3)c(=O)n(C3(C)CC3)c2n1] |
| 58 | 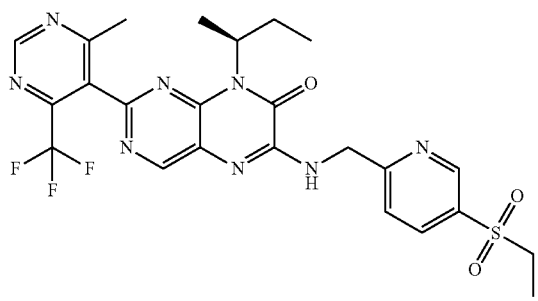 [SMILES: CC[C@H](C)n1c(=O)c(NCc2ccc(S(=O)(=O)CC)cn2)nc2cnc(-c3c(C)ncnc3C(F)(F)F)nc21] |
| 59 | 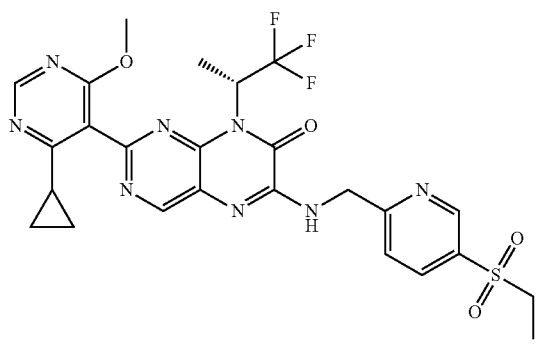 [SMILES: CCS(=O)(=O)c1ccc(CNc2nc3cnc(-c4c(OC)ncnc4C4CC4)nc3n([C@H](C)C(F)(F)F)c2=O)nc1] |

| Example | Structure |
|---|---|
| 60 | 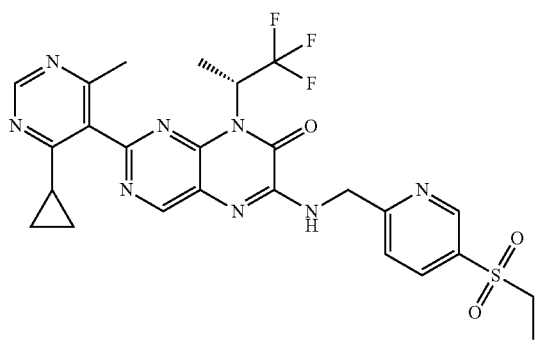 [SMILES: CCS(=O)(=O)c1ccc(CNc2nc3cnc(-c4c(C)ncnc4C4CC4)nc3n([C@H](C)C(F)(F)F)c2=O)nc1] |
| 61 | 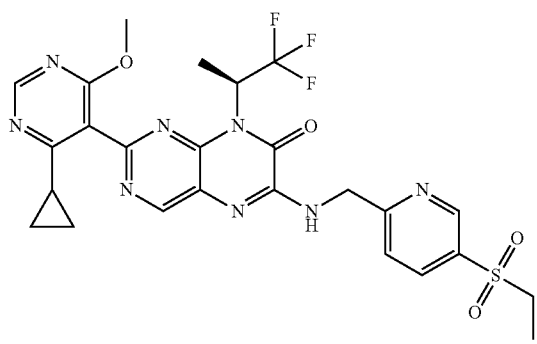 [SMILES: CCS(=O)(=O)c1ccc(CNc2nc3cnc(-c4c(OC)ncnc4C4CC4)nc3n([C@@H](C)C(F)(F)F)c2=O)nc1] |
| 62 | 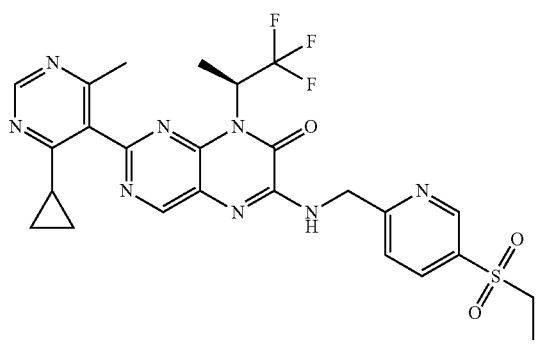 [SMILES: CCS(=O)(=O)c1ccc(CNc2nc3cnc(-c4c(C)ncnc4C4CC4)nc3n([C@@H](C)C(F)(F)F)c2=O)nc1] |
| 63 | 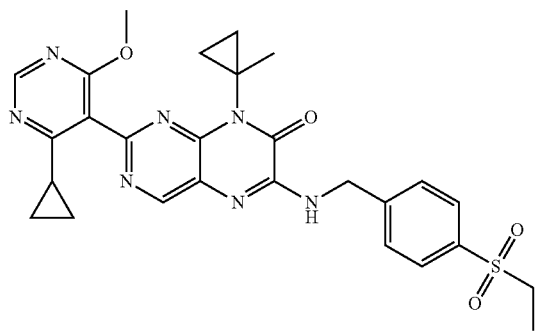 [SMILES: CCS(=O)(=O)c1ccc(CNc2nc3cnc(-c4c(OC)ncnc4C4CC4)nc3n(C3(C)CC3)c2=O)cc1] |

-continued

| Example | Structure |
|---|---|
| 64 | 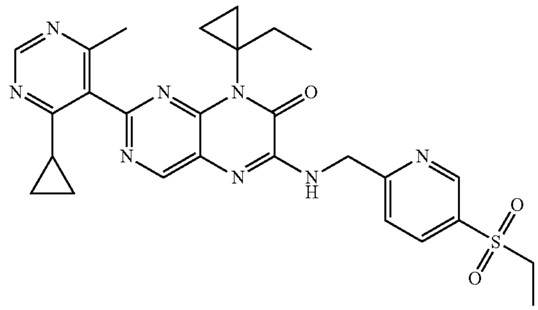 [SMILES: CCC1(n2c(=O)c(NCc3ccc(S(=O)(=O)CC)cn3)nc3cnc(-c4c(C)ncnc4C4CC4)nc32)CC1] |
| 65 | 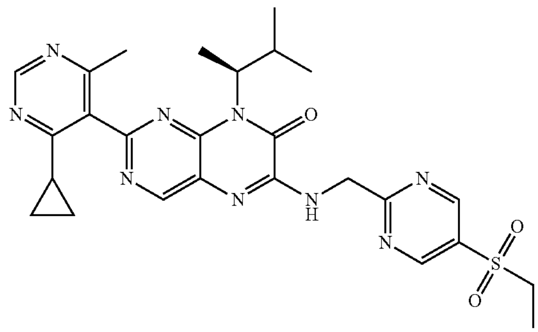 [SMILES: CCS(=O)(=O)c1cnc(CNc2nc3cnc(-c4c(C)ncnc4C4CC4)nc3n([C@@H](C)C(C)C)c2=O)nc1] |
| 66 | 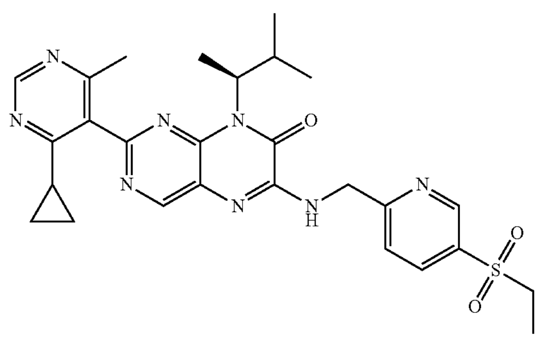 [SMILES: CCS(=O)(=O)c1ccc(CNc2nc3cnc(-c4c(C)ncnc4C4CC4)nc3n([C@@H](C)C(C)C)c2=O)nc1] |
| 67 | 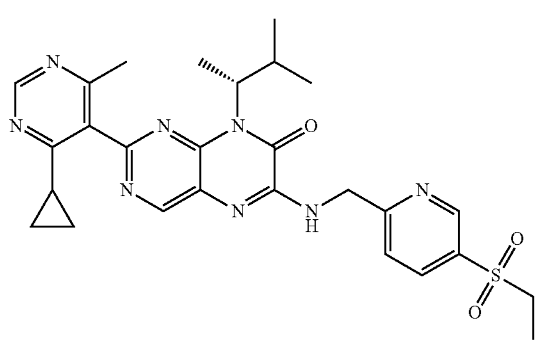 [SMILES: CCS(=O)(=O)c1ccc(CNc2nc3cnc(-c4c(C)ncnc4C4CC4)nc3n([C@H](C)C(C)C)c2=O)nc1] |

| Example | Structure |
|---------|-----------|
| 68 | 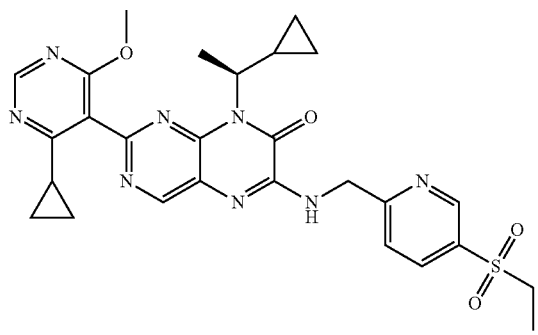 [SMILES: CCS(=O)(=O)c1ccc(CNc2nc3cnc(-c4c(OC)ncnc4C4CC4)nc3n([C@@H](C)C3CC3)c2=O)nc1] |
| 69 | 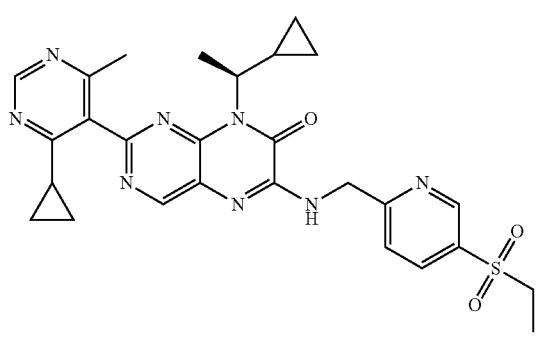 [SMILES: CCS(=O)(=O)c1ccc(CNc2nc3cnc(-c4c(C)ncnc4C4CC4)nc3n([C@@H](C)C3CC3)c2=O)nc1] |
| 70 | 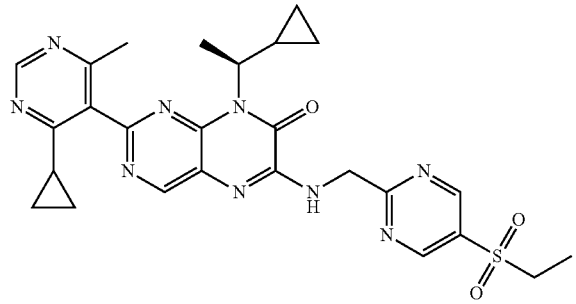 [SMILES: CCS(=O)(=O)c1cnc(CNc2nc3cnc(-c4c(C)ncnc4C4CC4)nc3n([C@@H](C)C3CC3)c2=O)nc1] |
| 71 | 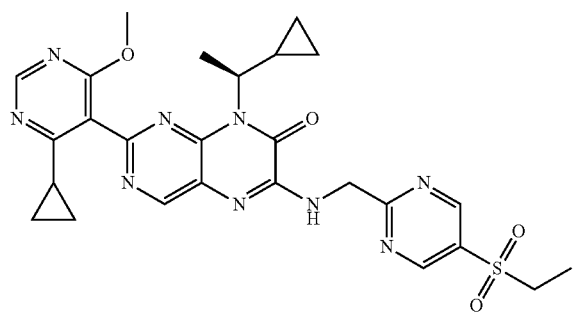 [SMILES: CCS(=O)(=O)c1cnc(CNc2nc3cnc(-c4c(OC)ncnc4C4CC4)nc3n([C@@H](C)C3CC3)c2=O)nc1] |
| 72 | 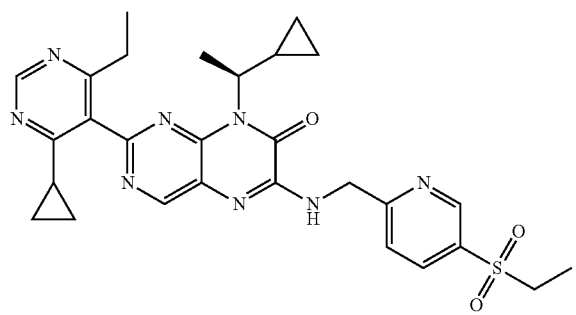 [SMILES: CCc1ncnc(C2CC2)c1-c1ncc2nc(NCc3ccc(S(=O)(=O)CC)cn3)c(=O)n([C@@H](C)C3CC3)c2n1] |

-continued
| Example | Structure |
|---------|-----------|
| 73 | 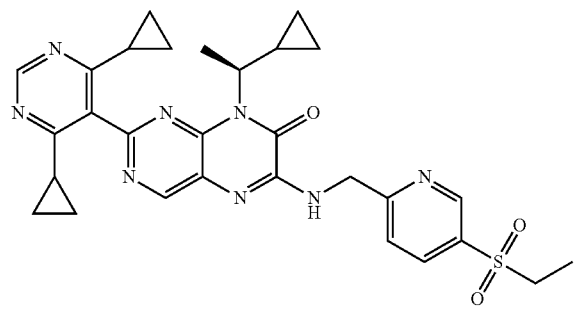 [SMILES: CCS(=O)(=O)c1ccc(CNc2nc3cnc(-c4c(C5CC5)ncnc4C4CC4)nc3n([C@@H](C)C3CC3)c2=O)nc1] |
| 74 | 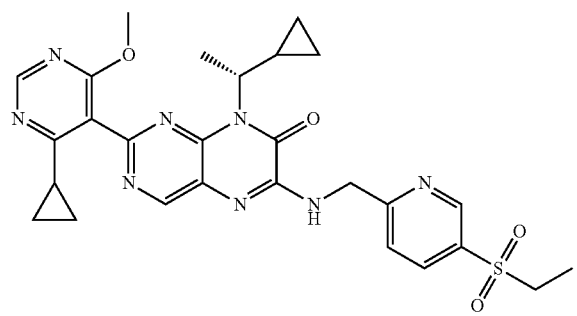 [SMILES: CCS(=O)(=O)c1ccc(CNc2nc3cnc(-c4c(OC)ncnc4C4CC4)nc3n([C@H](C)C3CC3)c2=O)nc1] |
| 75 | 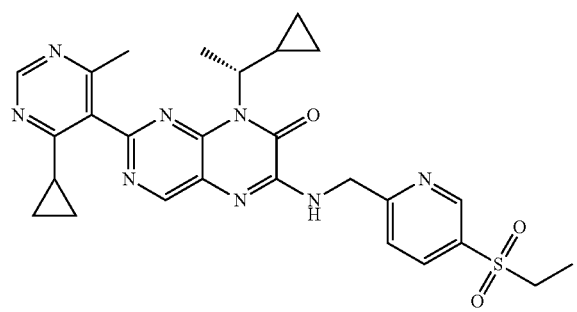 [SMILES: CCS(=O)(=O)c1ccc(CNc2nc3cnc(-c4c(C)ncnc4C4CC4)nc3n([C@H](C)C3CC3)c2=O)nc1] |
| 76 | 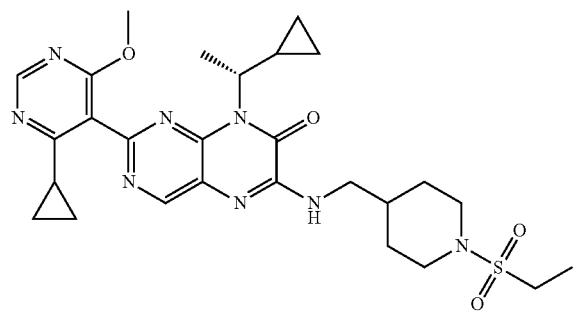 [SMILES: CCS(=O)(=O)N1CCC(CNc2nc3cnc(-c4c(OC)ncnc4C4CC4)nc3n([C@H](C)C3CC3)c2=O)CC1] |
| 77 | 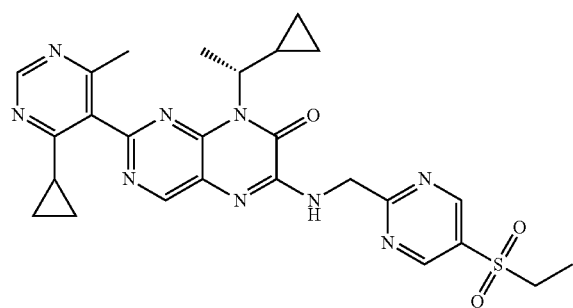 [SMILES: CCS(=O)(=O)c1cnc(CNc2nc3cnc(-c4c(C)ncnc4C4CC4)nc3n([C@H](C)C3CC3)c2=O)nc1] |

-continued

| Example | Structure |
|---|---|
| 78 | 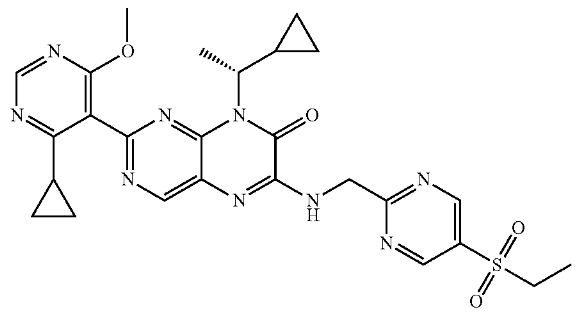 [SMILES: CCS(=O)(=O)c1cnc(CNc2nc3cnc(-c4c(OC)ncnc4C4CC4)nc3n([C@H](C)C3CC3)c2=O)nc1] |
| 79 | 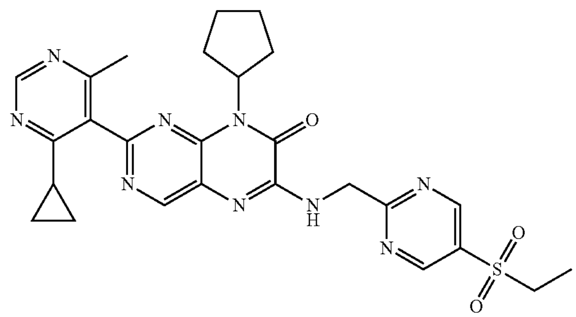 [SMILES: CCS(=O)(=O)c1cnc(CNc2nc3cnc(-c4c(C)ncnc4C4CC4)nc3n(C3CCCC3)c2=O)nc1] |
| 80 | 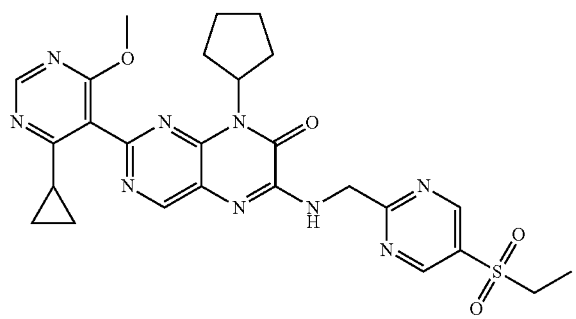 [SMILES: CCS(=O)(=O)c1cnc(CNc2nc3cnc(-c4c(OC)ncnc4C4CC4)nc3n(C3CCCC3)c2=O)nc1] |
| 81 | 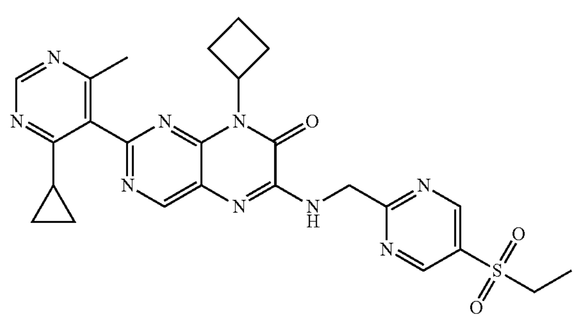 [SMILES: CCS(=O)(=O)c1cnc(CNc2nc3cnc(-c4c(C)ncnc4C4CC4)nc3n(C3CCC3)c2=O)nc1] |
| 82 | 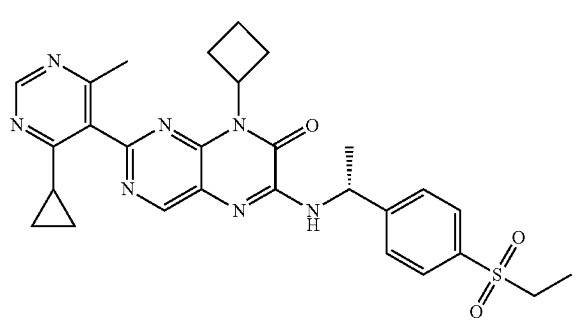 [SMILES: CCS(=O)(=O)c1ccc([C@@H](C)Nc2nc3cnc(-c4c(C)ncnc4C4CC4)nc3n(C3CCC3)c2=O)cc1] |

-continued
| Example | Structure |
|---------|-----------|
| 83 | 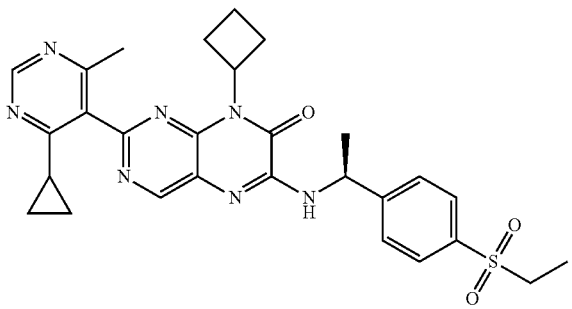 [SMILES: CCS(=O)(=O)c1ccc([C@H](C)Nc2nc3cnc(-c4c(C)ncnc4C4CC4)nc3n(C3CCC3)c2=O)cc1] |
| 84 | 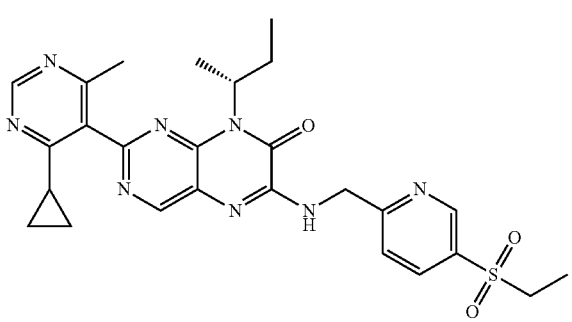 [SMILES: CC[C@@H](C)n1c(=O)c(NCc2ccc(S(=O)(=O)CC)cn2)nc2cnc(-c3c(C)ncnc3C3CC3)nc21] |
| 85 | 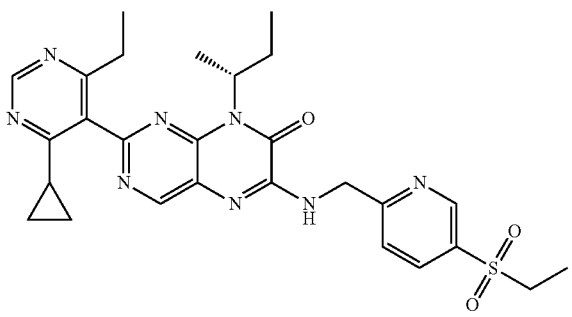 [SMILES: CCc1ncnc(C2CC2)c1-c1ncc2nc(NCc3ccc(S(=O)(=O)CC)cn3)c(=O)n([C@H](C)CC)c2n1] |
| 86 | 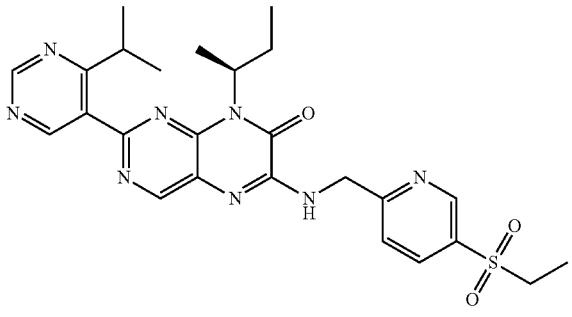 [SMILES: CC[C@H](C)n1c(=O)c(NCc2ccc(S(=O)(=O)CC)cn2)nc2cnc(-c3cncnc3C(C)C)nc21] |
| 87 | 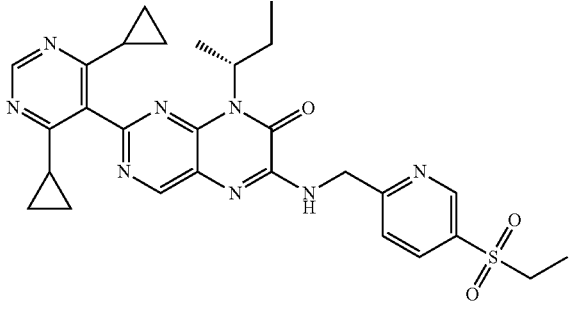 |

-continued

| Example | Structure |
|---|---|
| 88 | 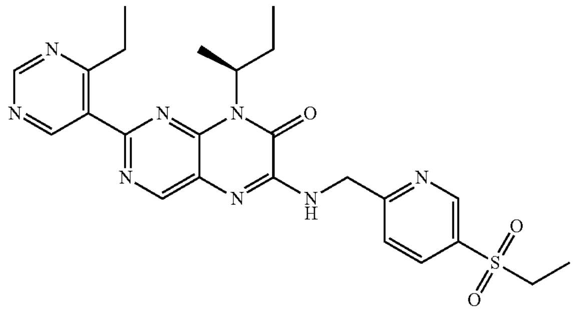 [SMILES: CCc1ncncc1-c1ncc2nc(NCc3ccc(S(=O)(=O)CC)cn3)c(=O)n([C@@H](C)CC)c2n1] |
| 89 | 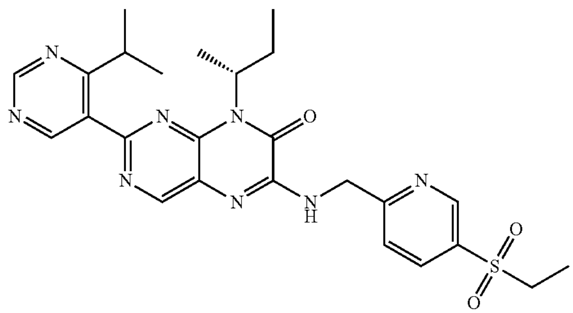 [SMILES: CC[C@@H](C)n1c(=O)c(NCc2ccc(S(=O)(=O)CC)cn2)nc2cnc(-c3cncnc3C(C)C)nc21] |
| 90 | 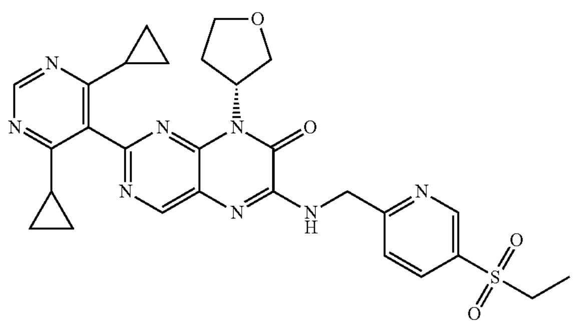 [SMILES: CCS(=O)(=O)c1ccc(CNc2nc3cnc(-c4c(C5CC5)ncnc4C4CC4)nc3n([C@@H]3CCOC3)c2=O)nc1] |
| 91 | 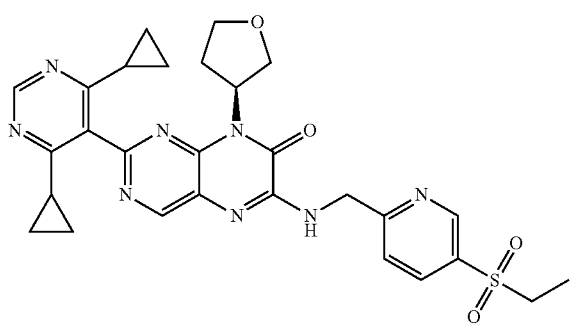 [SMILES: CCS(=O)(=O)c1ccc(CNc2nc3cnc(-c4c(C5CC5)ncnc4C4CC4)nc3n([C@H]3CCOC3)c2=O)nc1] |
| 92 | 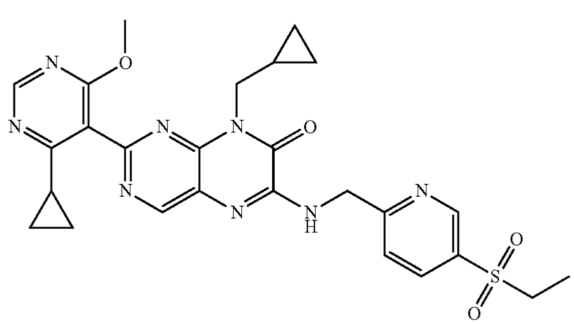 [SMILES: CCS(=O)(=O)c1ccc(CNc2nc3cnc(-c4c(OC)ncnc4C4CC4)nc3n(CC3CC3)c2=O)nc1] |

| Example | Structure |
|---|---|
| 93 | 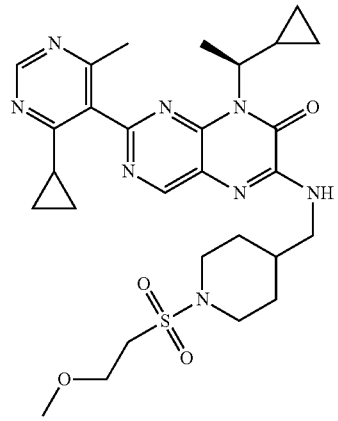 [SMILES: COCCS(=O)(=O)N1CCC(CNc2nc3cnc(-c4c(C)ncnc4C4CC4)nc3n([C@@H](C)C3CC3)c2=O)CC1] |
| 94 | 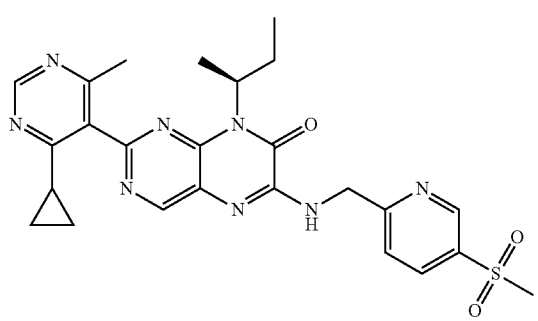 [SMILES: CC[C@H](C)n1c(=O)c(NCc2ccc(S(C)(=O)=O)cn2)nc2cnc(-c3c(C)ncnc3C3CC3)nc21] |
| 95 | 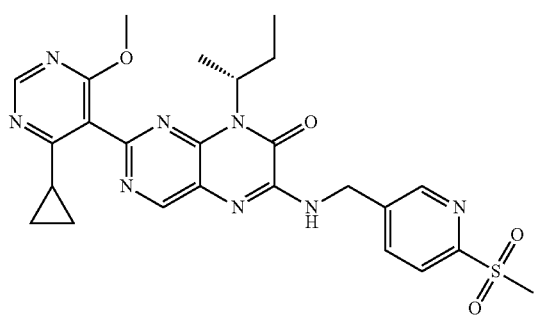 |
| 96 | 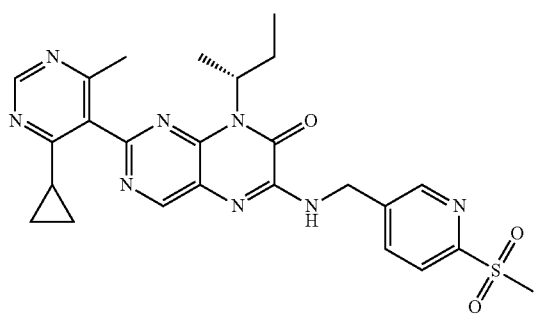 [SMILES: CC[C@@H](C)n1c(=O)c(NCc2ccc(S(C)(=O)=O)nc2)nc2cnc(-c3c(C)ncnc3C3CC3)nc21] |

| Example | Structure |
|---|---|
| 97 | 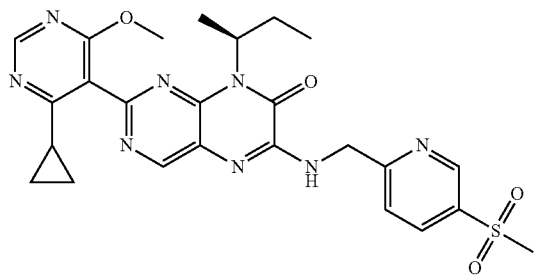 [SMILES: CC[C@H](C)n1c(=O)c(NCc2ccc(S(C)(=O)=O)cn2)nc2cnc(-c3c(OC)ncnc3C3CC3)nc21] |
| 98 | 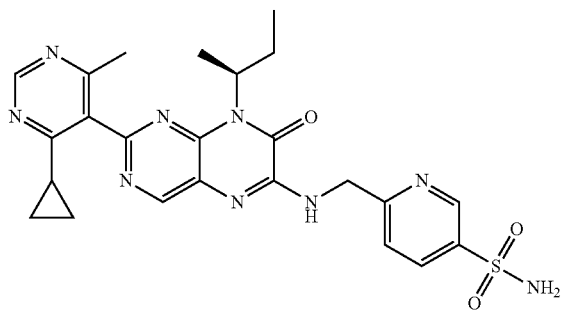 [SMILES: CC[C@H](C)n1c(=O)c(NCc2ccc(S(N)(=O)=O)cn2)nc2cnc(-c3c(C)ncnc3C3CC3)nc21] |
| 99 | 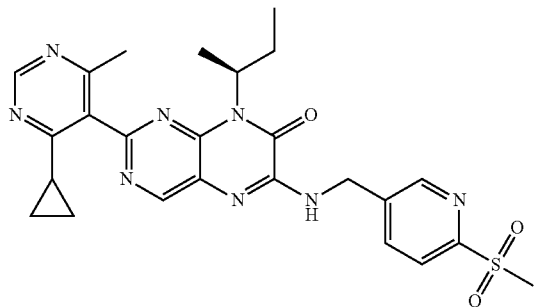 [SMILES: CC[C@H](C)n1c(=O)c(NCc2ccc(S(C)(=O)=O)nc2)nc2cnc(-c3c(C)ncnc3C3CC3)nc21] |
| 100 | 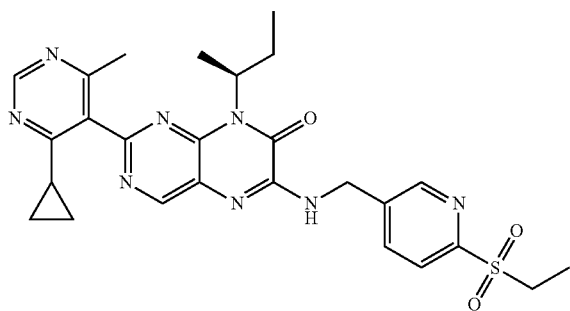 [SMILES: CC[C@H](C)n1c(=O)c(NCc2ccc(S(=O)(=O)CC)nc2)nc2cnc(-c3c(C)ncnc3C3CC3)nc21] |
| 101 | 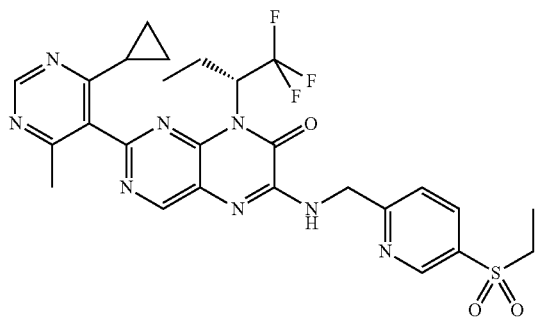 [SMILES: CC[C@@H](n1c(=O)c(NCc2ccc(S(=O)(=O)CC)cn2)nc2cnc(-c3c(C)ncnc3C3CC3)nc21)C(F)(F)F] |

| Example | Structure |
|---|---|
| 102 | 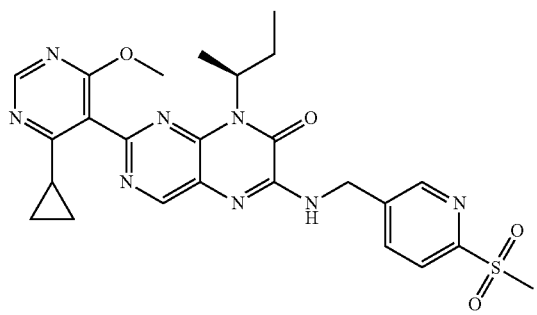 [SMILES: CC[C@H](C)n1c(=O)c(NCc2ccc(S(C)(=O)=O)nc2)nc2cnc(-c3c(OC)ncnc3C3CC3)nc21] |
| 103 | 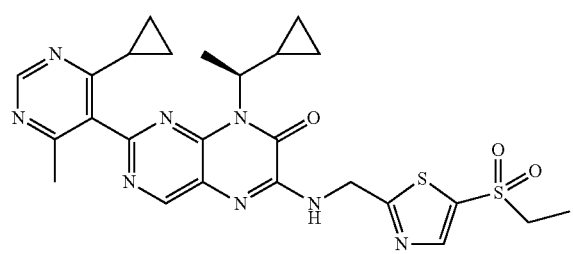 [SMILES: CCS(=O)(=O)c1cnc(CNc2nc3cnc(-c4c(C)ncnc4C4CC4)nc3n([C@@H](C)C3CC3)c2=O)s1] |
| 104 | 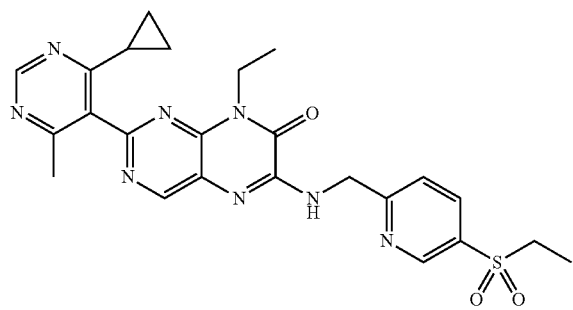 [SMILES: CCn1c(=O)c(NCc2ccc(S(=O)(=O)CC)cn2)nc2cnc(-c3c(C)ncnc3C3CC3)nc21] |
| 105 | 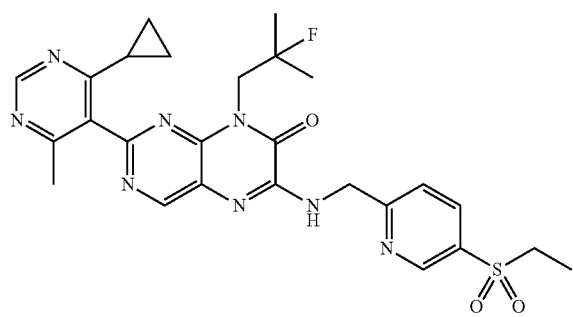 [SMILES: CCS(=O)(=O)c1ccc(CNc2nc3cnc(-c4c(C)ncnc4C4CC4)nc3n(CC(C)(C)F)c2=O)nc1] |
| 106 | 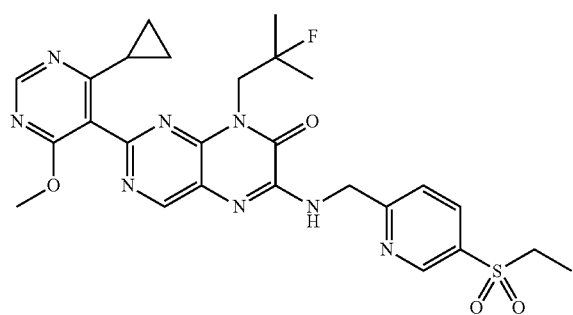 [SMILES: CCS(=O)(=O)c1ccc(CNc2nc3cnc(-c4c(OC)ncnc4C4CC4)nc3n(CC(C)(C)F)c2=O)nc1] |

| Example | Structure |
|---|---|
| 107 | 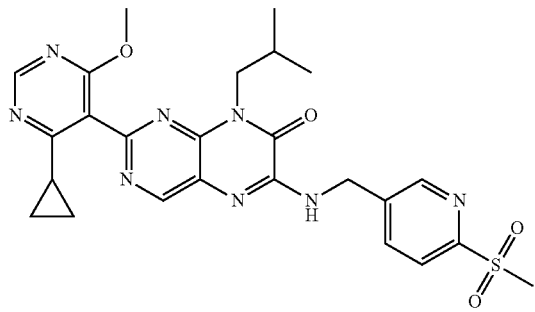 [SMILES: COc1ncnc(C2CC2)c1-c1ncc2nc(NCc3ccc(S(C)(=O)=O)nc3)c(=O)n(CC(C)C)c2n1] |
| 108 | 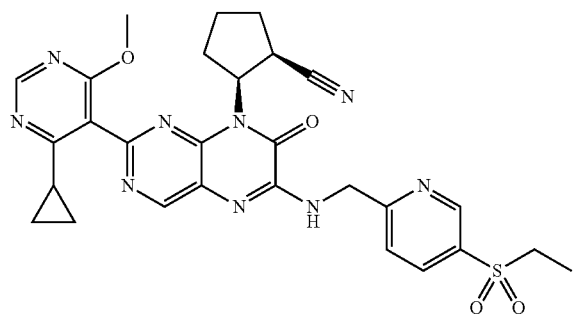 [SMILES: CCS(=O)(=O)c1ccc(CNc2nc3cnc(-c4c(OC)ncnc4C4CC4)nc3n([C@H]3CCC[C@H]3C#N)c2=O)nc1] |
| 109 | 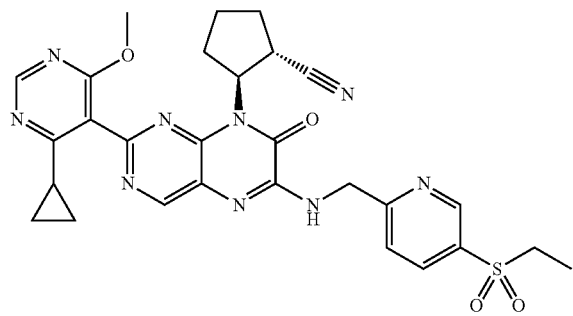 [SMILES: CCS(=O)(=O)c1ccc(CNc2nc3cnc(-c4c(OC)ncnc4C4CC4)nc3n([C@H]3CCC[C@@H]3C#N)c2=O)nc1] |
| 110 | 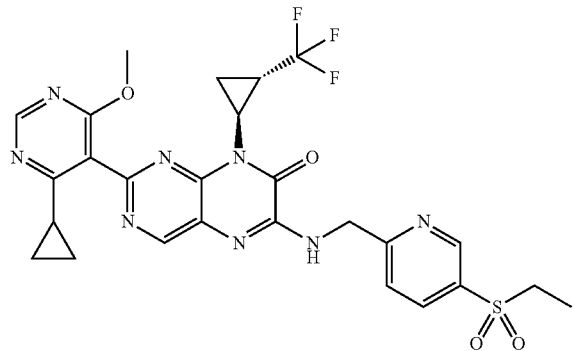 [SMILES: CCS(=O)(=O)c1ccc(CNc2nc3cnc(-c4c(OC)ncnc4C4CC4)nc3n([C@H]3C[C@@H]3C(F)(F)F)c2=O)nc1] |

-continued

| Example | Structure |
|---|---|
| 111 | 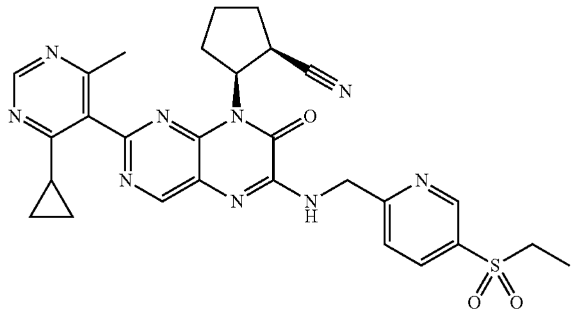 [SMILES: CCS(=O)(=O)c1ccc(CNc2nc3cnc(-c4c(C)ncnc4C4CC4)nc3n([C@H]3CCC[C@H]3C#N)c2=O)nc1] |
| 112 | 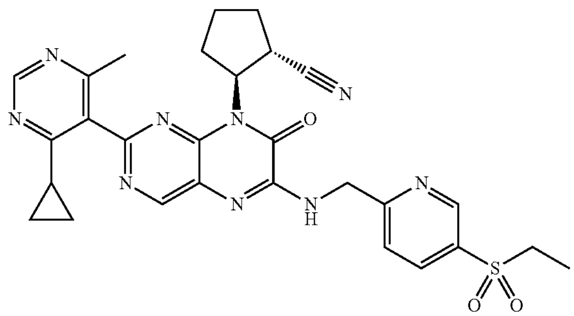 [SMILES: CCS(=O)(=O)c1ccc(CNc2nc3cnc(-c4c(C)ncnc4C4CC4)nc3n([C@H]3CCC[C@@H]3C#N)c2=O)nc1] |
| 113 | 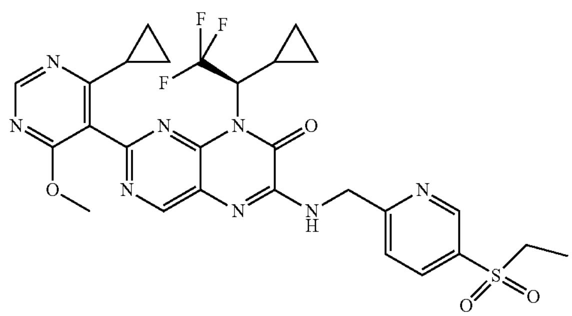 [SMILES: CCS(=O)(=O)c1ccc(CNc2nc3cnc(-c4c(OC)ncnc4C4CC4)nc3n([C@H](C3CC3)C(F)(F)F)c2=O)nc1] |
| 114 | 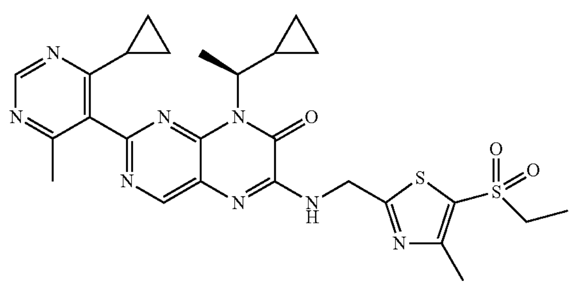 [SMILES: CCS(=O)(=O)c1sc(CNc2nc3cnc(-c4c(C)ncnc4C4CC4)nc3n([C@@H](C)C3CC3)c2=O)nc1C] |
| 115 | 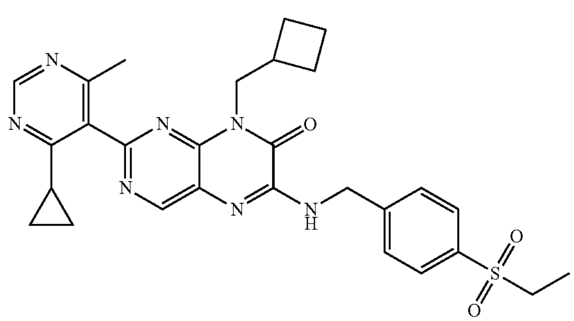 [SMILES: CCS(=O)(=O)c1ccc(CNc2nc3cnc(-c4c(C)ncnc4C4CC4)nc3n(CC3CCC3)c2=O)cc1] |

-continued
| Example | Structure |
|---------|-----------|
| 116 | 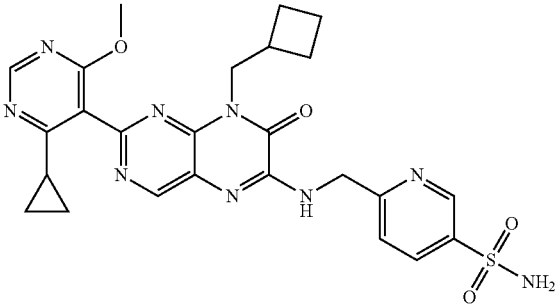 [SMILES: COc1ncnc(C2CC2)c1-c1ncc2nc(NCc3ccc(S(N)(=O)=O)cn3)c(=O)n(CC3CCC3)c2n1] |
| 117 | 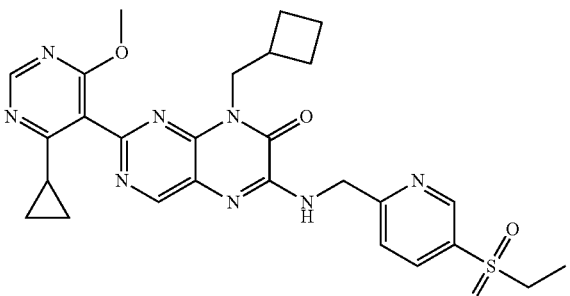 |
| 118 | 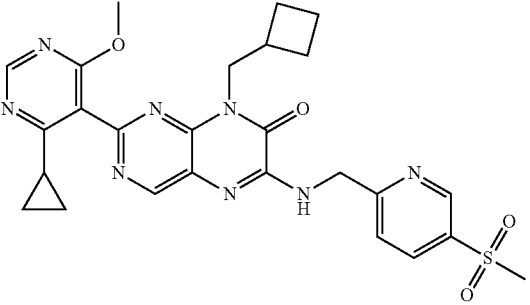 [SMILES: COc1ncnc(C2CC2)c1-c1ncc2nc(NCc3ccc(S(C)(=O)=O)cn3)c(=O)n(CC3CCC3)c2n1] |
| 119 | 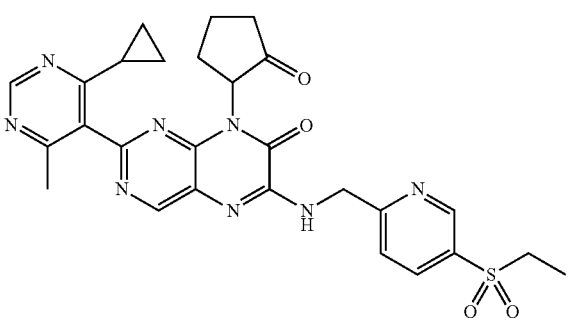 [SMILES: CCS(=O)(=O)c1ccc(CNc2nc3cnc(-c4c(C)ncnc4C4CC4)nc3n(C3CCCC3=O)c2=O)nc1] |
| 120 | 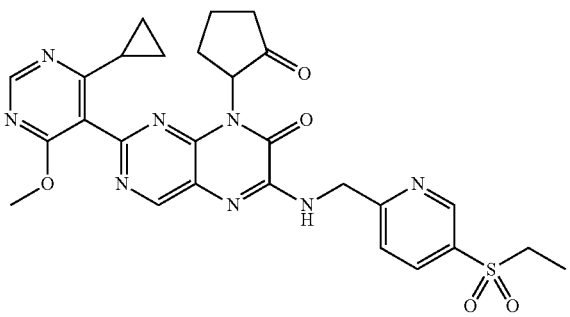 [SMILES: CCS(=O)(=O)c1ccc(CNc2nc3cnc(-c4c(OC)ncnc4C4CC4)nc3n(C3CCCC3=O)c2=O)nc1] |

| Example | Structure |
|---|---|
| 121 | 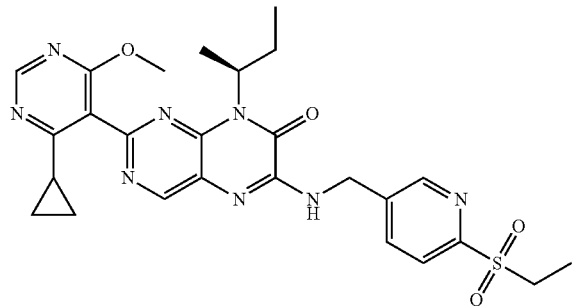 [SMILES: CC[C@H](C)n1c(=O)c(NCc2ccc(S(=O)(=O)CC)nc2)nc2cnc(-c3c(OC)ncnc3C3CC3)nc21] |
| 122 | 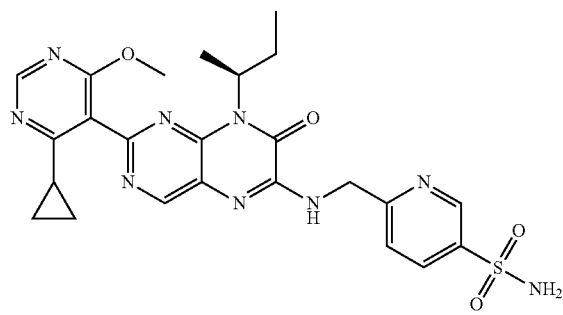 [SMILES: CC[C@H](C)n1c(=O)c(NCc2ccc(S(N)(=O)=O)cn2)nc2cnc(-c3c(OC)ncnc3C3CC3)nc21] |
| 123 | 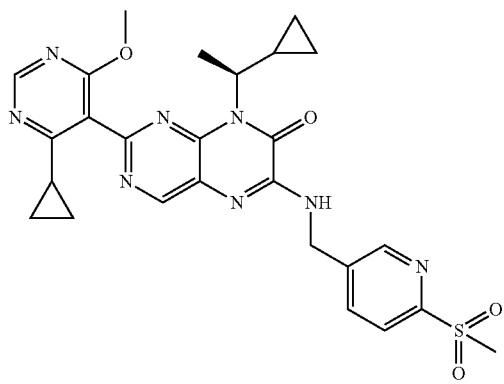 [SMILES: COc1ncnc(C2CC2)c1-c1ncc2nc(NCc3ccc(S(C)(=O)=O)nc3)c(=O)n([C@@H](C)C3CC3)c2n1] |
| 124 | 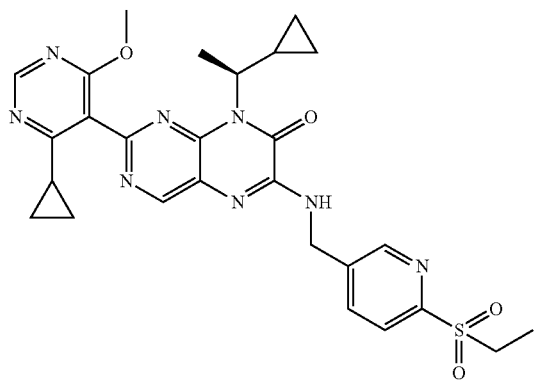 [SMILES: CCS(=O)(=O)c1ccc(CNc2nc3cnc(-c4c(OC)ncnc4C4CC4)nc3n([C@@H](C)C3CC3)c2=O)cn1] |

| Example | Structure |
|---|---|
| 125 | 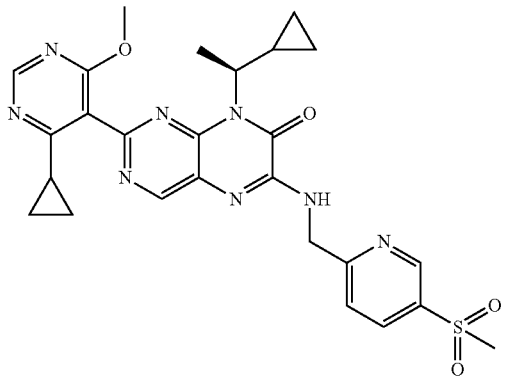 [SMILES: COc1ncnc(C2CC2)c1-c1ncc2nc(NCc3ccc(S(C)(=O)=O)cn3)c(=O)n([C@@H](C)C3CC3)c2n1] |
| 126 | 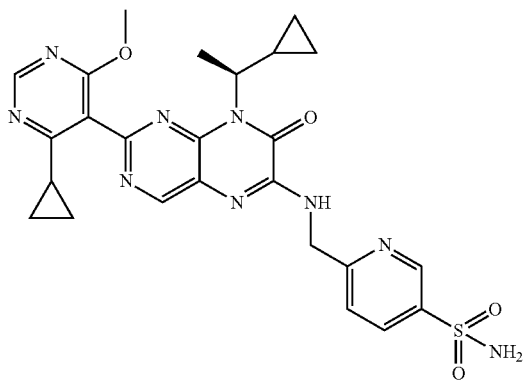 [SMILES: COc1ncnc(C2CC2)c1-c1ncc2nc(NCc3ccc(S(N)(=O)=O)cn3)c(=O)n([C@@H](C)C3CC3)c2n1] |
| 127 | 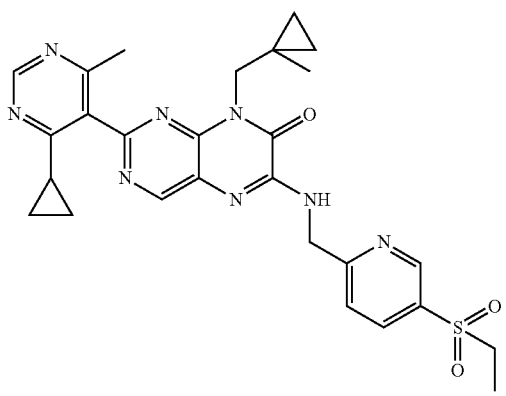 [SMILES: CCS(=O)(=O)c1ccc(CNc2nc3cnc(-c4c(C)ncnc4C4CC4)nc3n(CC3(C)CC3)c2=O)nc1] |
| 128 | 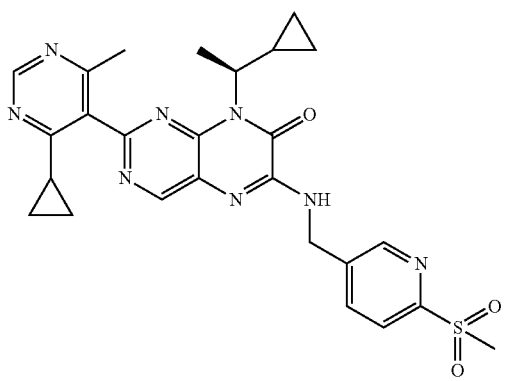 [SMILES: Cc1ncnc(C2CC2)c1-c1ncc2nc(NCc3ccc(S(C)(=O)=O)nc3)c(=O)n([C@@H](C)C3CC3)c2n1] |

-continued
| Example | Structure |
|---|---|
| 129 | 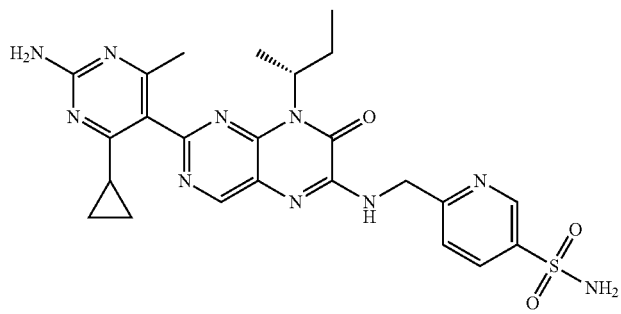 [SMILES: CC[C@@H](C)n1c(=O)c(NCc2ccc(S(N)(=O)=O)cn2)nc2cnc(-c3c(C)nc(N)nc3C3CC3)nc21] |
| 130 | 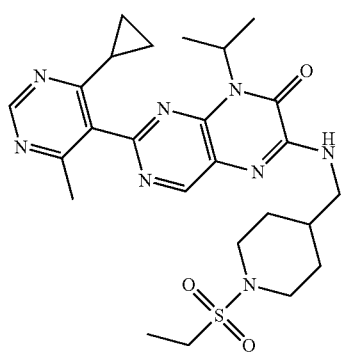 [SMILES: CCS(=O)(=O)N1CCC(CNc2nc3cnc(-c4c(C)ncnc4C4CC4)nc3n(C(C)C)c2=O)CC1] |
| 131 | 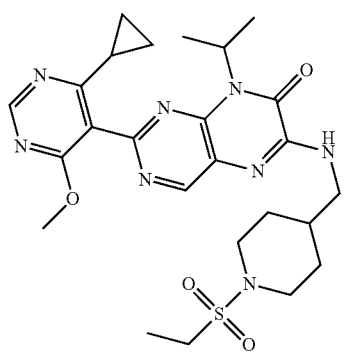 [SMILES: CCS(=O)(=O)N1CCC(CNc2nc3cnc(-c4c(OC)ncnc4C4CC4)nc3n(C(C)C)c2=O)CC1] |
| 132 | 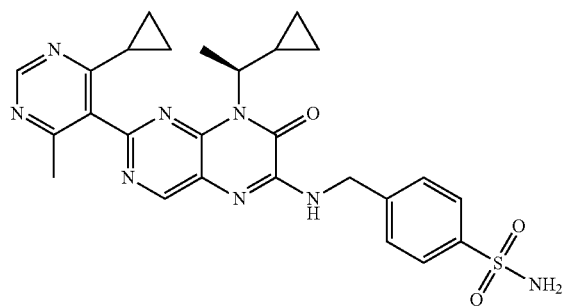 [SMILES: Cc1ncnc(C2CC2)c1-c1ncc2nc(NCc3ccc(S(N)(=O)=O)cc3)c(=O)n([C@@H](C)C3CC3)c2n1] |

| Example | Structure |
|---|---|
| 133 | 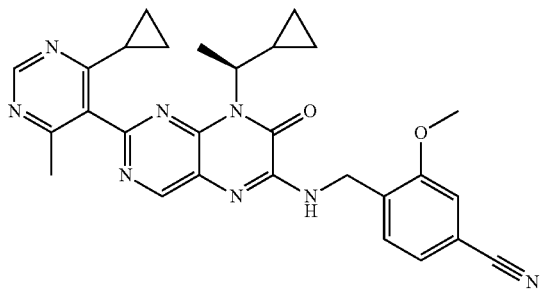 [SMILES: COc1cc(C#N)ccc1CNc1nc2cnc(-c3c(C)ncnc3C3CC3)nc2n([C@@H](C)C2CC2)c1=O] |
| 134 | 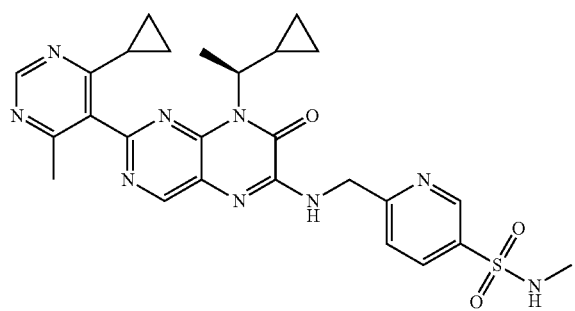 [SMILES: CNS(=O)(=O)c1ccc(CNc2nc3cnc(-c4c(C)ncnc4C4CC4)nc3n([C@@H](C)C3CC3)c2=O)nc1] |
| 135 | 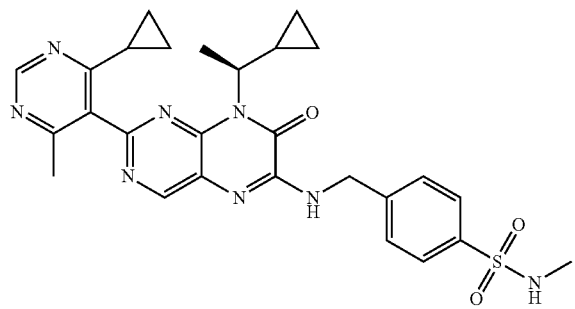 [SMILES: CNS(=O)(=O)c1ccc(CNc2nc3cnc(-c4c(C)ncnc4C4CC4)nc3n([C@@H](C)C3CC3)c2=O)cc1] |
| 136 | 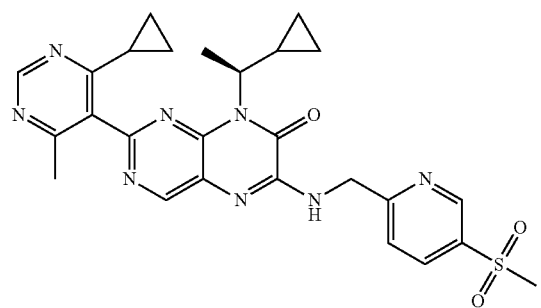 [SMILES: Cc1ncnc(C2CC2)c1-c1ncc2nc(NCc3ccc(S(C)(=O)=O)cn3)c(=O)n([C@@H](C)C3CC3)c2n1] |
| 137 | 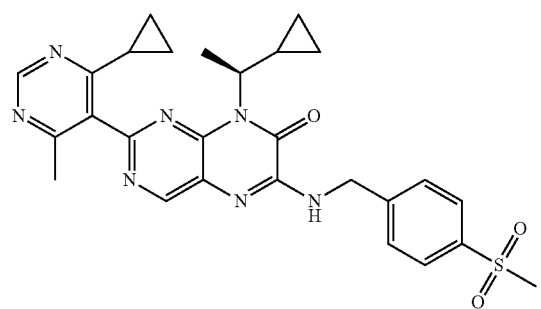 [SMILES: Cc1ncnc(C2CC2)c1-c1ncc2nc(NCc3ccc(S(C)(=O)=O)cc3)c(=O)n([C@@H](C)C3CC3)c2n1] |

-continued
| Example | Structure |
|---|---|
| 138 | 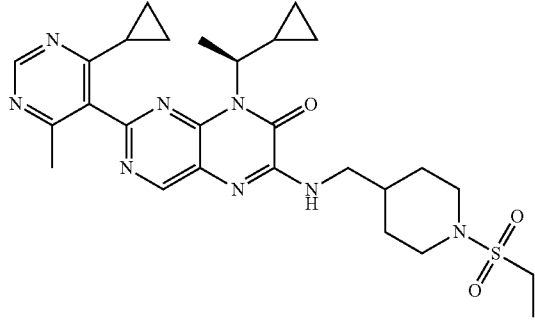 [SMILES: CCS(=O)(=O)N1CCC(CNc2nc3cnc(-c4c(C)ncnc4C4CC4)nc3n([C@@H](C)C3CC3)c2=O)CC1] |
| 139 | 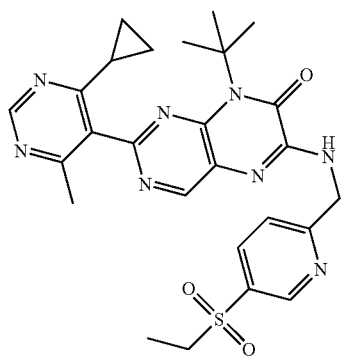 [SMILES: CCS(=O)(=O)c1ccc(CNc2nc3cnc(-c4c(C)ncnc4C4CC4)nc3n(C(C)(C)C)c2=O)nc1] |
| 140 | 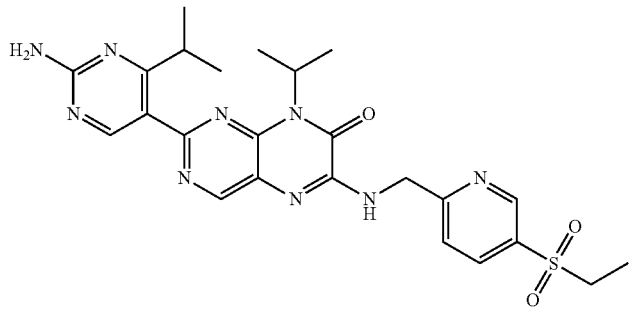 [SMILES: CCS(=O)(=O)c1ccc(CNc2nc3cnc(-c4cnc(N)nc4C(C)C)nc3n(C(C)C)c2=O)nc1] |
| 141 | 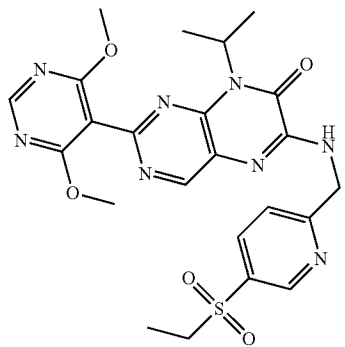 [SMILES: CCS(=O)(=O)c1ccc(CNc2nc3cnc(-c4c(OC)ncnc4OC)nc3n(C(C)C)c2=O)nc1] |

-continued

| Example | Structure |
|---|---|
| 142 | 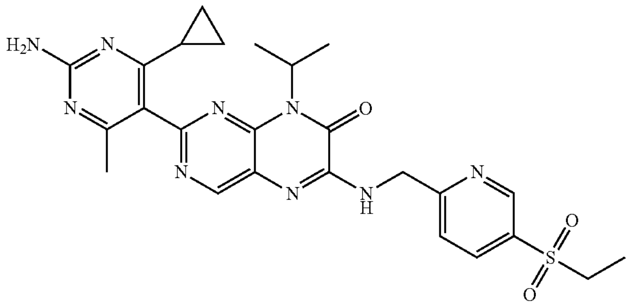 [SMILES: CCS(=O)(=O)c1ccc(CNc2nc3cnc(-c4c(C)nc(N)nc4C4CC4)nc3n(C(C)C)c2=O)nc1] |
| 143 | 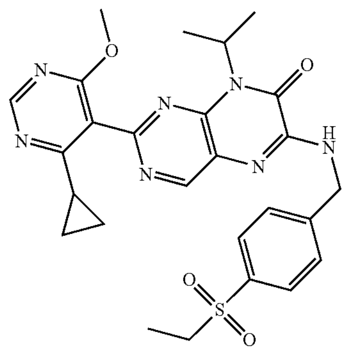 [SMILES: CCS(=O)(=O)c1ccc(CNc2nc3cnc(-c4c(OC)ncnc4C4CC4)nc3n(C(C)C)c2=O)cc1] |
| 144 | 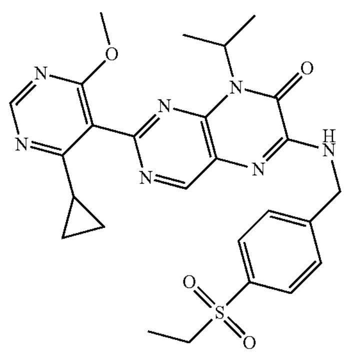 [SMILES: CCS(=O)(=O)c1ccc(CNc2nc3cnc(-c4c(OC)ncnc4C4CC4)nc3n(C(C)C)c2=O)cc1] |
| 145 | 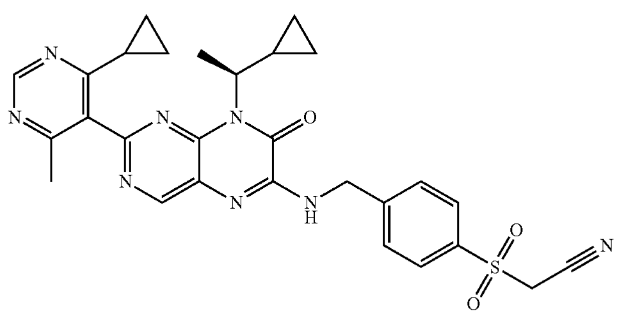 [SMILES: Cc1ncnc(C2CC2)c1-c1ncc2nc(NCc3ccc(S(=O)(=O)CC#N)cc3)c(=O)n([C@@H](C)C3CC3)c2n1] |
| 146 | 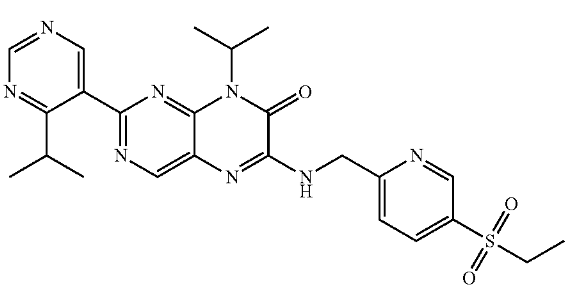 [SMILES: CCS(=O)(=O)c1ccc(CNc2nc3cnc(-c4cncnc4C(C)C)nc3n(C(C)C)c2=O)nc1] |

| Example | Structure |
|---|---|
| 147 | 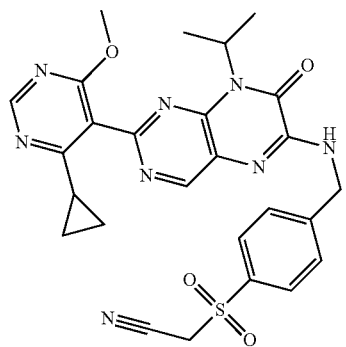 [SMILES: COc1ncnc(C2CC2)c1-c1ncc2nc(NCc3ccc(S(=O)(=O)CC#N)cc3)c(=O)n(C(C)C)c2n1] |
| 148 | 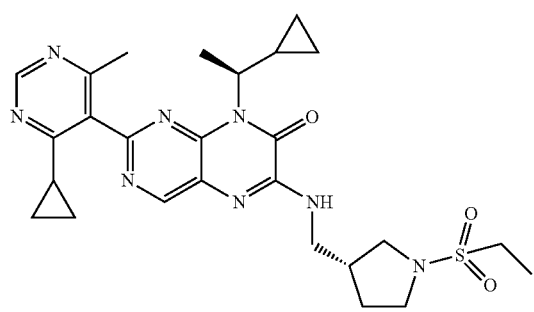 [SMILES: CCS(=O)(=O)N1CC[C@H](CNc2nc3cnc(-c4c(C)ncnc4C4CC4)nc3n([C@@H](C)C3CC3)c2=O)C1] |
| 149 | 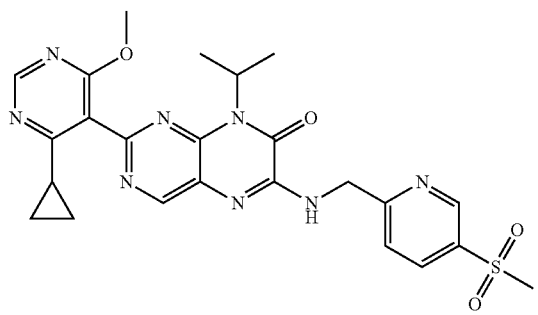 [SMILES: COc1ncnc(C2CC2)c1-c1ncc2nc(NCc3ccc(S(C)(=O)=O)cn3)c(=O)n(C(C)C)c2n1] |
| 150 | 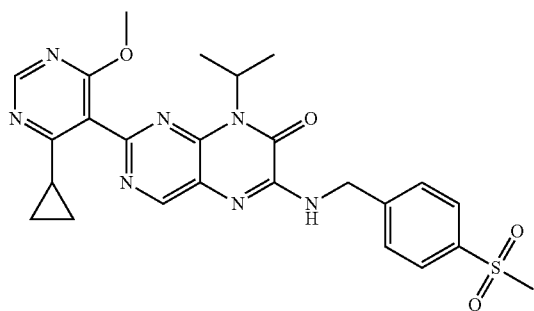 [SMILES: COc1ncnc(C2CC2)c1-c1ncc2nc(NCc3ccc(S(C)(=O)=O)cc3)c(=O)n(C(C)C)c2n1] |

| Example | Structure |
|---|---|
| 151 | 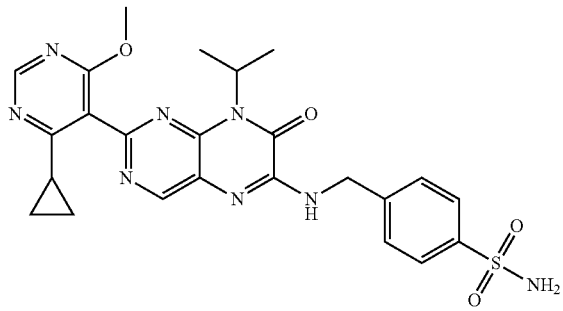 [SMILES: COc1ncnc(C2CC2)c1-c1ncc2nc(NCc3ccc(S(N)(=O)=O)cc3)c(=O)n(C(C)C)c2n1] |
| 152 | 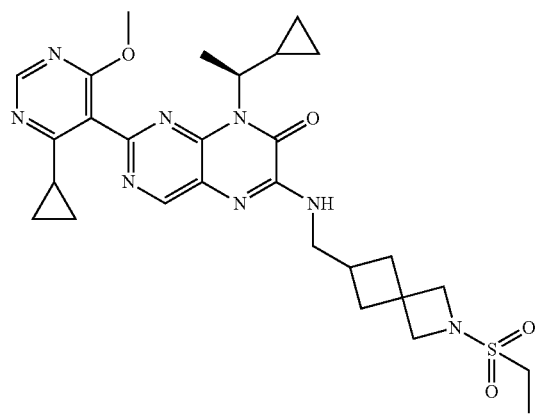 [SMILES: CCS(=O)(=O)N1CC2(CC(CNc3nc4cnc(-c5c(OC)ncnc5C5CC5)nc4n([C@@H](C)C4CC4)c3=O)C2)C1] |
| 153 | 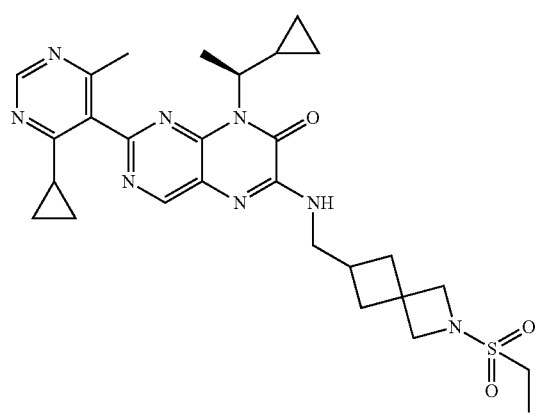 [SMILES: CCS(=O)(=O)N1CC2(CC(CNc3nc4cnc(-c5c(C)ncnc5C5CC5)nc4n([C@@H](C)C4CC4)c3=O)C2)C1] |
| 154 | 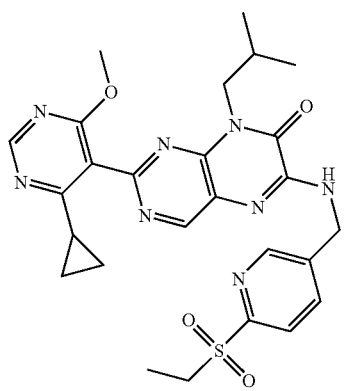 [SMILES: CCS(=O)(=O)c1ccc(CNc2nc3cnc(-c4c(OC)ncnc4C4CC4)nc3n(CC(C)C)c2=O)cn1] |

| Example | Structure |
|---|---|
| 155 | 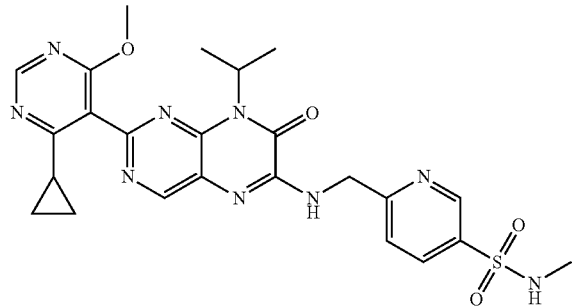 [SMILES: CNS(=O)(=O)c1ccc(CNc2nc3cnc(-c4c(OC)ncnc4C4CC4)nc3n(C(C)C)c2=O)nc1] |
| 156 | 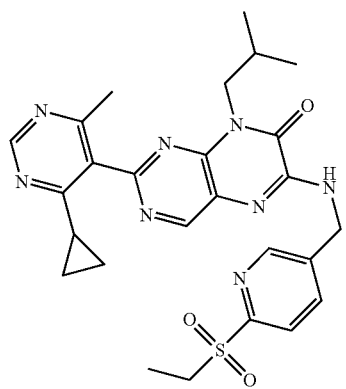 [SMILES: CCS(=O)(=O)c1ccc(CNc2nc3cnc(-c4c(C)ncnc4C4CC4)nc3n(CC(C)C)c2=O)cn1] |
| 157 | 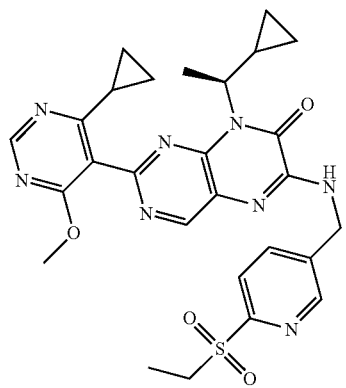 [SMILES: CCS(=O)(=O)c1ccc(CNc2nc3cnc(-c4c(OC)ncnc4C4CC4)nc3n([C@@H](C)C3CC3)c2=O)cn1] |
| 158 | 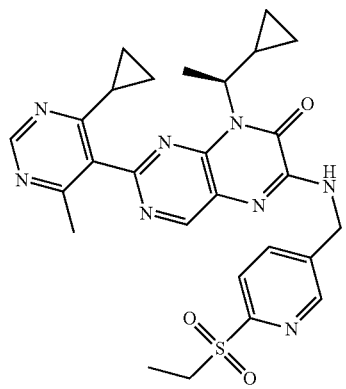 [SMILES: CCS(=O)(=O)c1ccc(CNc2nc3cnc(-c4c(C)ncnc4C4CC4)nc3n([C@@H](C)C3CC3)c2=O)cn1] |

| Example | Structure |
|---|---|
| 159 | 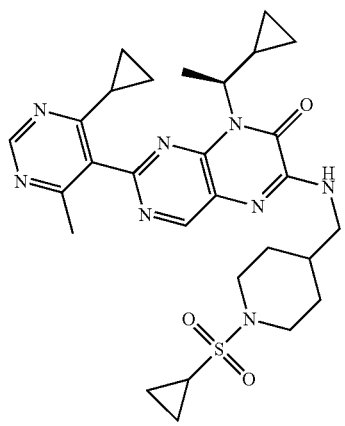 [SMILES: Cc1ncnc(C2CC2)c1-c1ncc2nc(NCC3CCN(S(=O)(=O)C4CC4)CC3)c(=O)n([C@@H](C)C3CC3)c2n1] |
| 160 | 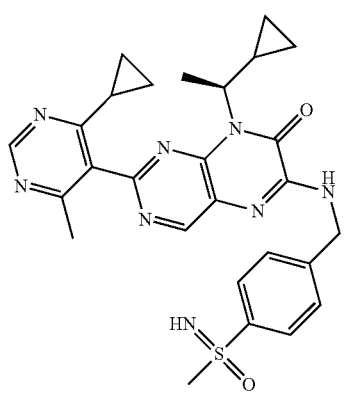 [SMILES: Cc1ncnc(C2CC2)c1-c1ncc2nc(NCc3ccc(S(C)(=N)=O)cc3)c(=O)n([C@@H](C)C3CC3)c2n1] |
| 161 | 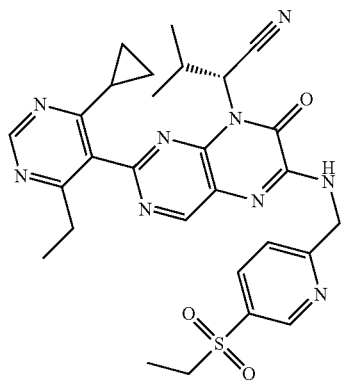 [SMILES: CCc1ncnc(C2CC2)c1-c1ncc2nc(NCc3ccc(S(=O)(=O)CC)cn3)c(=O)n([C@@H](C#N)C(C)C)c2n1] |
| 162 | 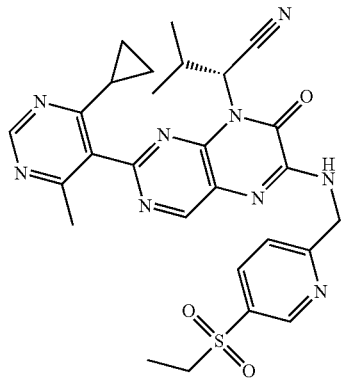 [SMILES: CCS(=O)(=O)c1ccc(CNc2nc3cnc(-c4c(C)ncnc4C4CC4)nc3n([C@@H](C#N)C(C)C)c2=O)nc1] |

| Example | Structure |
|---------|-----------|
| 163 | 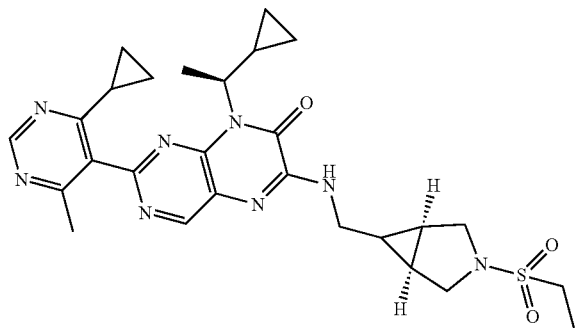 [SMILES: CCS(=O)(=O)N1C[C@@H]2C(CNc3nc4cnc(-c5c(C)ncnc5C5CC5)nc4n([C@@H](C)C4CC4)c3=O)[C@@H]2C1] |
| 164 | 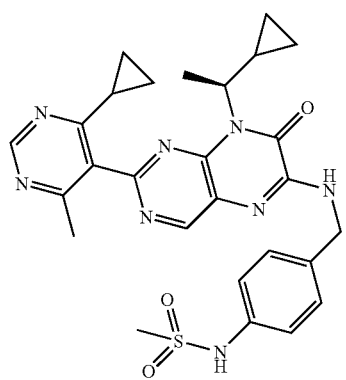 [SMILES: Cc1ncnc(C2CC2)c1-c1ncc2nc(NCc3ccc(NS(C)(=O)=O)cc3)c(=O)n([C@@H](C)C3CC3)c2n1] |
| 165 | 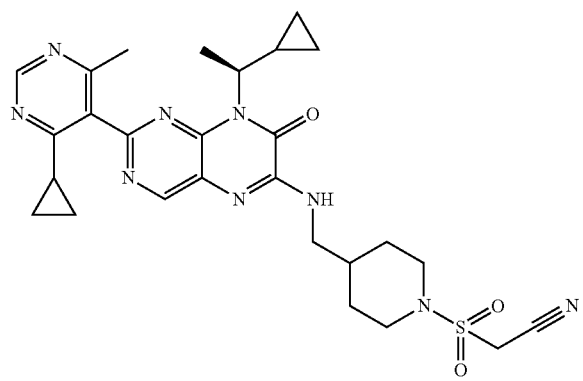 [SMILES: Cc1ncnc(C2CC2)c1-c1ncc2nc(NCC3CCN(S(=O)(=O)CC#N)CC3)c(=O)n([C@@H](C)C3CC3)c2n1] |
| 166 | 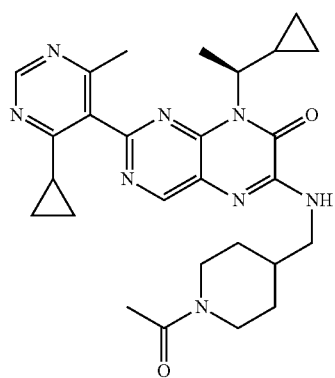 [SMILES: CC(=O)N1CCC(CNc2nc3cnc(-c4c(C)ncnc4C4CC4)nc3n([C@@H](C)C3CC3)c2=O)CC1] |

| Example | Structure |
|---|---|
| 167 | 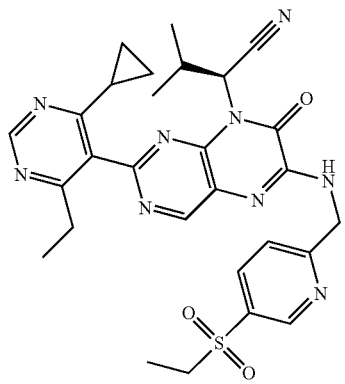 [SMILES: CCc1ncnc(C2CC2)c1-c1ncc2nc(NCc3ccc(S(=O)(=O)CC)cn3)c(=O)n([C@H](C#N)C(C)C)c2n1] |
| 168 | 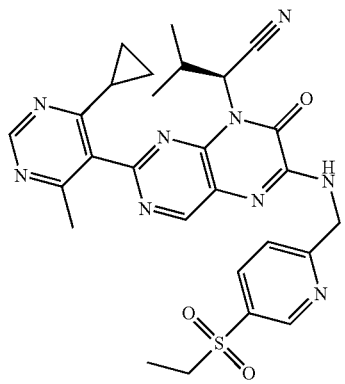 [SMILES: CCS(=O)(=O)c1ccc(CNc2nc3cnc(-c4c(C)ncnc4C4CC4)nc3n([C@H](C#N)C(C)C)c2=O)nc1] |
| 169 | 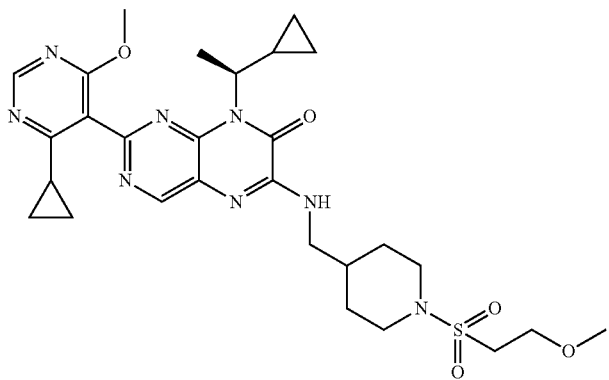 [SMILES: COCCS(=O)(=O)N1CCC(CNc2nc3cnc(-c4c(OC)ncnc4C4CC4)nc3n([C@@H](C)C3CC3)c2=O)CC1] |
| 170 | 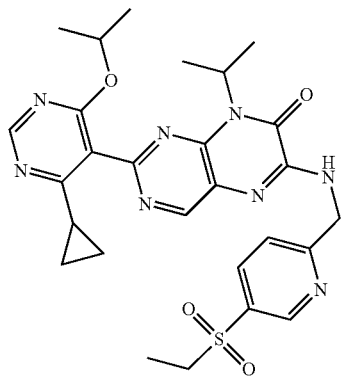 [SMILES: CCS(=O)(=O)c1ccc(CNc2nc3cnc(-c4c(OC(C)C)ncnc4C4CC4)nc3n(C(C)C)c2=O)nc1] |

| Example | Structure |
|---|---|
| 171 | 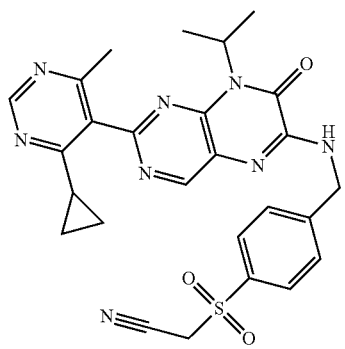 [SMILES: Cc1ncnc(C2CC2)c1-c1ncc2nc(NCc3ccc(S(=O)(=O)CC#N)cc3)c(=O)n(C(C)C)c2n1] |
| 172 | 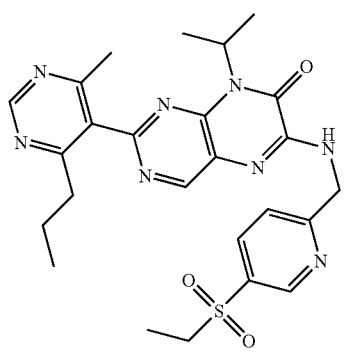 [SMILES: CCCc1ncnc(C)c1-c1ncc2nc(NCc3ccc(S(=O)(=O)CC)cn3)c(=O)n(C(C)C)c2n1] |
| 173 | 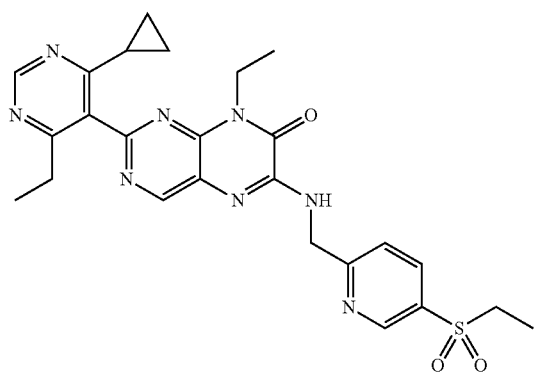 [SMILES: CCc1ncnc(C2CC2)c1-c1ncc2nc(NCc3ccc(S(=O)(=O)CC)cn3)c(=O)n(CC)c2n1] |
| 174 | 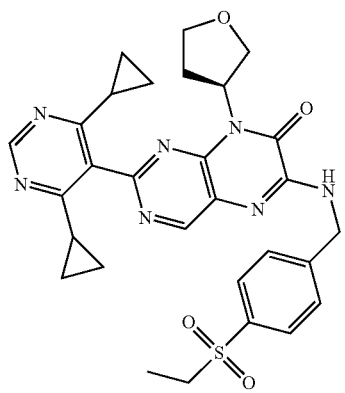 [SMILES: CCS(=O)(=O)c1ccc(CNc2nc3cnc(-c4c(C5CC5)ncnc4C4CC4)nc3n([C@H]3CCOC3)c2=O)cc1] |

| Example | Structure |
|---|---|
| 175 | 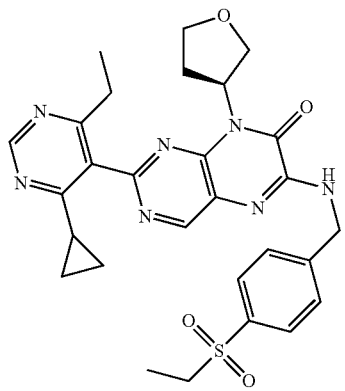 |
| 176 | 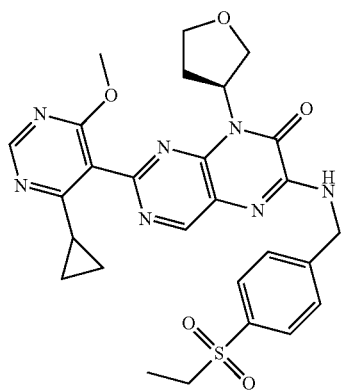 |
| 177 | 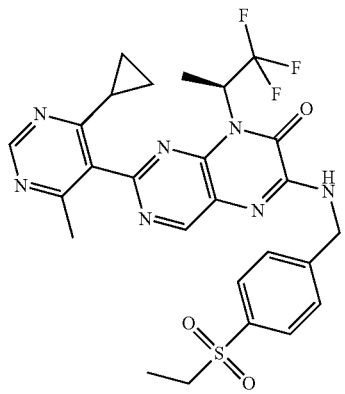 [SMILES: CCS(=O)(=O)c1ccc(CNc2nc3cnc(-c4c(C)ncnc4C4CC4)nc3n([C@@H](C)C(F)(F)F)c2=O)cc1] |
| 178 | 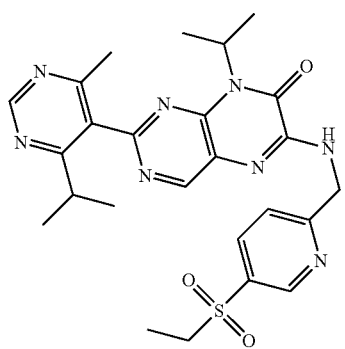 [SMILES: CCS(=O)(=O)c1ccc(CNc2nc3cnc(-c4c(C)ncnc4C(C)C)nc3n(C(C)C)c2=O)nc1] |

| Example | Structure |
|---|---|
| 179 | 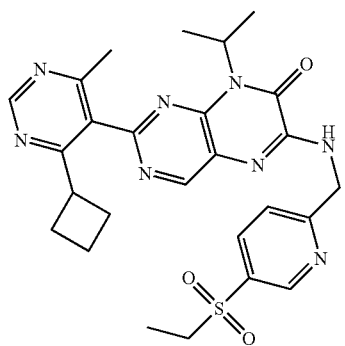 [SMILES: CCS(=O)(=O)c1ccc(CNc2nc3cnc(-c4c(C)ncnc4C4CCC4)nc3n(C(C)C)c2=O)nc1] |
| 180 | 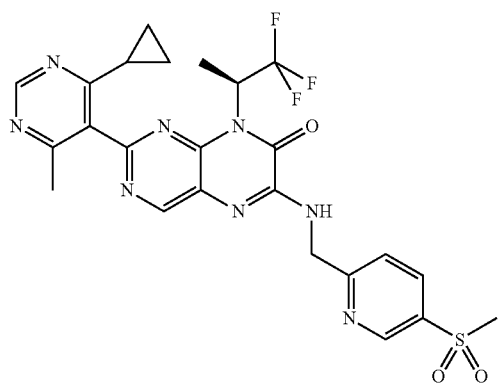 |
| 181 | 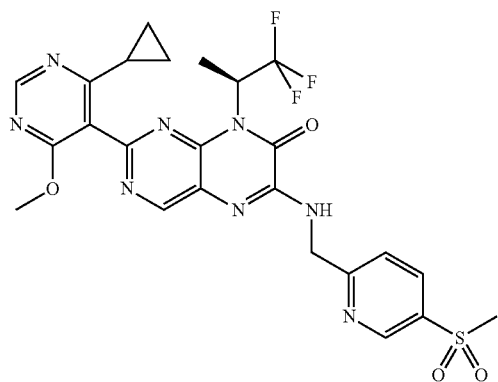 [SMILES: COc1ncnc(C2CC2)c1-c1ncc2nc(NCc3ccc(S(C)(=O)=O)cn3)c(=O)n([C@@H](C)C(F)(F)F)c2n1] |
| 182 | 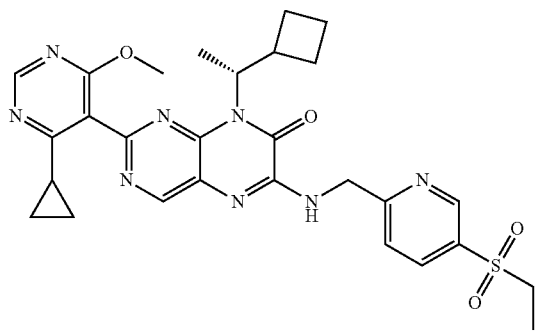 [SMILES: CCS(=O)(=O)c1ccc(CNc2nc3cnc(-c4c(OC)ncnc4C4CC4)nc3n([C@H](C)C3CCC3)c2=O)nc1] |

-continued

| Example | Structure |
|---------|-----------|
| 183 | 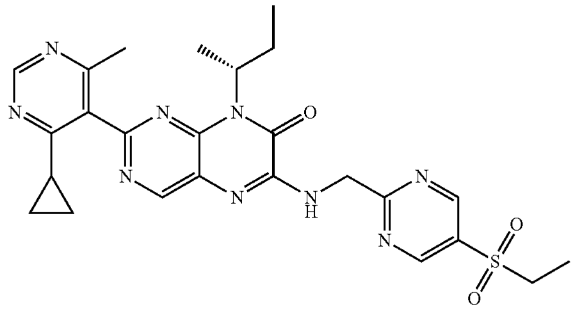 [SMILES: CC[C@@H](C)n1c(=O)c(NCc2ncc(S(=O)(=O)CC)cn2)nc2cnc(-c3c(C)ncnc3C3CC3)nc21] |
| 184 | 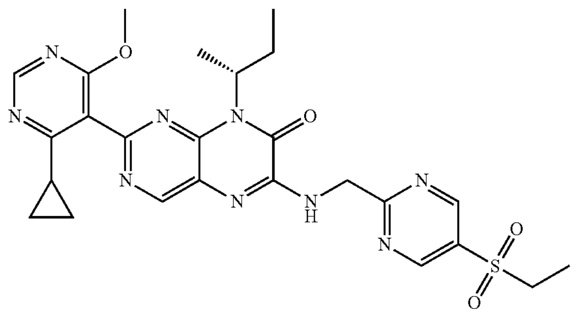 [SMILES: CC[C@@H](C)n1c(=O)c(NCc2ncc(S(=O)(=O)CC)cn2)nc2cnc(-c3c(OC)ncnc3C3CC3)nc21] |
| 185 | 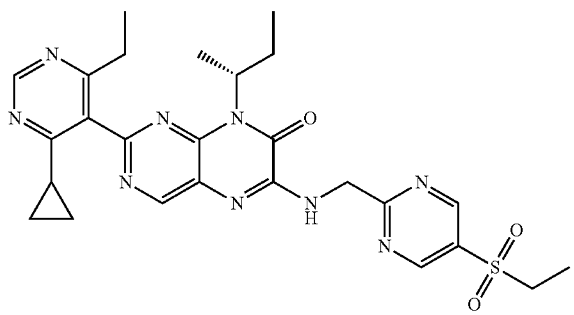 [SMILES: CCc1ncnc(C2CC2)c1-c1ncc2nc(NCc3ncc(S(=O)(=O)CC)cn3)c(=O)n([C@H](C)CC)c2n1] |
| 186 | 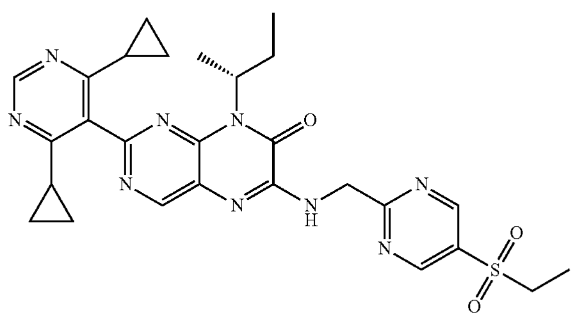 [SMILES: CC[C@@H](C)n1c(=O)c(NCc2ncc(S(=O)(=O)CC)cn2)nc2cnc(-c3c(C4CC4)ncnc3C3CC3)nc21] |
| 187 | 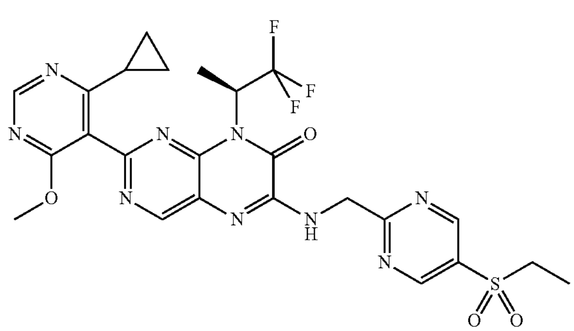 [SMILES: CCS(=O)(=O)c1cnc(CNc2nc3cnc(-c4c(OC)ncnc4C4CC4)nc3n([C@@H](C)C(F)(F)F)c2=O)nc1] |

| Example | Structure |
|---|---|
| 188 | 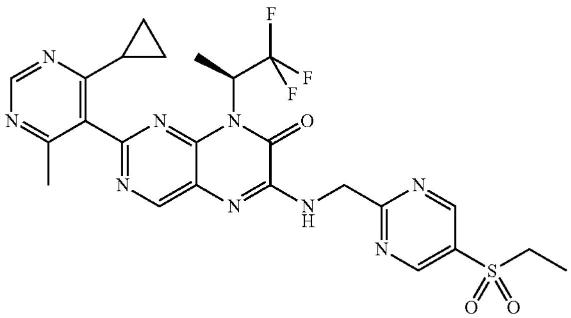 [SMILES: CCS(=O)(=O)c1cnc(CNc2nc3cnc(-c4c(C)ncnc4C4CC4)nc3n([C@@H](C)C(F)(F)F)c2=O)nc1] |
| 189 | 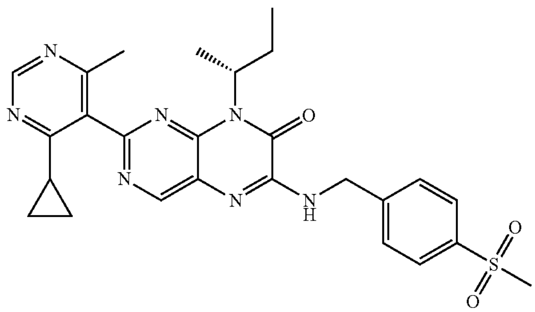 [SMILES: CC[C@@H](C)n1c(=O)c(NCc2ccc(S(C)(=O)=O)cc2)nc2cnc(-c3c(C)ncnc3C3CC3)nc21] |
| 190 | 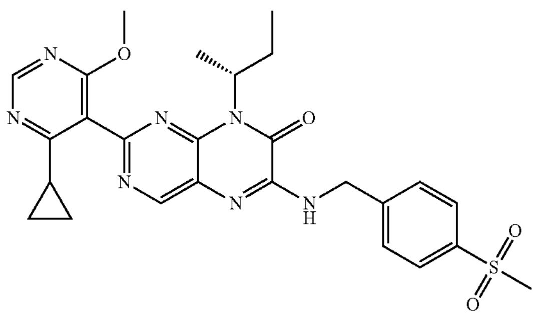 [SMILES: CC[C@@H](C)n1c(=O)c(NCc2ccc(S(C)(=O)=O)cc2)nc2cnc(-c3c(OC)ncnc3C3CC3)nc21] |
| 191 | 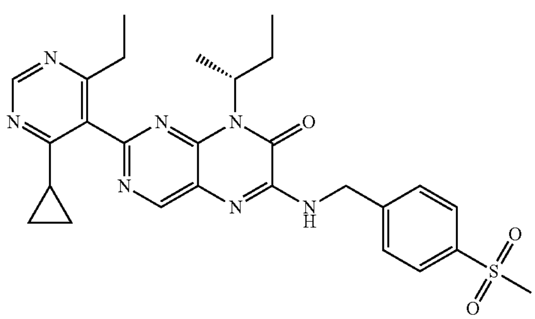 [SMILES: CCc1ncnc(C2CC2)c1-c1ncc2nc(NCc3ccc(S(C)(=O)=O)cc3)c(=O)n([C@H](C)CC)c2n1] |
| 192 | 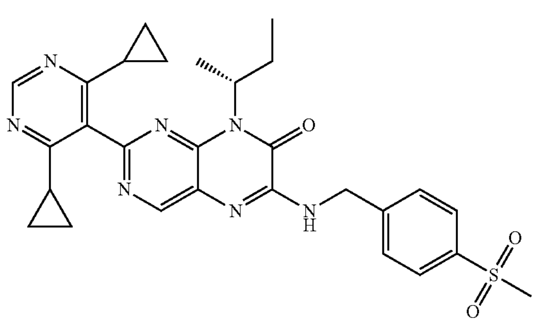 [SMILES: CC[C@@H](C)n1c(=O)c(NCc2ccc(S(C)(=O)=O)cc2)nc2cnc(-c3c(C4CC4)ncnc3C3CC3)nc21] |

-continued
| Example | Structure |
|---|---|
| 193 | 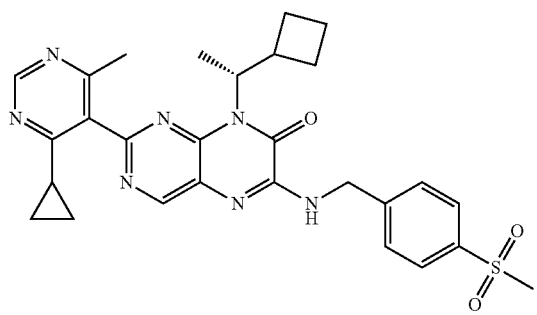 [SMILES: Cc1ncnc(C2CC2)c1-c1ncc2nc(NCc3ccc(S(C)(=O)=O)cc3)c(=O)n([C@H](C)C3CCC3)c2n1] |
| 194 | 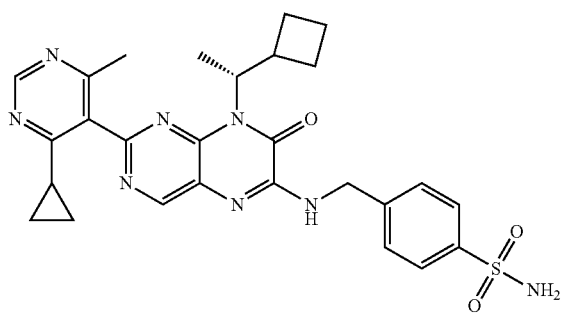 [SMILES: Cc1ncnc(C2CC2)c1-c1ncc2nc(NCc3ccc(S(N)(=O)=O)cc3)c(=O)n([C@H](C)C3CCC3)c2n1] |
| 195 | 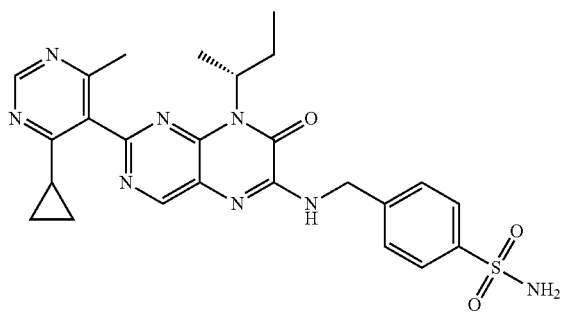 [SMILES: CC[C@@H](C)n1c(=O)c(NCc2ccc(S(N)(=O)=O)cc2)nc2cnc(-c3c(C)ncnc3C3CC3)nc21] |
| 196 | 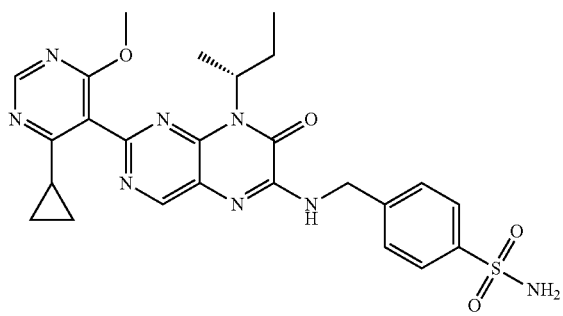 [SMILES: CC[C@@H](C)n1c(=O)c(NCc2ccc(S(N)(=O)=O)cc2)nc2cnc(-c3c(OC)ncnc3C3CC3)nc21] |
| 197 | 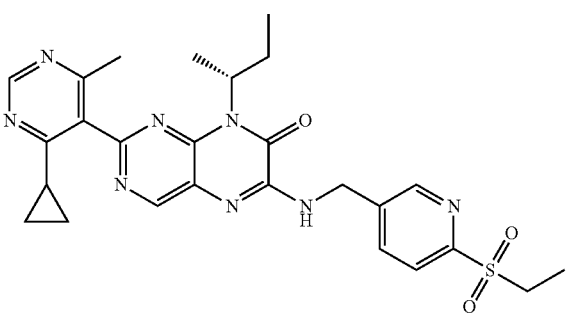 [SMILES: CC[C@@H](C)n1c(=O)c(NCc2ccc(S(=O)(=O)CC)nc2)nc2cnc(-c3c(C)ncnc3C3CC3)nc21] |

| Example | Structure |
|---------|-----------|
| 198 | 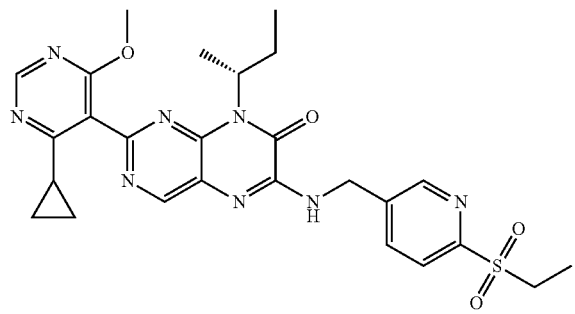 [SMILES: CC[C@@H](C)n1c(=O)c(NCc2ccc(S(=O)(=O)CC)nc2)nc2cnc(-c3c(OC)ncnc3C3CC3)nc21] |
| 199 | 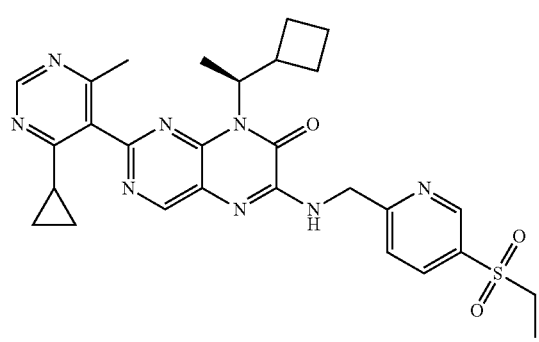 [SMILES: CCS(=O)(=O)c1ccc(CNc2nc3cnc(-c4c(C)ncnc4C4CC4)nc3n([C@@H](C)C3CCC3)c2=O)nc1] |
| 200 | 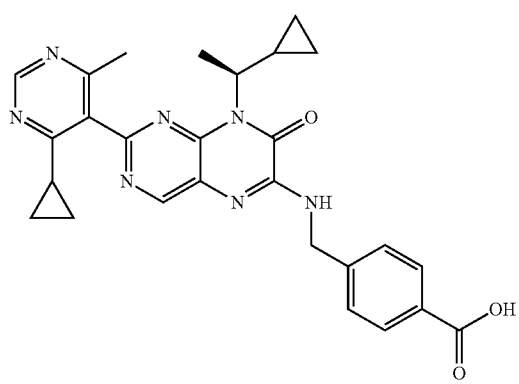 [SMILES: Cc1ncnc(C2CC2)c1-c1ncc2nc(NCc3ccc(C(=O)O)cc3)c(=O)n([C@@H](C)C3CC3)c2n1] |
| 201 | 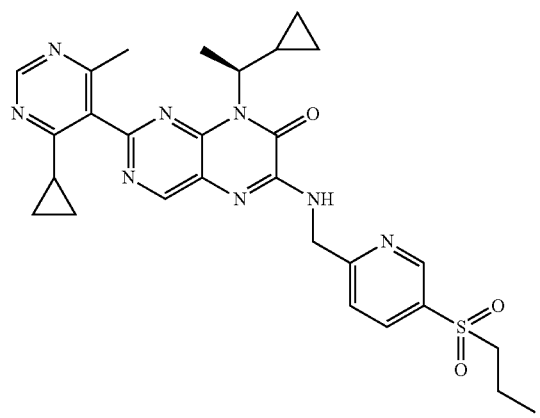 [SMILES: CCCS(=O)(=O)c1ccc(CNc2nc3cnc(-c4c(C)ncnc4C4CC4)nc3n([C@@H](C)C3CC3)c2=O)nc1] |

-continued
| Example | Structure |
|---|---|
| 202 | 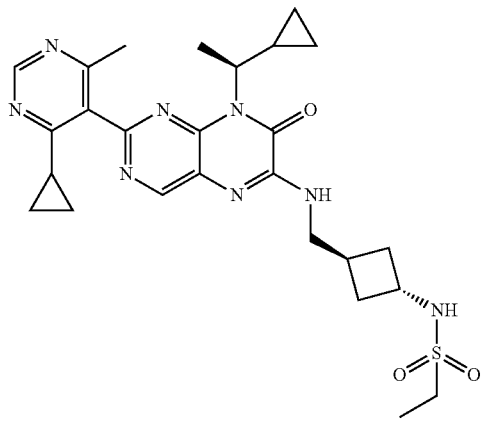 [SMILES: CCS(=O)(=O)N[C@H]1C[C@H](CNc2nc3cnc(-c4c(C)ncnc4C4CC4)nc3n([C@@H](C)C3CC3)c2=O)C1] |
| 203 | 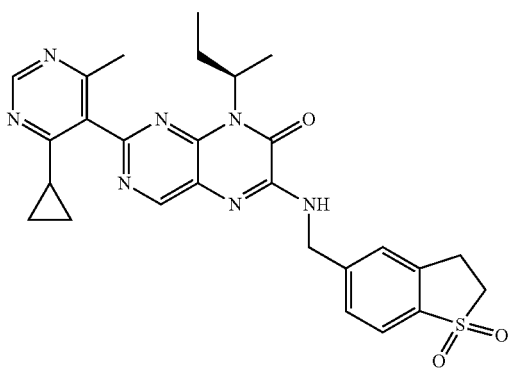 [SMILES: CC[C@@H](C)n1c(=O)c(NCc2ccc3c(c2)CCS3(=O)=O)nc2cnc(-c3c(C)ncnc3C3CC3)nc21] |
| 204 | 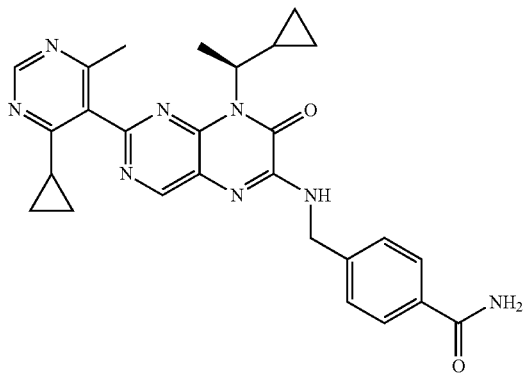 [SMILES: Cc1ncnc(C2CC2)c1-c1ncc2nc(NCc3ccc(C(N)=O)cc3)c(=O)n([C@@H](C)C3CC3)c2n1] |
| 205 | 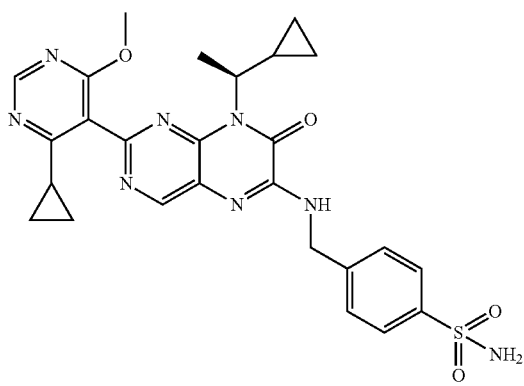 |

| Example | Structure |
|---|---|
| 206 | 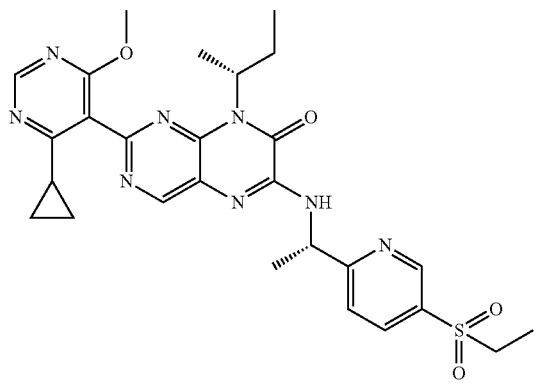 [SMILES: CC[C@@H](C)n1c(=O)c(N[C@@H](C)c2ccc(S(=O)(=O)CC)cn2)nc2cnc(-c3c(OC)ncnc3C3CC3)nc21] |
| 207 | 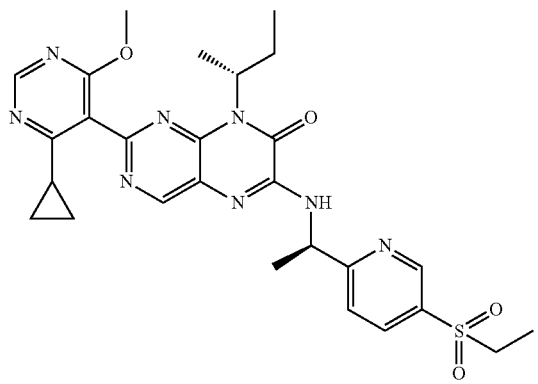 [SMILES: CC[C@@H](C)n1c(=O)c(N[C@H](C)c2ccc(S(=O)(=O)CC)cn2)nc2cnc(-c3c(OC)ncnc3C3CC3)nc21] |
| 208 | 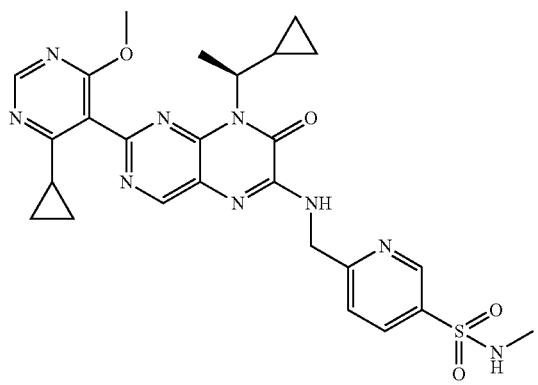 [SMILES: CNS(=O)(=O)c1ccc(CNc2nc3cnc(-c4c(OC)ncnc4C4CC4)nc3n([C@@H](C)C3CC3)c2=O)nc1] |
| 209 | 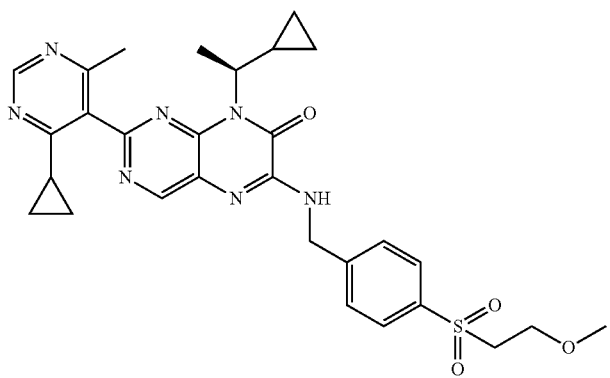 [SMILES: COCCS(=O)(=O)c1ccc(CNc2nc3cnc(-c4c(C)ncnc4C4CC4)nc3n([C@@H](C)C3CC3)c2=O)cc1] |

| Example | Structure |
|---|---|
| 210 | 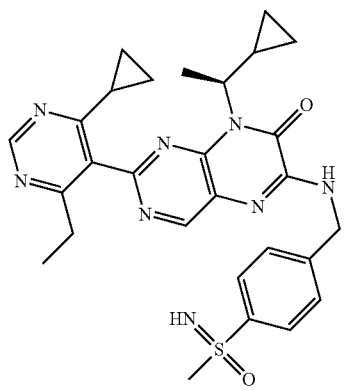 [SMILES: CCc1ncnc(C2CC2)c1-c1ncc2nc(NCc3ccc(S(C)(=N)=O)cc3)c(=O)n([C@@H](C)C3CC3)c2n1] |
| 211 | 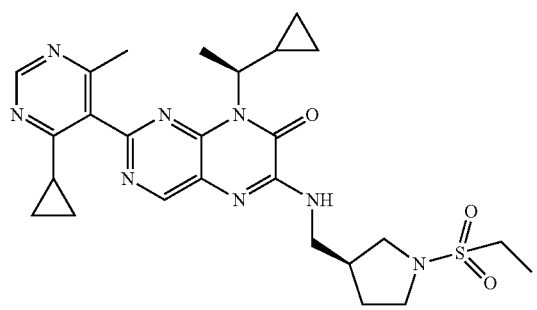 [SMILES: CCS(=O)(=O)N1CC[C@@H](CNc2nc3cnc(-c4c(C)ncnc4C4CC4)nc3n([C@@H](C)C3CC3)c2=O)C1] |
| 212 | 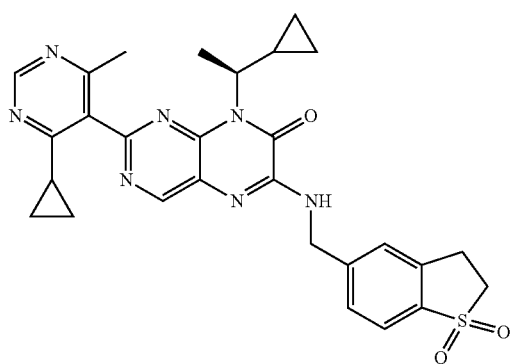 [SMILES: Cc1ncnc(C2CC2)c1-c1ncc2nc(NCc3ccc4c(c3)CCS4(=O)=O)c(=O)n([C@@H](C)C3CC3)c2n1] |
| 213 | 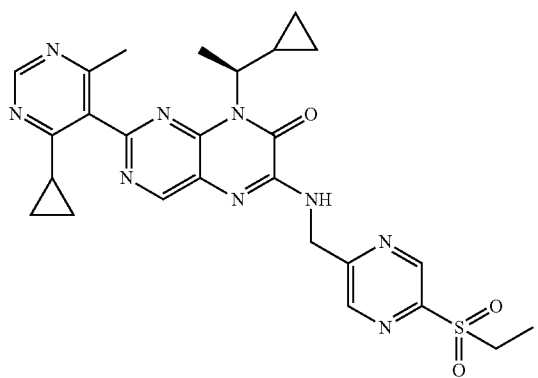 [SMILES: CCS(=O)(=O)c1cnc(CNc2nc3cnc(-c4c(C)ncnc4C4CC4)nc3n([C@@H](C)C3CC3)c2=O)cn1] |

| Example | Structure |
|---------|-----------|
| 214 | 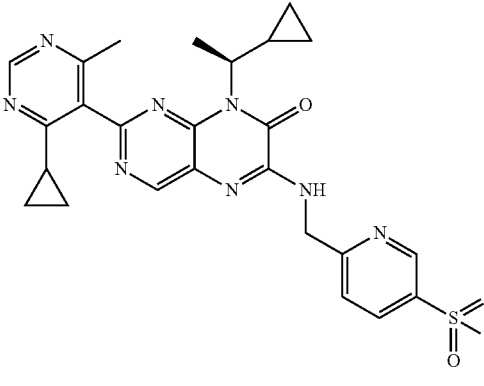 |
| 215 | 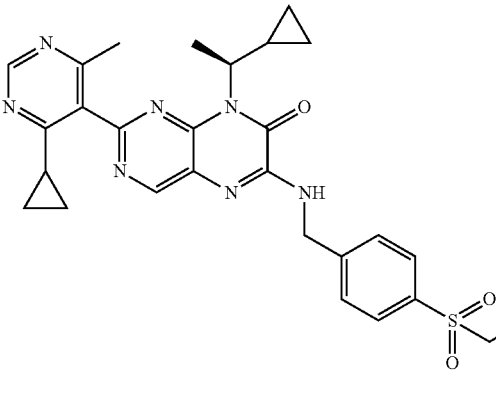 |
| 216 | 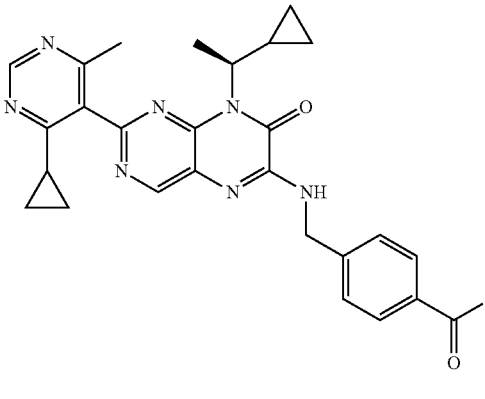 |
| 217 | 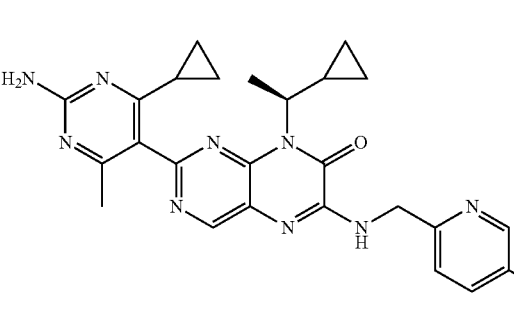 |

| Example | Structure |
|---|---|
| 218 | 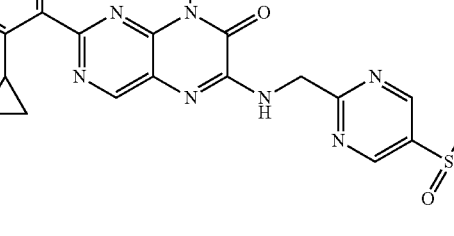 |
| 219 | 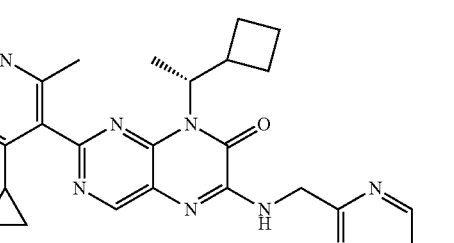 |
| 220 | 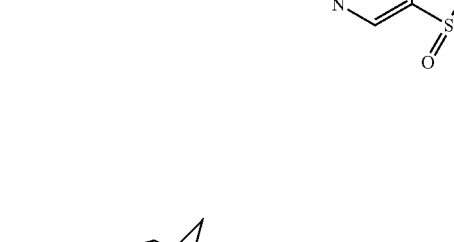 |
| 221 | 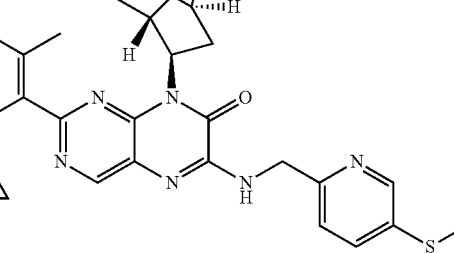 |

-continued
| Example | Structure |
|---|---|
| 222 | 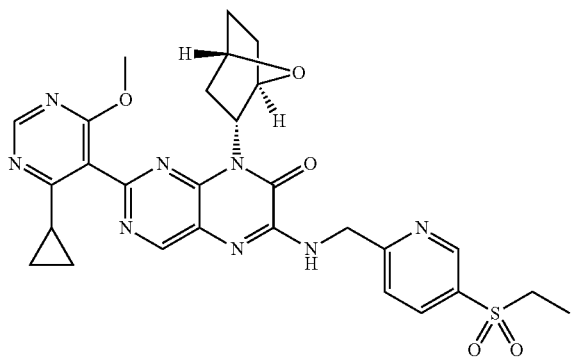 [SMILES: CCS(=O)(=O)c1ccc(CNc2nc3cnc(-c4c(OC)ncnc4C4CC4)nc3n([C@@H]3C[C@@H]4CC[C@H]3O4)c2=O)nc1] |
| 223 | 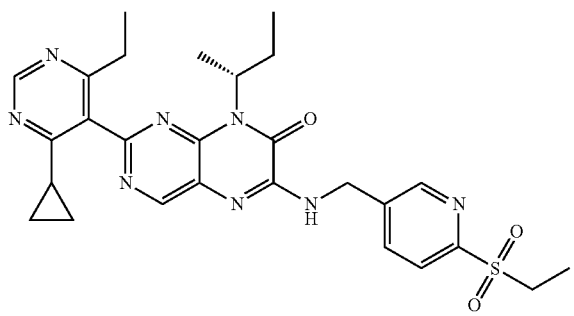 [SMILES: CCc1ncnc(C2CC2)c1-c1ncc2nc(NCc3ccc(S(=O)(=O)CC)nc3)c(=O)n([C@H](C)CC)c2n1] |
| 224 | 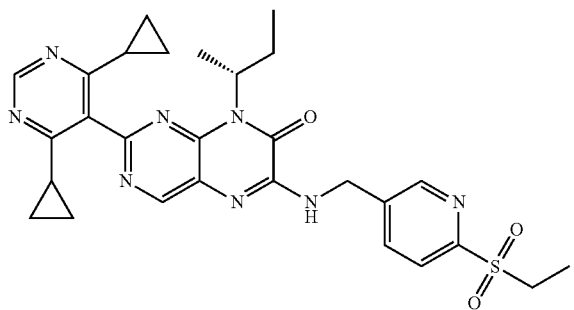 [SMILES: CC[C@@H](C)n1c(=O)c(NCc2ccc(S(=O)(=O)CC)nc2)nc2cnc(-c3c(C4CC4)ncnc3C3CC3)nc21] |
| 225 | 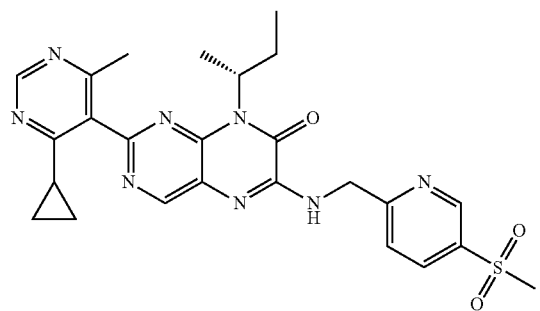 |

-continued

| Example | Structure |
|---|---|
| 226 | 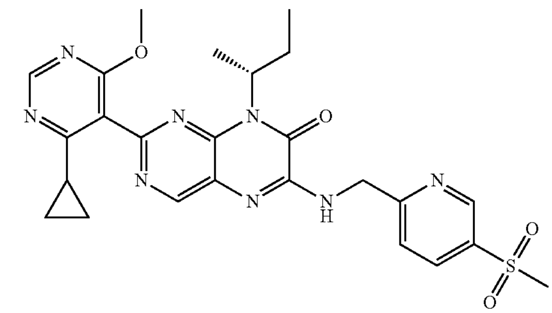 |
| 227 | 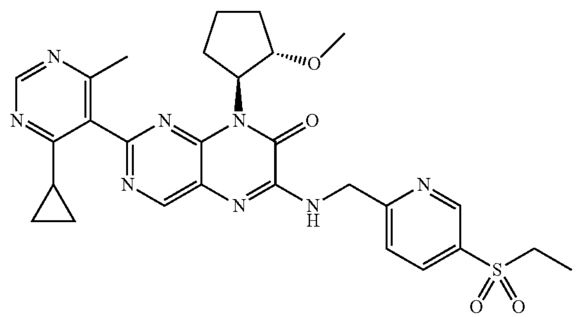 [SMILES: CCS(=O)(=O)c1ccc(CNc2nc3cnc(-c4c(C)ncnc4C4CC4)nc3n([C@H]3CCC[C@@H]3OC)c2=O)nc1] |
| 228 | 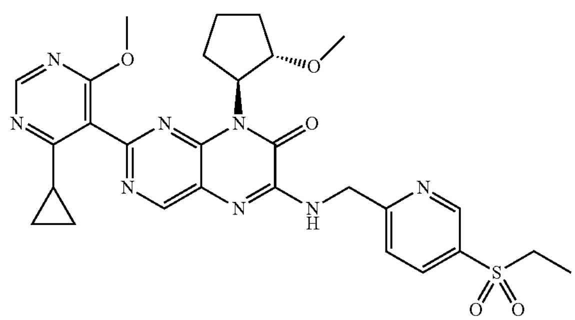 [SMILES: CCS(=O)(=O)c1ccc(CNc2nc3cnc(-c4c(OC)ncnc4C4CC4)nc3n([C@H]3CCC[C@@H]3OC)c2=O)nc1] |
| 229 | 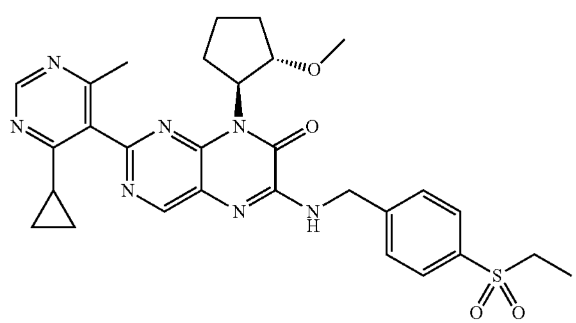 [SMILES: CCS(=O)(=O)c1ccc(CNc2nc3cnc(-c4c(C)ncnc4C4CC4)nc3n([C@H]3CCC[C@@H]3OC)c2=O)cc1] |
| 230 | 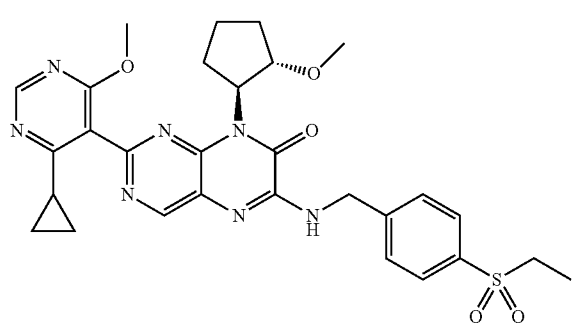 [SMILES: CCS(=O)(=O)c1ccc(CNc2nc3cnc(-c4c(OC)ncnc4C4CC4)nc3n([C@H]3CCC[C@@H]3OC)c2=O)cc1] |

| Example | Structure |
|---|---|
| 231 | 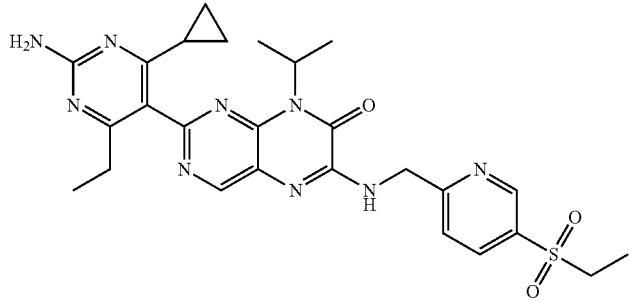 [SMILES: CCc1nc(N)nc(C2CC2)c1-c1ncc2nc(NCc3ccc(S(=O)(=O)CC)cn3)c(=O)n(C(C)C)c2n1] |
| 232 | 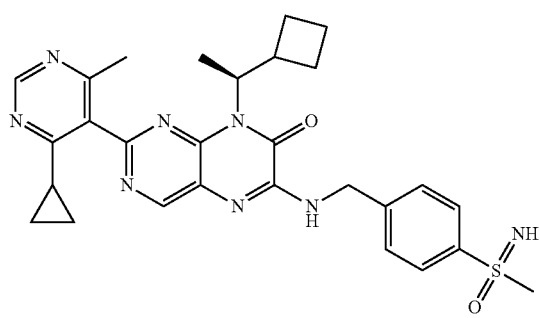 |
| 233 | 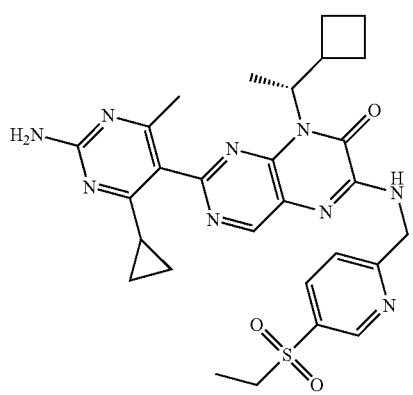 [SMILES: CCS(=O)(=O)c1ccc(CNc2nc3cnc(-c4c(C)nc(N)nc4C4CC4)nc3n([C@H](C)C3CCC3)c2=O)nc1] |
| 234 | 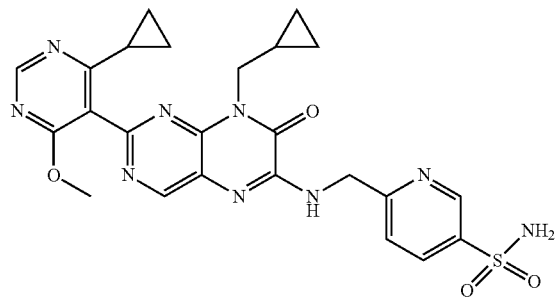 [SMILES: COc1ncnc(C2CC2)c1-c1ncc2nc(NCc3ccc(S(N)(=O)=O)cn3)c(=O)n(CC3CC3)c2n1] |

| Example | Structure |
|---|---|
| 235 | 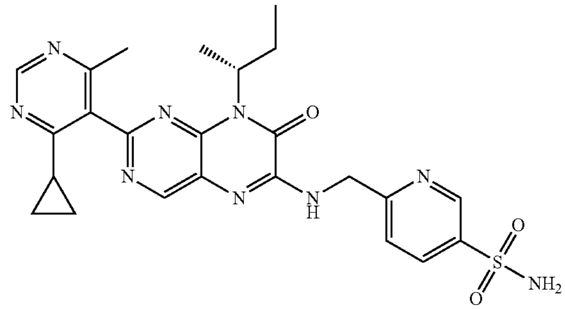 [SMILES: CC[C@@H](C)n1c(=O)c(NCc2ccc(S(N)(=O)=O)cn2)nc2cnc(-c3c(C)ncnc3C3CC3)nc21] |
| 236 | 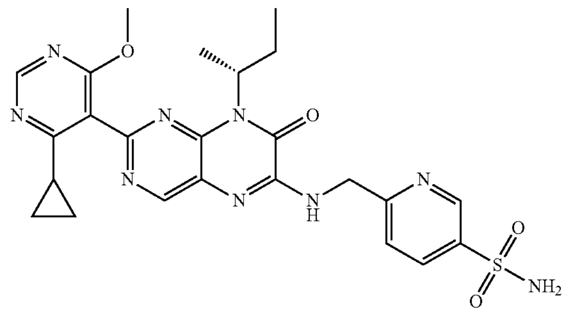 [SMILES: CC[C@@H](C)n1c(=O)c(NCc2ccc(S(N)(=O)=O)cn2)nc2cnc(-c3c(OC)ncnc3C3CC3)nc21] |
| 237 | 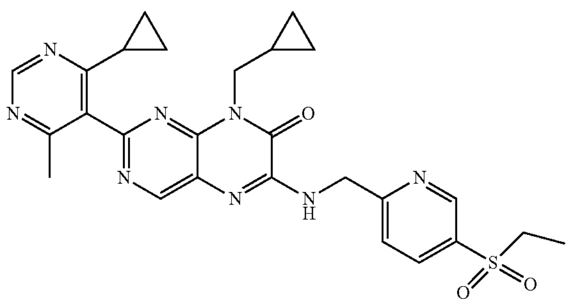 [SMILES: CCS(=O)(=O)c1ccc(CNc2nc3cnc(-c4c(C)ncnc4C4CC4)nc3n(CC3CC3)c2=O)nc1] |
| 238 | 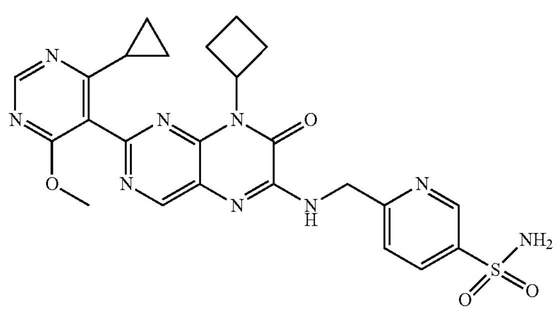 [SMILES: COc1ncnc(C2CC2)c1-c1ncc2nc(NCc3ccc(S(N)(=O)=O)cn3)c(=O)n(C3CCC3)c2n1] |
| 239 | 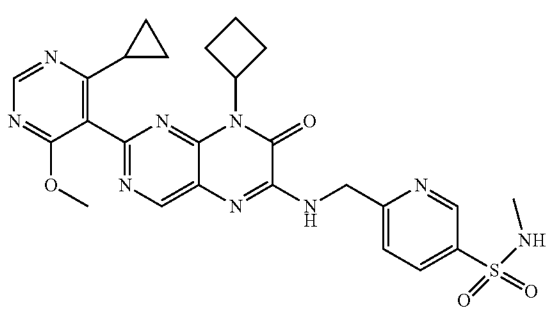 [SMILES: CNS(=O)(=O)c1ccc(CNc2nc3cnc(-c4c(OC)ncnc4C4CC4)nc3n(C3CCC3)c2=O)nc1] |

| Example | Structure |
|---|---|
| 240 | 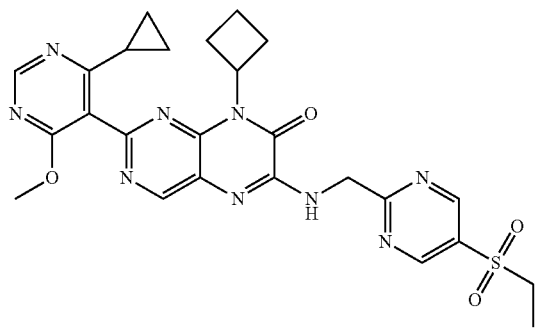 [SMILES: CCS(=O)(=O)c1cnc(CNc2nc3cnc(-c4c(OC)ncnc4C4CC4)nc3n(C3CCC3)c2=O)nc1] |
| 241 | 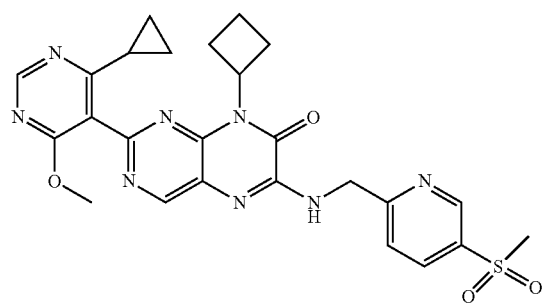 [SMILES: COc1ncnc(C2CC2)c1-c1ncc2nc(NCc3ccc(S(C)(=O)=O)cn3)c(=O)n(C3CCC3)c2n1] |
| 242 | 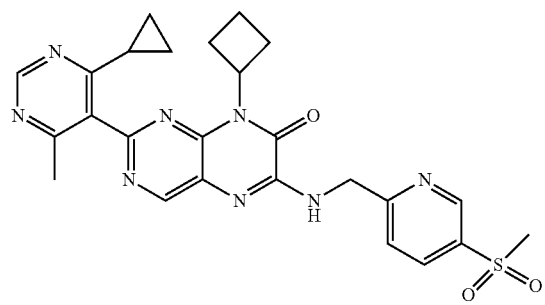 [SMILES: Cc1ncnc(C2CC2)c1-c1ncc2nc(NCc3ccc(S(C)(=O)=O)cn3)c(=O)n(C3CCC3)c2n1] |
| 243 | 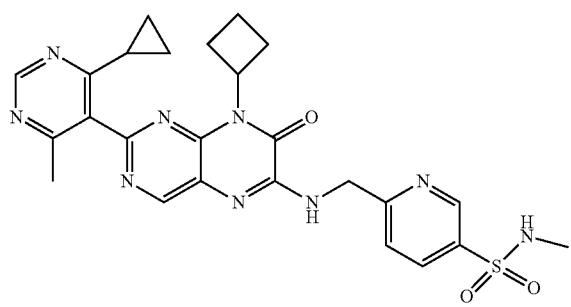 [SMILES: CNS(=O)(=O)c1ccc(CNc2nc3cnc(-c4c(C)ncnc4C4CC4)nc3n(C3CCC3)c2=O)nc1] |
| 244 | 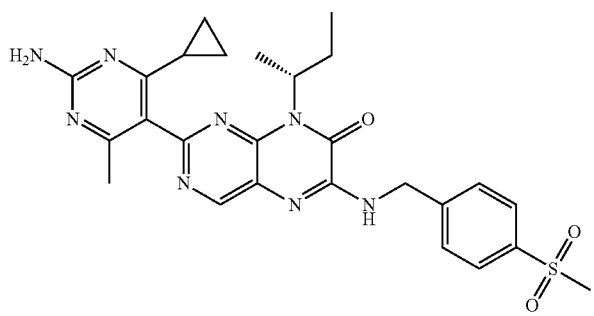 [SMILES: CC[C@@H](C)n1c(=O)c(NCc2ccc(S(C)(=O)=O)cc2)nc2cnc(-c3c(C)nc(N)nc3C3CC3)nc21] |

| Example | Structure |
|---|---|
| 245 | 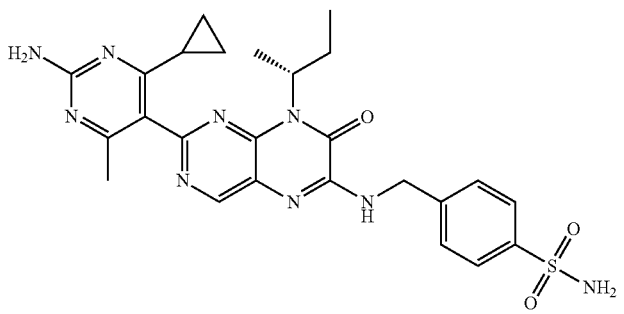 [SMILES: CC[C@@H](C)n1c(=O)c(NCc2ccc(S(N)(=O)=O)cc2)nc2cnc(-c3c(C)nc(N)nc3C3CC3)nc21] |
| 246 | 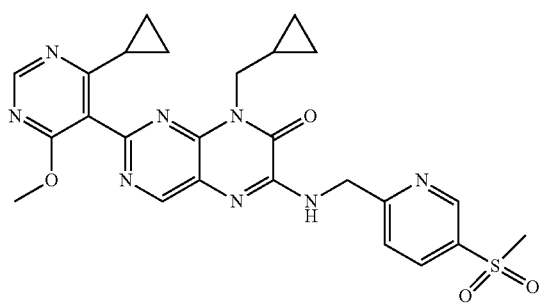 [SMILES: COc1ncnc(C2CC2)c1-c1ncc2nc(NCc3ccc(S(C)(=O)=O)cn3)c(=O)n(CC3CC3)c2n1] |
| 247 | 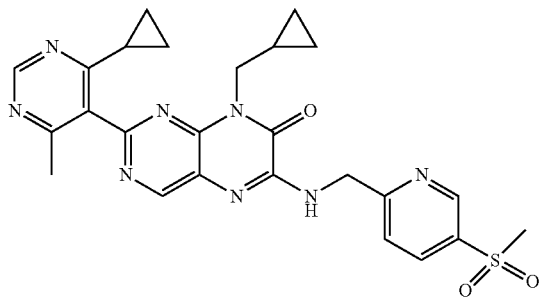 [SMILES: Cc1ncnc(C2CC2)c1-c1ncc2nc(NCc3ccc(S(C)(=O)=O)cn3)c(=O)n(CC3CC3)c2n1] |
| 248 | 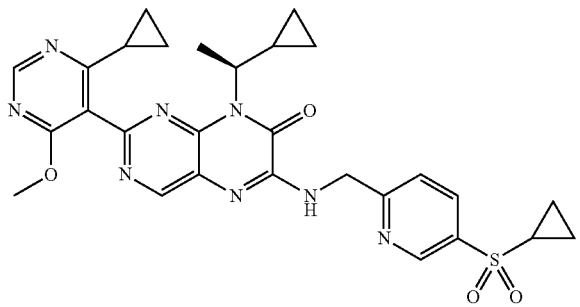 [SMILES: COc1ncnc(C2CC2)c1-c1ncc2nc(NCc3ccc(S(=O)(=O)C4CC4)cn3)c(=O)n([C@@H](C)C3CC3)c2n1] |
| 249 | 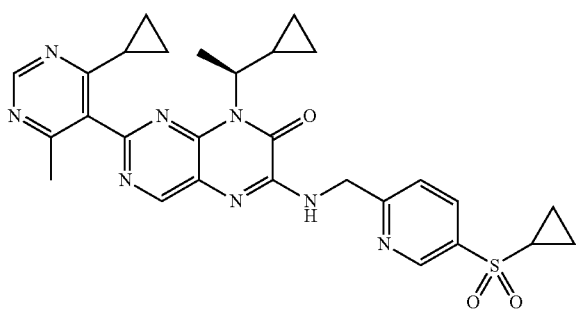 [SMILES: Cc1ncnc(C2CC2)c1-c1ncc2nc(NCc3ccc(S(=O)(=O)C4CC4)cn3)c(=O)n([C@@H](C)C3CC3)c2n1] |

-continued

| Example | Structure |
|---|---|
| 250 | 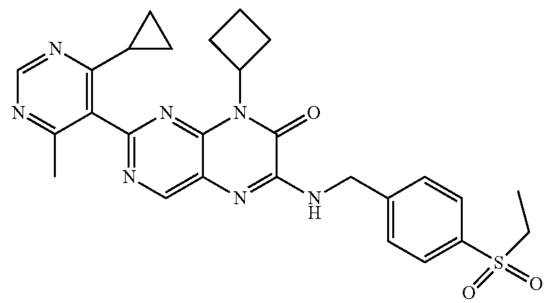 [SMILES: CCS(=O)(=O)c1ccc(CNc2nc3cnc(-c4c(C)ncnc4C4CC4)nc3n(C3CCC3)c2=O)cc1] |
| 251 | 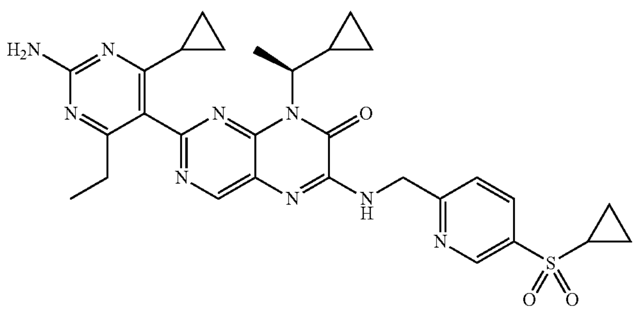 [SMILES: CCc1nc(N)nc(C2CC2)c1-c1ncc2nc(NCc3ccc(S(=O)(=O)C4CC4)cn3)c(=O)n([C@@H](C)C3CC3)c2n1] |
| 252 | 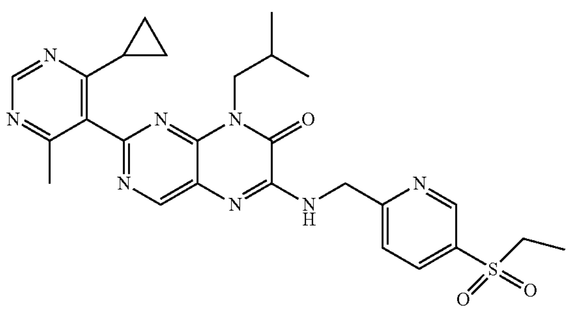 [SMILES: CCS(=O)(=O)c1ccc(CNc2nc3cnc(-c4c(C)ncnc4C4CC4)nc3n(CC(C)C)c2=O)nc1] |
| 253 | 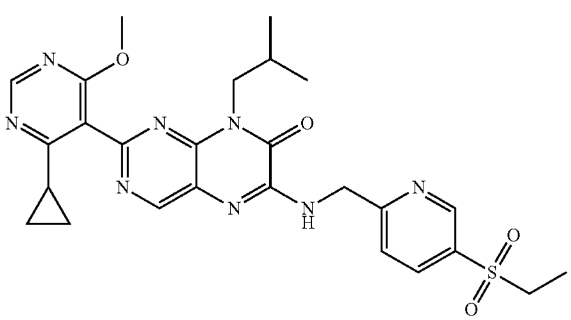 [SMILES: CCS(=O)(=O)c1ccc(CNc2nc3cnc(-c4c(OC)ncnc4C4CC4)nc3n(CC(C)C)c2=O)nc1] |
| 254 | 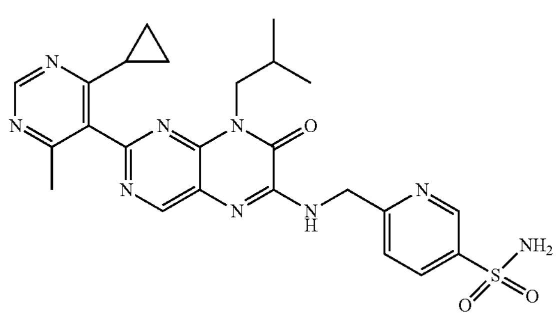 [SMILES: Cc1ncnc(C2CC2)c1-c1ncc2nc(NCc3ccc(S(N)(=O)=O)cn3)c(=O)n(CC(C)C)c2n1] |

| Example | Structure |
|---|---|
| 255 | 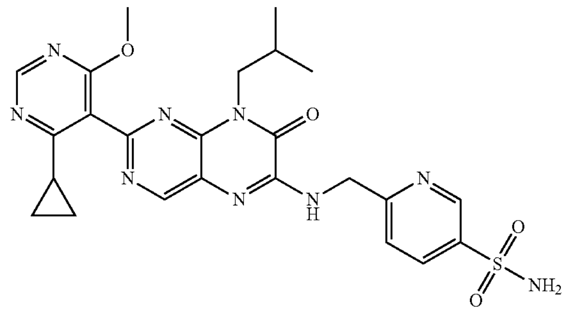 [SMILES: COc1ncnc(C2CC2)c1-c1ncc2nc(NCc3ccc(S(N)(=O)=O)cn3)c(=O)n(CC(C)C)c2n1] |
| 256 | 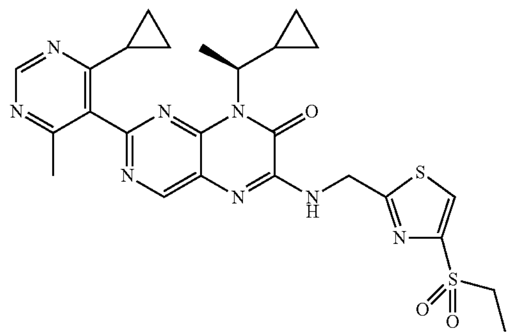 [SMILES: CCS(=O)(=O)c1csc(CNc2nc3cnc(-c4c(C)ncnc4C4CC4)nc3n([C@@H](C)C3CC3)c2=O)n1] |
| 257 | 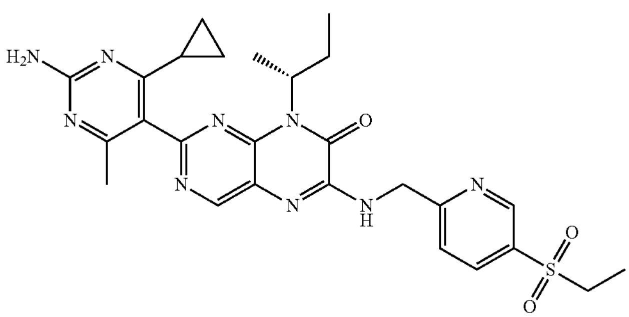 [SMILES: CC[C@@H](C)n1c(=O)c(NCc2ccc(S(=O)(=O)CC)cn2)nc2cnc(-c3c(C)nc(N)nc3C3CC3)nc21] |
| 258 | 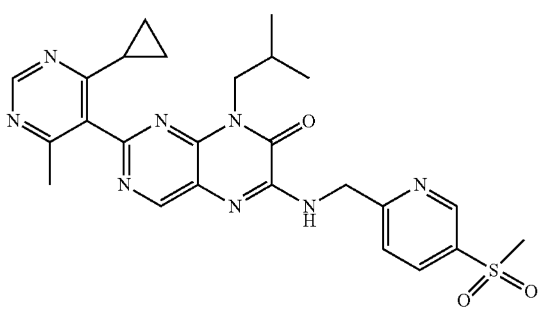 [SMILES: Cc1ncnc(C2CC2)c1-c1ncc2nc(NCc3ccc(S(C)(=O)=O)cn3)c(=O)n(CC(C)C)c2n1] |
| 259 | 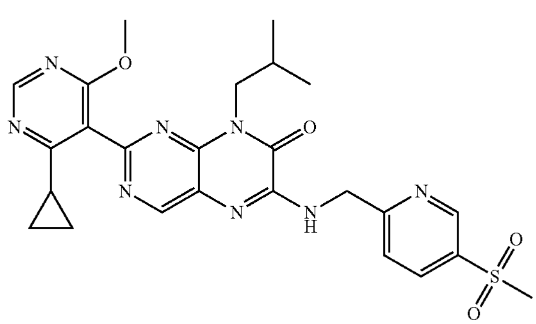 [SMILES: COc1ncnc(C2CC2)c1-c1ncc2nc(NCc3ccc(S(C)(=O)=O)cn3)c(=O)n(CC(C)C)c2n1] |

| Example | Structure |
|---|---|
| 260 | 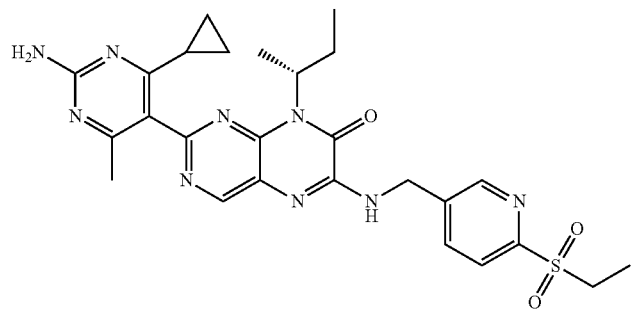 [SMILES: CC[C@@H](C)n1c(=O)c(NCc2ccc(S(=O)(=O)CC)nc2)nc2cnc(-c3c(C)nc(N)nc3C3CC3)nc21] |
| 261 | 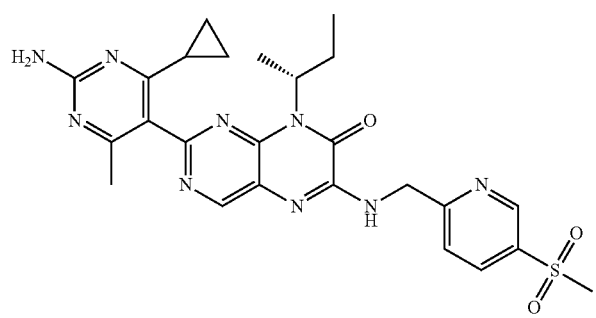 [SMILES: CC[C@@H](C)n1c(=O)c(NCc2ccc(S(C)(=O)=O)cn2)nc2cnc(-c3c(C)nc(N)nc3C3CC3)nc21] |
| 262 | 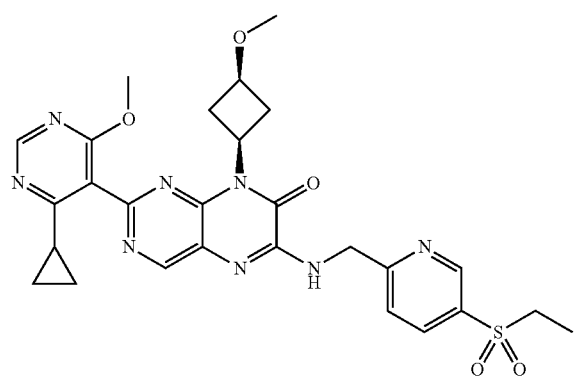 [SMILES: CCS(=O)(=O)c1ccc(CNc2nc3cnc(-c4c(OC)ncnc4C4CC4)nc3n([C@H]3C[C@@H](OC)C3)c2=O)nc1] |
| 263 | 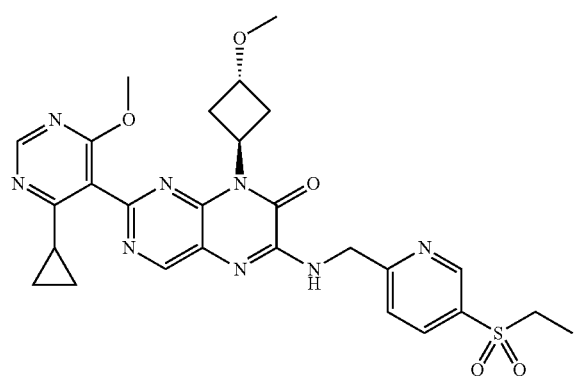 [SMILES: CCS(=O)(=O)c1ccc(CNc2nc3cnc(-c4c(OC)ncnc4C4CC4)nc3n([C@H]3C[C@H](OC)C3)c2=O)nc1] |

| Example | Structure |
|---|---|
| 264 | 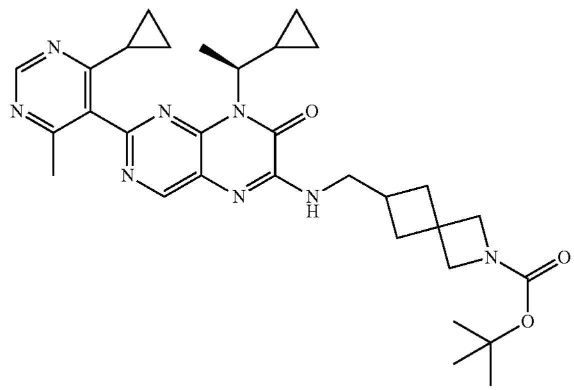 [SMILES: Cc1ncnc(C2CC2)c1-c1ncc2nc(NCC3CC4(C3)CN(C(=O)OC(C)(C)C)C4)c(=O)n([C@@H](C)C3CC3)c2n1] |
| 265 | | or a pharmaceutically acceptable salt thereof.

21. A pharmaceutical composition comprising a compound of formula (I) according to claim 1, or a pharmaceutically acceptable salt thereof, and at least one pharmaceutically acceptable carrier.

22. A method for treating an autoimmune disease or allergic disorder in a patient comprising administering to said patient a therapeutically effective amount of a compound of formula (I) according to claim 1, or a pharmaceutically acceptable salt thereof.

23. A method according to claim 22, wherein the autoimmune disease or allergic disorder is selected from rheumatoid arthritis, psoriasis, systemic lupus erythromatosis, lupus nephritis, scleroderma, asthma, allergic rhinitis, allergic eczema, multiple sclerosis, juvenile rheumatoid arthritis, juvenile idiopathic arthritis, type I diabetes, inflammatory bowel disease, graft versus host disease, psoriatic arthritis, reactive arthritis, ankylosing spondylitis, Crohn's disease, ulcerative colitis, uveitis and non-radiographic spondyloarthropathy.

24. The compound according to claim 1, wherein the compound is

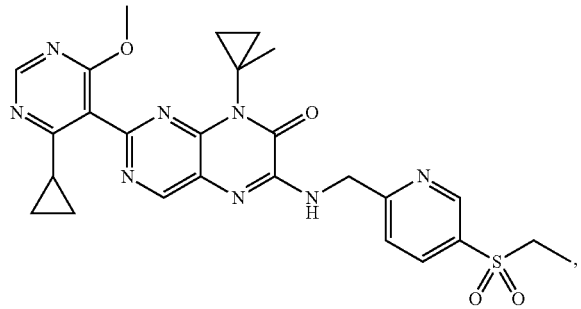 [SMILES: CCS(=O)(=O)c1ccc(CNc2nc3cnc(-c4c(OC)ncnc4C4CC4)nc3n(C3(C)CC3)c2=O)nc1]

or a pharmaceutically acceptable salt thereof.

25. The compound according to claim 1, wherein the compound is

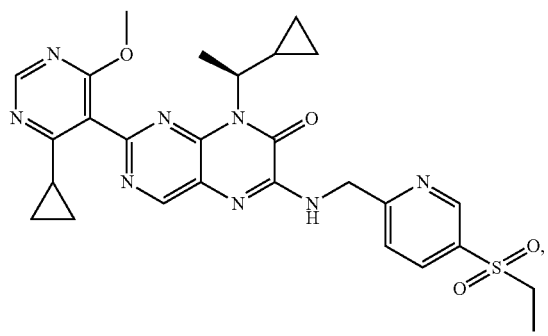 [SMILES: CCS(=O)(=O)c1ccc(CNc2nc3cnc(-c4c(OC)ncnc4C4CC4)nc3n([C@@H](C)C3CC3)c2=O)nc1]

or a pharmaceutically acceptable salt thereof.

26. The compound according to claim 1, wherein the compound is

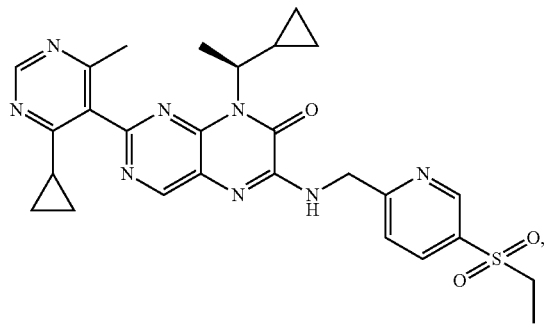 [SMILES: CCS(=O)(=O)c1ccc(CNc2nc3cnc(-c4c(C)ncnc4C4CC4)nc3n([C@@H](C)C3CC3)c2=O)nc1]

or a pharmaceutically acceptable salt thereof.

27. The compound according to claim 1, wherein the compound is

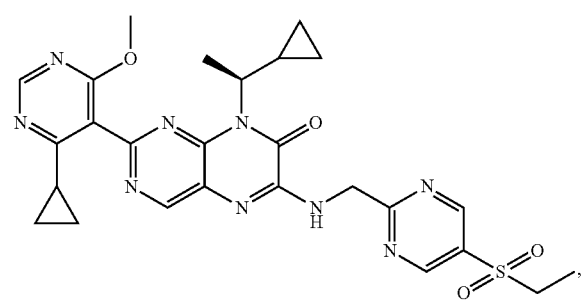 [SMILES: CCc1ncnc(C2CC2)c1-c1ncc2nc(NCc3ccc(S(=O)(=O)CC)cn3)c(=O)n([C@@H](C)C3CC3)c2n1]

or a pharmaceutically acceptable salt thereof.

28. The compound according to claim 1, wherein the compound is

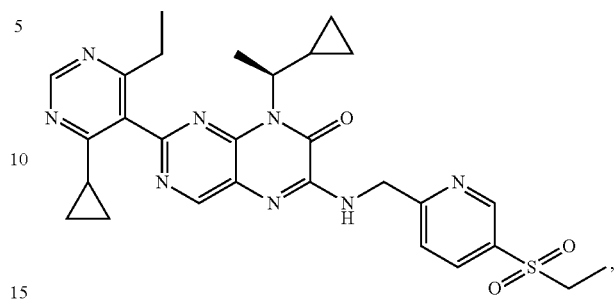

or a pharmaceutically acceptable salt thereof.

29. The compound according to claim 1, wherein the compound is

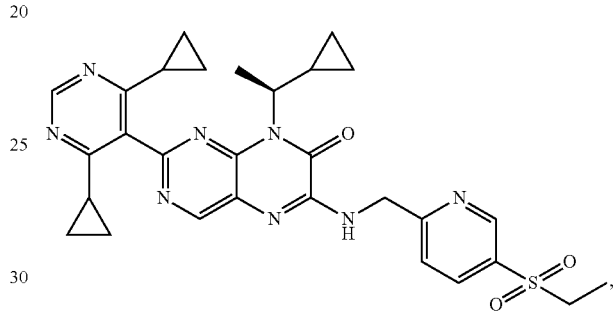

or a pharmaceutically acceptable salt thereof.

30. The compound according to claim 1, wherein the compound is

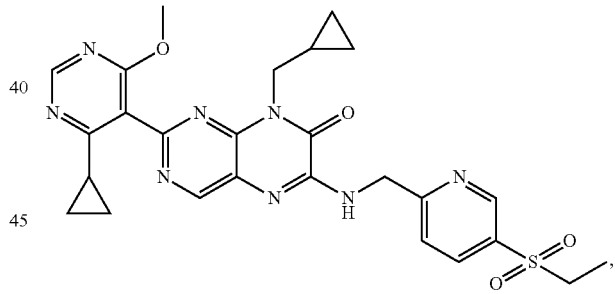

or a pharmaceutically acceptable salt thereof.

31. The compound according to claim 1, wherein the compound is

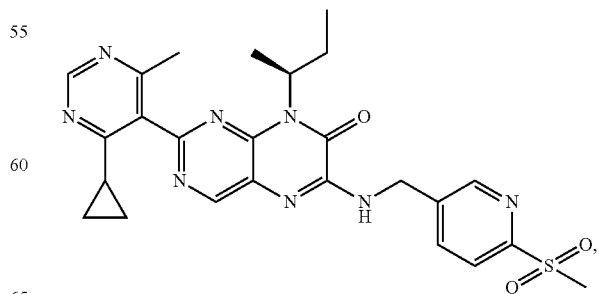

or a pharmaceutically acceptable salt thereof.

32. The new compound according to claim 1, wherein the compound is

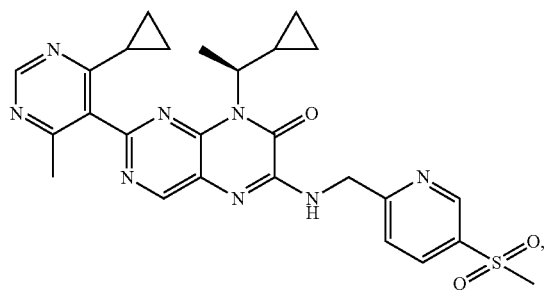 [SMILES: Cc1ncnc(C2CC2)c1-c1ncc2nc(NCc3ccc(S(C)(=O)=O)cn3)c(=O)n([C@@H](C)C3CC3)c2n1]

or a pharmaceutically acceptable salt thereof.

33. The compound according to claim 1, wherein the compound is

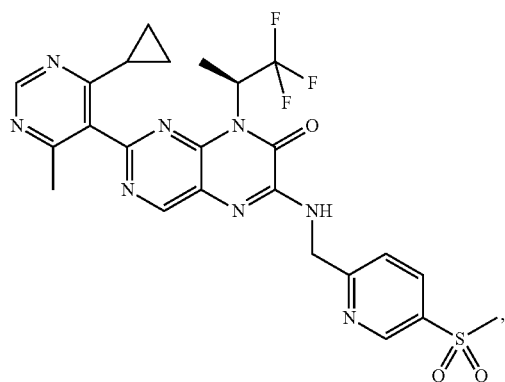 [SMILES: Cc1ncnc(C2CC2)c1-c1ncc2nc(NCc3ccc(S(C)(=O)=O)cn3)c(=O)n([C@@H](C)C(F)(F)F)c2n1]

or a pharmaceutically acceptable salt thereof.

34. A pharmaceutical composition comprising the compound according to claim 24, or a pharmaceutically acceptable salt thereof, and at least one pharmaceutically acceptable carrier.

35. A pharmaceutical composition comprising the compound according to claim 25, or a pharmaceutically acceptable salt thereof, and at least one pharmaceutically acceptable carrier.

36. A pharmaceutical composition comprising the compound according to claim 26, or a pharmaceutically acceptable salt thereof, and at least one pharmaceutically acceptable carrier.

37. A pharmaceutical composition comprising the compound according to claim 27, or a pharmaceutically acceptable salt thereof, and at least one pharmaceutically acceptable carrier.

38. A pharmaceutical composition comprising the compound according to claim 28, or a pharmaceutically acceptable salt thereof, and at least one pharmaceutically acceptable carrier.

39. A pharmaceutical composition comprising the compound according to claim 29, or a pharmaceutically acceptable salt thereof, and at least one pharmaceutically acceptable carrier.

40. A pharmaceutical composition comprising the compound according to claim 30, or a pharmaceutically acceptable salt thereof, and at least one pharmaceutically acceptable carrier.

41. A pharmaceutical composition comprising the compound according to claim 31, or a pharmaceutically acceptable salt thereof, and at least one pharmaceutically acceptable carrier.

42. A pharmaceutical composition comprising the compound according to claim 32, or a pharmaceutically acceptable salt thereof, and at least one pharmaceutically acceptable carrier.

43. A pharmaceutical composition comprising the compound according to claim 33, or a pharmaceutically acceptable salt thereof, and at least one pharmaceutically acceptable carrier.

44. The method according to claim 22, wherein the compound of formula (I) is

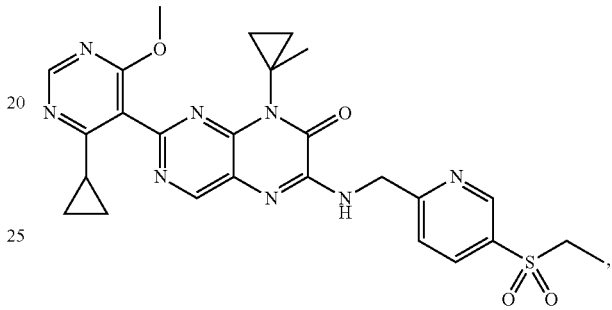

or a pharmaceutically acceptable salt thereof.

45. The method according to claim 22, wherein the compound of formuls (I) is

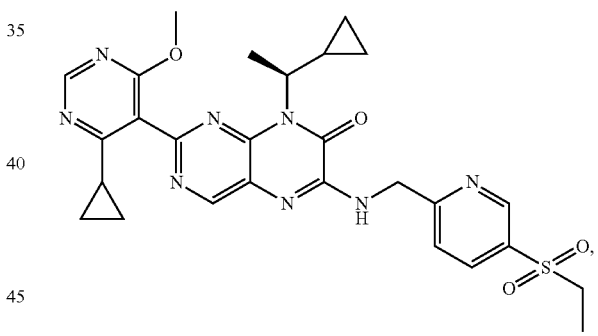

or a pharmaceutically acceptable salt thereof.

46. The method according to claim 22, wherein the compound of formula (I) is

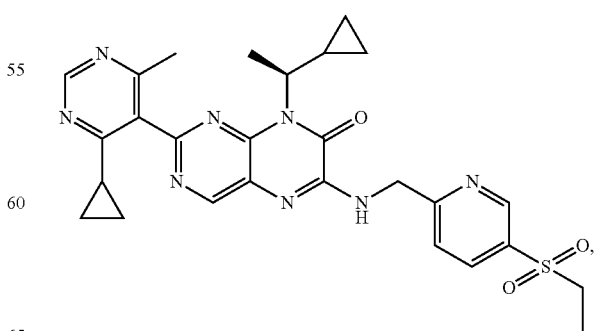

or a pharmaceutically acceptable salt thereof.

47. The method according to claim 22, wherein the compound of formula (I) is

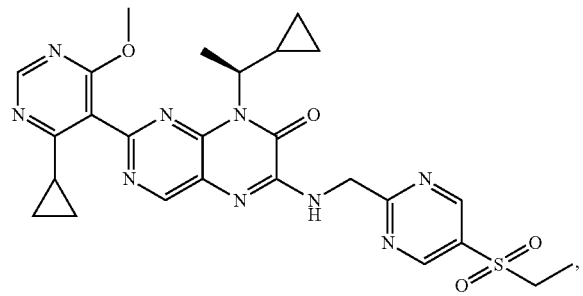

or a pharmaceutically acceptable salt thereof.

48. The method according to claim 22, wherein the compound of fomula (I) is

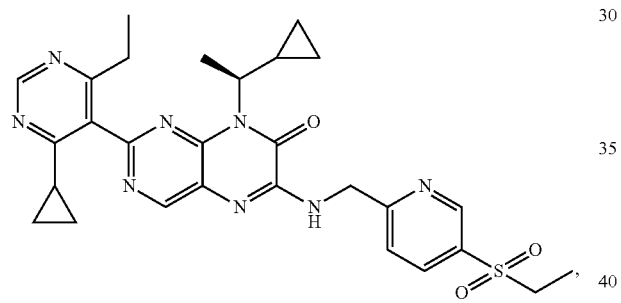

or a pharmaceutically acceptable salt thereof.

49. The method according to claim 22, wherein the compound of formula (I) is

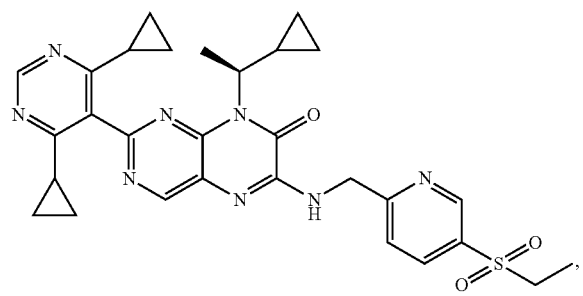 [SMILES: CCS(=O)(=O)c1ccc(CNc2nc3cnc(-c4c(C5CC5)ncnc4C4CC4)nc3n([C@@H](C)C3CC3)c2=O)nc1]

or a pharmaceutically acceptable salt thereof.

50. The method according to claim 22, wherein the compound of formula (I) is

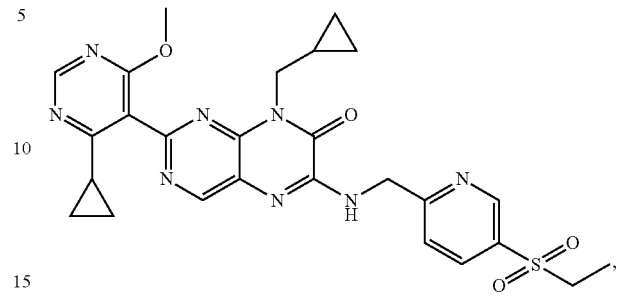

or a pharmaceutically acceptable salt thereof.

51. The method according to claim 22, wherein the compound of formula (I) is or a pharmaceutically acceptable salt thereof.

52. The method according to claim 22, wherein the compound of formula (I) is or a pharmaceutically acceptable salt thereof.

53. The method according to claim 22, wherein the compound of formula (I) is
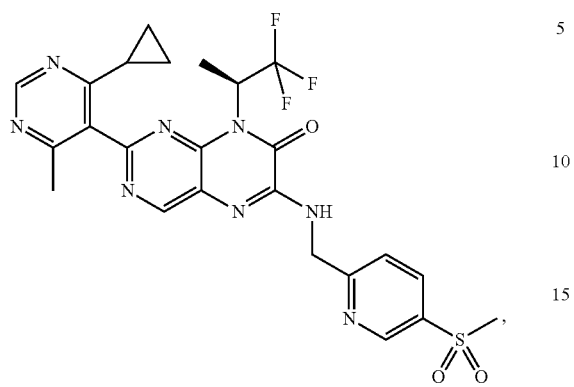
or a pharmaceutically acceptable salt thereof.
* * * * *

UNITED STATES PATENT AND TRADEMARK OFFICE
CERTIFICATE OF CORRECTION

PATENT NO.        : 9,242,989 B2
APPLICATION NO.   : 14/683682
DATED             : January 26, 2016
INVENTOR(S)       : Bakonyi et al.

It is certified that error appears in the above-identified patent and that said Letters Patent is hereby corrected as shown below:

Specification

Table, structure 229: " 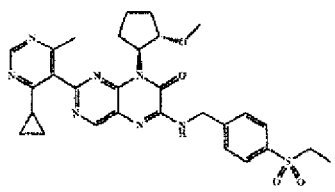 " to read as -- 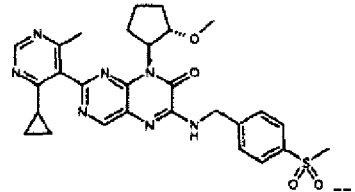 --

Column 247, line 40, methods: "systemic lupus erythromatosis" to read as --systemic lupus erythematosus--

Claims

Column 249, line 67, claim 1: "-S(O)$_n$NR$^7$R$^{8}$" to read as -- -S(O)$_n$NR$^7$R$^8$;--

Column 250, line 66, claim 2: "-N(H)S(O)-R$^6$;" to read as -- -N(H)S(O)$_n$R$^6$;--

Column 251, line 21, claim 3: "-S(O)-R$^6$," to read as --S(O)$_n$R$^6$,--

Column 254, line 59, claim 17: "-NR$^7$R$^{8}$" to read as -- -NR$^7$R$^8$;--

Column 256, line 08, claim 18: "R$^7$, R$^8$R$^{9}$" to read as --R$^7$, R$^8$ and R$^9$--

Signed and Sealed this
Tenth Day of May, 2016

Michelle K. Lee
*Director of the United States Patent and Trademark Office*